United States Patent
Ince et al.

(10) Patent No.: US 8,975,265 B2
(45) Date of Patent: Mar. 10, 2015

(54) SUBSTITUTED IMIDAZO[1,2-A]PYRIMIDINES AND —PYRIDINES

(75) Inventors: Stuart Ince, Berlin (DE); Andrea Hägebarth, Berlin (DE); Oliver Politz, Panketal OT Zepernick (DE); Roland Neuhaus, Berlin (DE); Ulf Bömer, Glienicke (DE); William Scott, Guilford, CT (US)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/808,430

(22) PCT Filed: Jul. 7, 2011

(86) PCT No.: PCT/EP2011/061508
§ 371 (c)(1),
(2), (4) Date: Mar. 22, 2013

(87) PCT Pub. No.: WO2012/007345
PCT Pub. Date: Jan. 19, 2012

(65) Prior Publication Data
US 2013/0190332 A1    Jul. 25, 2013

Related U.S. Application Data

(60) Provisional application No. 61/392,779, filed on Oct. 13, 2010.

(30) Foreign Application Priority Data

Jul. 12, 2010   (EP) .................................... 10169205

(51) Int. Cl.
| | | |
|---|---|---|
| A01N 43/90 | (2006.01) |
| A61K 31/519 | (2006.01) |
| A61K 31/437 | (2006.01) |
| C07D 471/04 | (2006.01) |
| C07D 487/04 | (2006.01) |
| A61K 45/06 | (2006.01) |
| C07F 5/04 | (2006.01) |

(52) U.S. Cl.
CPC ............ *A61K 31/437* (2013.01); *C07D 471/04* (2013.01); *C07D 487/04* (2013.01); *A61K 31/519* (2013.01); *A61K 45/06* (2013.01); *C07F 5/04* (2013.01)
USPC ...................................................... 514/259.5

(58) Field of Classification Search
None
See application file for complete search history.

(56) References Cited

FOREIGN PATENT DOCUMENTS

| WO | 2008/070016 A2 | 6/2008 |
| WO | 2009/021990 A1 | 2/2009 |
| WO | WO 2009021990 A1 * | 2/2009 |
| WO | 2010/088177 A1 | 8/2010 |
| WO | 2010/104705 A1 | 9/2010 |
| WO | 2010/114780 A1 | 10/2010 |
| WO | 2011/033265 A1 | 3/2011 |
| WO | 2011/055115 A1 | 3/2011 |

OTHER PUBLICATIONS

Y. Li et al., Bioorg. Med. Chem. Lett. 2009, 19, 834-836.

* cited by examiner

*Primary Examiner* — Dennis Heyer
*Assistant Examiner* — Daniel M Podgorski

(57) ABSTRACT

Compounds of formula (I) which are effective inhibitors of the Pi3K/Akt pathway, processes for their production and their use as pharmaceuticals.

10 Claims, No Drawings

SUBSTITUTED IMIDAZO[1,2-A]PYRIMIDINES AND —PYRIDINES

FIELD OF APPLICATION OF THE INVENTION

The invention relates to substituted Imidazo[1,2-a]pyrimidine and Imidazo[1,2-a]pyridine compounds, a process for their production and the use thereof.

KNOWN TECHNICAL BACKGROUND

Cancer is the second most prevalent cause of death in the United States, causing 450,000 deaths per year. While substantial progress has been made in identifying some of the likely environmental and hereditary causes of cancer, there is a need for additional therapeutic modalities that target cancer and related diseases. In particular there is a need for therapeutic methods for treating diseases associated with dysregulated growth/proliferation.

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

One pathway that has been shown to mediate important survival signals for mammalian cells comprises receptor tyrosine kinases like platelet-derived growth factor receptor (PDGF-R), human epidermal growth factor 2/3 receptor (HER2/3), or the insulin-like growth factor 1 receptor (IGF-1R). After activation the respectives by ligand, these receptors activate the phoshatidylinositol 3-kinase (Pi3K)/Akt pathway. The phoshatidylinositol 3-kinase (Pi3K)/Akt protein kinase pathway is central to the control of cell growth, proliferation and survival, driving progression of tumors. Therefore within the class of serine-threonine specific signalling kinases, Akt (protein kinase B; PKB) with the isoenzmyes Akt1 (PKBα), Akt2 (PKB β) and Akt3 (PKB γ) is of high interest for therapeutic intervention. Akt is mainly activated in a Pi3-kinase dependent manner and the activation is regulated through the tumor suppressor PTEN (phosphatase and tensin homolog), which works essentially as the functional antagonist of Pi3K.

The Pi3K/Akt pathway regulates fundamental cellular functions (e.g. transcription, translation, growth and survival), and is implicated in human diseases including diabetes and cancer. The pathway is frequently overactivated in a wide range of tumor entities like breast and prostate carcinomas. Upregulation can be due to overexpression or constitutively activation of receptor tyrosine kinases (e.g. EGFR, HER2/3), which are upstream and involved in its direct activation, or gain- or loss-of-function mutants of some of the components like loss of PTEN. The pathway is targeted by genomic alterations including mutation, amplification and rearrangement more frequently than any other pathway in human cancer, with the possible exception of the p53 and retinoblastoma pathways. The alterations of the Pi3K/Akt pathway trigger a cascade of biological events, that drive tumor progression, survival, angiogenesis and metastasis.

Activation of Akt kinases promotes increased nutrient uptake, converting cells to a glucose-dependent metabolism that redirects lipid precursors and amino acids to anabolic processes that support cell growth and proliferation. These metabolic phenotype with overactivated Akt lead to malignancies that display a metabolic conversion to aerobic glycolysis (the Warburg effect). In that respect the Pi3K/Akt pathway is discussed to be central for survival despite unfavourable growth conditions such as glucose depletion or hypoxia.

A further aspect of the activated PI3K/Akt pathway is to protect cells from programmed cell death ("apoptosis") and is hence considered to transduce a survival signal. By acting as a modulator of anti-apoptotic signalling in tumor cells, the Pi3K/Akt pathway, particular Akt itself is a target for cancer therapy. Activated Akt phosphorylates and regulates several targets, e.g. BAD, GSK3 or FKHRL1, that affect different signalling pathways like cell survival, protein synthesis or cell movement. This Pi3K/Akt pathway also plays a major part in resistance of tumor cells to conventional anti-cancer therapies. Blocking the Pi3K/Akt pathway could therefore simultaneously inhibit the proliferation of tumor cells (e.g. via the inhibition of the metabolic effect) and sensitize towards pro-apoptotic agents.

Akt inhibition selectively sensitized tumor cells to apoptotic stimuli like Trail, Campthothecin and Doxorubicin. Dependent on the genetic background/molecular apperations of tumors, Akt inhibitors might induce apoptotic cell death in monotherapy as well.

From WO 2008/070016 tricyclic Akt inhibitors are known which are alleged to be unspecific Akt kinase inhibitors. No data for any specific compounds are disclosed. Different Akt inhibitors are disclosed in WO 2009/021990, WO2010088177, WO2010104705, WO2010114780, WO2011033265, WO2011055115. In a recent disclosure, Y. Li et al (Bioorg. Med. Chem. Lett. 2009, 19, 834-836 and cited references therein) detail the difficulty in finding optimal Akt inhibitors. The potential application of Akt inhibitors in multiple disease settings, such as for example, cancer, makes the provision of new, improved Akt inhibitors to those currently available still highly desirable.

DESCRIPTION OF THE INVENTION

A solution to the above problem is the provision of improved Akt inhibitors, whereby the current compounds have an improved pharmacokinetic profile. It has now been found that the new substituted Imidazo[1,2-a]pyrimidine and Imidazo[1,2-a]pyridine compounds, which are described in detail below, are Akt inhibitors with an improved pharmacokinetic profile.

In accordance with a first aspect, the invention relates to compounds of formula (I)

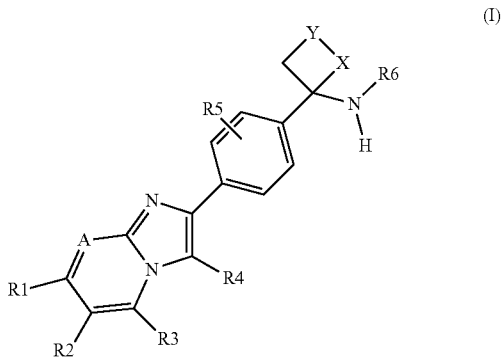

in which
R1 is hydrogen, hydroxy, halogen, cyano, —CO-(1-6C-alkyl), —C(O)OR10, —CO(NR8R9), —NR8R9, —NH—C(O)NR8R9, —NH—C(O)R11, 2-6C-alkinyl, or a group selected from 1-6C-alkyl, 2-6C-alkenyl, 1-6C-alkoxy, 3-7C-cycloalkyl, aryl, heteroaryl, -(1-6C-alkylen)-aryl, -(1-6C-alkylen)-heteroaryl, —O-(3-7C-cycloalkyl), —O-aryl, —O-(3-7C-heterocyclyl), —O-heteroaryl, —O-(1-6C-alkylen)-heteroaryl, —O-(1-6C-alkylen)-(3-7C-heterocyclyl), —O-(1-6C-alkylen)-aryl, —O-(1-6C-alkyl)-(3-7C-cycloalkyl),
  wherein said group being optionally substituted, one or more times, identically or differently, with a substituent selected from:
    hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, heteroaryl,
    wherein said substituent can be optionally substituted with 1-6C-alkoxy,
R2 is hydrogen, hydroxy, halogen, cyano, —C(O)OR10, —CO(NR8R9), —NR8R9, —NH—C(O)R11, —NH—C(O)NR8R9, —NHS(O)$_2$R11 or
a group selected from 1-6C-alkyl, 2-6C-alkenyl, 1-6C-alkoxy, 3-7C-cycloalkyl, aryl, heteroaryl,
  wherein said group is optionally substituted, one or more times, identically or differently, with a substituent selected from:
    hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, NH-(1-6C-alkyl)-O-(1-60-alkyl),
R3 is hydrogen, 1-6C-alkyl,
R4 is phenyl optionally substituted by 1-6C-alkyl, halogen, cyano,
R5 is hydrogen, halogen,
R6 is hydrogen, 1-6C-alkyl,
A is N, C(R7),
R7 is hydrogen, hydroxy, halogen, cyano, —C(O)OR10, —CO(NR8R9), 3-7C-cycloalkyl, or
a group selected from 1-6C-alkyl, 2-6C-alkenyl, 1-6C-alkoxy, aryl, heteroaryl,
  wherein said group is optionally substituted, one or more times, identically or differently, with a substituent selected from:
    hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
X is —CH$_2$—,
Y is —CH$_2$—, —CH(OH)—,
R8, R9 which can be the same or different, is hydrogen, hydroxy, 3-7C-cycloalkyl or
a group selected from 1-4C-alkyl, 1-6C-alkoxy, wherein said group is optionally substituted, one or more times, identically or differently, with a substituent selected from:
  halogen, hydroxy, mono- or di-(1-4C-alkylamino), 1-4C-alkoxy, or 3-7C-cycloalkyl, or,
R8 and R9 together with the nitrogen to which they are attached may also form a saturated or unsaturated 3-6C-heterocyclic ring,
  which is optionally substituted by (═O)
R10 is hydrogen, 1-6C-alkyl,
R11 is 1-4C-alkyl (optionally substituted in the same way of differently one or more times with halogen, hydroxy) or 3-7C-cycloalkyl,
or an N-oxide, a salt, a tautomer or a stereoisomer of said compound, or a salt of said N-oxide, tautomer or stereoisomer.

A further aspect of the invention are compounds of formula (I) according to claim 1, wherein
R1 is hydrogen, hydroxy, halogen, cyano, CO-(1-3C-alkyl), C(O)OR10, CO(NR8R9), NR8R9, NH—C(O)NR8R9, NH—C(O)R11, 2-3C-alkinyl, or a group selected from 1-3C-alkyl, 2-3C-alkenyl, 1-3C-alkoxy, 3-6C-cycloalkyl, aryl, heteroaryl, -(1-3C-alkyl en)-aryl, -(1-3C-alkylen)-heteroaryl, —O-(3-6C-cycloalkyl), —O-aryl, —O-(3-6C-heterocyclyl), —O-heteroaryl, —O-(1-3C-alkyl en)-heteroaryl, —O-(1-3C-alkylen)-(3-6C-heterocyclyl), —O-(1-3C-alkylen)-aryl, —O-(1-6C-alkyl)en-(3-7C-cycloalkyl),
  wherein said group being optionally substituted, one or more times, identically or differently, with a substituent selected from:
    hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)$_2$R11, heteroaryl,
    wherein said substituent can be optionally substituted with 1-6C-alkoxy,
R2 is hydrogen, hydroxy, halogen, cyano, —C(O)OR10, —CO(NR8R9), —NR8R9, —NH—C(O)R11, —NH—C(O)NR8R9, —NHS(O)$_2$R11 or
a group selected from 1-3C-alkyl, 2-3C-alkenyl, 1-3C-alkoxy, 3-6C-cycloalkyl, aryl, heteroaryl,
  wherein said group is optionally substituted, one or more times, identically or differently, with a substituent selected from:
    hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)$_2$R11, NH-(1-3C-alkylen)-O-(1-3C-alkyl),
R3 is hydrogen, 1-3C-alkyl,
R4 is phenyl optionally substituted by 1-3C-alkyl, halogen, cyano,
R5 is hydrogen, halogen,
R6 is hydrogen, 1-3C-alkyl,
A is N, C(R7),
R7 is hydrogen, hydroxy, halogen, cyano, C(O)OR10, CO(NR8R9), 3-6C-cycloalkyl, or
a group selected from 1-3C-alkyl, 2-3C-alkenyl, 1-3C-alkoxy, aryl, heteroaryl,
  wherein said group is optionally substituted, one or more times, identically or differently, with a substituent selected from:
    hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)$_2$R11,
X is —CH$_2$—,
Y is —CH$_2$—, —CH(OH)—,
R8, R9 which can be the same or different, is hydrogen, hydroxy, 3-6C-cycloalkyl or
a group selected from 1-3C-alkyl, 1-3C-alkoxy, wherein said group is optionally substituted, one or more times, identically or differently, with a substituent selected from:
  halogen, hydroxy, mono- or di-1-3C-alkylamino), 1-3C-alkoxy, or 3-6C-cycloalkyl, or,
R8 and R9 together with the nitrogen to which they are attached may also form a saturated or unsaturated 3-6C-heterocyclic ring,
  which is optionally substituted by (═O)
R10 is hydrogen, 1-3C-alkyl,
R11 is 1-3C-alkyl (optionally substituted in the same way of differently one or more times with halogen, hydroxy) or 3-6C-cycloalkyl,
or an N-oxide, a salt, a tautomer or a stereoisomer of said compound, or a salt of said N-oxide, tautomer or stereoisomer.
wherein
R1 is hydrogen, hydroxy, halogen, cyano, CO(NR8R9), or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-60-alkyl)-aryl, wherein said group being optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, R2 is hydrogen, 1-6C-alkyl, 1-6C-alkoxy, halogen, cyano, CO(NR8R9), aryl, heteroaryl,
wherein said 1-6C-alkyl, 1-6C-alkoxy, aryl, heteroaryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, R3 is hydrogen,
R4 is phenyl optionally substituted by 1-6C-alkyl, halogen, cyano,
R5 is hydrogen, halogen,
R6 is hydrogen, 1-6C-alkyl,
A is N, C(R7),
R7 is hydrogen, 1-6C-alkyl, 1-6C-alkoxy, halogen, cyano, CO(NR8R9), aryl, wherein said
1-6C-alkyl, 1-6C-alkoxy, aryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, X is —CH$_2$—,
Y is —CH$_2$—, —CH(OH)—,
R8, R9 which can be the same or different, is hydrogen, 1-4C-alkyl (optionally substituted in the same way of differently one or more times with halogen, hydroxy, mono- or di-1-4C-alkylamino), 1-4C-alkoxy, or 3-7C-cycloalkyl, or,
in the case of —NR8R9, R8 and R9 together with the nitrogen to which they are attached may also form a 3-6C-heterocyclic ring,
R10 is hydrogen, 1-6C-alkyl,
R11 is 1-4C-alkyl (optionally substituted in the same way of differently one or more times with halogen, hydroxy) or 3-7C-cycloalkyl,
or an N-oxide, a salt, a tautomer or a stereoisomer of said compound, or a salt of said N-oxide, tautomer or stereoisomer.

Another aspect of the invention relates to compounds of formula (I), wherein
R1 is hydrogen, hydroxy, or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl,
wherein said group being optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, R2 is hydrogen, 1-6C-alkyl, 1-6C-alkoxy, halogen, cyano, CO(NR8R9), aryl, heteroaryl,
wherein said 1-6C-alkyl, 1-6C-alkoxy, aryl, heteroaryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, R3 is hydrogen,
R4 is phenyl optionally substituted by 1-6C-alkyl, halogen, cyano,
R5 is hydrogen, halogen,
R6 is hydrogen, 1-6C-alkyl,
A is N, C(R7),
R7 is hydrogen, 1-6C-alkyl, 1-6C-alkoxy, halogen, cyano, CO(NR8R9), aryl, wherein said
1-6C-alkyl, 1-6C-alkoxy, aryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, X is —CH$_2$—,
Y is —CH$_2$—, —CH(OH)—,
R8, R9 which can be the same or different, are hydrogen, 1-4C-alkyl (optionally substituted in the same way of differently one or more times with halogen, hydroxy, mono- or di-1-4C-alkylamino), 1-4C-alkoxy, or 3-7C-cycloalkyl, or,
in the case of —NR8R9, R8 and R9 together with the nitrogen to which they are attached may also form a 3-6C-heterocyclic ring,
R10 is hydrogen, 1-6C-alkyl,
R11 is 1-4C-alkyl (optionally substituted in the same way of differently one or more times with halogen, hydroxy) or 3-7C-cycloalkyl,
or an N-oxide, a salt, a tautomer or a stereoisomer of said compound, or a salt of said N-oxide, tautomer or stereoisomer.

A further aspect of the invention are compounds of formula (I)
R1 is hydrogen, hydroxy, halogen, cyano, —CO-(1-6C-alkyl), —C(O)OR10, —CO(NR8R9), —NR8R9, —NH—C(O)NR8R9, —NH—C(O)R11, 2-6C-alkinyl, or
a group selected from 1-6C-alkyl, 2-6C-alkenyl, 1-6C-alkoxy, 3-7C-cycloalkyl, aryl, heteroaryl, -(1-6C-alkylen)-aryl, -(1-6C-alkylen)-heteroaryl, —O-(3-7C-cycloalkyl), —O-aryl, —O-(3-7C-heterocyclyl), —O-heteroaryl, —O-(1-6C-alkylen)-heteroaryl, —O-(1-6C-alkylen)-(3-7C-heterocyclyl), —O-(1-6C-alkylen)-aryl, —O-(1-6C-alkyl)-(3-7C-cycloalkyl)
wherein said group being optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, heteroaryl, wherein said substituent can be optionally substituted with 1-6C-alkoxy, R2 is hydrogen, hydroxy, halogen, cyano, —C(O)OR10, —CO(NR8R9), —NR8R9, —NH—C(O)R11, —NH—C(O)NR8R9, —NHS(O)$_2$R11 or
a group selected from 1-6C-alkyl, 2-6C-alkenyl, 1-6C-alkoxy, 3-7C-cycloalkyl, aryl, heteroaryl,
wherein said group is optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11, NH-(1-6C-alkylen)-O-(1-6C-alkyl), R3 is hydrogen, R4 is phenyl optionally substituted by 1-6C-alkyl, halogen, cyano, R5 is hydrogen, halogen, R6 is hydrogen, A is N, C(R7), R7 is hydrogen, hydroxy, halogen, cyano, —C(O)OR10, —CO(NR8R9), 3-7C-cycloalkyl, or a group selected from 1-6C-alkyl, 2-6C-alkenyl, 1-6C-alkoxy, aryl, heteroaryl,
  wherein said group is optionally substituted, one or more times, identically or differently, with a substituent selected from:
    hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11, X is —CH₂—, Y is —CH₂—, —CH(OH)—, R8, R9 which can be the same or different, is hydrogen, hydroxy, 3-7C-cycloalkyl or a group selected from 1-4C-alkyl, 1-6C-alkoxy, wherein said group is optionally substituted, one or more times, identically or differently, with a substituent selected from:
  halogen, hydroxy, mono- or di-(1-4C-alkylamino), 1-4C-alkoxy, or 3-7C-cycloalkyl, or, R8 and R9 together with the nitrogen to which they are attached may also form a saturated or unsaturated 3-6C-heterocyclic ring,
  which is optionally substituted by (=O)

R10 is hydrogen, 1-6C-alkyl,

R11 is 1-4C-alkyl (optionally substituted in the same way of differently one or more times with halogen, hydroxy) or 3-7C-cycloalkyl, or an N-oxide, a salt, a tautomer or a stereoisomer of said compound, or a salt of said N-oxide, tautomer or stereoisomer.

Another aspect of the invention are compounds of formula (I)

R1 is hydrogen, hydroxy, halogen, cyano, —CO-(1-3C-alkyl), —C(O)OR10, —CO(NR8R9), —NR8R9, —NH—C(O)NR8R9, —NH—C(O)R11, 2-3C-alkinyl, or a group selected from 1-3C-alkyl, 2-3C-alkenyl, 1-3C-alkoxy, 3-6C-cycloalkyl, aryl, heteroaryl, -(1-3C-alkylen)-aryl, -(1-3C-alkylen)-heteroaryl, —O-(3-6C-cycloalkyl), —O-aryl, —O-(3-6C-heterocyclyl), —O-heteroaryl, —O-(1-3C-alkylen)-heteroaryl, —O-(1-3C-alkylen)-(3-6C-heterocyclyl), —O-(1-3C-alkylen)-aryl, —O-(1-3C-alkyl)-(3-6C-cycloalkyl)
  wherein said group being optionally substituted, one or more times, identically or differently, with a substituent selected from:
    hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)₂R11, heteroaryl,
    wherein said substituent can be optionally substituted with 1-3C-alkoxy, R2 is hydrogen, hydroxy, halogen, cyano, —C(O)OR10, —CO(NR8R9), —NR8R9, —NH—C(O)R11, —NH—C(O)NR8R9, —NHS(O)₂R11 or a group selected from 1-3C-alkyl, 2-3C-alkenyl, 1-3C-alkoxy, 3-6C-cycloalkyl, aryl, heteroaryl, wherein said group is optionally substituted, one or more times, identically or differently, with a substituent selected from:
  hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)₂R11, NH-(1-3C-alkylen)-O-(1-3C-alkyl), R3 is hydrogen, R4 is phenyl optionally substituted by 1-3C-alkyl, halogen, cyano, R5 is hydrogen, halogen, R6 is hydrogen, A is N, C(R7), R7 is hydrogen, hydroxy, halogen, cyano, —C(O)OR10, —CO(NR8R9), 3-6C-cycloalkyl, or a group selected from 1-3C-alkyl, 2-3C-alkenyl, 1-3C-alkoxy, aryl, heteroaryl,
  wherein said group is optionally substituted, one or more times, identically or differently, with a substituent selected from:
    hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)₂R11, X is —CH₂—, Y is —CH₂—, —CH(OH)—, R8, R9 which can be the same or different, is hydrogen, hydroxy, 3-6C-cycloalkyl or a group selected from 1-3C-alkyl, 1-3C-alkoxy, wherein said group is optionally substituted, one or more times, identically or differently, with a substituent selected from:
  halogen, hydroxy, mono- or di-(1-3C-alkylamino), 1-3C-alkoxy, or 3-6C-cycloalkyl, or, R8 and R9 together with the nitrogen to which they are attached may also form a saturated or unsaturated 3-6C-heterocyclic ring,
    which is optionally substituted by (=O)

R10 is hydrogen, 1-3C-alkyl,

R11 is 1-3C-alkyl (optionally substituted in the same way of differently one or more times with halogen, hydroxy) or 3-6C-cycloalkyl, or an N-oxide, a salt, a tautomer or a stereoisomer of said compound, or a salt of said N-oxide, tautomer or stereoisomer.

A further aspect of the invention are compounds of formula (I)

wherein

R1 is hydrogen, hydroxy, halogen, cyano, CO(NR8R9), or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)heteroaryl, —O-(1-6C-alkyl)-(3-7C-heterocyclyl), —O-(1-6C-alkyl)-aryl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11, R2 is hydrogen, 1-6C-alkyl, 1-6C-alkoxy, halogen, cyano, CO(NR8R9), aryl, heteroaryl,
  wherein said 1-6C-alkyl, 1-6C-alkoxy, aryl, heteroaryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11, R3 is hydrogen,
R4 is phenyl optionally substituted by 1-6C-alkyl, halogen, cyano,
R5 is hydrogen, halogen,
R6 is hydrogen,
A is N, C(R7),
R7 is hydrogen, 1-6C-alkyl, 1-6C-alkoxy, halogen, cyano, CO(NR8R9), aryl, wherein said
1-6C-alkyl, 1-6C-alkoxy, aryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
X is —CH$_2$—,
Y is —CH$_2$—, —CH(OH)—,
R8, R9 which can be the same or different, are hydrogen, 1-4C-alkyl (optionally substituted in the same way of differently one or more times with halogen, hydroxy, mono- or di-1-4C-alkylamino), 1-4C-alkoxy, or 3-7C-cycloalkyl, or,
in the case of —NR8R9, R8 and R9 together with the nitrogen to which they are attached may also form a 3-6C-heterocyclic ring,
R10 is hydrogen, 1-6C-alkyl,
R11 is 1-4C-alkyl (optionally substituted in the same way of differently one or more times with halogen, hydroxy) or 3-7C-cycloalkyl,
or an N-oxide, a salt, a tautomer or a stereoisomer of said compound, or a salt of said N-oxide, tautomer or stereoisomer.

Another aspect of the invention are compounds of formula (I) wherein
R1 is hydrogen, hydroxy, or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl,
wherein said group being optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
R2 is hydrogen, 1-6C-alkyl, 1-6C-alkoxy, halogen, cyano, CO(NR8R9), aryl, heteroaryl,
wherein said 1-6C-alkyl, 1-6C-alkoxy, aryl, heteroaryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
R3 is hydrogen,
R4 is phenyl optionally substituted by 1-6C-alkyl, halogen, cyano,
R5 is hydrogen, halogen,
R6 is hydrogen,
A is N, C(R7),
R7 is hydrogen, 1-6C-alkyl, 1-6C-alkoxy, halogen, cyano, CO(NR8R9), aryl, wherein said
1-6C-alkyl, 1-6C-alkoxy, aryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
X is —CH$_2$—,
Y is —CH$_2$—, —CH(OH)—,
R8, R9 which can be the same or different, are hydrogen, 1-4C-alkyl (optionally substituted in the same way of differently one or more times with halogen, hydroxy, mono- or di-1-4C-alkylamino), 1-4C-alkoxy, or 3-7C-cycloalkyl, or,
in the case of —NR8R9, R8 and R9 together with the nitrogen to which they are attached may also form a 3-6C-heterocyclic ring,
R10 is hydrogen, 1-6C-alkyl,
R11 is 1-4C-alkyl (optionally substituted in the same way of differently one or more times with halogen, hydroxy) or 3-7C-cycloalkyl,
or an N-oxide, a salt, a tautomer or a stereoisomer of said compound, or a salt of said N-oxide, tautomer or stereoisomer.

A further aspect of the invention are compounds of formula (I) wherein
R1 is hydrogen, hydroxy, halogen, cyano, —CO-(1-6C-alkyl), —C(O)OR10, —CO(NR8R9), —NR8R9, —NH—C(O)NR8R9, —NH—C(O)R11, 2-6C-alkinyl, or
a group selected from 1-6C-alkyl, 2-6C-alkenyl, 1-6C-alkoxy, 3-7C-cycloalkyl, aryl, heteroaryl, -(1-6C-alkylen)-aryl, -(1-6C-alkylen)-heteroaryl, —O-(3-7C-cycloalkyl), —O-aryl, —O-(3-7C-heterocyclyl), —O-heteroaryl, —O-(1-6C-alkylen)-heteroaryl, —O-(1-6C-alkylen)-(3-7C-heterocyclyl), —O-(1-6C-alkylen)-aryl, —O-(1-6C-alkylen)-(3-7C-cycloalkyl)
wherein said group being optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, heteroaryl, wherein said substituent can be optionally substituted with 1-6C-alkoxy,
R2 is hydrogen, hydroxy, halogen, cyano, —C(O)OR10, —CO(NR8R9), —NR8R9, —NH—C(O)R11, —NH—C(O)NR8R9, —NHS(O)$_2$R11 or
a group selected from 1-6C-alkyl, 2-6C-alkenyl, 1-6C-alkoxy, 3-7C-cycloalkyl, aryl, heteroaryl,
wherein said group is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, NH-(1-6C-alkylen)-O-(1-6C-alkyl),
R3 is hydrogen,
R4 is phenyl
R5 is hydrogen,
R6 is hydrogen,
A is N, C(R7),
R7 is hydrogen, hydroxy, halogen, cyano, C(O)OR10, CO(NR8R9), 3-7C-cycloalkyl, or
a group selected from 1-6C-alkyl, 2-6C-alkenyl, 1-6C-alkoxy, aryl, heteroaryl,
wherein said group is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, X is —CH₂—,
Y is —CH₂—, —CH(OH)—,
R8, R9 which can be the same or different, is hydrogen, hydroxy, 3-7C-cycloalkyl or
  a group selected from 1-4C-alkyl, 1-6C-alkoxy, wherein said group is optionally substituted, one or more times, identically or differently, with a substituent selected from:
    halogen, hydroxy, mono- or di-(1-4C-alkylamino, 1-4C-alkoxy, or 3-7C-cycloalkyl, or,
  R8 and R9 together with the nitrogen to which they are attached may also form a saturated or unsaturated 3-6C-heterocyclic ring,
    which is optionally substituted by (=O)
R10 is hydrogen, 1-6C-alkyl,
R11 is 1-4C-alkyl (optionally substituted in the same way of differently one or more times with halogen, hydroxy) or 3-7C-cycloalkyl,
or an N-oxide, a salt, a tautomer or a stereoisomer of said compound, or a salt of said N-oxide, tautomer or stereoisomer.

A further aspect of the invention are compounds of formula (I) wherein
R1 is hydrogen, hydroxy, halogen, cyano, —CO-(1-3C-alkyl), —C(O)OR10, —CO(NR8R9), —NR8R9, —NH—C(O)NR8R9, —NH—C(O)R11, 2-3C-alkinyl, or
  a group selected from 1-3C-alkyl, 2-3C-alkenyl, 1-3C-alkoxy, 3-6C-cycloalkyl, aryl, heteroaryl, -(1-3C-alkylen)-aryl, -(1-3C-alkylen)-heteroaryl, —O-(3-6C-cycloalkyl), —O-aryl, —O-(3-6C-heterocyclyl), —O-heteroaryl, —O-(1-3C-alkylen)-heteroaryl, —O-(1-3C-alkylen)-(3-6C-heterocyclyl), —O-(1-3C-alkylen)-aryl, —O-(1-3C-alkylen)-(3-6C-cycloalkyl)
    wherein said group being optionally substituted, one or more times, identically or differently, with a substituent selected from:
      hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)₂R11, heteroaryl,
      wherein said substituent can be optionally substituted with 1-3C-alkoxy,
R2 is hydrogen, hydroxy, halogen, cyano, —C(O)OR10, —CO(NR8R9), —NR8R9, —NH—C(O)R11, —NH—C(O)NR8R9, —NHS(O)₂R11 or
  a group selected from 1-3C-alkyl, 2-3C-alkenyl, 1-3C-alkoxy, 3-6C-cycloalkyl, aryl, heteroaryl,
    wherein said group is optionally substituted, one or more times, identically or differently, with a substituent selected from:
      hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)₂R11, —NH-(1-3C-alkylen)-O-(1-3C-alkyl),
R3 is hydrogen,
R4 is phenyl
R5 is hydrogen,
R6 is hydrogen,
A is N, C(R7),
R7 is hydrogen, hydroxy, halogen, cyano, C(O)OR10, CO(NR8R9), 3-7C-cycloalkyl, or
  a group selected from 1-3C-alkyl, 2-3C-alkenyl, 1-3C-alkoxy, aryl, heteroaryl,
    wherein said group is optionally substituted, one or more times, identically or differently, with a substituent selected from:
      hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)₂R11,
X is —CH₂—,
Y is —CH₂—, —CH(OH)—,
R8, R9 which can be the same or different, is hydrogen, hydroxy, 3-6C-cycloalkyl or
  a group selected from 1-3C-alkyl, 1-3C-alkoxy, wherein said group is optionally substituted, one or more times, identically or differently, with a substituent selected from:
    halogen, hydroxy, mono- or di-(1-3C-alkylamino, 1-3C-alkoxy, or 3-6C-cycloalkyl, or,
  R8 and R9 together with the nitrogen to which they are attached may also form a saturated or unsaturated 3-6C-heterocyclic ring,
    which is optionally substituted by (=O)
R10 is hydrogen, 1-3C-alkyl,
R11 is 1-3C-alkyl (optionally substituted in the same way of differently one or more times with halogen, hydroxy) or 3-6C-cycloalkyl,
or an N-oxide, a salt, a tautomer or a stereoisomer of said compound, or a salt of said N-oxide, tautomer or stereoisomer.

A further aspect of the invention are compounds of formula (I) wherein
R1 is hydrogen, hydroxy, halogen, cyano, —CO-(1-6C-alkyl), C(O)OR10, CO(NR8R9), NR8R9, NH—C(O)NR8R9, NH—C(O)R11, 2-6C-alkinyl, or
  a group selected from 1-6C-alkyl, 2-6C-alkenyl, 1-6C-alkoxy, 3-7C-cycloalkyl, aryl, heteroaryl, —O-(3-7C-cycloalkyl), —O-aryl, —O-(1-6C-alkyl)-heteroaryl, —O-(1-6C-alkyl)-(3-7C-cycloalkyl)
    wherein said group being optionally substituted, one or more times, identically or differently, with a substituent selected from:
      hydroxy, halogen, 1-6C-alkyl, 1-6C-alkoxy, —NR8R9, cyano, —C(O)NR8R9, —C(O)OR10,
      wherein said substituent can be optionally substituted with 1-6C-alkoxy,
R2 is hydrogen, hydroxy, halogen, cyano, C(O)OR10, CO(NR8R9), NR8R9, —NH—C(O)R11, —NH—C(O)NR8R9, —NHS(O)₂R11 or
  a group selected from 1-6C-alkyl, 2-6C-alkenyl, 1-6C-alkoxy, 3-7C-cycloalkyl, aryl, heteroaryl,
    wherein said group is optionally substituted, one or more times, identically or differently, with a substituent selected from:
      hydroxy, halogen, 1-6C-alkyl, 1-6C-alkoxycyano, —C(O)NR8R9, —C(O)OR10, —NHC(O)R11, NH-(1-6C-alkyl)-O-(1-6C-alkyl),
R3 is hydrogen,
R4 is phenyl
R5 is hydrogen,
R6 is hydrogen,
A is N, C(R7),
R7 is hydrogen, hydroxy, halogen, cyano, C(O)OR10, CO(NR8R9), 3-7C-cycloalkyl, or
  a group selected from 1-6C-alkyl, 2-6C-alkenyl, 1-6C-alkoxy, aryl, heteroaryl,
    wherein said group is optionally substituted, one or more times, identically or differently, with a substituent selected from:
      hydroxy, halogen, 1-6C-alkoxy,
X is —CH₂—,
Y is —CH₂—, —CH(OH)—, R8, R9 which can be the same or different, is hydrogen, hydroxy, 3-7C-cycloalkyl or
a group selected from 1-4C-alkyl, 1-6C-alkoxy, wherein said group is optionally substituted, one or more times, identically or differently, with a substituent selected from:
halogen, hydroxy, 1-4C-alkoxy, or 3-7C-cycloalkyl, or,
R8 and R9 together with the nitrogen to which they are attached may also form a saturated or unsaturated 3-6C-heterocyclic ring,
which is optionally substituted by (=O)
R10 is hydrogen, 1-6C-alkyl,
R11 is 1-4C-alkyl
or an N-oxide, a salt, a tautomer or a stereoisomer of said compound, or a salt of said N-oxide, tautomer or stereoisomer.

Another aspect of the invention are compounds of formula (I) wherein
R1 is hydrogen, hydroxy, halogen, cyano, CO(NR8R9), or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)aryl,
wherein said group being optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
R2 is hydrogen, 1-6C-alkyl, 1-6C-alkoxy, halogen, cyano, CO(NR8R9), aryl, heteroaryl,
wherein said 1-6C-alkyl, 1-6C-alkoxy, aryl, heteroaryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
R3 is hydrogen,
R4 is phenyl,
R5 is hydrogen,
R6 is hydrogen,
A is N, C(R7),
R7 is hydrogen, 1-6C-alkyl, 1-6C-alkoxy, halogen, cyano, CO(NR8R9), aryl, wherein said
1-6C-alkyl, 1-6C-alkoxy, aryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
X is —CH$_2$—,
Y is —CH$_2$—, —CH(OH)—,
R8, R9 which can be the same or different, is hydrogen, 1-4C-alkyl (optionally substituted in the same way of differently one or more times with halogen, hydroxy, mono- or di-1-4C-alkylamino), 1-4C-alkoxy, or 3-7C-cycloalkyl, or,
in the case of —NR8R9, R8 and R9 together with the nitrogen to which they are attached may also form a 3-6C-heterocyclic ring,
R10 is hydrogen, 1-6C-alkyl,
R11 is 1-4C-alkyl (optionally substituted in the same way of differently one or more times with halogen, hydroxy) or 3-7C-cycloalkyl,
or an N-oxide, a salt, a tautomer or a stereoisomer of said compound, or a salt of said N-oxide, tautomer or stereoisomer.

A further aspect of the invention are compounds of formula (I) wherein
R1 is hydrogen, hydroxy, or a group selected from 1-6C-alkyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)-aryl,
wherein said group being optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
R2 is hydrogen, 1-6C-alkyl, 1-6C-alkoxy, halogen, cyano, CO(NR8R9), aryl, heteroaryl,
wherein said 1-6C-alkyl, 1-6C-alkoxy, aryl, heteroaryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
R3 is hydrogen,
R4 is phenyl,
R5 is hydrogen,
R6 is hydrogen,
A is N, C(R7),
R7 is hydrogen, 1-6C-alkyl, 1-6C-alkoxy, halogen, cyano, CO(NR8R9), aryl, wherein said
1-6C-alkyl, 1-6C-alkoxy, aryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
X is —CH$_2$—,
Y is —CH$_2$—, —CH(OH)—,
R8, R9 which can be the same or different, is hydrogen, 1-4C-alkyl (optionally substituted in the same way of differently one or more times with halogen, hydroxy, mono- or di-1-4C-alkylamino), 1-4C-alkoxy, or 3-7C-cycloalkyl, or,
in the case of —NR8R9, R8 and R9 together with the nitrogen to which they are attached may also form a 3-6C-heterocyclic ring,
R10 is hydrogen, 1-6C-alkyl,
R11 is 1-4C-alkyl (optionally substituted in the same way of differently one or more times with halogen, hydroxy) or 3-7C-cycloalkyl,
or an N-oxide, a salt, a tautomer or a stereoisomer of said compound, or a salt of said N-oxide, tautomer or stereoisomer.

A further aspect of the invention are compounds of formula (I) wherein
R1 is hydrogen, hydroxy, halogen, cyano, —CO-(1-3C-alkyl), —C(O)OR10, —CO(NR8R9), —NR8R9, —NH—C(O)NR8R9, —NH—C(O)R11, 2-3C-alkinyl, or
a group selected from 1-3C-alkyl, 2-3C-alkenyl, 1-3C-alkoxy, 5-6C-cycloalkyl, aryl, heteroaryl, -(1-3C-alkylen)-aryl, -(1-3C-alkylen)-heteroaryl, —O-(5-6C-cycloalkyl), —O-aryl, —O-(5-6C-heterocyclyl), —O-heteroaryl, —O-(1-3C-alkylen)-heteroaryl, —O-(1-3C-alkylen)-(5-6C-heterocyclyl), —O-(1-3C-alkylen)-aryl, —O-(1-3C-alkylen)-(5-6C-cycloalkyl)

wherein said group being optionally substituted, one or more times, identically or differently, with a substituent selected from:

hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)₂R11, heteroaryl, wherein said substituent can be optionally substituted with 1-3C-alkoxy, R2 is hydrogen, hydroxy, halogen, cyano, —C(O)OR10, —CO(NR8R9), —NR8R9, —NH—C(O)R11, —NH—C(O)NR8R9, —NHS(O)₂R11 or a group selected from 1-3C-alkyl, 2-3C-alkenyl, 1-3C-alkoxy, 5-6C-cycloalkyl, aryl, heteroaryl, wherein said group is optionally substituted, one or more times, identically or differently, with a substituent selected from:

hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)₂R11, NH-(1-3C-alkyl)-O-(1-3C-alkyl), R3 is hydrogen,
R4 is phenyl
R5 is hydrogen,
R6 is hydrogen,
A is N, C(R7),
R7 is hydrogen, hydroxy, halogen, cyano, C(O)OR10, CO(NR8R9), 56C-cycloalkyl, or a group selected from 1-3C-alkyl, 2-3C-alkenyl, 1-3C-alkoxy, aryl, heteroaryl, wherein said group is optionally substituted, one or more times, identically or differently, with a substituent selected from:

hydroxy, halogen, 1-3C-alkyl, 1-3C-haloalkyl, 1-3C-alkoxy, —NR8R9, cyano, —C(O)NR8R9, —C(O)OR10, —NHC(O)R11, —NHS(O)₂R11, X is —CH₂—,
Y is —CH₂—, —CH(OH)—, R8, R9 which can be the same or different, is hydrogen, hydroxy, or a group selected from 1-3C-alkyl, 1-3C-alkoxy, wherein said group is optionally substituted, one or more times, identically or differently, with a substituent selected from:

halogen, hydroxy, mono- or di-(1-3C-alkylamino), 1-3C-alkoxy, or 5-6C-cycloalkyl, or, R8 and R9 together with the nitrogen to which they are attached may also form a saturated or unsaturated 5-6C-heterocyclic ring, which is optionally substituted by (═O)

R10 is hydrogen, 1-3C-alkyl,
R11 is 1-3C-alkyl (optionally substituted in the same way of differently one or more times with halogen, hydroxy) or 5-6C-cycloalkyl, or an N-oxide, a salt, a tautomer or a stereoisomer of said compound, or a salt of said N-oxide, tautomer or stereoisomer.

Another aspect of the invention are compounds of formula (I)
wherein,

R1 is hydrogen, 1-6C-alkyl, 1-6C-alkoxy, hydroxy, 3-7C-cycloalkyl, aryl,

R2 is hydrogen, 1-6C-alkyl, 1-6C-alkoxy, halogen, cyano, aryl,

R3 is hydrogen,
R4 is phenyl,
R5 is hydrogen,
R6 is hydrogen,
A is N, C(R7),
R7 is hydrogen, X is —CH₂—,
Y is —CH₂—, —CH(OH)—, or an N-oxide, a salt, a tautomer or a stereoisomer of said compound, or a salt of said N-oxide, tautomer or stereoisomer.

Another aspect of the invention are compounds of formula (I) according to claim 1, wherein, R1 is hydrogen, 1-3C-alkyl, -(1-3C-alkylen)C(O)O(1-3C-alkyl), -(2-3Calkenylen)C(O)O(1-3C-alkyl), -(2-3Calkenylen)C(O)NH₂, -(1-3C-alkylen)C(O)NH₂, halogen, hydroxy, ONa, 1-3C-alkoxy, —O-cyclohexyl, —O-phenyl, —O-(1-3C-alkylen)-heteroaryl, —O-(1-3C-alkylen)-[(1-3C-alkoxy)heteroaryl], —O-(1-3C-alkylen)NH₂, —O-(1-3C-alkylen)O-(1-3C-alkyl), —O-(1-3C-alkylen)-cyclopropane-C(O)NH₂, —O-(1-3C-alkylen)-CN, —O-(1-3C-alkylen)-C(O)O(1-3C-alkyl), —O-(1-3C-alkylen)-C(O)N(1-3C-alkyl)₂, —O-(1-3C-alkylen)-(heterocyclyl), -heteroaryl-(1-3Calkoxy), —O-(1-3C-alkylen)-(heteroaryl)-(1-3alkoxy), 3-7C-cycloalkyl, phenyl (which is optionally substituted with 1-3C-alkyl, halogen), cyano, —C(O)(1-3C-alkyl), —C(O)OH, —C(O)O(1-3C-alkyl), —CONH₂, —C(O)NH(1-3C-alkyl), —C(O)NH—OH, —C(O)-heterocycyl, heteroaryl (which is optionally substituted with 1-3C-alkyl, (═O), 1-3Calkoxy,), NH—C(O)—NH-(1-3C-alkyl), amino, NH—C(O)-(1-3C-alkyl), NH—C(O)—NH₂, N(1-3C-alkyl)-O-(1-3C-alkyl), R2 is hydrogen, 1-3C-alkyl, trifluoromethyl, -(1-3C-alkylen)C(O)O-(1-3C-alkyl), 2-3C-alkenyl, -(2-3C-alkenylen)C(O)O-(1-3C-alkyl), -(2-3C-alkenylen)C(O)NH₂, -(1-3C-alkylen)-NH-(1-3C-alkylen)-O-(1-3C-alkyl), 1-3C-alkoxy, —O-(1-3C-alkylen)-CN, —O-(1-3C-alkylen)-C(O)O-(1-3C-alkyl), hydroxy, halogen, cyano, 3-7C-cycloalkyl, phenyl, —C(O)(1-3C-alkyl), C(O)O(1-3C-alkyl), —CONH₂, —CONH-(1-3C-alkyl), C(O)—N(1-3C-alkyl), C(O)—NH-(1-3C-alkylen)F, C(O)—NH-(1-3C-alkylen)OH, C(O)—NH-(1-3C-alkylen)O-(1-3C-alkyl), C(O)NH-3-7C-cycloalkyl, C(O)NH-(1-3C-alkylen)-3-7C-cycloalkyl, C(O)NH—OH, -(1-3C-alkylen)O-(1-3C-alkyl), —CH(OH)-(1-3C-alkyl), -(1-3C-alkylen)OH, heteroaryl (which is optionally substituted with 1-3C-alkyl), amino, NH—C(O)-(1-3C-alkyl), NH—C(O)—NH₂, NH—C(O)—NH-(1-3C-alkyl), NH—S(O)₂-(1-3C-alkyl), R3 is hydrogen, 1-3C-alkyl,
R4 is phenyl,
R5 is hydrogen,
R6 is hydrogen,
A is N, C(R7),
R7 is hydrogen, hydroxy, cyano, halogen, 1-3C-alkyl, 2-3C-alkenyl, 1-3C-alkoxy, -(1-3C-alkylen)OH, C(O)O-(1-3C-alkyl), —CONH₂, 3-7C-cycloalkyl, phenyl (which is optionally substituted with halogen, 1-3C-alkox),
R8 is hydrogen, 1-3C-alkyl, hydroxy, 1-3C-alkoxy, 3-7C-cycloalkyl, whereby 1-3C-alkyl are optionally substituted one or more times, identically or differently with a substituent selected from halogen, hydroxy, 1-3C-alkoxy, 3-7C-cycloalkyl,
R9 is hydrogen, 1-3C-alkyl,
or
R8 and R9 together with the nitrogen to which they are attached may also form a saturated or unsaturated 5- or 6-membered heterocyclic ring which optionally is substituted with (═O),
X is —CH₂—,
Y is —CH₂—, —CH(OH)—, or an N-oxide, a salt, a tautomer or a stereoisomer of said compound, or a salt of said N-oxide, tautomer or stereoisomer.

A further aspect of the invention are compounds of formula (I) according to claim 1,
wherein,
R1 is hydrogen, methyl, ethyl, bromine, methoxy, ethoxy, propyloxy, cyclohexyloxy, —O-phenyl, —O—OH$_2$-pyridyl, —O—CH$_2$-methoxypyridyl, —OCH$_2$CH$_2$NH$_2$, —OCH$_2$CH$_2$OCH$_3$, hydroxy, cyclopropyl, phenyl, cyano, —CONR8R9, pyrazole,
R2 is hydrogen, methyl, ethyl, methoxy, ethoxy, hydroxyl, bromine, chlorine, cyano, phenyl, —CONR8R9, —CONHCH$_3$, —CH$_2$OCH$_3$, —CH(OH)CH$_3$, —CH$_2$OH,
R3 is hydrogen,
R4 is phenyl,
R5 is hydrogen,
R6 is hydrogen,
A is N, C(R7),
R7 is hydrogen, cyano, bromine, methyl, ethyl, methoxy, ethoxy, —CH$_2$OH, —CONR8R9,
R8 is hydrogen, methyl
R9 is hydrogen,
X is —CH$_2$—,
Y is —CH$_2$—, —CH(OH)—,
or an N-oxide, a salt, a tautomer or a stereoisomer of said compound, or a salt of said N-oxide, tautomer or stereoisomer.

Another aspect of the invention are compounds of formula (I) according to claim 1, wherein,
R1 is hydrogen, methyl, ethyl, —(CH$_2$)$_2$C(O)OCH$_3$, —(CH═CH)C(O)OCH$_3$, —(CH═CH)C(O)NH$_2$, —(CH$_2$)$_2$C(O)NH$_2$, bromine, chlorine, fluorine, hydroxy ONa, methoxy, ethoxy, propyloxy, isopropoxy, —O-cyclohexyl, —O-phenyl, —O—CH$_2$-pyridyl, —O—CH$_2$-methoxypyridyl, —OCH$_2$CH$_2$NH$_2$, —OCH$_2$CH$_2$OCH$_3$, —O—CH$_2$-cyclopropane-C(O)NH$_2$, —O—CH$_2$—CN, —O—CH$_2$—C(O)OCH$_3$, —O—CH$_2$—C(O)N(CH$_3$)$_2$, —O—CH$_2$— (pyrrolidin-2-one-1-yl), (2-methoxypyridine-5-yl), —O—CH$_2$-(2-methoxypyridine-4-yl), cyclopropyl, phenyl, 2-methylphenyl, 4-fluorophenyl, cyano, —C(O)CH$_3$, —C(O)OH, —C(O)OCH$_3$, —C(O)OCH$_2$CH$_3$, —CONH$_2$, —C(O)NHCH$_3$, —C(O)NHCH$_2$CH$_3$, —C(O)-pyrrolidin-1yl, 1-pyrazolyl, imidazol-2-yl, imidazol-4-yl, 1-methyl-imidazol-5-yl, tetratzol-4-yl, NH—C(O)—NHCH$_3$, 1H-pyridine-2-one-1yl, pyridine-2-yl, pyridine-3-yl, pyridine-4-yl, 3-methoxy-pyridine-5-yl, amino, NH—C(O)—CH$_3$, NH—C(O)—NH$_2$, N(CH$_3$)—OCH$_3$,
R2 is hydrogen, methyl, ethyl, trifluoromethyl, —(CH$_2$)$_2$C(O)OCH$_3$, vinyl, —(CH═CH)C(O)OCH$_3$, —(CH═CH)C(O)NH$_2$, —CH$_2$—NH—(CH$_2$)$_2$—O—CH$_3$, methoxy, ethoxy, —O—CH$_2$—CN, —O—CH$_2$—C(O)OCH$_3$, hydroxy, bromine, chlorine, fluorine, cyano, cyclopropyl, phenyl, —C(O)CH$_3$, C(O)OCH$_3$, C(O)OCH$_2$CH$_3$, —CONH$_2$, —CONHCH$_3$, —CONHC$_2$H$_5$, C(O)—N(CH$_3$)$_2$, C(O)—NH—(CH$_2$)$_2$F, C(O)—NH—(CH$_2$)$_2$OH, C(O)—NH—(CH$_2$)$_2$OCH$_3$, C(O)NH-cyclopropyl, C(O)NH—CH$_2$-cyclopropyl, C(O)NH—OH, —CH$_2$OCH$_3$, —CH(OH)CH$_3$, —CH$_2$OH, pyrazol-3-yl, pyrazol-4-yl, pyrrazol-5-yl, 1-methyl-pyrrazol-4-yl, 3-methyl-pyrazol-5-yl, imidazol-2-yl, imidazol-4-yl, imidazol-5-yl, 1-methyl-imidazol-5-yl, 1-methyl-imidazol-4-yl, tetrazol-4-yl, pyridine-2-yl, pyridine-3-yl, pyridine-4-yl, amino, NH—C(O)—CH$_3$, NH—C(O)—NH$_2$, NH—C(O)—NH—CH$_3$, NH—S(O)$_2$—CH$_3$,
R3 is hydrogen, methyl,
R4 is phenyl,
R5 is hydrogen,
R6 is hydrogen,
A is N, C(R7),
R7 is hydrogen, hydroxy, cyano, bromine, chlorine, fluorine, methyl, ethyl, vinyl, methoxy, ethoxy, —CH$_2$OH, C(O)OC$_2$H$_5$, —CONH$_2$, cyclopropyl, 4-fluoro-phenyl, 3-fluoro-phenyl, 3-methoxy-pyridine-5-yl, pyrazol-5-yl, pyrazol-4-yl, indazol-6-yl,
R8 is hydrogen, methyl, ethyl, hydroxy, methoxy, cyclopropyl, whereby methyl, ethyl are optionally substituted one or more times, identically or differently with a substituent selected from fluorine, hydroxy, methoxy, cyclopropyl,
R9 is hydrogen, methyl,
or
R8 and R9 together with the nitrogen to which they are attached may also form a saturated or unsaturated 5- or 6-membered heterocyclic ring which optionally is substituted with (═O),
X is —CH$_2$—,
Y is —CH$_2$—, —CH(OH)—,
or an N-oxide, a salt, a tautomer or a stereoisomer of said compound, or a salt of said N-oxide, tautomer or stereoisomer.

A further aspect of the invention are compounds of formula (I) according to claim 1,
wherein,
R1 is hydrogen, methyl, ethyl, bromine, methoxy, ethoxy, propyloxy, cyclohexyloxy, —O-phenyl, —O—CH$_2$-pyridyl, —O—CH$_2$-methoxypyridyl, —OCH$_2$CH$_2$NH$_2$, —OCH$_2$CH$_2$OCH$_3$, hydroxy, cyclopropyl, phenyl, cyano, —CONH$_2$, pyrazole,
R2 is hydrogen, methyl, ethyl, methoxy, ethoxy, hydroxyl, bromine, chlorine, cyano, phenyl, —CONH$_2$, —CONHCH$_3$, —CH$_2$OCH$_3$, —CH(OH)CH$_3$, —CH$_2$OH,
R3 is hydrogen,
R4 is phenyl,
R5 is hydrogen,
R6 is hydrogen,
A is N, C(R7),
R7 is hydrogen, cyano, bromine, methyl, ethyl, methoxy, ethoxy, —CH$_2$OH, —CONH$_2$,
R8 is hydrogen, methyl
R9 is hydrogen,
X is —CH$_2$—,
Y is —CH$_2$—, —CH(OH)—,
or an N-oxide, a salt, a tautomer or a stereoisomer of said compound, or a salt of said N-oxide, tautomer or stereoisomer.

A further aspect of the invention are compounds of formula (I) according to claim 1,
wherein,
R1 is hydrogen, methyl, ethyl, bromine, methoxy, ethoxy, propyloxy, cyclohexyloxy, —O-phenyl, —O—CH$_2$-pyridyl, —O—CH$_2$-methoxypyridyl, —OCH$_2$CH$_2$NH$_2$, —OCH$_2$CH$_2$OCH$_3$, hydroxy, cyclopropyl, phenyl, cyano, —CONH$_2$, pyrazole,
R2 is hydrogen, methyl, ethyl, methoxy, ethoxy, hydroxyl, bromine, chlorine, cyano, phenyl, —CONH$_2$, —CONHCH$_3$, —CH$_2$OCH$_3$, —CH(OH)CH$_3$, —CH$_2$OH,
R3 is hydrogen,
R4 is phenyl,
R5 is hydrogen,
R6 is hydrogen,
A is N, C(R7),
R7 is hydrogen, cyano, bromine, methyl, ethyl, methoxy, ethoxy, —CH$_2$OH, —CONH$_2$, X is —CH$_2$—,
Y is —CH$_2$—, —CH(OH)—,
or an N-oxide, a salt, a tautomer or a stereoisomer of said compound, or a salt of said N-oxide, tautomer or stereoisomer.

Another aspect of the invention are compounds of formula (I)
wherein,
R1 is hydrogen, methyl, methoxy, hydroxy, cyclopropyl, phenyl,
R2 is hydrogen, methyl, methoxy, ethoxy, chlorine, cyano, phenyl,
R3 is hydrogen,
R4 is phenyl,
R5 is hydrogen,
R6 is hydrogen,
A is N, C(R7),
R7 is hydrogen,
X is —CH$_2$—,
Y is —CH$_2$—, —CH(OH)—,
or an N-oxide, a salt, a tautomer or a stereoisomer of said compound, or a salt of said N-oxide, tautomer or stereoisomer.

In one aspect of the invention compounds of formula (I) as described above are selected from the group consisting of:
1-[4-(3-phenyl-imidazo[1,2-a]pyrimidin-2-yl)-phenyl]-cyclobutylamine,
1-[4-(7-methyl-3-phenyl-imidazo[1,2-a]pyrimidin-2-yl)-phenyl]-cyclobutylamine,
1-[4-(7-cyclopropyl-3-phenyl-imidazo[1,2-a]pyrimidin-2-yl)-phenyl]-cyclobutylamine,
1-[4-(3,7-diphenyl-imidazo[1,2-a]pyrimidin-2-yl)-phenyl]-cyclobutylamine,
1-[4-(3-phenyl-7-o-tolyl-imidazo[1,2-a]pyrimidin-2-yl)-phenyl]-cyclobutylamine,
1-[4-(6-chloro-3-phenyl-imidazo[1,2-a]pyrimidin-2-yl)-phenyl]-cyclobutylamine,
1-[4-(6-methyl-3-phenyl-imidazo[1,2-a]pyrimidin-2-yl)-phenyl]-cyclobutylamine,
1-[4-(6-methoxy-3-phenyl-imidazo[1,2-a]pyrimidin-2-yl)-phenyl]-cyclobutylamine,
1-[4-(6-ethoxy-3-phenyl-imidazo[1,2-a]pyrimidin-2-yl)-phenyl]-cyclobutylamine,
1-[4-(3,6-diphenyl-imidazo[1,2-a]pyrimidin-2-yl)-phenyl]-cyclobutylamine,
2-[4-(1-amino-cyclobutyl)-phenyl]-3-phenyl-imidazo[1,2-a]pyridine-6-carbonitrile,
1-[4-(7-methoxy-3-phenyl-imidazo[1,2-a]pyrimidin-2-yl)-phenyl]-cyclobutylamine,
2-[4-(1-amino-cyclobutyl)-phenyl]-3-phenyl-imidazo[1,2-a]pyrimidin-7-ol,
1-[4-(3-phenyl-7-propoxy-imidazo[1,2-a]pyrimidin-2-yl)-phenyl]-cyclobutylamine,
2-[4-(cis-1-amino-3-hydroxy-cyclobutyl)-phenyl]-3-phenyl-imidazo[1,2-a]pyrimidin-7-ol, A further aspect of the invention are compounds of formula (I) as described above selected from the group consisting of:
2-[4-(1-amino-cyclobutyl)-phenyl]-3-phenyl-imidazo[1,2-a]pyridine-8-carbonitrile,
1-[4-(7-methyl-3-phenyl-imidazo[1,2-a]pyridin-2-yl)-phenyl]-cyclobutyl amine,
1-[4-(8-methyl-3-phenyl-imidazo[1,2-a]pyridin-2-yl)-phenyl]-cyclobutyl amine,
2-[4-(1-amino-cyclobutyl)-phenyl]-3-phenyl-imidazo[1,2-a]pyridine-7-carbonitrile,
1-[4-(6-methyl-3-phenyl-imidazo[1,2-a]pyridin-2-yl)-phenyl]-cyclobutyl amine,
1-[4-(7-methoxy-3-phenyl-imidazo[1,2-a]pyridin-2-yl)-phenyl]-cyclobutylamine,
2-[4-(1-amino-cyclobutyl)-phenyl]-3-phenyl-imidazo[1,2-a]pyridine-6-carboxylic acid methylamide,
1-[4-(6-methoxymethyl-3-phenyl-imidazo[1,2-a]pyridin-2-yl)-phenyl]-cyclobutylamine,
1-[4-(3-phenyl-imidazo[1,2-a]pyridin-2-yl)-phenyl]-cyclobutylamine,
1-[4-(8-methoxy-3-phenyl-imidazo[1,2-a]pyridin-2-yl)-phenyl]-cyclobutylamine,
1-{2-[4-(1-amino-cyclobutyl)-phenyl]-3-phenyl-imidazo[1,2-a]pyridin-6-yl}-ethanol,
{2-[4-(1-amino-cyclobutyl)-phenyl]-3-phenyl-imidazo[1,2-a]pyridin-7-yl}-methanol,
{2-[4-(1-amino-cyclobutyl)-phenyl]-3-phenyl-imidazo[1,2-a]pyridin-8-yl}-methanol,
1-[4-(6-bromo-3-phenyl-imidazo[1,2-a]pyridin-2-yl)-phenyl]-cyclobutylamine,
1-[4-(6-methoxy-3-phenyl-imidazo[1,2-a]pyridin-2-yl)-phenyl]-cyclobutylamine,
2-[4-(1-amino-cyclobutyl)-phenyl]-3-phenyl-imidazo[1,2-a]pyridine-6-carboxylic acid amide,
1-[4-(8-ethoxy-3-phenyl-imidazo[1,2-a]pyridin-2-yl)-phenyl]-cyclobutylamine,
1-[4-(7-ethoxy-3-phenyl-imidazo[1,2-a]pyridin-2-yl)-phenyl]-cyclobutylamine,
1-[4-(7-ethyl-3-phenyl-imidazo[1,2-a]pyridin-2-yl)-phenyl]-cyclobutylamine,
1-{4-[3-phenyl-7-(1H-pyrazol-4-yl)-imidazo[1,2-a]pyridin-2-yl]-phenyl}-cyclobutylamine,
{2-[4-(1-amino-cyclobutyl)-phenyl]-3-phenyl-imidazo[1,2-a]pyridin-6-yl}-methanol,
1-{4-[7-(6-methoxy-pyridin-3-ylmethoxy)-3-phenyl-imidazo[1,2-a]pyrimidin-2-yl]-phenyl}-cyclobutylamine,
1-{4-[7-(2-methoxy-ethoxy)-3-phenyl-imidazo[1,2-a]pyrimidin-2-yl]-phenyl}-cyclobutylamine, 1-{4-[7-(2-methoxy-pyridin-4-ylmethoxy)-3-phenyl-imidazo[1,2-a]pyrimidin-2-yl]-phenyl}-cyclobutylamine,
1-[4-(7-ethoxy-3-phenyl-imidazo[1,2-a]pyrimidin-2-yl)-phenyl]-cyclobutylamine,
1-[4-(7-isopropoxy-3-phenyl-imidazo[1,2-a]pyrimidin-2-yl)-phenyl]-cyclobutylamine,
1-[4-(7-cyclohexyloxy-3-phenyl-imidazo[1,2-a]pyrimidin-2-yl)-phenyl]-cyclobutylamine,
1-[4-(7-phenoxy-3-phenyl-imidazo[1,2-a]pyrimidin-2-yl)-phenyl]-cyclobutylamine,
1-[4-(6-ethyl-3-phenyl-imidazo[1,2-a]pyrimidin-2-yl)-phenyl]-cyclobutylamine,
1-{4-[7-(4-fluoro-phenyl)-3-phenyl-imidazo[1,2-a]pyridin-2-yl]-phenyl}-cyclobutylamine,
1-[4-(7-cyclopropyl-3-phenyl-imidazo[1,2-a]pyridin-2-yl)-phenyl]-cyclobutylamine,
1-[4-(6-ethyl-3-phenyl-imidazo[1,2-a]pyridin-2-yl)-phenyl]-cyclobutylamine,
1-[4-(8-bromo-3-phenyl-imidazo[1,2-a]pyridin-2-yl)-phenyl]-cyclobutylamine,
1-[4-(7-bromo-3-phenyl-imidazo[1,2-a]pyridin-2-yl)-phenyl]-cyclobutylamine,
2-[4-(1-amino-cyclobutyl)-phenyl]-3-phenyl-imidazo[1,2-a]pyridine-7-carboxylic acid amide,
1-{4-[7-(2-amino-ethoxy)-3-phenyl-imidazo[1,2-a]pyrimidin-2-yl]-phenyl}-cyclobutylamine,
2-[4-(1-amino-cyclobutyl)-phenyl]-3-phenyl-imidazo[1,2-a]pyridin-6-ol,
2-[4-(1-amino-cyclobutyl)-phenyl]-3-phenyl-imidazo[1,2-a]pyridine-8-carboxylic acid amide, In another aspect of the invention compounds of formula (I) as described above are selected from the group consisting of:
1-[4-(3-phenyl-imidazo[1,2-a]pyrimidin-2-yl)-phenyl]-cyclobutylamine,
1-[4-(7-methyl-3-phenyl-imidazo[1,2-a]pyrimidin-2-yl)-phenyl]-cyclobutylamine,
1-[4-(7-cyclopropyl-3-phenyl-imidazo[1,2-a]pyrimidin-2-yl)-phenyl]-cyclobutylamine,
1-[4-(3,7-diphenyl-imidazo[1,2-a]pyrimidin-2-yl)-phenyl]-cyclobutylamine,
1-[4-(3-phenyl-7-o-tolyl-imidazo[1,2-a]pyrimidin-2-yl)-phenyl]-cyclobutylamine,
1-[4-(6-chloro-3-phenyl-imidazo[1,2-a]pyrimidin-2-yl)-phenyl]-cyclobutylamine,
1-[4-(6-methyl-3-phenyl-imidazo[1,2-a]pyrimidin-2-yl)-phenyl]-cyclobutylamine,
1-[4-(6-methoxy-3-phenyl-imidazo[1,2-a]pyrimidin-2-yl)-phenyl]-cyclobutylamine,
1-[4-(6-ethoxy-3-phenyl-imidazo[1,2-a]pyrimidin-2-yl)-phenyl]-cyclobutylamine,
1-[4-(3,6-diphenyl-imidazo[1,2-a]pyrimidin-2-yl)-phenyl]-cyclobutylamine,
2-[4-(1-amino-cyclobutyl)-phenyl]-3-phenyl-imidazo[1,2-a]pyridine-6-carbonitrile,
1-[4-(7-methoxy-3-phenyl-imidazo[1,2-a]pyrimidin-2-yl)-phenyl]-cyclobutylamine,
2-[4-(1-amino-cyclobutyl)-phenyl]-3-phenyl-imidazo[1,2-a]pyrimidin-7-ol,
1-[4-(3-phenyl-7-propoxy-imidazo[1,2-a]pyrimidin-2-yl)-phenyl]-cyclobutylamine,
2-[4-(1-amino-cyclobutyl)-phenyl]-3-phenyl-imidazo[1,2-a]pyridine-8-carbonitrile,
1-[4-(7-methyl-3-phenyl-imidazo[1,2-a]pyridin-2-yl)-phenyl]-cyclobutyl amine,
1-[4-(8-methyl-3-phenyl-imidazo[1,2-a]pyridin-2-yl)-phenyl]-cyclobutyl amine,
2-[4-(1-amino-cyclobutyl)-phenyl]-3-phenyl-imidazo[1,2-a]pyridine-7-carbonitrile,
1-[4-(6-methyl-3-phenyl-imidazo[1,2-a]pyridin-2-yl)-phenyl]-cyclobutyl amine,
1-[4-(7-methoxy-3-phenyl-imidazo[1,2-a]pyridin-2-yl)-phenyl]-cyclobutylamine,
2-[4-(1-amino-cyclobutyl)-phenyl]-3-phenyl-imidazo[1,2-a]pyridine-6-carboxylic acid methylamide,
1-[4-(6-methoxymethyl-3-phenyl-imidazo[1,2-a]pyridin-2-yl)-phenyl]-cyclobutylamine,
1-[4-(3-phenyl-imidazo[1,2-a]pyridin-2-yl)-phenyl]-cyclobutylamine,
1-[4-(8-methoxy-3-phenyl-imidazo[1,2-a]pyridin-2-yl)-phenyl]-cyclobutylamine,
1-{2-[4-(1-amino-cyclobutyl)-phenyl]-3-phenyl-imidazo[1,2-a]pyridin-6-yl}-ethanol,
{2-[4-(1-amino-cyclobutyl)-phenyl]-3-phenyl-imidazo[1,2-a]pyridin-7-yl}-methanol,
{2-[4-(1-amino-cyclobutyl)-phenyl]-3-phenyl-imidazo[1,2-a]pyridin-8-yl}-methanol,
1-[4-(6-bromo-3-phenyl-imidazo[1,2-a]pyridin-2-yl)-phenyl]-cyclobutylamine,
1-[4-(6-methoxy-3-phenyl-imidazo[1,2-a]pyridin-2-yl)-phenyl]-cyclobutylamine,
2-[4-(1-amino-cyclobutyl)-phenyl]-3-phenyl-imidazo[1,2-a]pyridine-6-carboxylic acid amide,
1-[4-(8-ethoxy-3-phenyl-imidazo[1,2-a]pyridin-2-yl)-phenyl]-cyclobutylamine,
1-{4-(7-ethoxy-3-phenyl-imidazo[1,2-a]pyridin-2-yl)-phenyl}-cyclobutylamine,
1-[4-(7-ethyl-3-phenyl-imidazo[1,2-a]pyridin-2-yl)-phenyl]-cyclobutylamine,
1-{4-[3-phenyl-7-(1H-pyrazol-4-yl)-imidazo[1,2-a]pyridin-2-yl]-phenyl}-cyclobutylamine,
{2-[4-(1-amino-cyclobutyl)-phenyl]-3-phenyl-imidazo[1,2-a]pyridin-6-yl}-methanol,
1-{4-[7-(6-methoxy-pyridin-3-ylmethoxy)-3-phenyl-imidazo[1,2-a]pyrimidin-2-yl]-phenyl}-cyclobutylamine,
1-{4-[7-(2-methoxy-ethoxy)-3-phenyl-imidazo[1,2-a]pyrimidin-2-yl]-phenyl}-cyclobutylamine, 1-{4-[7-(2-methoxy-pyridin-4-ylmethoxy)-3-phenyl-imidazo[1,2-a]pyrimidin-2-yl]-phenyl}-cyclobutylamine,
1-[4-(7-ethoxy-3-phenyl-imidazo[1,2-a]pyrimidin-2-yl)-phenyl]-cyclobutylamine,
1-[4-(7-isopropoxy-3-phenyl-imidazo[1,2-a]pyrimidin-2-yl)-phenyl]-cyclobutylamine,
1-[4-(7-cyclohexyloxy-3-phenyl-imidazo[1,2-a]pyrimidin-2-yl)-phenyl]-cyclobutylamine,
1-[4-(7-phenoxy-3-phenyl-imidazo[1,2-a]pyrimidin-2-yl)-phenyl]-cyclobutylamine,
1-[4-(6-ethyl-3-phenyl-imidazo[1,2-a]pyrimidin-2-yl)-phenyl]-cyclobutylamine,
1-{4-[7-(4-fluoro-phenyl)-3-phenyl-imidazo[1,2-a]pyridin-2-yl]-phenyl}-cyclobutylamine,
1-[4-(7-cyclopropyl-3-phenyl-imidazo[1,2-a]pyridin-2-yl)-phenyl]-cyclobutylamine,
1-[4-(6-ethyl-3-phenyl-imidazo[1,2-a]pyridin-2-yl)-phenyl]-cyclobutylamine,
1-[4-(8-bromo-3-phenyl-imidazo[1,2-a]pyridin-2-yl)-phenyl]-cyclobutylamine,
1-[4-(7-bromo-3-phenyl-imidazo[1,2-a]pyridin-2-yl)-phenyl]-cyclobutylamine,
2-[4-(1-amino-cyclobutyl)-phenyl]-3-phenyl-imidazo[1,2-a]pyridine-7-carboxylic acid amide,
2-[4-(cis-1-amino-3-hydroxy-cyclobutyl)-phenyl]-3-phenyl-imidazo[1,2-a]pyrimidin-7-ol
1-{4-[7-(2-amino-ethoxy)-3-phenyl-imidazo[1,2-a]pyrimidin-2-yl]-phenyl}-cyclobutylamine,
2-[4-(1-amino-cyclobutyl)-phenyl]-3-phenyl-imidazo[1,2-a]pyridin-6-ol,
2-[4-(1-amino-cyclobutyl)-phenyl]-3-phenyl-imidazo[1,2-a]pyridine-8-carboxylic acid amide,
or an N-oxide, a salt, a tautomer or a stereoisomer of said compound, or a salt of said N-oxide, tautomer or stereoisomer.

One aspect of the invention are compounds of formula (I) as described in the examples as characterized by their names in the title as claimed in claim 5 and their structures as well as the subcombinations of all residues specifically disclosed in the compounds of the examples.

One aspect of the present invention are the compounds disclosed in the examples as well as the intermediates as used for their synthesis.

One aspect of the invention is intermediate (II) wherein Rx=—C(O)OtBu, Ry=H

Another aspect of the invention is intermediate III wherein all residues are defined as in claims 1-4.

If embodiments of the invention as disclosed herein relate to compounds of formula (I), it is understood that those embodiments refer to the compounds of formula (I) as disclosed in the claims and the examples.

Another aspect of the invention are compounds of formula (I), wherein
R1 is hydrogen, hydroxy, or a group selected from 1-6C-alkyl, 1-6C-alkoxy, 3-7C-cycloalkyl, aryl, heteroaryl, -(1-6C-alkyl)-aryl, -(1-6C-alkyl)heteroaryl, —O-(3-7C-cycloalkyl), —O-aryl, —O-(3-7C-heterocyclyl), —O-heteroaryl, —O-(1-6C-alkyl)-heteroaryl, —O-(1-6C-alkyl)-(3-7C-heterocyclyl), —O-(1-6C-alkyl)aryl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11.

Another aspect of the invention are compounds of formula (I), wherein

R1 is hydrogen, hydroxy, or a group selected from 1-6C-alkyl, 1-6C-alkoxy, 3-7C-cycloalkyl, aryl, —O-(3-7C-cycloalkyl), —O-aryl, —O-(3-7C-heterocyclyl), —O-heteroaryl, —O-(1-6C-alkyl)heteroaryl, —O-(1-6C-alkyl)-(3-7C-heterocyclyl), —O-(1-6C-alkyl)-aryl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11.

Another aspect of the invention are compounds of formula (I), wherein

R1 is hydrogen, hydroxy, or a group selected from 1-6C-alkyl, 1-6C-alkoxy, 3-7C-cycloalkyl, aryl, —O-(3-7C-cycloalkyl), —O-aryl, —O-(3-7C-heterocyclyl), —O-heteroaryl, —O-(1-6C-alkyl)heteroaryl, —O-(1-6C-alkyl)-(3-7C-heterocyclyl), —O-(1-6C-alkyl)-aryl, wherein said group being optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11.

Another aspect of the invention are compounds of formula (I), wherein

R1 is hydrogen, hydroxy, or a group selected from 1-6C-alkyl, 1-6C-alkoxy, 3-7C-cycloalkyl, aryl, —O-aryl, —O-(3-7C-heterocyclyl), —O-heteroaryl, —O-(-1-6C-alkyl)-heteroaryl, —O-(1-6C-alkyl)-(3-7C-heterocyclyl), —O-(1-6C-alkyl)-aryl, wherein said group being optionally substituted, one or more times, identically or differently, with a substituent selected from:

hydroxy, halogen, 1-6C-alkyl, 1-6C-alkoxy.

Yet another aspect of the invention are compounds of formula (I) according to claim 1, 2 or 3, wherein R1 is halogen, cyano or CO(NR8R9).

Another aspect of the invention are compounds of formula (I), wherein

R1 is hydrogen, 1-6C-alkyl-, 1-6C-alkoxy, hydroxy, 3-7C-cycloalkyl, phenyl.

Another aspect of the invention are compounds of formula (I), wherein

R1 is hydrogen, methyl, methoxy, hydroxy, cyclopropyl, phenyl

Another aspect of the invention are compounds of formula (I) according to claim 1, 2 or 3, wherein R1 is ethyl, bromine, ethoxy, propyloxy, cycloheyloxy, —O-phenyl, —O-pyridiyl, —O—CH2-(methoxy-pyridyl), —OCH2-CH2-NH2, —O—CH2-CH2-O—CH3, cyano, —C(O)NH2, pyrazole.

Another aspect of the invention are compounds of formula (I) according to claim 1, 2 or 3, wherein R1 is hydrogen, methyl, ethyl, hydroxy, cyclopropyl, phenyl, bromine, methoxy, ethoxy, propyloxy, cycloheyloxy, —O-phenyl, —O-pyridiyl, —O—CH2-(methoxypyridyl), —OCH2-CH2-NH2, —O—CH2-CH2-O—CH3, cyano, —C(O)NH2, pyrazole.

Another aspect of the invention are compounds of formula (I), wherein

R2 is hydrogen, 1-6C-alkyl, 1-6C-alkoxy, halogen, cyano, CO(NR8R9), aryl, heteroaryl, wherein said 1-6C-alkyl, 1-6C-alkoxy, aryl, heteroaryl is optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11.

Another aspect of the invention are compounds of formula (I), wherein

R2 is hydrogen, 1-6C-alkyl, 1-6C-alkoxy, halogen, cyano, CO(NR8R9), aryl, wherein said 1-6C-alkyl, 1-6C-alkoxy, aryl, is optionally substituted, one or more times, identically or differently, with a substituent selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11.

Another aspect of the invention are compounds of formula (I), wherein

R2 is hydrogen, 1-6C-alkyl, 1-6C-alkoxy, halogen, cyano, aryl, wherein said aryl, is optionally substituted, one or more times, identically or differently, with a substituent selected from:

hydroxy, halogen, 1-6C-alkyl, 1-4C-haloalkyl, 1-6C-alkoxy

Another aspect of the invention are compounds of formula (I), wherein

R2 is hydrogen, 1-6C-alkyl, 1-6C-alkoxy, halogen, cyano, aryl, wherein said 1-6C-alkyl, 1-6C-alkoxy, is optionally substituted, one or more times with halogen.

Another aspect of the invention are compounds of formula (I), wherein

R2 is hydrogen, 1-6C-alkyl-, 1-6C-alkoxy, halogen, cyano, phenyl.

Another aspect of the invention are compounds of formula (I), wherein

R2 is hydrogen, methyl, methoxy, ethoxy, chlorine, cyano, phenyl.

Another aspect of the invention are compounds of formula (I) according to claim 1, 2 or 3, wherein R2 is ethyl, hydroxy, bromine, —C(O)NH2, —C(O)NHCH3, —CH2-O—CH3, —CH(OH)CH3, —CH2OH.

Another aspect of the invention are compounds of formula (I) according to claim 1, 2 or 3, wherein R2 is hydrogen, methyl, methoxy, ethoxy, chlorine, cyano, phenyl ethyl, hydroxy, bromine, —C(O)NH2, —C(O)NHCH3, —CH2-O—CH3, —CH(OH)CH3, —CH2OH.

Another aspect of the invention are compounds of formula (I), wherein

R3 is hydrogen.

Another aspect of the invention are compounds of formula (I), wherein

R3 is 1-6Calkyl, preferably methyl.

Another aspect of the invention are compounds of formula (I), wherein

R4 is phenyl optionally substituted by 1-6C-alkyl, halogen, cyano.

Another aspect of the invention are compounds of formula (I), wherein
R4 is phenyl, optionally substituted with halogen.

Another aspect of the invention are compounds of formula (I), wherein
R4 is phenyl, optionally substituted with fluorine.

In another embodiment of the above-mentioned aspects, the invention relates to compounds of formula (I), wherein R4 is an unsubstituted phenyl moiety.

Another aspect of the invention are compounds of formula (I), wherein
R5 is hydrogen, halogen.

Another aspect of the invention are compounds of formula (I), wherein
R5 is hydrogen, or fluorine.

Another aspect of the invention are compounds of formula (I), wherein
R5 is hydrogen.

Another aspect of the invention are compounds of formula (I), wherein
R6 is hydrogen, 1-6C-alkyl.

Another aspect of the invention are compounds of formula (I), wherein
R6 is hydrogen.

Another aspect of the invention are compounds of formula (I), wherein
A is N, C(R7).

In a further embodiment of the above-mentioned aspects, the invention relates to compounds of formula (I), wherein A is —CH2-.

In a further embodiment of the above-mentioned aspects, the invention relates to compounds of formula (I), wherein A is N.

Another aspect of the invention are compounds of formula (I), wherein
R7 is hydroxy, C(O)OR10,), 3-7C-cycloalkyl, or a group selected from 2-6C-alkenyl, aryl, heteroaryl.
wherein said group is optionally substituted, one or more times, identically or differently, with a substituent selected from: hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11.

Another aspect of the invention are compounds of formula (I), wherein
R7 is hydrogen, 1-6C-alkyl, 1-6C-alkoxy, halogen, cyano, CO(NR8R9), aryl, wherein said 1-6C-alkyl, 1-6C-alkoxy, aryl is optionally substituted, one or more times, identically or differently, with a substituent selected from:
hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11.

Another aspect of the invention are compounds of formula (I), wherein
R7 is hydrogen, cyano, bromine, methyl, ethyl, methoxy, ethoxy, —CH2OH, —C(O)NH2.

Another aspect of the invention are compounds of formula (I), wherein
R7 is cyano, bromine, methyl, ethyl, methoxy, ethoxy, —CH2OH, —C(O)NH2.

Another aspect of the invention are compounds of formula (I), wherein
R7 is hydrogen.

Another aspect of the invention are compounds of formula (I), wherein
R8/R9 which can be the same or different is hydrogen, hydroxy, 3-7C-cycloalkyl or 1-6C-alkoxy, wherein the 1-6C-alkoxy group is optionally substituted, one or more times, identically or differently, with a substituent selected from:
halogen, hydroxy, mono- or di-1-4C-alkylamino), 1-4C-alkoxy, or 3-7C-cycloalkyl or,
R8 and R9 together with the nitrogen to which they are attached may also form a saturated or unsaturated 3-6C-heterocyclic ring, which is optionally substituted by (═O)

Another aspect of the invention are compounds of formula (I), wherein
R8 hydrogen, hydroxy, 3-7C-cycloalkyl or a group selected from 1-4C-alkyl, 1-6C-alkoxy, wherein said group is optionally substituted, one or more times, identically or differently, with a substituent selected from:
halogen, hydroxy, mono- or di-(1-4C-alkylamino), 1-4C-alkoxy, or 3-7C-cycloalkyl and R9 is hydrogen or,
R8 and R9 together with the nitrogen to which they are attached may also form a saturated or unsaturated 3-6C-heterocyclic ring, which is optionally substituted by (═O)

Another aspect of the invention are compounds of formula (I), wherein
R8 and R9 together with the nitrogen to which they are attached may also form a saturated or unsaturated 3-6C-heterocyclic ring, preferably a 5- or 6-membered heterocyclic ring, especially the rings as disclosed in the examples.

Another aspect of the invention are compounds of formula (I), wherein
R8 is hydrogen or methyl.

Another aspect of the invention are compounds of formula (I), wherein
R9 is hydrogen.

Another aspect of the invention are compounds of formula (I), wherein
X is —CH$_2$—.

Another aspect of the invention are compounds of formula (I), wherein
X is —CH$_2$—.

Another aspect of the invention are compounds of formula (I), wherein
Y is —CH$_2$—, —CH(OH)—.

Another aspect of the invention are compounds of formula (I), wherein
Y is —CH$_2$—.

Another aspect of the invention are compounds of formula (I), wherein
R8, R9 which can be the same or different, are hydrogen, 1-4C-alkyl (optionally substituted in the same way of differently one or more times with halogen, hydroxy, mono- or di-1-4C-alkylamino), 1-4C-alkoxy, or 3-7C-cycloalkyl, or,
in the case of —NR8R9, R8 and R9 together with the nitrogen to which they are attached may also form a 3-6C-heterocyclic ring.

Another aspect of the invention are compounds of formula (I), wherein
R10 is hydrogen, 1-6C-alkyl.

Another aspect of the invention are compounds of formula (I), wherein
R11 is 1-4C-alkyl (optionally substituted in the same way of differently one or more times with halogen, hydroxy) or 3-7C-cycloalkyl.

In a further embodiment of the above-mentioned aspects, the invention relates to compounds of formula (I), wherein R6 is hydrogen and R5 is hydrogen.

In another embodiment of the above-mentioned aspects, the invention relates to compounds of formula (I), wherein R6 is hydrogen, R5 is hydrogen and R4 is an unsubstituted phenyl moiety.

In a further embodiment of the above-mentioned aspects, the invention relates to compounds of formula (I), wherein R5 is hydrogen and R4 is an unsubstituted phenyl moiety.

In a preferred embodiment the invention relates to compounds of formula (I), wherein R6 is hydrogen, R5 is hydrogen and R4 is an unsubstituted phenyl moiety and A is N.

In a further embodiment of the above-mentioned aspects, the invention relates to compounds of formula (I), wherein from R1, R2, R3 and R7 at least two of them are not hydrogen.

In a further embodiment of the above-mentioned aspects, the invention relates to compounds of formula (I), wherein R2 and R7 are not hydrogen, R2 is preferably 1-3Calkoxy, C(O)NR8R9, R7 halogen, 1-3Calkoxy, heterocyclyl.

Another embodiment of the invention are the compounds of the claims as disclosed in the Claims section wherein the definitions are limited according to the preferred or more preferred definitions as disclosed below or specifically disclosed residues of the exemplified compounds and subcombinations thereof.

Definitions

Unless defined otherwise in the claims the constituents defined below can optionally be substituted, one or more times, identically or differently, with a substituent selected from:

hydroxy, halogen, cyano, 1-6C-alkyl, 1-4C-haloalkyl, 1-6C-alkoxy, —NR8R9, cyano, (=O), —C(O)NR8R9, —C(O)OR10, —NHC(O)R11, —NHS(O)$_2$R11. An alkyl constituent being substituted more times by halogen includes also a completely halogenated alkyl moiety such as e.g. CF3.

Should a constituent be composed of more than one part, e.g. —O-(1-6Calkyl)-3-7C-cycloalkyl, the position of a possible substituent can be at any of these parts at any suitable position. A hyphen at the beginning of the constituent marks the point of attachment to the rest of the molecule. Should a ring be substituted the substituent could be at any suitable position of the ring, also on a ring nitrogen atom.

The term "comprising" when used in the specification includes "consisting of".

If it is referred to "as mentioned above" or "mentioned above" within the description it is referred to any of the disclosures made within the specification in any of the preceding pages.

"suitable" within the sense of the invention means chemically possible to be made by methods within the knowledge of a skilled person.

"1-6C-alkyl" is a straight-chain or branched alkyl group having 1 to 6 carbon atoms. Examples are methyl, ethyl, n propyl, iso-propyl, n butyl, iso-butyl, sec-butyl and tert-butyl, pentyl, hexyl, preferably 1-4 carbon atoms (1-4C-alkyl), more preferably 1-3 carbon atoms (1-3C-alkyl). Other alkyl constituents mentioned herein having another number of carbon atoms shall be defined as mentioned above taking into account the different length of their chain. Those parts of constituents containing an alkyl chain as a bridging moiety between two other parts of the constituent which usually is called an "alkylene" moiety is defined in line with the definition for alkyl above including the preferred length of the chain e.g. methylen, ethylene, n-propylen, iso-propylen, n-butylen, isobutylene, tert-butylen.

"2-6C-Alkenyl" is a straight chain or branched alkenyl radical having 2 to 4 carbon atoms. Examples are the but-2-enyl, but-3-enyl (homoallyl), prop-1-enyl, prop-2-enyl (allyl) and the ethenyl (vinyl) radicals.

"2-6C-Alkynyl" is a straight chain or branched alkynyl radical having 2 to 4 carbon atoms. Examples are the but-2-ynyl, but-3-ynyl (homopropargyl), prop-1-ynyl, 1-methyl-prop-2-ynyl (1-methylpropargyl), prop-2-ynyl (propargyl) and the ethinyl radicals.

"Mono- or di-1-4C-alkylamino" radicals contain in addition to the nitrogen atom, independently one or two of the above mentioned 1-4C-alkyl radicals. Examples are the methyamino, the ethylamino, the isopropylamino, the dimethylamino, the diethylamino and the diisopropylamino radical.

"Halogen" within the meaning of the present invention is iodine, bromine, chlorine or fluorine, preferably "halogen" within the meaning of the present invention is chlorine or fluorine, should a halogen atom be needed as leaving group within the synthesis iodine or bromine are preferred.

"1-4C-Haloalkyl" is a straight-chain or branched alkyl group having 1 to 4 carbon atoms in which at least one hydrogen is substituted by a halogen atom. Examples are chloromethyl or 2-bromoethyl. For a partially or completely fluorinated C1-C4-alkyl group, the following partially or completely fluorinated groups are considered, for example: fluoromethyl, difluoromethyl, trifluoromethyl, fluoroethyl, 1,1-difluoroethyl, 1,2-difluoroethyl, 1,1,1-trifluoroethyl, tetrafluoroethyl, and pentafluoroethyl, whereby fluoromethyl, difluoromethyl, trifluoromethyl, fluoroethyl, 1,1-difluoroethyl, or 1,1,1-trifluoroethyl are preferred. Partially or completely fluorinated C1-C4-alkyl groups are considered to be encompassed by the term 1-4C-haloalkyl.

"1-6C-Alkoxy" represents radicals, which in addition to the oxygen atom, contain a straight-chain or branched alkyl radical having 1 to 6 carbon atoms. Examples which may be mentioned are the hexoxy, pentoxy, butoxy, iso-butoxy, sec-butoxy, tert-butoxy, propoxy, isopropoxy, ethoxy and methoxy radicals, preferred are methoxy, ethoxy, propoxy, isopropoxy.

"3-7C-Cycloalkyl" stands for cyclopropyl, cyclobutyl, cyclopentyl, cyclohexyl or cycloheptyl, preferably cyclopropyl.

"3-7C-Cycloalkyloxy" or "—O-(3-7C-cycloalkyl)" stands for e.g. cyclopropyloxy, cyclobutyloxy, cyclopentyloxy, cyclohexyloxy or cycloheptyloxy, preferably cyclopropyloxy.

"—O-(1-6C-alkylen)-(3-7C-cycloalkyl)" stands for e.g. —O—CH2-cyclopropyl, —O—CH2-CH2-cyclopropyl, —O—CH2-cyclobutyl, —O—CH2—CH2-cyclobutyl, —O—CH2-cyclopentyl, —O—CH2—CH2-cyclopentyl, —O—CH2-cyclohexyl, —O—CH2—CH2-cyclohexyl.

"3-7C-Heterocyclyl", or "heterocyclyl" represents a mono- or polycyclic, preferably mono- or bicyclic, more preferably monocyclic, nonaromatic heterocyclic radical containing, 4 to 10, preferably 4 to 7, ring atoms, and up to 3, preferably up to 2, hetero atoms and/or hetero groups from the series consisting of N, O, S, SO, SO$_2$. The heterocyclyl radicals can be saturated or partially unsaturated and, unless stated otherwise, may be optionally substituted, one or more times, identically or differently, with a substituent selected from: 1-4C-alkyl, 1-4C-haloalkyl, 1-4C-alkoxy, hydroxy, fluorine or (=O) whereby the 1-4C-alkyl may be optionally further substituted with hydroxy and the double bonded oxygen atom leads to a carbonyl group together with the carbon atom of the heterocyclyl ring at any suitable position. Particularly preferred heterocyclyl radicals are 4- to 7-membered monocyclic saturated heterocyclyl radicals having up to two hetero atoms from the series consisting of O, N and S. The following may be mentioned by way of example and by preference: oxetanyl, tetrahydrofuranyl, azetidinyl, 3-hydroxyazetidinyl, 3-fluoroazetidinyl, 3,3-difluoroazetidinyl, pyrrolidinyl, 3-hydroxypyrrolidinyl, pyrrolinyl, piperidinyl, 3-hydroxypiperidinyl, 4-hydroxypiperidinyl, 3-fluoropiperidinyl, 3,3-difluoropiperidinyl, 4-fluoropiperidinyl, 4,4-difluoropiperidinyl, piperazinyl, N-methylpiperazinyl, N-(2-hydroxyethyl)-piperazinyl, morpholinyl, thiomorpholinyl, azepanyl, homopiperazinyl, N-methyl-homopiperazinyl.

In the case of —NR8R9, when R8 and R9 together with the nitrogen atom to which they are attached form a 3-6C-heterocyclic ring, the term "3-6C-heterocyclic ring" includes all saturated or unsaturated non-arylic heterocyclic rings containing 4 to 7 ring atoms and having 1 or 2 nitrogen atoms, or 1 nitrogen atom and 1 oxygen atom. The 3-6C-heterocyclic ring may be optionally substituted one or more times, identically or differently, with a substituent selected from: 1-4C-alkyl, 1-4C-haloalkyl, 1-4C-alkoxy, hydroxy, fluorine, or (=O)—an oxygen atom being connected via a double bond to a carbon atom of the ring thus forming a carbonyl group which can be positioned besides the nitrogen atom resulting in a lactame moiety or at any other carbon atom of the ring, whereby the 1-4C-alkyl may be optionally further substituted with hydroxy. Preferred examples are azetidine, 3-hydroxyazetidine, 3-fluoroazetidine, 3,3-difluoroazetidine, pyrrolidine, pyrrolidin-2-one, 3-hydroxypyrrolidine, piperidine, 3-hydroxypiperidine, 4-hydroxypiperidine, 3-fluoropiperidine, 3,3-difluoropiperidine, 4-fluoropiperidine, 4,4-difluoropiperidine, 1H-pyridine-2-one, piperazine, N-methyl-piperazine, N-(2-hydroxyethyl)-piperazine, morpholine.

The term "heterocyclyloxy" or "—O-heterocyclyl" represents the same heterocyclic moieties as defined for the term heterocyclyl whereby a C atom in the ring is connected via an oxygen atom to the rest of the molecule. Preferred heterocyclic moieties are either unsubstituted, or may be optionally substituted on a ring nitrogen atom with a substituent selected from: 1-4C-alkyl, 1-4C-haloalkyl, 1-4C-alkoxy.

The term "—O-(1-6C-alkyl)-heterocyclyl" or "—O-(1-6C-alkylen)-heterocyclyl" represents the same heterocyclyl moieties as defined for the term heterocyclyl whereby the ring is connected via a —O-(1-6Calkyl) spacer to the rest of the molecule. Heterocyclic moieties containing one or more ring nitrogen atom are preferably connected to the —O-(1-6-alkyl) spacer via one of the ring nitrogen atoms.

"Aryl" represents a mono-, or bicyclic aromatic carbocyclic radical having, as a rule, 6 to 10 carbon atoms; by way of example phenyl or naphthyl. Phenyl is preferred. The aryl moiety can be substituted one or more times, identically or differently by hydroxy, halogen, cyano, 1-6C-alkyl, 1-4C-haloalkyl, 1-6C-alkoxy, —NR8R9, cyano, —C(O)NR8R9, —C(O)OR10, —NHC(O)R11, —NHS(O)₂R11. In one embodiment of the invention if the phenyl moiety were a substitutent it is not substituted or only substituted once.

The term "-(1-6C-alkyl)-aryl" or "-(1-6C-alkylen)-aryl" represents an aryl radical as defined above which is connected to the rest of the molecule via a straight or branched alkyl chain, preferably —(CH₂)-aryl, or —(CH₂CH₂)-aryl. Benzyl is particularly preferred.

The term "aryloxy" or "—O-aryl" represents the same aryl moieties as defined for the term aryl whereby the ring is connected via an oxygen atom to the rest of the molecule.

The term "—O-(1-6C-alkyl)-aryl" or "—O-(1-6C-alkylen)-aryl" represents the same aryl moieties as defined for the term aryl whereby the ring is connected via a —O-(1-6Calkyl) spacer to the rest of the molecule. Preferred —O-(1-6Calkyl) spacers in this context are —O—(CH₂)—, or —O—(CH₂CH₂)—. Benzyloxy is particularly preferred.

The term "heteroaryl" represents a monocyclic 5- or 6-membered aromatic heterocycle or a fused bicyclic aromatice moiety comprising without being restricted thereto, the 5-membered heteroaryl radicals furyl, thienyl, pyrrolyl, oxazolyl, isoxazolyl, thiazolyl, isothiazolyl, imidazolyl, pyrazolyl, triazolyl (1,2,4-triazolyl, 1,3,4-triazolyl or 1,2,3-triazolyl), thiadiazolyl (1,3,4-thiadiazolyl, 1,2,5-thiadiazolyl, 1,2,3-thiadiazolyl or 1,2,4-thiadiazolyl) and oxadiazolyl (1,3,4-oxadiazolyl, 1,2,5-oxadiazolyl, 1,2,3-oxadiazolyl or 1,2,4-oxadiazolyl), as well as the 6-membered heteroaryl radicals pyridinyl, pyrimidinyl, pyrazinyl and pyridazinyl as well as the fused ring systems such as e.g. phthalidyl-, thiophthalidyl-, indolyl-, isoindolyl-, dihydroindolyl-, dihydroisoindolyl-, indazolyl-, benzothiazolyl-, benzofuranyl-, beximidazolyl-, benzoxazinonyl-, chinolinyl-, isochinolinyl-, chinazolinyl-, chinoxalinyl-, cinnolinyl-, phthalzinyl-, 1,7- or 1,8-naphthridinyl-, cumarinyl-, isocumarinyl-, indolizinyl-, isobenzofuranyl-, azaindolyl-, azaisoindolyl-, furanopyridiyl-, furanopyrimidinyl-, furanopyrazinyl-, furanopyidazinyl-, preferred fused ring system indazolyl. Preferred 5- or 6-membered heteroaryl radicals are furanyl, thienyl, pyrrolyl, thiazolyl, oxazolyl, thiadiazolyl, oxadiazolyl, pyridinyl, pyrimidinyl, pyrazinyl or pyridazinyl. More preferred 5- or 6-membered heteroaryl radicals are furan-2-yl, thien-2-yl, pyrrol-2-yl, thiazolyl, oxazolyl, 1,3,4-thiadiazolyl, 1,3,4-oxadiazolyl, pyridin-2-yl, pyridin-4-yl, pyrimidin-2-yl, pyrimidin-4-yl, pyrazin-2-yl or pyridazin-3-yl.

The term "-(1-6C-alkyl)-heteroaryl" represents a heteroaryl radical as defined above which is connected to the rest of the molecule via a straight or branched alkyl chain, preferably —(CH₂)-heteroaryl, or —(CH₂CH₂)-heteroaryl, whereby —(CH₂)— heteroaryl is particularly preferred.

The term "Heteroaryloxy" or "—O-heteroaryl" represents the same heteroaryl moieties as defined for the term heteroaryl whereby the ring is connected via an oxygen atom to the rest of the molecule.

The term "—O-(1-6C-alkylen)-heteroaryl" represents the same heteraryl moieties as defined for the term heteroaryl whereby the ring is connected via a —O-(1-6Calkyl) spacer to the rest of the molecule.

The term "—O-(1-6C-alkylen) spacer" can vary in the sense of the invention to have an alkylene chain having from 1-6, 1-5, 1-4, 1-3, 1-2 or 1 carbon atoms.

The NR8R9 group includes, for example, NH2, N(H)CH3, N(CH3)2, N(H)CH2CH3 and N(CH3)CH2CH3. In the case of —NR8R9, when R8 and R9 together with the nitrogen atom to which they are attached form a 3-6C-heterocyclic ring, the term "3-6C-heterocyclic ring" is defined above. Especially preferred are pyrrolidin-2-one, 1H-pyridine-2-one.

The NH(CO)R11 group includes for example NH(CO) CH3, NH(CO)C2H5, NH(CO)C3H7, NH(CO)CH(CH3)2.

The NHS(O)₂R11 group includes for example NHS(O) 2CH3, NHS(O)2C2H5, NHS(O)2C3H7, NHS(O)2CH(CH3) 2.

The C(O)NR8R9 group includes, for example, C(O)NH2, C(O)N(H)CH3, C(O)N(CH3)2, C(O)N(H)CH2CH3, C(O)N (CH3)CH2CH3 or C(O)N(CH2CH3)2. In the case of —NR8R9, when R8 and R9 together with the nitrogen atom to which they are attached form a 3-6C-heterocyclic ring, the term "3-6C-heterocyclic ring" is defined above.

The C(O)OR10 group includes for example C(O)OH, C(O)OCH3, C(O)OC2H5, C(O)C3H7, C(O)CH(CH3)2, C(O)OC4H9, C(O)OC5H11, C(O)OC6H13; for C(O)O(1-6Calkyl) the alkyl part may be straight or branched.

In general and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

Constituents which are optionally substituted as stated herein, may be substituted, unless otherwise noted, one or more times, independently from one another at any possible position. When any variable occurs more than one time in any constituent, each definition is independent.

In case of R1 or R2 it is understood that the groups selected from 1-6C-alkyl, 2-6C-alkenyl, 1-6C-alkoxy, 3-7C-cycloalkyl, aryl, heteroaryl, -(1-6C-alkyl)-aryl, -(1-6C-alkyl)-heteroaryl, —O-(3-7C-cycloalkyl), —O-aryl, —O-(3-7C-heterocyclyl), —O-heteroaryl, —O-(1-6C-alkyl en)-(3-7C-cycloalkyl), —O-(1-6C-alkyl)-aryl, —O-(1-6C-alkyl)-(3-7C-heterocyclyl), —O-(1-6C-alkyl)-heteroaryl may be optionally substituted, one or more times, identically or differently, with a substituent selected from: hydroxy, halogen, 1-6C-alkyl, 1-4C-haloalkyl, 1-6C-alkoxy, —NR8R9, cyano, (═O), —C(O)NR8R9, —C(O)OR10, —NHC(O)R11, —NHS(O)2R11, heteroaryl, Preferably the groups -(1-6C-alkyl)-aryl, -(1-6C-alkyl)-heteroaryl, —O-(1-6C-alkyl)-heteroaryl, —O-(1-6C-alkyl en)-(3-7C-cycloalkyl), —O-(1-6C-alkyl)-(3-7C-heterocyclyl), —O-(1-6C-alkyl)-aryl-O-(1-6C-alkyl)heteroaryl are either not substituted within the 1-6C-alkyl part, or the 1-6C-alkyl part is optionally substituted with one or two fluorine atoms.

The heteroarylic, heteroarylenic, or heterocyclic groups mentioned herein may be substituted by their given substituents or parent molecular groups, unless otherwise noted, at any possible position, such as e.g. at any substitutable ring carbon or ring nitrogen atom. Analogously it is being understood that it is possible for any heteroaryl or heterocyclyl group to be attached to the rest of the molecule via any suitable atom if chemically suitable. Unless otherwise noted, any heteroatom of a heteroarylic or heteroarylenic ring with unsatisfied valences mentioned herein is assumed to have the hydrogen atom(s) to satisfy the valences. Unless otherwise noted, rings containing quaternizable amino- or imino-type ring nitrogen atoms (—N═) may be preferably not quaternized on these amino- or imino-type ring nitrogen atoms by the mentioned substituents or parent molecular groups.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

Salts of the compounds according to the invention include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

One aspect of the invention are salts of the compounds according to the invention including all inorganic and organic acid addition salts, especially all pharmaceutically acceptable inorganic and organic acid addition salts, particularly all pharmaceutically acceptable inorganic and organic acid addition salts customarily used in pharmacy. Another aspect of the invention are the salts with di- and tricarboxylic acids.

Examples of acid addition salts include, but are not limited to, hydrochlorides, hydrobromides, phosphates, nitrates, sulfates, salts of sulfamic acid, formates, acetates, propionates, citrates, D-gluconates, benzoates, 2-(4-hydroxybenzoyl)-benzoates, butyrates, salicylates, sulfosalicylates, lactates, maleates, laurates, malates, fumarates, succinates, oxalates, malonates, pyruvates, acetoacetates, tartarates, stearates, benzensulfonates, toluenesulfonates, methanesulfonates, trifluoromethansulfonates, 3-hydroxy-2-naphthoates, benzenesulfonates, naphthalinedisulfonates and trifluoroacetates.

Examples of salts with bases include, but are not limited to, lithium, sodium, potassium, calcium, aluminum, magnesium, titanium, meglumine, ammonium, salts optionally derived from $NH_3$ or organic amines having from 1 to 16 C-atoms such as e.g. ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylendiamine, N-methylpiperindine and guanidinium salts.

The salts include water-insoluble and, particularly, water-soluble salts.

According to the person skilled in the art the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The term "(chemotherapeutic) anti-cancer agents", includes but is not limited to (i) alkylating/carbamylating agents such as Cyclophosphamid (Endoxan®), Ifosfamid (Holoxan®), Thiotepa (Thiotepa Lederle®), Melphalan (Alkeran®), or chloroethyl-nitrosourea (BCNU); (ii) platinum derivatives like cis-platin (Platinex® BMS), oxaliplatin (Eloxatin®), satraplatin or carboplatin (Cabroplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof (like the nanoparticle formulation Abraxane® with paclitaxel bound to albumin), epothilones such as Epothilone B (Patupilone®), Azaepothilone (Ixabepilone®) or Sagopilone; (iv) topoisomerase inhibitors such as anthracyclines (exemplified by Doxorubicin/Adriblastin®), epipodophyllotoxines (exemplified by Etoposide/Etopophos®) and camptothecin and camptothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and (vii) folic acid antagonists such as methotrexate (Farmitrexat®) or premetrexed (Alimta®).

The term "target specific anti-cancer agent", includes but is not limited to (i) kinase inhibitors such as e.g. Imatinib (Glivec®), ZD-1839/Gefitinib (Iressa®), Bay43-9006 (Sorafenib, Nexavar®), SU11248/Sunitinib (Sutent®), OSI-774/Erlotinib (Tarceva®), Dasatinib (Sprycel®), Lapatinib (Tykerb®), or, see also below, Vatalanib, Vandetanib (Zactima®) or Pazopanib; (ii) proteasome inhibitors such as PS-341/Bortezumib (Velcade®); (iii) histone deacetylase inhibitors like SAHA (Zolinza®), PXD101, MS275, MGCD0103, Depsipeptide/FK228, NVP-LBH589, Valproic acid (VPA), CRA/PCI-24781, ITF2357, SB939 and butyrates (iv) heat shock protein 90 inhibitors like 17-allylaminogeldanamycin (17-AAG) or 17-dimethylaminogeldanamycin (17-DMAG); (v) vascular targeting agents (VTAs) like combretastin A4 phosphate or AVE8062/AC7700 and anti-angiogenic drugs like the VEGF antibodies, such as Bevacizumab (Avastin®), or KDR tyrosine kinase inhibitors such as PTK787/ZK222584 (Vatalanib®) or Vandetanib (Zactima®) or Pazopanib; (vi) monoclonal antibodies such as Trastuzumab (Herceptin®), Rituximab (MabThera/Rituxan®), Alemtuzumab (Campath®), Tositumomab (Bexxar®), C225/Cetuximab (Erbitux®), Avastin (see above) or Panitumumab (Vectibix®) as well as mutants and conjugates of monoclonal antibodies, e.g. Gemtuzumab ozogamicin (Mylotarg®) or Ibritumomab tiuxetan (Zevalin®), and antibody fragments; (vii) oligonucleotide based therapeutics like G-3139/Oblimersen (Genasense®) or the DNMT1 inhibitor MG98; (viii) Toll-like receptor/TLR 9 agonists like Promune®, TLR 7 agonists like Imiquimod (Aldara®) or Isatoribine and analogues thereof, or TLR 7/8 agonists like Resiquimod as well as immunostimulatory RNA as TLR 7/8 agonists; (ix) protease inhibitors; (x) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors (e.g. Femara, Arimedex or Aromasin).

Other "target specific anti-cancer agents" include bleomycin, retinoids such as all-trans retinoic acid (ATRA), DNA methyltransferase inhibitors such as 5-Aza-2'-deoxycytidine (Decitabine, Dacogen®) and 5-azacytidine (Vidaza®), alanosine, cytokines such as interleukin-2, interferons such as interferon α2 or interferon-γ, bcl2 antagonists (e.g. ABT-737 or analogs), death receptor agonists, such as TRAIL, DR4/5 agonistic antibodies, FasL and TNF-R agonists (e.g. TRAIL receptor agonists like mapatumumab or lexatumumab).

Specific examples of anti-cancer agents include, but are not limited to 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DASATINIB, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LAPATINIB, LETROZOLE, LEUPRORELIN, LOBAPLATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PANITUMUMAB, PATUPILONE, PAZOPANIB, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SAGOPILONE, SARGRAMOSTIM, SATRAPLATIN, SIROLIMUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VANDETANIB, VERTEPORFIN, VINBLASTINE, VINCRISTINE, VINDESINE, VINORELBINE, VOROZOLE, ZEVALIN and ZOLINZA.

The compounds according to the invention and their salts can exist in the form of tautomers which are included in the embodiments of the invention.

The compounds of the invention may, depending on their structure, exist in different stereoisomeric forms. These forms include configurational isomers or optionally conformational isomers (enantiomers and/or diastereoisomers including those of atropisomers). The present invention therefore includes enantiomers, diastereoisomers as well as mixtures thereof. From those mixtures of enantiomers and/or disastereoisomers pure stereoisomeric forms can be isolated with methods known in the art, preferably methods of chromatography, especially high pressure liquid chromatography (HPLC) using achiral or chiral phase. The invention further includes all mixtures of the stereoisomers mentioned above independent of the ratio, including the racemates.

Some of the compounds and salts according to the invention may exist in different crystalline forms (polymorphs) which are within the scope of the invention.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

The intermediates used for the synthesis of the compounds of claims 1-5 as described below, as well as their use for the synthesis of the compounds of claims 1-5, are one further aspect of the present invention. Preferred intermediates are the Intermediate Examples as disclosed below.

The compounds according to the invention can be prepared as follows. The compounds according to the invention can be prepared according to the following schemes 1 or 2, Scheme 1:

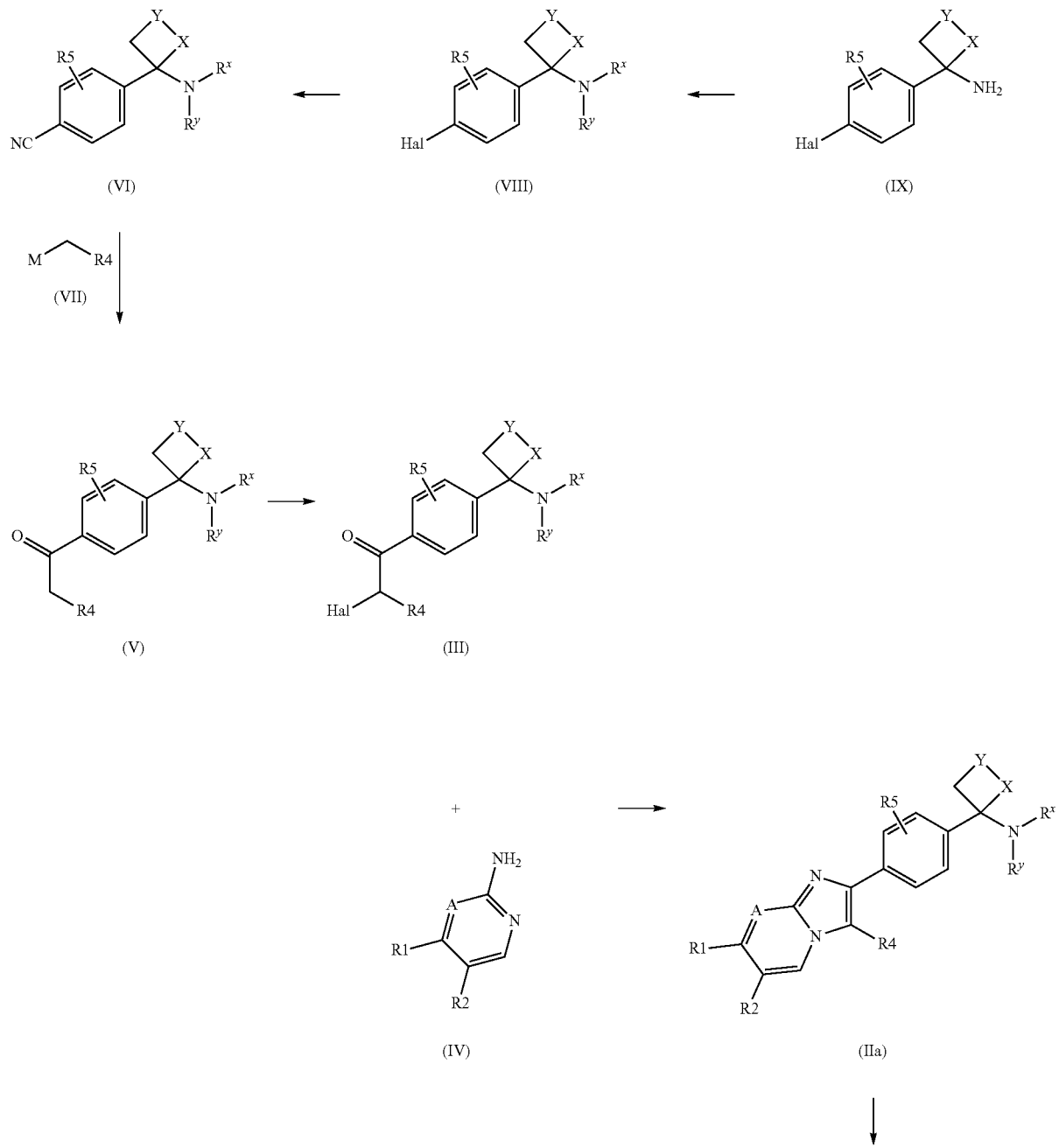

-continued
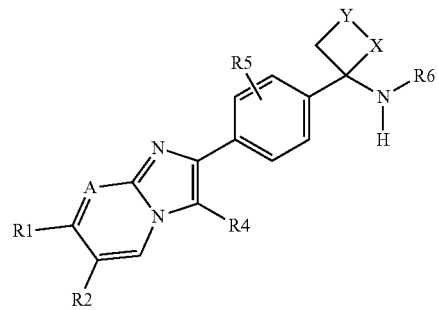
(Ia)
Scheme 2:
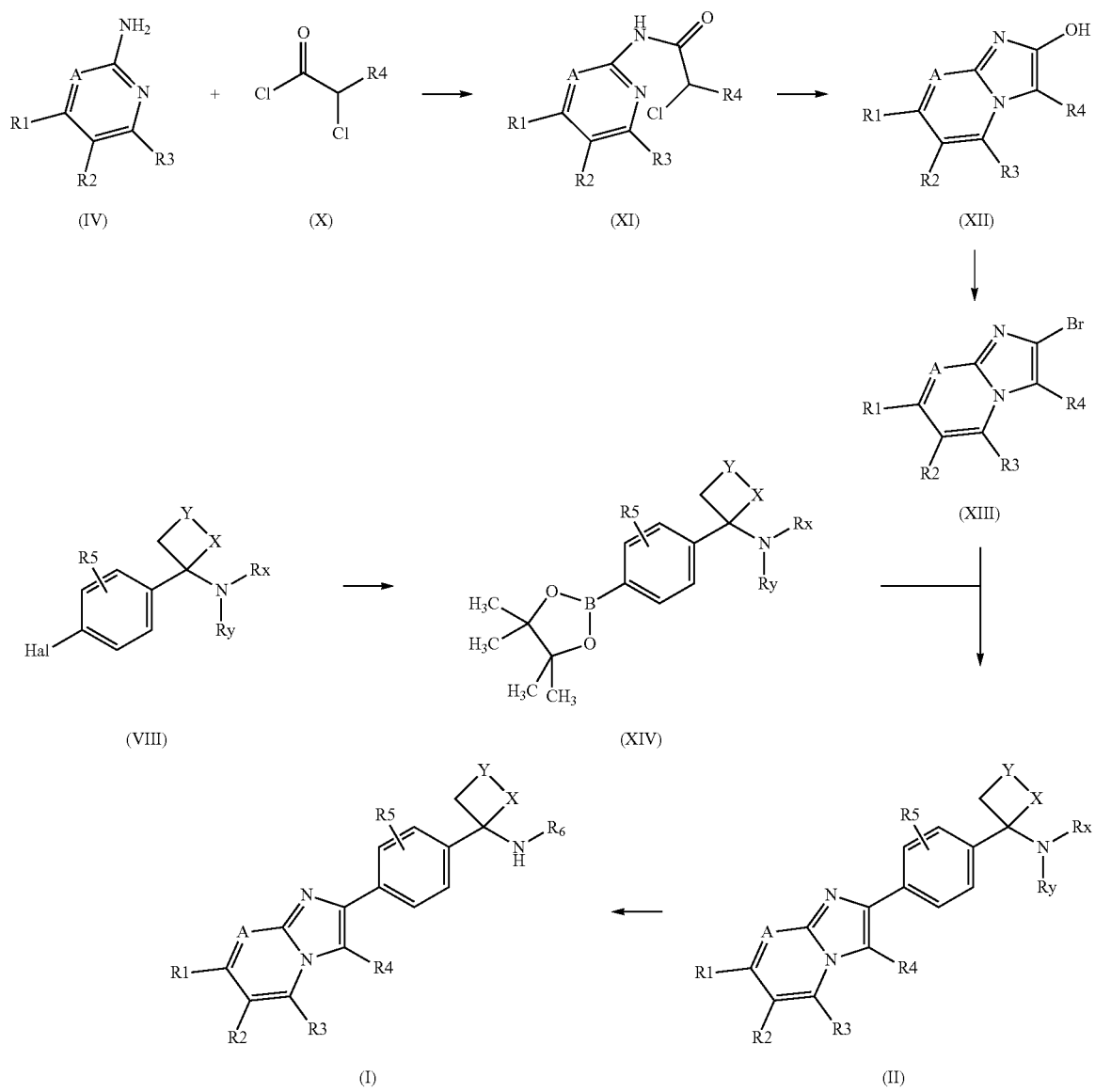

wherein A, X, Y, R1, R2, R3, R4, R5 and R6 have the meanings defined above and in the claims, whereby Rx has the meaning of R6 and may also be a protecting group; Ry is H, or a protecting group, whereby Rx and Ry together, or Y and Rx together, may form a cyclic protecting group; Hal is halogen, preferably Cl, Br, or I; M is a metal moiety, such as —Li, —MgCl, —MgBr.

Compounds of formula (I) according to scheme 2 encompass compounds of formula (Ia) according to scheme 1 as well as compounds of formula (II) according to scheme 2 encompass compounds of formula (IIa) according to scheme 1. Compounds of general formula (I)/(Ia) may be prepared from compounds of general formula (II)/(IIa). Ry may optionally be R6, or a protecting group, or other such precursor which requires further manipulation. For example, Rx in compounds of general formula (II) may be a protecting group such as the Boc group, —CO(OtBu). Thus in special embodiment of the invention the protecting group is a Boc group. Preparation of compounds of general formula (I) may thus be accomplished by use of an appropriate deprotection reaction, such as in the case of a Boc group, acidic reaction conditions, for example, with a solution of 4M hydrogen chloride in dioxane, in an appropriate solvent, such as for example DCM and methanol, at ambient temperature. The resulting ammonium salts are usually converted to the free amines by using, e.g., bases known to the skilled person, e.g., bicarbonate, amine bases such as Hunig's base (diisopropylethylamine), sodium hydroxide, ammonia, or by eluting the compounds with methanol/ammonia from a PoraPak™ column. Further conditions to deprotect the Boc group, or further protecting groups that may be suitable for use in blocking the amino functionality in compounds of general formula (II), including their synthesis and deprotection, are found, for example, in T. W. Greene, Protective Groups in Organic Synthesis, John Wiley & Sons, 1999, 3rd Ed., or in P. Kocienski, Protecting Groups, Thieme Medical Publishers, 2000. Similarly, when Ry is not H, then Ry is a protecting group, such as for example when Rx and Ry together form a cyclic protecting group such as for example a phthalamide.

Furthermore, compounds of general formula (II)/(IIa) may contain functionality that may itself be further modified, thus allowing introduction of the desired functionality in the A, R1 or R2 groups. Such transformations include oxidations, reductions, nucleophilic substitutions, electrophilic substitutions, radical reactions, or metal promoted reactions such as metal assisted cross-coupling reactions, such as for example Suzuki, Stille, or Heck reactions, or the like. Similarly, compounds of general formula (I) may also be modified in this way to provide further compounds according to the invention, providing the transformations do not cause unwanted side reactions at the —NHR6 group.

Compounds of general formula (IIa) may be prepared from an intermediate ketone of general formula (III) and a heterocyclic amine of general formula (IV), by use of an appropriate cyclisation reaction. For example, compounds of general formula (IIa) may be prepared by reacting (III) and (IV) in an appropriate solvent, such as for example DMF, ethanol or isopropanol, at elevated temperatures from 50° C. to 150° C. The use of basic additives such as a tertiary amine, for example triethylamine or diisopropylamine, or additives such as molecular sieves may be beneficial.

Compounds of general formula (IV) are either commercially available, may be prepared using the methods described in the examples, may be prepared using known methods, or may be prepared by analogous methods to those known by the person skilled in the art.

Compounds of general formula (III) may be prepared from a ketone of general formula (V) by use of an appropriate halogenation reaction. For example in the case of halogen is Br, a suitable bromination reaction, such as for example by reacting a ketone of general formula (V) with pyridinium hydrobromide perbromide in a suitable solvent, such as THF, at suitable temperatures, such as for example from 0° C. to ambient temperature.

Compounds of general formula (V) may be prepared from a compound of general formula (VI) using known methods, such as by addition of a suitable organometallic reagent (VII), in a suitable solvent, such as ethereal solvents, for example THF, at low temperatures, for example from −78° C. to −10° C., preferably from −30° C. to -10° C. Preferred organometallic reagents are for example organomagnesium reagents in which M is —MgCl or —MgBr, more preferably —MgCl.

Compounds of general formula (VI) may be prepared from compounds of general formula (VIII) using known methods, such as by way of a palladium catalysed cyanation reaction, using a suitable catalyst such as tetrakis(triphenylphosphine)palladium(0)[Pd(PPh$_3$)$_4$], a suitable cyano source, such as zinc dicyanide, a suitable solvent, such as DMF, whereby dry DMF may be beneficial, and elevated temperatures, such as up to the boiling point of the solvent, preferably at 80° C.

Compounds of general formula (VIII) and (IX) are either commercially available, may be prepared using the methods described below, may be prepared using known methods, or may be prepared by analogous methods to those known by the person skilled in the art.

Thus one aspect of the invention is the process for the manufacture of compounds of general formula (I), characterized in that a compound of formula (III)

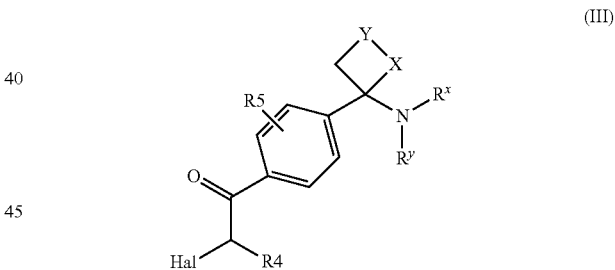

whereby R4, R5 and R6, X and Y have the meaning according to claim 1 and Rx is R6 or a protecting group; Ry is hydrogen or a protecting group, or Rx and Ry together, or Y and Rx together, may form a cyclic protecting group, Hal is halogen, is reacted with a compound of formula (IV)

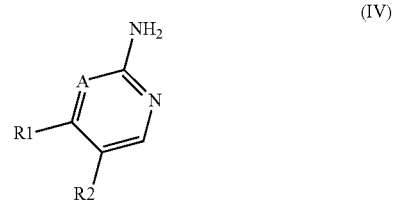

whereby R1, R2, R3 and A have the meaning according to claim 1, forming a compound of formula (II)

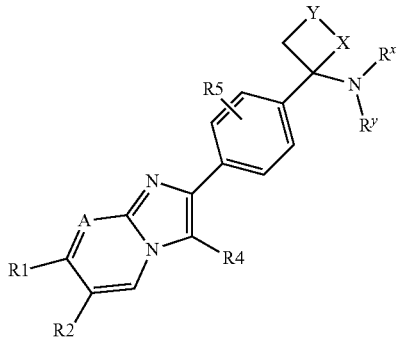
(II)

which is optionally subsequently deprotected to form a compound of general formula (I).

One preferred aspect of the invention is the process for the preparation of the compounds of claims 1-5 according to the Examples.

Another aspect of the invention is the intermediate of general formula (III)

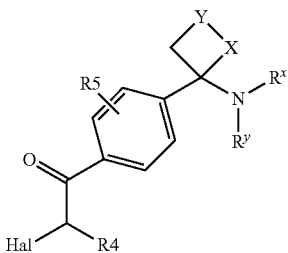
(III)

wherein R4, R5 and R6, X and Y have the meaning according to claim 1 and Rx is R6 or a protecting group; Ry is hydrogen or a protecting group, or Rx and Ry together, or Y and Rx together, may form a cyclic protecting group, Hal is halogen as well as its use for the production of the compounds of general formula (I).

A further aspect of the invention is the process for the manufacture of compounds of general formula (I) according to claim 1, characterized in that a compound of formula (XIV)

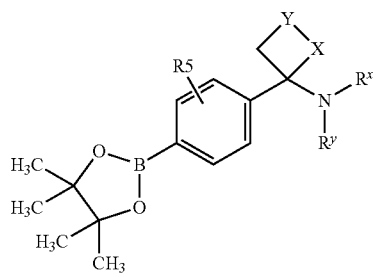
(XIV)

wherein R5, R6 and X and Y have the meaning as defined in claim 1 and Rx is R6 or a protecting group; Ry is hydrogen or a protecting group, or Rx and Ry together, or Y and Rx together, may form a cyclic protecting group, optionally the amino group is thus protected, is reacted with a compound of formula

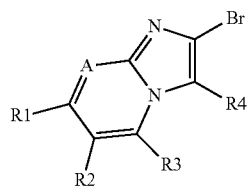
(XIII)

wherein R1, R2, R3, A and R4 have the meaning as defined in claim 1, to obtain, optionally after deprotection, a compound of formula (I)

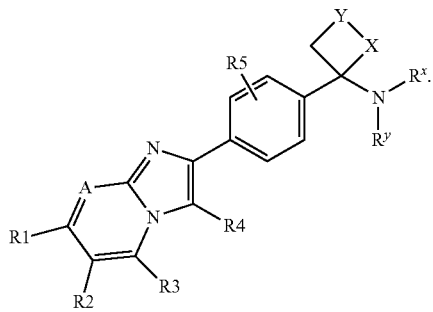

Another aspect of the invention is the intermediate compound of general formula XIV

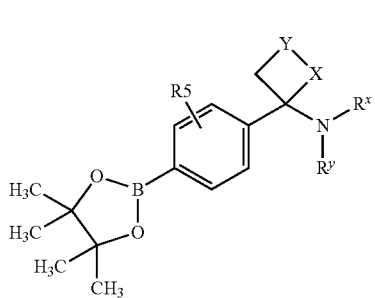
(XIV)

wherein R5, R6 and X and Y have the meaning as defined in claim 1 and Rx is R6 or a protecting group; Ry is hydrogen or a protecting group, or Rx and Ry together, or Y and Rx together, may form a cyclic protecting group as well as its use for the manufacture of compounds of general formula (I).

For both processes described above it is preferred that Rx is R6 or a protecting group and Ry is hydrogen or a protecting group. In one embodiment of the invention one of Rx/Ry is a protecting group and the other is hydrogen. Especially preferred protecting groups are the ones disclosed in the experimental section.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1-5 according to the examples.

Optionally, compounds of the formula (I) can be converted into their salts, or, optionally, salts of the compounds of the formula (I) can be converted into the free compounds. Corresponding processes are customary for the skilled person.

Optionally, compounds of the formula (I) can be converted into their N-oxides. The N-oxide may also be introduced by way of an intermediate. N-oxides may be prepared by treating an appropriate precursor with an oxidizing agent, such as metachloroperbenzoic acid, in an appropriate solvent, such as dichloromethane, at suitable temperatures, such as from 0° C. to 40° C., whereby room temperature is generally preferred. Further corresponding processes for forming N-oxides are customary for the skilled person.

Commercial Utility

The compounds of formula (I) and the stereoisomers of the compounds of formula (I) according to the invention are hereinafter referred to as the compounds of the invention. In particular, the compounds of the invention are pharmaceutically acceptable. The compounds according to the invention have valuable pharmaceutical properties, which make them commercially utilizable. In particular, they inhibit the Pi3K/Akt pathway and exhibit cellular activity. They are expected to be commercially applicable in the therapy of diseases (e.g. diseases dependent on overactivated Pi3K/Akt). An abnormal activation of the PI3K/AKT pathway is an essential step towards the initiation and maintenance of human tumors and thus its inhibition, for example with AKT inhibitors, is understood to be a valid approach for treatment of human tumors. For a recent review see Garcia-Echeverria et al (Oncogene, 2008, 27, 551-5526).

Cellular activity and analogous terms in the present invention is used as known to persons skilled in the art, as an example, inhibition of phosphorylation, inhibition of cellular proliferation, induction of apoptosis or chemosensitization.

Chemosensitization and analogous terms in the present invention is used as known to persons skilled in the art. These stimuli include, for example, effectors of death receptor and survival pathways as well as cytotoxic/chemotherapeutic and targeted agents and finally radiation therapy. Induction of apoptosis and analogous terms according to the present invention are used to identify a compound which executes programmed cell death in cells contacted with that compound or in combination with other compounds routinely used for therapy.

Apoptosis in the present invention is used as known to persons skilled in the art. Induction of apoptosis in cells contacted with the compound of this invention might not necessarily be coupled with inhibition of cell proliferation. Preferably, the inhibition of proliferation and/or induction of apoptosis are specific to cells with aberrant cell growth.

Furthermore, the compounds according to the present invention inhibit protein kinase activity in cells and tissues, causing a shift towards dephosphorylated substrate proteins and as functional consequence, for example the induction of apoptosis, cell cycle arrest and/or sensitization towards chemotherapeutic and target-specific cancer drugs. In a preferred embodiment, inhibition of the Pi3K/Akt pathway induces cellular effects as mentioned herein, alone, or in combination with standard cytotoxic or targeted cancer drugs.

In addition inhibition of AKT signaling pathway was found to inhibit retinal neovascularisation in the oxygene induced retinopathy model as well as a potential therapeutic use of a AKT inhibition on choroidal neovascularisation was shown (Wang et al., Acta Histochem. Cytochem. 44(2): 103-111, 2011; Yang et al., Investigative Ophthalmology & Visual Science (IOVS), April 2009, Vol. 50, No. 4) These results lead to the conclusion that AKT inhibition could provide a useful therapy for ocular diseases associated with ocular neovascularisation like e.g. AMD, MD und diabetic retinopathy.

Thus one embodiment of the invention includes methods of treatment of ocular diseases associated with ocular neovasculariation especially AMD, MD und diabetic retinopathy comprising administering a compound of general formula (I) as well as the use of those compounds for the treatment of said diseases.

Compounds according to the present invention exhibit anti-proliferative and/or proapoptotic and/or chemosensitizing properties. Accordingly, the compounds of the present invention are useful for the treatment of hyperproliferative disorders, in particular cancer. Therefore the compounds of the present invention are useful to induce an anti-proliferative and/or pro-apoptotic and/or chemosensitizing effect in mammals, such as humans, suffering from a hyperproliferative disorders, like cancer.

The invention further relates to a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, especially malignant neoplasia, including cancer and the tumor types as disclosed below.

Compounds according to the present invention exhibit anti-proliferative and/or proapoptotic properties in mammals such as humans due to inhibition of metabolic activity of cancer cells which are able to survive despite of unfavourable growth conditions such as glucose depletion, hypoxia or other chemo stress.

Thus, the compounds according to the present invention are useful for treating, ameliorating or preventing diseases of benign or malignant behaviour as described herein, such as e.g. for inhibiting cellular neoplasia.

Neoplasia in the present invention is used as known to persons skilled in the art. A benign neoplasia is described by hyperproliferation of cells, incapable of forming an aggressive, metastasizing tumor in-vivo. In contrast, a malignant neoplasia is described by cells with multiple cellular and biochemical abnormalities, capable of forming a systemic disease, for example forming tumor metastasis in distant organs.

The compounds according to the present invention can be preferably used for the treatment of malignant neoplasia. Examples of malignant neoplasia treatable with the compounds according to the present invention include solid and hematological tumors. Solid tumors can be exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). Hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

The invention further includes as a preferred embodiment methods for treatment of melanoma, NSCLC, brain- breast- and prostate cancer comprising administering a compound of general formula (I) as well as the use of the compounds of general formula (I) for said treatment.

It is noted that a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function and death.

Drug resistance is of particular importance for the frequent failure of standard cancer therapeutics. This drug resistance is caused by various cellular and molecular mechanisms. One aspect of drug resistance is caused by constitutive activation of anti-apoptotic survival signals with PKB/Akt as a key signalling kinase. Inhibition of the Pi3K/Akt pathway leads to a resensitization towards standard chemotherapeutic or target specific cancer therapeutics. As a consequence, the commercial applicability of the compounds according to the present invention is not limited to $1^{st}$ line treatment of cancer patients. In a preferred embodiment, cancer patients with resistance to cancer chemotherapeutics or target specific anti-cancer drugs are also amenable for treatment with these compounds for e.g. $2^{nd}$ or $3^{rd}$ line treatment cycles. In particular, the compounds according to the present invention might be used in combination with standard chemotherapeutic or targeted drugs to resensitize tumors towards these agents.

Compounds according to the present invention are suitable for treatment, prevention or amelioration of the diseases of benign and malignant behavior as described above, such as e.g. benign or malignant neoplasia, particularly cancer, especially a cancer that is sensitive to Pi3K/Akt pathway inhibition.

The present invention further includes a method for treating, preventing or ameliorating mammals, including humans, preferably treating mammals, including humans, which are suffering from one of the abovementioned conditions, illnesses, disorders or diseases. The method is characterized in that a pharmacologically active and therapeutically effective and tolerable amount of one or more of the compounds according to the present invention is administered to the subject in need of such treatment.

The present invention further includes a method for treating, preventing or ameliorating diseases responsive to inhibition of the Pi3K/Akt pathway, in a mammal, including human, preferably treating diseases responsive to inhibition of the Pi3K/Akt pathway, in a mammal, including human, comprising administering a pharmacologically active and therapeutically effective and tolerable amount of one or more of the compounds according to the present invention to said mammal.

The present invention further includes a method for inhibiting protein kinase activity in cells comprising administering a pharmacologically active and therapeutically effective and tolerable amount of one or more of the compounds according to the present invention to a patient in need of such therapy.

The present invention further includes a method for treating hyperproliferative diseases of benign or malignant behaviour and/or disorders responsive to induction of apoptosis, such as e.g. cancer, particularly any of those cancer diseases described above, in a mammal, comprising administering a pharmacologically active and therapeutically effective and tolerable amount of one or more of the compounds according to the present invention to said mammal.

The present invention further includes a method for inhibiting cellular hyperproliferation or arresting aberrant cell growth in a mammal, comprising administering a pharmacologically active and therapeutically effective and tolerable amount of one or more of the compounds according to the present invention to said mammal.

The present invention further includes a method for inducing apoptosis in the therapy of benign or malignant neoplasia, particularly cancer, comprising administering a pharmacologically active and therapeutically effective and tolerable amount of one or more of the compounds according to the present invention to a subject in need of such therapy.

The present invention further includes a method for inhibiting protein kinase activity in cells comprising administering a pharmacologically active and therapeutically effective and tolerable amount of one or more of the compounds according to the present invention to a patient in need of such therapy.

The present invention further includes a method for sensitizing towards chemotherapeutic or target-specific anti-cancer agents in a mammal, comprising administering a pharmacologically active and therapeutically effective and tolerable amount of one or more of the compounds according to the present invention to said mammal.

The present invention further includes a method for treating benign and/or malignant neoplasia, especially malignant neoplasia, particularly cancer, in a mammal, including human, comprising administering a pharmacologically active and therapeutically effective and tolerable amount of one or more of the compounds according to the present invention to said mammal.

The present invention further includes a method for treating solid and hematological tumors, whereby solid tumors can be exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). and hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

The present invention further relates to the use of the compounds for the production of pharmaceutical compositions, which are employed for the treatment, prophylaxis, and/or amelioration of one or more of the illnesses mentioned, preferably for the treatment of one or more of the illnesses mentioned.

The present invention further relates to the use of the compounds for the manufacture of pharmaceutical compositions for treating, preventing or ameliorating, preferably treating hyperproliferative diseases and/or disorders responsive to the induction of apoptosis, such as e.g. benign or malignant neoplasia, especially malignant neoplasia, in particular cancer, especially those cancer diseases and tumor types mentioned above.

The present invention further relates to the use of the compounds according to this invention for the production of pharmaceutical compositions for treating, preventing or ameliorating, preferably treating benign or malignant neoplasia, especially malignant neoplasia, particularly cancer, such as e.g. any of those cancer diseases and tumor types described above.

The invention further relates to a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, including cancer.

The invention further related to the use of a compound according to the invention or a pharmaceutically acceptable salt thereof, for the production of a pharmaceutical composition for the treatment, prevention or amelioration of a disease mediated by a dysregulated function of a single protein kinase or multiple protein kinases and/or disorders responsive to the induction of apoptosis.

The invention further relates to a pharmaceutical composition, comprising a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, including cancer.

The present invention further relates to the use of compounds and pharmaceutically acceptable salts according to the present invention for the manufacture of pharmaceutical compositions, which can be used for sensitizing towards chemotherapeutic and/or target specific anti-cancer agents.

The present invention further relates to the use of compounds according to the present invention for the manufacture of pharmaceutical compositions, which can be used for sensitizing towards radiation therapy of those diseases mentioned herein, particularly cancer.

The present invention further relates to the use of the compounds according to the present invention for the manufacture of pharmaceutical compositions, which can be used in the treatment of diseases sensitive to protein kinase inhibitor therapy and different to cellular neoplasia. These non-malignant diseases include, but are not limited to benign prostate hyperplasia, neurofibromatosis, dermatoses, and myelodysplastic syndromes.

The present invention further relates to pharmaceutical compositions comprising one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

The pharmaceutical compositions according to this invention are prepared by processes, which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, dragees, pills, cachets, granules, capsules, caplets, suppositories, patches (e.g. as TTS), emulsions (such as e.g. micro-emulsions or lipid emulsions), suspensions (such as e.g. nano suspensions), gels, solubilisates or solutions (e.g. sterile solutions), or encapsuled in liposomes or as beta-cyclodextrine or beta-cyclodextrin derivative inclusion complexes or the like, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers (such as e.g. polyoxyethylenglyceroltriricinoleat 35, PEG 400, Tween 80, Captisol, Solutol HS15 or the like), colorants, complexing agents, permeation promoters, stabilizers, fillers, binders, thickeners, disintegrating agents, buffers, pH regulators (e.g. to obtain neutral, alkaline or acidic formulations), polymers, lubricants, coating agents, propellants, tonicity adjusting agents, surfactants, flavorings, sweeteners or dyes, can be used.

In particular, auxiliaries and/or excipients of a type appropriate to the desired formulation and the desired mode of administration are used.

The administration of the compounds, pharmaceutical compositions or combinations according to the invention may be performed in any of the generally accepted modes of administration available in the art. Illustrative examples of suitable modes of administration include intravenous, oral, nasal, parenteral, topical, trans-dermal and rectal delivery. Oral and intravenous deliveries are preferred.

Generally, the pharmaceutical compositions according to the invention can be administered such that the dose of the active compound is in the range customary for Pi3K/Akt pathway inhibitors. In particular, a dose in the range of from 0.01 to 4000 mg of the active compound per day is preferred for an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination.

The pharmaceutical composition can be administered in a single dose per day or in multiple subdoses, for example, 2 to 4 doses per day. A single dose unit of the pharmaceutical composition can contain e.g. from 0.01 mg to 4000 mg, preferably 0.1 mg to 2000 mg, more preferably 0.5 to 1500 mg, most preferably 1 to 500 mg, of the active compound. Furthermore, the pharmaceutical composition can be adapted to weekly, monthly or even more infrequent administration, for example by using an implant, e.g. a subcutaneous or intramuscular implant, by using the active compound in form of a sparingly soluble salt or by using the active compound coupled to a polymer.

The present invention further relates to combinations comprising one or more first active ingredients selected from the compounds of the invention and one or more second active ingredients selected from chemotherapeutic anti-cancer agents and target-specific anti-cancer agents e.g. for treating, preventing or ameliorating diseases responsive or sensitive to inhibition of the Pi3K/Akt pathway, such as hyperproliferative diseases of benign or malignant behaviour and/or disorders responsive to the induction of apoptosis, particularly cancer, such as e.g. any of those cancer diseases described above.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware of the total daily dosage(s) and administration form(s) of the additional therapeutic agent(s) coadministered. Said total daily dosage(s) can vary within a wide range depending from the agent combined.

In practicing the present invention, the compounds according to this invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics (chemotherapeutic and/or target specific anti-cancer agents), in particular art-known anti-cancer agents, such as any of e.g. those mentioned above.

In this context, the present invention further relates to a combination comprising a first active ingredient, which is at least one compound according to this invention, and a second active ingredient, which is at least one art-known anti-cancer agent, such as e.g. one or more of those mentioned herein above, for separate, sequential, simultaneous, concurrent or chronologically staggered use in therapy, such as e.g. in therapy of any of those diseases mentioned herein.

The present invention further relates to a pharmaceutical composition comprising a first active ingredient, which is at least one compound according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy.

The present invention further relates to a combination product comprising a.) at least one compound according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat hyperproliferative diseases and diseases responsive or sensitive to inhibition of the Pi3K/Akt pathway, such as e.g. benign or malignant neoplasia, particularly cancer, more precisely, any of those cancer diseases described above.

The present invention further relates to a combined preparation comprising at least one compound according to this invention and at least one art-known anti-cancer agent for simultaneous, concurrent, sequential or separate administration.

The present invention further relates to combinations, compositions, formulations, preparations or kits according to the present invention having Pi3K/Akt pathway inhibitory activity.

In addition, the present invention further relates to a method for treating in combination therapy hyperproliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating hyperproliferative diseases of benign or malignant behaviour and/or disorders responsive to the induction of apoptosis, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating hyperproliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating, especially treating hyperproliferative diseases and/or disorders responsive to induction of apoptosis, such as e.g. benign or malignant neoplasia, especially malignant neoplasia, e.g. cancer, particularly any of those cancer diseases and tumor types mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing or ameliorating, especially treating hyperproliferative diseases, and/or disorders responsive to the induction of apoptosis, such as e.g. malignant or benign neoplasia, especially malignant neoplasia, such as e.g. cancer, particularly those diseases and tumor types mentioned herein.

The present invention further relates to a commercial package comprising one or more compounds of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be according, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a hyperproliferative diseases and/or a disorder responsive to the induction of apoptosis, particularly one of those diseases mentioned herein, such as e.g. malignant or benign neoplasia, especially malignant neoplasia, e.g. cancer, like any of those cancer diseases and tumor types mentioned herein.

In addition, compounds according to the present invention can be used in the pre- or post-surgical treatment of cancer.

In further addition, compounds of the present invention can be used in combination with radiation therapy.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

EXPERIMENTAL PART

The following table lists the abbreviations used in this paragraph and in the Intermediate Examples and Examples section as far as they are not explained within the text body. NMR peak forms are stated as they appear in the spectra, possible higher order effects have not been considered. Chemical names were generated using AutoNom2000 as implemented in MDL ISIS Draw. In some cases generally accepted names of commercially available reagents were used in place of AutoNom2000 generated names.

| Abbreviation | Meaning |
| --- | --- |
| boc | t-Butoxycarbonyl |
| br | broad |
| CI | chemical ionisation |
| d | doublet |
| dd | doublet of doublet |
| DAD | diode array detector |
| DCM | dichloromethane |
| EtOAc | ethyl acetate |
| Eq. | equivalent |
| ESI | electrospray (ES) ionisation |
| HATU | 2-(7-aza-1H-benzotriazole-1-yl)-1,1,3,3-tetramethyluronium hexafluorophosphate (CAS number 148893-10-1) |
| HPLC | high performance liquid chromatography |
| LC-MS | liquid chromatography mass spectrometry |
| m | multiplet |
| MS | mass spectrometry |
| n-BuLi | n-Butyllithium |
| NMR | nuclear magnetic resonance spectroscopy: chemical shifts (δ) are given in ppm. The chemical shifts were corrected by setting the DMSO signal to 2.50 ppm using unless otherwise stated. |
| PoraPak ™; | a HPLC column obtainable from Waters |
| q | quartet |
| r.t. or rt | room temperature |
| RT | retention time (as measured either with HPLC or UPLC) in minutes |
| s | singlet |
| t | triplet |
| THF | tetrahydrofuran |
| UPLC | ultra performance liquid chromatography |

Other abbreviations have their meanings customary per se to the skilled person. The various aspects of the invention described in this application are illustrated by the following examples which are not meant to limit the invention in any way.

EXAMPLES

UPLC-MS Standard Procedures

Analytical UPLC-MS was performed using UPLC-MS Method 1 unless otherwise stated. The masses (m/z) are reported from the positive mode electrospray ionisation unless the negative mode is indicated (ES−).

UPLC-MS Method 1
Instrument: Waters Acquity UPLC-MS SQD 3001; Column: Acquity UPLC BEH C18 1.7 50×2.1 mm; Eluent A: water+0.1% formic acid, Eluent B: acetonitrile; Gradient: 0-1.6 min 1-99% B, 1.6-2.0 min 99% B; Flow rate 0.8 ml/min; Temperature: 60° C.; Injection: 2 µl; DAD scan: 210-400 nm, ELSD.

UPLC-MS Method 2
Instrument: Waters Acquity UPLC-MS SQD 3001; Column: Acquity UPLC BEH C18 1.7 50×2.1 mm; Eluent A: water+0.2% ammonia, Eluent B: acetonitrile; Gradient: 0-1.6 min 1-99% B, 1.6-2.0 min 99% B; Flow rate 0.8 ml/min; Temperature: 60° C.; Injection: 2 µl; DAD scan: 210-400 nm; ELSD.

UPLC-MS Method 3
Instrument: Waters Acquity UPLC-MS ZQ4000; Column: Acquity UPLC BEH C18 1.7 50×2.1 mm; Eluent A: water+0.05% formic acid, Eluent B: Acetonitrile+0.05% formic acid; Gradient: 0-1.6 min 1-99% B, 1.6-2.0 min 99% B; Flow rate 0.8 ml/min; Temperature: 60° C.; Injection: 2 µl; DAD scan: 210-400 nm; ELSD.

UPLC-MS Method 4
Instrument: Waters Acquity UPLC-MS ZQ4000; Column: Acquity UPLC BEH C18 1.7 50×2.1 mm; Eluent A: water+0.2% Ammonia, Eluent B: Acetonitrile; Gradient: 0-1.6 min 1-99% B, 1.6-2.0 min 99% B; Flow rate 0.8 ml/min; Temperature: 60° C.; Injection: 2 µl; DAD scan: 210-400 nm; ELSD.

INTERMEDIATE EXAMPLES

Intermediate Example Int-1-0

{1-[4-(3-phenyl-imidazo[1,2-a]pyrimidin-2-yl)-phenyl]-cyclobutyl}-carbamic acid tert-butyl ester

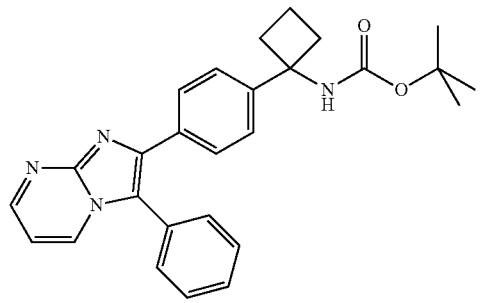 [SMILES: CC(C)(C)OC(=O)NC1(c2ccc(-c3nc4ncccn4c3-c3ccccc3)cc2)CCC1]

Step 1: [1-(4-bromo-phenyl)-cyclobutyl]-carbamic acid tert-butyl ester

The free base of commercially available [1-(4-bromo-phenyl)cyclobutyl]-amine hydrochloride [CAS 1193389-40-0] (8.99 g, 34.24 mmol) was prepared as follows: (8.99 g, 34.24 mmol) of the hydrochloride salt was taken up in DCM and washed sequentially with aqueous sodium bicarbonate and water and the organic portion was tried and concentrated.

The crude amine was taken up in dry THF (120 mL) and diisopropylethylamine (17.62 mL, 102.71 mmol) under nitrogen and a solution of di-tert-butyldicarbonate (8.22 g, 37.66 mmol) in THF (20 mL) was added. The reaction was stirred at rt overnight. The mixture was partitioned between EtOAc and water and the extracted organic phase was washed with brine and concentrated in vacuo to give the title compound.

Alternatively, the title compound may be prepared by known methods, such as those given in WO2008/70041, in particular from commercially available (4-bromophenyl)-acetonitrile.

Step 2: [1-(4-cyano-phenyl)-cyclobutyl]-carbamic acid tert-butyl ester

The title compound may be prepared from by known methods, such as those given in WO2008/70041, in particular from [1-(4-bromo-phenyl)cyclobutyl]-carbamic acid tert-butyl ester.

Alternatively, [1-(4-cyano-phenyl)-cyclobutyl]-carbamic acid tert-butyl ester (CAS 1032349-97-5) may be obtained commercially.

Step 3: [1-(4-phenylacetyl-phenyl)-cyclobutyl]-carbamic acid tert-butyl ester The title compound may be prepared by known methods, such as those given in WO2008/70041, in particular from [1-(4-cyano-phenyl)cyclobutyl]-carbamic acid tert-butyl ester.

Step 4: {1-[4-(2-bromo-2-phenyl-acetyl)-phenyl]-cyclobutyl}-carbamic acid tert-butyl ester Intermediate Example Int-1-A

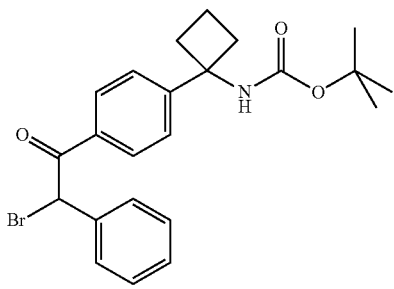 [SMILES: CC(C)(C)OC(=O)NC1(c2ccc(C(=O)C(Br)c3ccccc3)cc2)CCC1]

A mixture of [1-(4-phenylacetyl-phenyl)cyclobutyl]-carbamic acid tert-butyl ester (2.54 g, 6.74 mmol) and pyridinium hydrobromide perbromide (2.156 g, 6.74 mmol) in THF (38 mL) was stirred at rt for 2 hours. The mixture was partitioned between EtOAc and water and the organic phase washed respectively with aqueous sodium thiosulfate solution and brine, dried and concentrated in vacuo to give the crude title compound which was used without further purification.

Step 5: {1-[4-(3-phenyl-imidazo[1,2-a]pyrimidin-2-yl)-phenyl]-cyclobutyl}-carbamic acid tert-butyl ester Intermediate Example Int-1-0

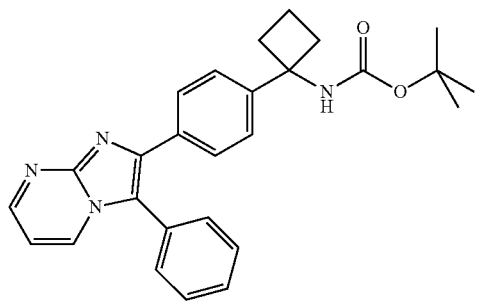 [SMILES: CC(C)(C)OC(=O)NC1(c2ccc(-c3nc4ncccn4c3-c3ccccc3)cc2)CCC1]

A mixture of crude {1-[4-(2-bromo-2-phenyl-acetyl)-phenyl]-cyclobutyl}-carbamic acid tert-butyl ester [Int-1-A] (465 mg) and 2-aminopyrimidine (199 mg) in DMF (15 mL) under argon was heated for 3 hours at 100° C. (bath temperature). On cooling the mixture was partitioned between EtOAc and water and the organic phase washed with brine, dried and concentrated in vacuo to give the crude title compound (390 mg) which was used without further purification.

UPLC-MS: RT=1.26 min; m/z=441.58 (M+1).

The following intermediate examples were prepared in analogy by reacting Intermediate Example Int-1-A with the appropriate amine.

| Intermediate Example | Structure/ Name | UPLC-MS |
|---|---|---|
| Int-1-1 | ![structure] {1-[4-(7-methyl-3-phenyl-imidazo[1,2-a]pyrimidin-2-yl)-phenyl]-cyclobutyl}-carbamic acid tert-butyl ester | RT = 1.22 min; m/z = 455.59 (M + 1) |

-continued

| Intermediate Example | Structure/ Name | UPLC-MS |
|---|---|---|
| Int-1-2 | 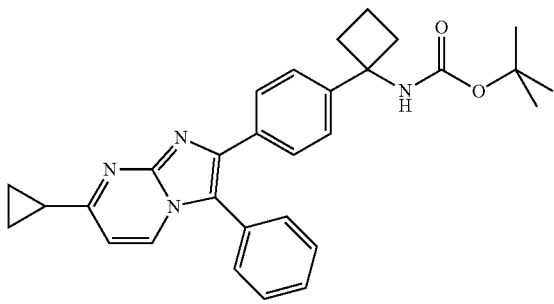<br>{1-[4-(7-cyclopropyl-3-phenyl-imidazo[1,2-a]pyrimidin-2-yl)-phenyl]-cyclobutyl}-carbamic acid tert-butyl ester | RT = 1.27 min; m/z = 481.63 (M + 1) |
| Int-1-3 | 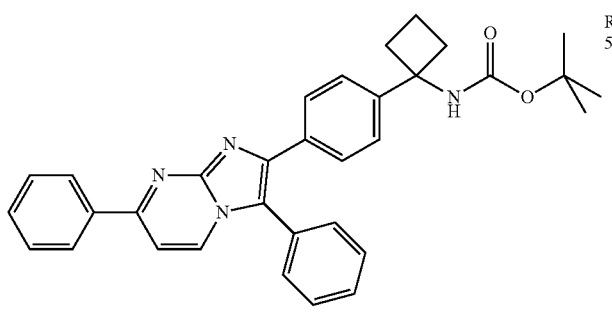<br>{1-[4-(3,7-diphenyl-imidazo[1,2-a]pyrimidin-2-yl)-phenyl]-cyclobutyl}-carbamic acid tert-butyl ester | RT = 1.43 min; m/z = 517.64 (M + 1) |
| Int-1-4 | 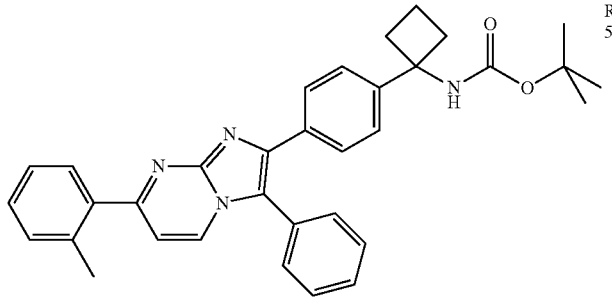<br>{1-[4-(3-Phenyl-7-o-tolyl-imidazo[1,2-a]pyrimidin-2-yl)-phenyl]-cyclobutyl}-carbamic acid tert-butyl ester | RT = 1.48 min; m/z = 531.35 (M) |
| Int-1-5 | 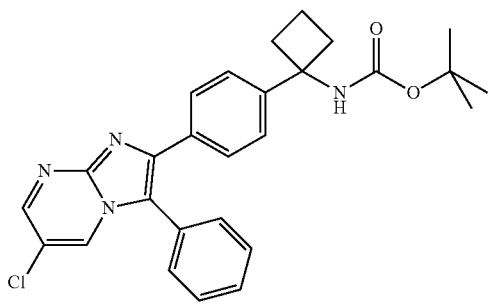<br>{1-[4-(6-chloro-3-phenyl-imidazo[1,2-a]pyrimidin-2-yl)-phenyl]-cyclobutyl}-carbamic acid tert-butyl ester | RT = 1.45 min; m/z = 475.54 (M + 1) |

| Intermediate Example | Structure/ Name | UPLC-MS |
|---|---|---|
| Int-1-6 | 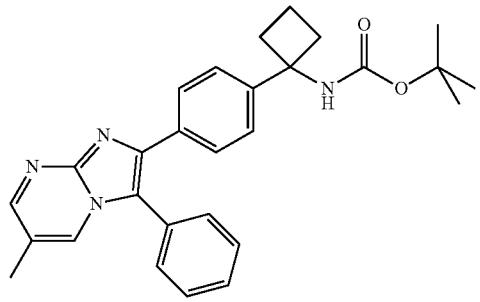<br>{1-[4-(6-methyl-3-phenyl-imidazo[1,2-a]pyrimidin-2-yl)-phenyl]-cyclobutyl}-carbamic acid tert-butyl ester | RT = 1.27 min; m/z = 455.59 (M + 1) |
| Int-1-7 | 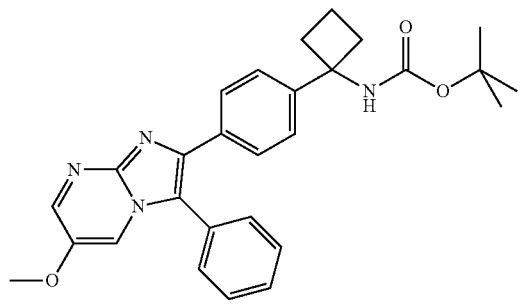<br>{1-[4-(6-methoxy-3-phenyl-imidazo[1,2-a]pyrimidin-2-yl)-phenyl]-cyclobutyl}-carbamic acid tert-butyl ester | RT = 1.34 min; m/z = 471.29 (M + 1) |
| Int-1-8 | 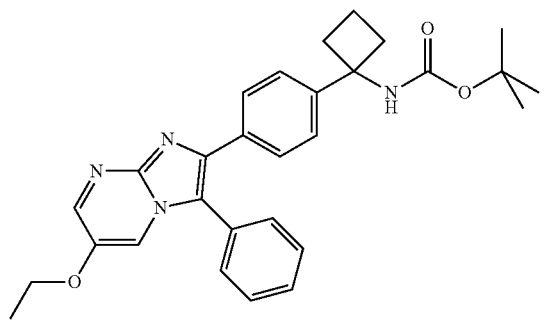<br>{1-[4-(6-ethoxy-3-phenyl-imidazo[1,2-a]pyrimidin-2-yl)-phenyl]-cyclobutyl}-carbamic acid tert-butyl ester | RT = 1.35 min; m/z = 485.62 (M + 1) |

-continued

| Intermediate Example | Structure/Name | UPLC-MS |
|---|---|---|
| Int-1-9 | 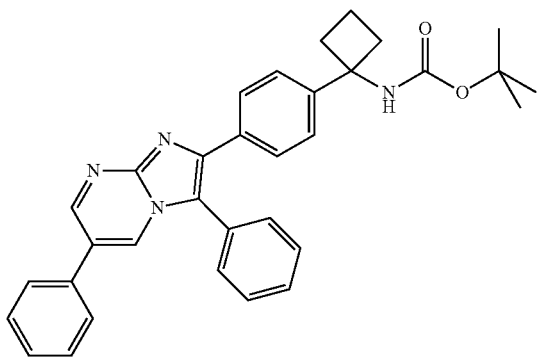<br>{1-[4-(3,6-diphenyl-imidazo[1,2-a]pyrimidin-2-yl)-phenyl]-cyclobutyl}-carbamic acid tert-butyl ester | RT = 1.51 min; m/z = 517.65 (M + 1) |
| Int-1-10 | 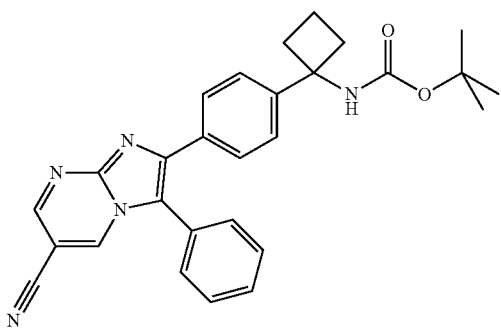<br>{1-[4-(6-cyano-3-phenyl-imidazo[1,2-a]pyridin-2-yl)-phenyl]-cyclobutyl} cabamic acid tert-butyl ester | RT = 1.42 min; m/z = 465.29 (M + 1) |

Intermediate Example Int-2-0

{1-[4-(7-methoxy-3-phenyl-imidazo[1,2-a]pyrimidin-2-yl)-phenyl]-cyclobutyl}-carbamic acid tert-butyl ester

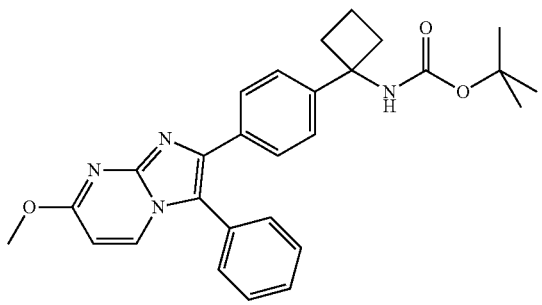 [SMILES: COc1ccn2c(-c3ccccc3)c(-c3ccc(C4(NC(=O)OC(C)(C)C)CCC4)cc3)nc2n1]

Step 1: 4-methoxy-pyrimidin-2-ylamine

A solution of 4-chloro-pyrimidin-2-ylamine (10 g, 77 mmol) in methanol (400 mL) under argon, was treated with a solution of sodium methoxide in methanol (25.7%, 51.59 mL, 0.232 mol) whereupon a cream yellow solution was obtained. The reaction was heated at reflux for 3 hours to give a clear yellow green solution. On cooling the volatiles were removed in vacuo and the residue taken up in 100 mL EtOAc and washed with 100 mL water. The organic phase was dried, filtered and concentrated in vacuo to give the title compound as a white solid (9.12 g).

1H NMR (300 MHz, d6-DMSO): δ 7.90 (d, 1H) 6.50 (br s, 2H), 5.95 (d, 1H), 3.74 (s, 3H) ppm.

Step 2: {1-[4-(7-methoxy-3-phenyl-imidazo[1,2-a]pyrimidin-2-yl)-phenyl]cyclobutyl}-carbamic acid tert-butyl ester Intermediate Example Int-2-0

Intermediate Example Int-2-1

{1-[4-(7-Hydroxy-3-phenyl-imidazo[1,2-a]pyrimidin-2-yl)-phenyl]-cyclobutyl}-carbamic acid tert-butyl ester

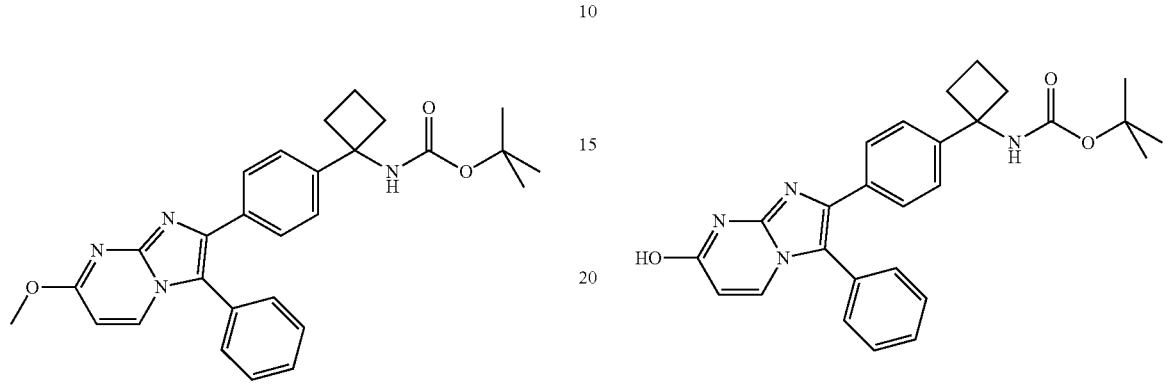

A mixture of crude {1-[4-(2-bromo-2-phenyl-acetyl)-phenyl]-cyclobutyl}-carbamic acid tert-butyl ester [Int-1-A] (3.38 g), 4-methoxypyrimidin-2-ylamine (1.90 g), and triethylamine (1.27 mL) in ethanol (94 mL) under argon, was heated for 3 h at 100° C. (bath temperature). On cooling the volatiles were removed in vacuo and the residue taken up in EtOAc and washed with water. The aqueous phase was extracted with EtOAc and the combined organic phases were washed with brine, dried and concentrated to give the crude title compound as a yellow solid.

UPLC-MS: RT=1.19 min; m/z=471.27 (M+1).

A mixture of crude {1-[4-(2-bromo-2-phenyl-acetyl)-phenyl]-cyclobutyl}-carbamic acid tert-butyl ester [Int-1-A] (1.26 g) and 4-methoxypyrimidin-2-ylamine (0.67 g) in DMF (21 mL) was heated overnight at 90° C. (bath temperature). On cooling the mixture was partitioned between EtOAc and water and the organic phase washed with brine, dried and concentrated to give a mixture of the title compound and Int-2-0. Purification was achieved by preparative HPLC to give the title compound.

The following intermediates may be prepared in analogy to Intermediate Example Int-2-0 from the corresponding 4-alkoxy-pyrimidin-2-ylamines, which in turn may be prepared in analogy to 4-methoxy-pyrimidin-2-ylamine from the corresponding alcohol and 4-chloro-pyrimidin-2-ylamine.

| Intermediate Example | Structure/ Name | UPLC-MS |
|---|---|---|
| Int-2-2 | | RT = 1.24 min; m/z = 499.0 (M + 1) |

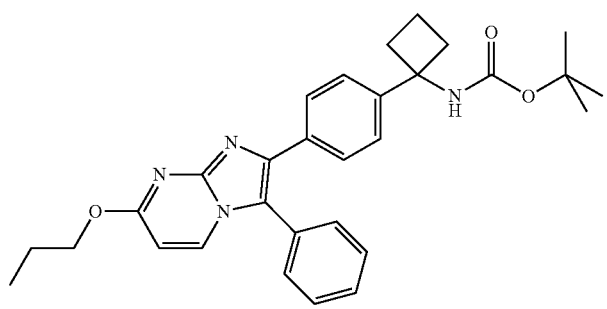

{1-[4-(3-phenyl-7-propoxy-imidazo[1,2-a]pyrimidin-2-yl)-phenyl]-cyclobutyl}-carbamic acid tert-butyl ester

Intermediate Example Int-3-0

5-[4-(7-methoxy-3-phenyl-imidazo[1,2-a]pyrimidin-2-yl)-phenyl]-2-oxa-4-aza-bicyclo[3.1.1]heptan-3-one

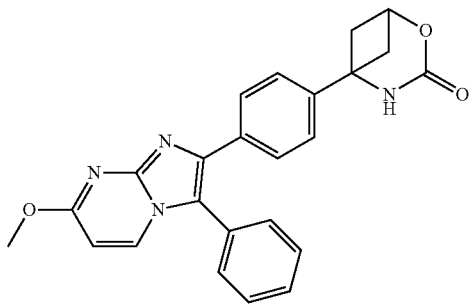

Step 1: 5-(4-phenylacetyl-phenyl)-2-oxa-4-aza-bicyclo[3.1.1]heptan-3-one

A solution of 5-(4-bromo-phenyl)-2-oxa-4-aza-bicyclo[3.1.1]heptan-3-one (prepared according to WO2009/148916, 4 g) in dry THF (60 mL) was cooled to −78° C. and treated with n-BuLi (6.56 mL of a 2.5M solution in hexane) and stirred for 30 minutes at this temperature before addition of further n-BuLi (13.1 mL of a 2.5M solution in hexane). Stirring was continued at this temperature for 30 minutes before a solution of N-methoxy-N-methyl-benzeneacetamide (prepared according to US6407119B1, 4.6 g) in THF (10 mL) was added. After 10 minutes the reaction was quenched with saturated aqueous ammonium chloride solution, extracted with EtOAc and the combined organic phases washed with brine, filtered and concentrated. The residue was triturated with hexane/EtOAc to give the title compound which was used in the next step without further purification.
UPLC-MS: RT=1.05 min; m/z=308.17 (M+1).

Step 2: 5-[4-(2-bromo-2-phenyl-acetyl)-phenyl]-2-oxa-4-aza-bicyclo[3.1.1]heptan-3-one A mixture of 5-(4-phenylacetyl-phenyl)-2-oxa-4-aza-bicyclo[3.1.1]heptan-3-one (2.34 g) and pyridinium hydrobromide perbromide (2.22 g) in THF (39 mL) was stirred at rt for 2 hours. The mixture was partitioned between EtOAc and water and the organic phase washed successively with dilute aqueous sodium thiosulfate and brine, dried and concentrated to give the crude title compound which was used in the next step without further purification.
UPLC-MS: RT=1.13 min; m/z=387.99 ($^{81}$Br-M+1).

Step 3: 5-[4-(7-methoxy-3-phenyl-imidazo[1,2-a]pyrimidin-2-yl)-phenyl]-2-oxa-4-aza-bicyclo[3.1.1]heptan-3-one A mixture of crude 5-[4-(2-bromo-2-phenyl-acetyl)-phenyl]-2-oxa-4-aza-bicyclo[3.1.1]heptan-3-one (2.5 g), 4-methoxypyrimidin-2-amine (1.26 g), triethylamine (0.84 mL) and ethanol (62 mL), under argon, was heated at 100° C. (bath temperature) for 6 hours. On cooling the reaction was concentrated and partitioned between EtOAc and water. The aqueous phase was extracted with EtOAc and the combined organic phases were washed with brine, dried and concentrated. Purification was achieved by chromatography on silica gel followed by preparative reverse phase HPLC to give the title compound.
UPLC-MS: RT=0.88 min; m/z=413.0 (M+1).
1H NMR (300 MHz, d6-DMSO): δ 8.18 (d, 1H), 8.08 (s, 1H), 7.45-7.57 (m, 7H), 7.24 (d, 2H), 6.52 (d, 1H), 4.88 (m, 1H), 3.95 (s, 3H), [2H obscured by solvent], 1.91-1.94 (m, 2H) ppm.

Intermediate Example Int-4-0

(1-{4-[7-(6-methoxy-pyridin-3-ylmethoxy)-3-phenyl-imidazo[1,2-a]pyrimidin-2-yl]-phenyl}-cyclobutyl)-carbamic acid tert-butyl ester

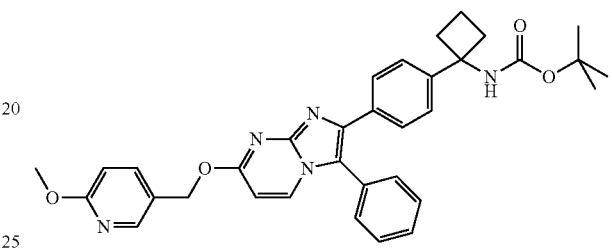

Step 1: 4-(6-methoxy-pyridin-3-ylmethoxy)-pyrimidin-2-ylamine

A mixture of commercially available (6-methoxypyridin-3-yl)-methanol (CAS 58584-63-7, 1 g, 7.19 mmol) and dry THF (9.3 mL) was cooled to 0° C. and sodium hydride (0.38 g of a 60% dispersion, 9.58 mmol) was added portionwise. Stirring was continued at 0° C. before portionwise addition of 2-amino-4-chloropyrimidine (0.62 g, 4.79 mmol). The mixture was heated at 100° C. (bath temperature) for 2 hours. On cooling, the mixture was poured onto ice, extracted with EtOAc (4×) and the combined organic phase washed with brine, dried and concentrated to give the title compound as a beige solid (1.33 g, 65% purity) which was used without further purification in the next step.

Step 2: (1-{4-[7-(6-methoxy-pyridin-3-ylmethoxy)-3-phenyl-imidazo[1,2-a]pyrimidin-2-yl]-phenyl}-cyclobutyl)-carbamic acid tert-butyl ester A mixture of crude {1-[4-(2-bromo-2-phenyl-acetyl)-phenyl]-cyclobutyl}-carbamic acid tert-butyl ester [Int-1-A] (1.2 g, 82% purity), crude 4-(6-methoxy-pyridin-3-ylmethoxy)-pyrimidin-2-ylamine (0.66 g, 65% purity) and activated 3 Å molecular sieves in EtOH (7.5 mL) was heated at reflux for 2 hours. LC-MS indicated the reaction to be incomplete. A further 0.66 g portion of 4-(6-methoxy-pyridin-3-ylmethoxy)-pyrimidin-2-ylamine was added and the mixture was heated at reflux for 3 hours. On cooling the mixture was partitioned between EtOAc and water, decanted and the separated organic phase washed with brine, dried and concentrated to give the title compound (1.86 g) as a yellow solid which was used in the next step without further purification.
UPLC-MS: RT=1.36 min; m/z=578.28 (M+1).

The following intermediates were prepared in analogy to Intermediate Example Int-4-0 (steps 1 and 2) from the corresponding pyrimidin-2-ylamines, which in turn were prepared from the corresponding alcohol and 4-chloro-pyrimidin-2-ylamine in analogy to the methods described above (see Intermediate Examples Int-2-0 Step 1 and Int-4-0 Step 1). Intermediate Examples Int-4-4, Int-4-5 and Int-4-6 in the Table below were prepared in analogy using a combination of methods in analogy to Int-4-0 Step 1 and Int-2-0 Step 2.

| Intermediate Example | Structure/ Name | UPLC-MS |
|---|---|---|
| Int-4-1 | 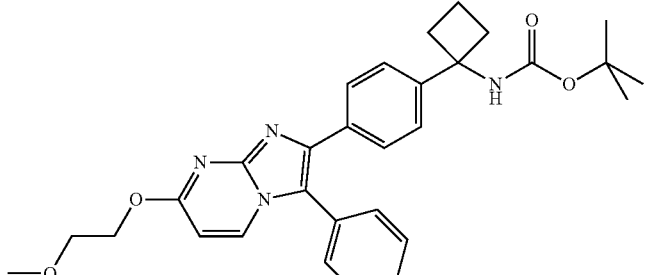<br>(1-{4-[7-(2-methoxy-ethoxy)-3-phenyl-imidazo[1,2-a]pyrimidin-2-yl]-phenyl}-cyclobutyl)-carbamic acid tert-butyl ester | UPLC-MS Method 2:<br>RT = 1.45 min;<br>m/z = 515.29 (M + H) |
| Int-4-2 | 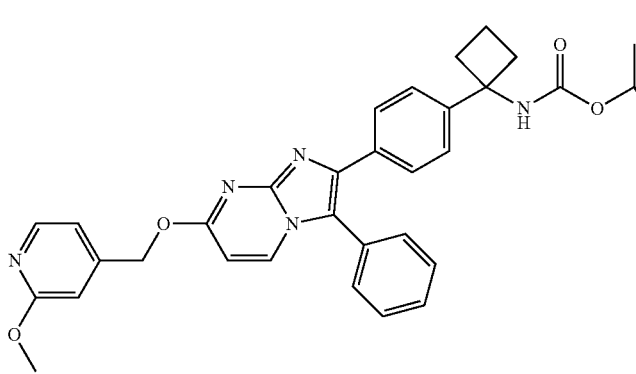<br>(1-{4-[7-(2-methoxy-pyridin-4-ylmethoxy)-3-phenyl-imidazo[1,2-a]pyrimidin-2-yl]-phenyl}-cyclobutyl)-carbamic acid tert-butyl ester | UPLC-MS Method 2:<br>RT = 1.55 min;<br>m/z = 578.33 (M + H) |
| Int-4-3 | 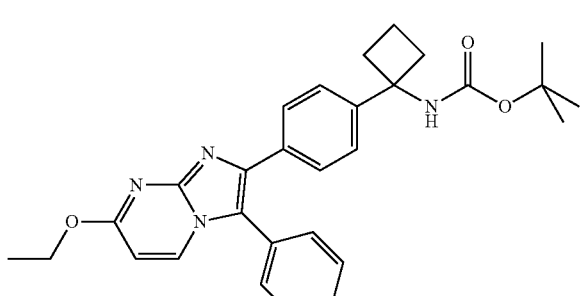<br>{1-[4-(7-ethoxy-3-phenyl-imidazo[1,2-a] pyrimidin-2-yl)-phenyl]-cyclobutyl}-carbamic acid tert-butyl ester | RT = 1.32 min;<br>m/z = 485.28 (M + H) |
| Int-4-4 | 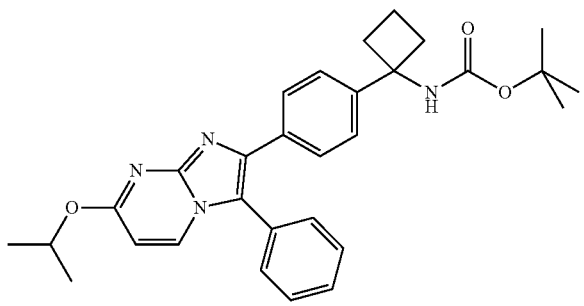<br>{1-[4-(7-isopropoxy-3-phenyl-imidazo[1,2-a] pyrimidin-2-yl)-phenyl]-cyclobutyl}-carbamic acid tert-butyl ester | RT = 1.35 min;<br>m/z = 499.30 (M + H) |

| Intermediate Example | Structure/ Name | UPLC-MS |
|---|---|---|
| Int-4-5 | 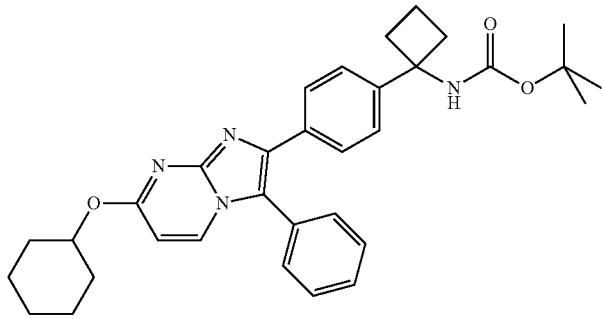<br>{1-[4-(7-cyclohexyloxy-3-phenyl-imidazo[1,2-a]pyrimidin-2-yl)-phenyl]-cyclobutyl}-carbamic acid tert-butyl ester | RT = 1.41 min;<br>m/z = 539.47 (M + H) |
| Int-4-6 | 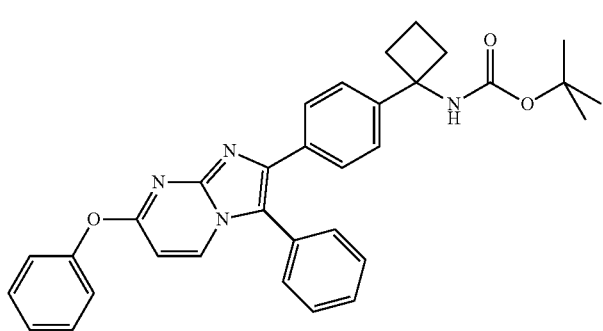<br>{1-[4-(7-phenoxy-3-phenyl-imidazo[1,2-a]pyrimidin-2-yl)-phenyl]-cyclobutyl}-carbamic acid tert-butyl ester | RT = 1.44 min;<br>m/z = 533.44 (M + H) |

The following intermediates were prepared in analogy to Intermediate Example Int-4-0 from the corresponding pyridin-2-ylamines or pyrimidin-2-ylamines.

| Intermediate Example | Structure/ Name | UPLC-MS |
|---|---|---|
| Int-4-7 | 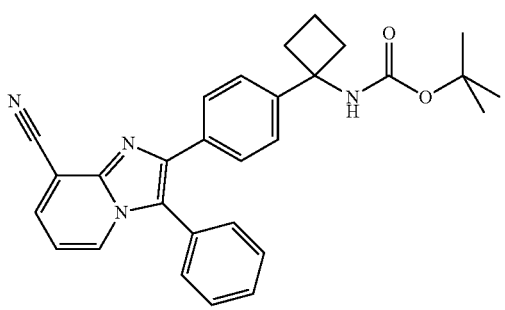<br>{1-[4-(8-cyano-3-phenyl-imidazo[1,2-a] pyridin-2-yl)-phenyl]-cyclobutyl}-carbamic acid tert-butyl ester | RT = 1.50 min; m/z = 465.23 (M + 1) |

| Intermediate Example | Structure/ Name | UPLC-MS |
|---|---|---|
| Int-4-8 | 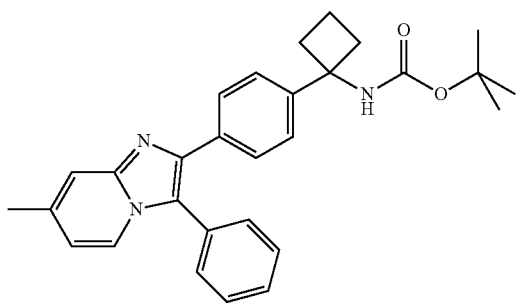<br>{1-[4-(7-methyl-3-phenyl-imidazo[1,2-a]pyridin-2-yl)-phenyl]-cyclobutyl}-carbamic acid tert-butyl ester | RT = 1.19 min; m/z = 454.26 (M + H) |
| Int-4-9 | 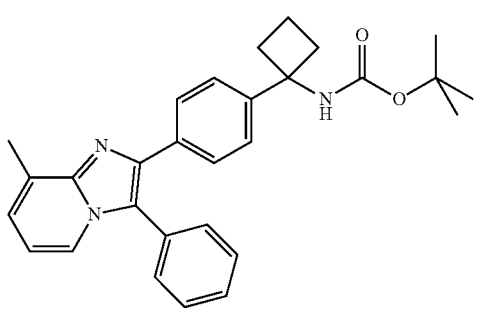<br>{1-[4-(8-methyl-3-phenyl-imidazo[1,2-a]pyridin-2-yl)-phenyl]-cyclobutyl}-carbamic acid tert-butyl ester | RT = 1.20 min; m/z = 454.25 (M + H) |
| Int-4-10 | 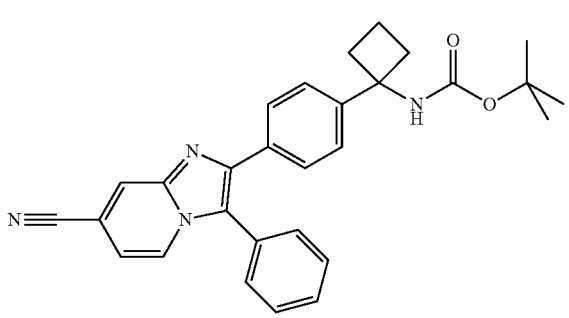<br>{1-[4-(7-cyano-3-phenyl-imidazo[1,2-a]pyridin-2-yl)-phenyl]-cyclobutyl}-carbamic acid tert-butyl ester | RT = 1.48 min; m/z = 465.24 (M + H) |
| Int-4-11 | 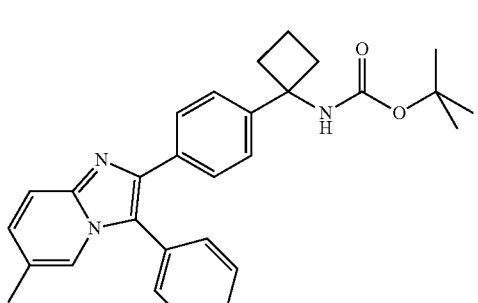<br>{1-[4-(6-methyl-3-phenyl-imidazo[1,2-a]pyridin-2-yl)-phenyl]-cyclobutyl}-carbamic acid tert-butyl ester | RT = 1.22 min; m/z = 454.25 (M + H) |

-continued

| Intermediate Example | Structure/ Name | UPLC-MS |
|---|---|---|
| Int-4-12 | 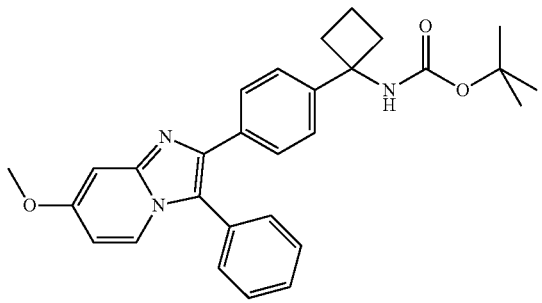 [SMILES: COc1ccn2c(-c3ccccc3)c(-c3ccc(C4(NC(=O)OC(C)(C)C)CCC4)cc3)nc2n1]<br>{1-[4-(7-methoxy-3-phenyl-imidazo[1,2-a]pyridin-2-yl)-phenyl]-cyclobutyl}-carbamic acid tert-butyl ester | RT = 1.21 min; m/z = 470.28 (M + H) |
| Int-4-13 | 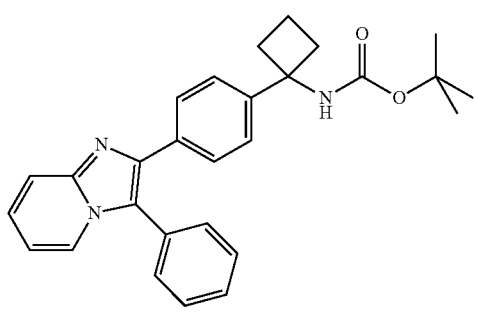<br>{1-[4-(3-phenyl-imidazo[1,2-a]pyridin-2-yl)-phenyl]-cyclobutyl}-carbamic acid tert-butyl ester | UPLC-MS Method 2:<br>RT = 1.50 min; m/z = 440.34 (M + H) |
| Int-4-14 | 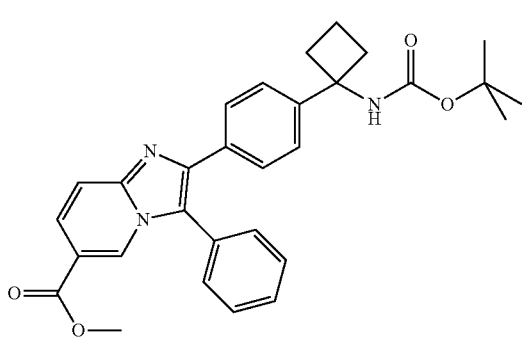<br>2-[4-(1-tert-butoxycarbonylamino-cyclobutyl)-phenyl]-3-phenyl-imidazo[1,2-a]pyridine-6-carboxylic acid methyl ester | RT = 1.47 min; m/z = 498.29 (M + H) |
| Int-4-15 | 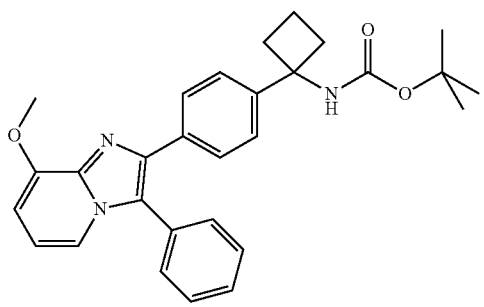<br>{1-[4-(8-methoxy-3-phenyl-imidazo[1,2-a]pyridin-2-yl)-phenyl]-cyclobutyl}-carbamic acid tert-butyl ester | RT = 1.19 min; m/z = 470.27 (M + H) |

-continued

| Intermediate Example | Structure/ Name | UPLC-MS |
|---|---|---|
| Int-4-16 | 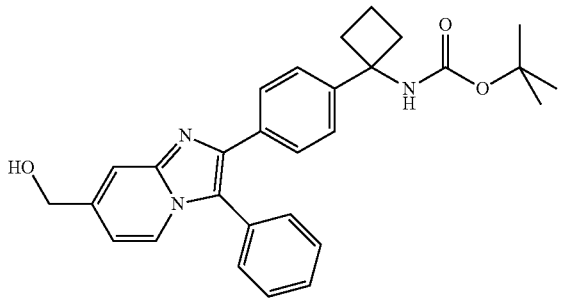<br>{1-[4-(7-Hydroxymethyl-3-phenyl-imidazo[1,2-a]pyridin-2-yl)-phenyl]-cyclobutyl}-carbamic acid tert-butyl ester | RT = 1.08 min; m/z = 470.28 (M + H) |
| Int-4-17 | 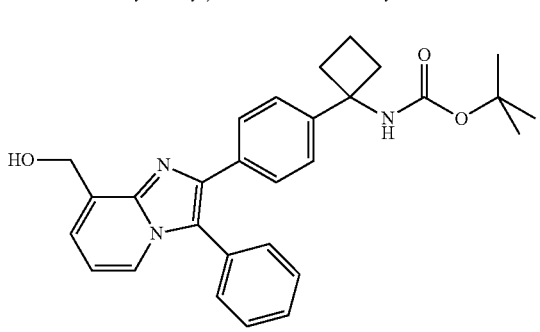<br>{1-[4-(8-hydroxymethyl-3-phenyl-imidazo[1,2-a]pyridin-2-yl)-phenyl]-cyclobutyl}-carbamic acid tert-butyl ester | RT = 1.14 min; m/z = 470.29 (M + H) |
| Int-4-18 | 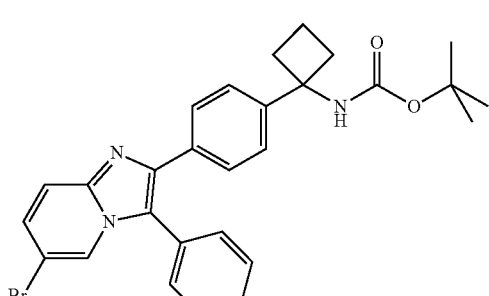<br>{1-[4-(6-bromo-3-phenyl-imidazo[1,2-a] pyridin-2-yl)-phenyl]-cyclobutyl}-carbamic acid tert-butyl ester | RT = 1.5 min; m/z= 520.21 ([$^{81}$Br] – M + H) |
| Int-4-19 | 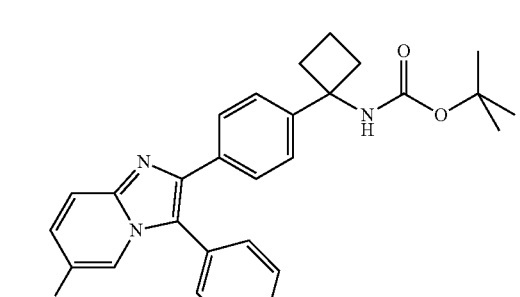<br>{1-[4-(6-methoxy-3-phenyl-imidazo[1,2-a] pyridin-2-yl)-phenyl]-cyclobutyl}-carbamic acid tert-butyl ester | UPLC-MS Method 2: RT = 1.49 min; m/z = 470.24 (M + H) |

| Intermediate Example | Structure/ Name | UPLC-MS |
|---|---|---|
| Int-4-20 | 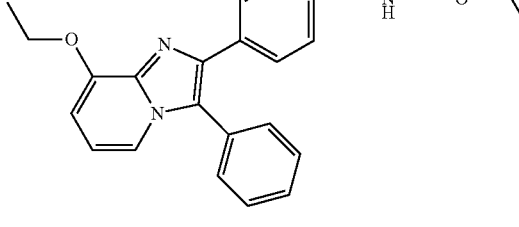<br>{1-[4-(8-ethoxy-3-phenyl-imidazo[1,2-a]pyridin-2-yl)-phenyl]-cyclobutyl}-carbamic acid tert-butyl ester | RT = 1.23 min; m/z = 484.28 (M + H) |
| Int-4-21 | 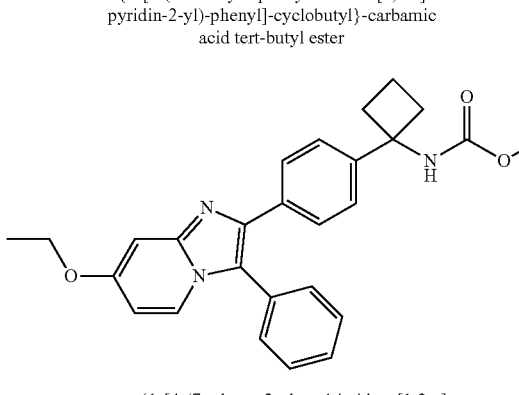<br>{1-[4-(7-ethoxy-3-phenyl-imidazo[1,2-a]pyridin-2-yl)-phenyl]-cyclobutyl}-carbamic acid tert-butyl ester | UPLC-MS Method 2:<br>RT = 1.58 min; m/z = 484.35 (M + H) |
| Int-4-22 | 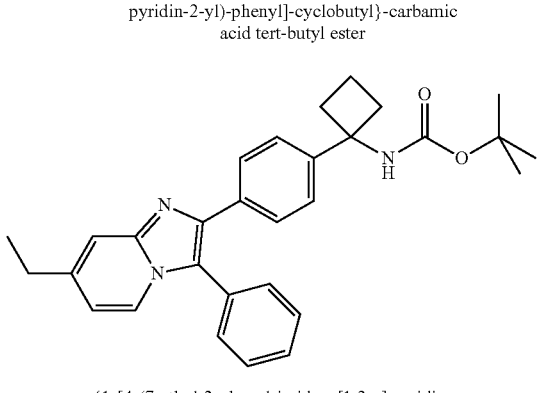<br>{1-[4-(7-ethyl-3-phenyl-imidazo[1,2-a] pyridin-2-yl)-phenyl]-cyclobutyl}-carbamic acid tert-butyl ester | UPLC-MS Method 2:<br>RT = 1.62 min; m/z = 468.36 (M + H) |
| Int-4-23a | 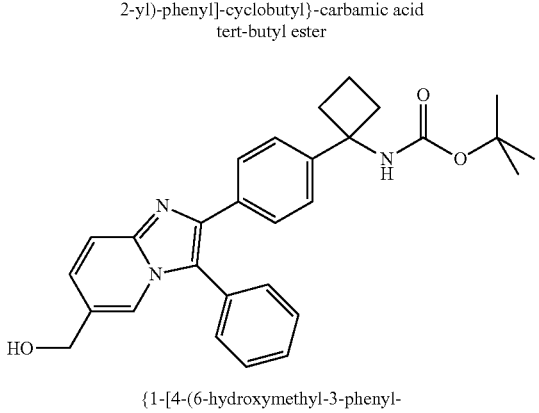<br>{1-[4-(6-hydroxymethyl-3-phenyl-imidazo[1,2-a]pyridin-2-yl)-phenyl]-cyclobutyl}-carbamic acid tert-butyl ester | RT = 1.03 min;<br>m/z = 470.28 (M + H) |

| Intermediate Example | Structure/ Name | UPLC-MS |
|---|---|---|
| Int-4-23b | 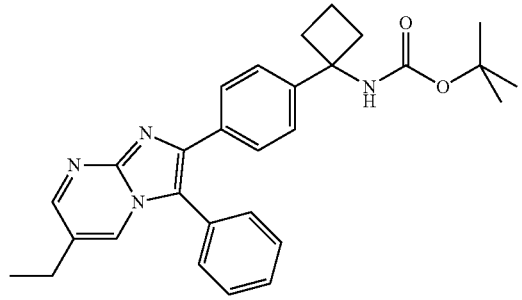<br>{1-[4-(6-ethyl-3-phenyl-imidazo[1,2-a] pyrimidin-2-yl)-phenyl]-cyclobutyl}-carbamic acid tert-butyl ester | RT = 1.37 min;<br>m/z = 469.29<br>(M + H) |
| Int-4-24 | 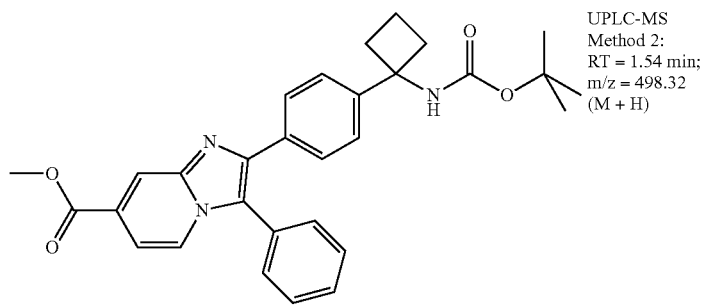<br>2-[4-(1-tert-butoxycarbonylamino-cyclobutyl)-phenyl]-3-phenyl-imidazo[1,2-a] pyridine-7-carboxylic acid methyl ester | UPLC-MS<br>Method 2:<br>RT = 1.54 min;<br>m/z = 498.32<br>(M + H) |
| Int-4-25 | 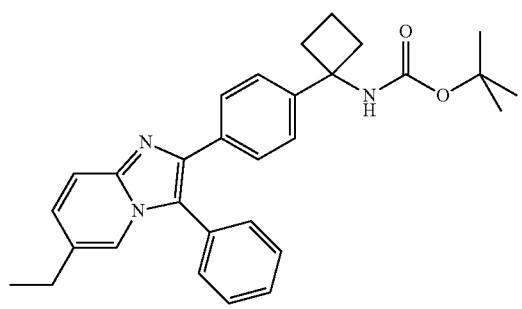<br>{1-[4-(6-ethyl-3-phenyl-imidazo[1,2-a] pyridin-2-yl)-phenyl]-cyclobutyl}-carbamic acid tert-butyl ester | UPLC-MS<br>Method 2:<br>RT = 1.63 min;<br>m/z = 468.30<br>(M + H) |
| Int-4-26 | 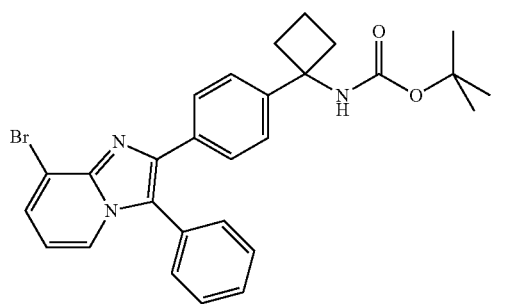<br>{1-[4-(8-bromo-3-phenyl-imidazo[1,2-a] pyridin-2-yl)-phenyl]-cyclobutyl}-carbamic acid tert-butyl ester | RT = 1.63 min;<br>m/z = 520.18 ($^{81}$Br – M + H) |

| Intermediate Example | Structure/Name | UPLC-MS |
|---|---|---|
| Int-4-27 | 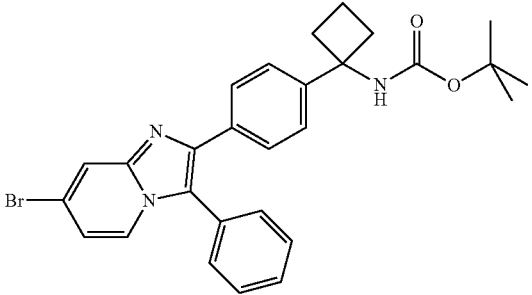<br>{1-[4-(7-bromo-3-phenyl-imidazo[1,2-a] pyridin-2-yl)-phenyl]-cyclobutyl}-carbamic acid tert-butyl ester | RT = 1.49 min;<br>m/z = 520.18<br>($^{81}$Br − M + H) |

Intermediate Example Int-4-28

2-[4-(1-tert-butoxycarbonylamino-cyclobutyl)-phenyl]-3-phenyl-imidazo[1,2-a]pyridine-8-carboxylic acid methyl ester

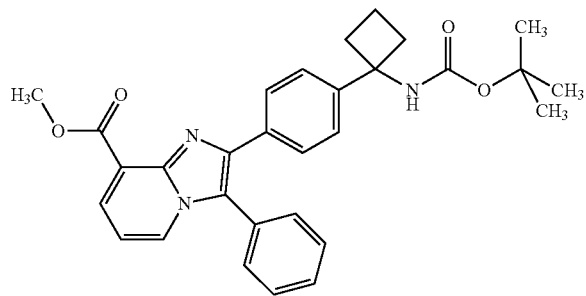 [SMILES: COC(=O)c1cccn2c(-c3ccccc3)c(-c3ccc(C4(NC(=O)OC(C)(C)C)CCC4)cc3)nc12]

This intermediate example was prepared in analogy to Intermediate Example Int-4-0 except that 2-propanol was used as the solvent for the reaction instead of ethanol and the mixture was heated at reflux.

UPLC-MS Method 2: RT=1.47 min; m/z=498.26 (M+H)

Intermediate Example Int-4-29

{1-[4-(3-phenyl-imidazo[1,2-a]pyridin-2-yl)-phenyl]-cyclobutyl}-carbamic acid tert-butyl ester

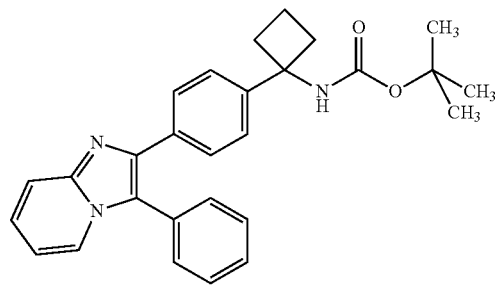 [SMILES: CC(C)(C)OC(=O)NC1(c2ccc(-c3nc4ccccn4c3-c3ccccc3)cc2)CCC1]

A mixture of {1-[4-(2-bromo-2-phenyl-acetyl)-phenyl]-cyclobutyl}-carbamic acid tert-butyl ester [Int-1-A] (0.89 g, 2.0 mmol), 2-aminopyridine (0.38 g, 4.0 mmol, 2 equiv) and powdered activated 3A sieves (10 g) in ethanol (7.5 mL) was heated for 5 h at the reflux temperature at which time HPLC-MS indicated that educt had been consumed. The resulting solution was separated between CH$_2$Cl$_2$ (25 mL) and an saturated aqueous NaHCO$_3$ solution (25 mL). The organic phase was washed with a saturated aqueous NaCl solution (25 mL), dried (Na$_2$SO$_4$ anh), and concentrated under reduced pressure. The remaining material was purified using MPLC (Biotage Isolera; 25 g SNAP cartridge: 90% hexane/10% EtOAc for 2.0 min., gradient to 70% hexane/30% EtOAc over 2.0 min., 70% hexane/30% EtOAc for 14.1 min., gradient to 65% hexane/35% EtOAc over 6.5 min., 65% hexane/35% EtOAc for 6.1 min.) to give {1-[4-(3-phenyl-imidazo[1,2-a]pyridin-2-yl)-phenyl]-cyclobutyl}-carbamic acid tert-butyl ester (0.31 g, 35%):

UPLC-MS (Method 2): RT=1.49 min; m/z (rel intensity) 440 (80, (M+H)$^+$).

MS: m/z (rel intensity) 440 (100, (M+H)$^+$).

1H-NMR (d6-DMSO): δ 1.06 (br s, 3H), 1.28 (br s, 6H), 1.64-1.79 (m, 1H), 1.85-1.98 (m, 1H), 2.26-2.36 (m, 4H), 6.85 (t, J=6.2 Hz, 1H), 7.22-7.30 (m, 3H), 7.43-7.59 (m, 8H), 7.62 (d, J=9.2 Hz, 1H), 7.96 (br d, J=5.1H, 1H) ppm.

Intermediate Example Int-4-30

{1-[4-(6-ethoxy-3-phenyl-imidazo[1,2-a]pyridin-2-yl)-phenyl]-cyclobutyl}-carbamic acid tert-butyl ester

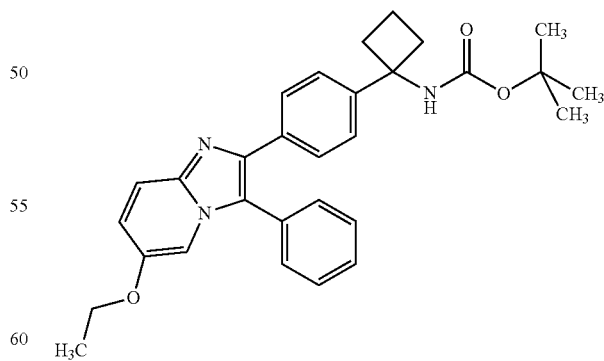

A mixture of {1-[4-(2-bromo-2-phenyl-acetyl)-phenyl]-cyclobutyl}-carbamic acid tert-butyl ester [Int-1-A] (0.87 g, 2.0 mmol), 2-amino-5-ethoxypyridine (0.54 g, 3.9 mmol, 2 equiv) and powdered activated 3A sieves (10 g) in ethanol (7.3 mL) was heated at the reflux temperature with monitoring by UPLC-MS. The resulting solution was separated between CH$_2$Cl$_2$ (25 mL) and an saturated aqueous NaHCO$_3$ solution (25 mL). The organic phase was washed with a saturated aqueous NaCl solution (25 mL), dried (Na$_2$SO$_4$ anh), and concentrated under reduced pressure. The remaining material was purified using MPLC (Biotage Isolera; 25 g SNAP cartridge: 100% hexane for 1.5 min., gradient to 80% hexane/20% EtOAc over 2.2 min., gradient to 70% hexane/30% EtOAc over 10.6 min., 70% hexane/30% EtOAc for 2.8 min., gradient to 65% hexane/35% EtOAc over 2.2 min., 65% hexane/35% EtOAc for 4.8 min.) to give {1-[4-(6-ethoxy-3-phenyl-imidazo[1,2-a]pyridin-2-yl)-phenyl]-cyclobutyl}-carbamic acid tert-butyl ester (0.26 g, 28%):

UPLC-MS (Method 2): RT=1.58 min; m/z (rel intensity) 484 (100, (M+H)$^+$).

MS: m/z (rel intensity) 484 (100, (M+H)$^+$).

1H-NMR (d6-DMSO): δ 1.11 (br s, 3H), 1.33 (br s, 6H), 1.39 (t, J=6.9 Hz, 3H), 1.77 (br s, 1H), 1.93-2.00 (m, 1H), 2.31-2.42 (m, 4H), 4.15 (q, J=7.1 Hz, 2H), 6.58 (dd, J=7.5, 2.6 Hz, 1H), 7.03 (d, J=2.3 Hz, 1H), 7.26 (d, J=8.3 Hz, 2H), 7.48 (d, J=7.2 Hz, 2H), 7.50-7.60 (m, 5H), 7.84 (br s, 1H) ppm.

The following examples were prepared in an analogous manner, substituting appropriate starting materials where necessary.

| Example | Structure/Name | UPLC-MS |
|---|---|---|
| Int-4-31 | 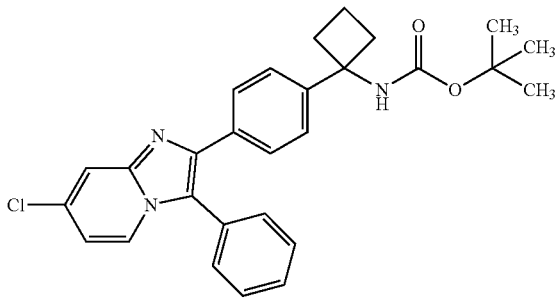 [SMILES: CC(C)(C)OC(=O)NC1(c2ccc(-c3nc4cc(Cl)ccn4c3-c3ccccc3)cc2)CCC1]<br>{1-[4-(7-Chloro-3-phenyl-imidazo[1,2-a]pyridin-2-yl)-phenyl]-cyclobutyl}-carbamic acid tert-butyl ester | Method 2: RT = 1.48 min; m/z (rel intensity) 474 (100, (M + H)$^+$), 947 (30, (2M + H)$^+$). |
| Int-4-32 | 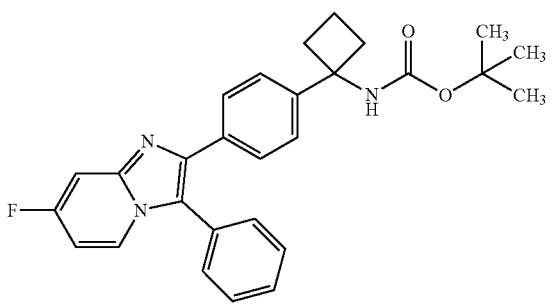 [SMILES: CC(C)(C)OC(=O)NC1(c2ccc(-c3nc4cc(F)ccn4c3-c3ccccc3)cc2)CCC1]<br>{1-[4-(7-Fluoro-3-phenyl-imidazo[1,2-a]pyridin-2-yl)-phenyl]-cyclobutyl}-carbamic acid tert-butyl ester | Method 2: RT = 1.29 min; m/z (rel intensity) 458 (60, (M + H)$^+$), 915 (30, (2M + H)$^+$). |
| Int-4-33 | 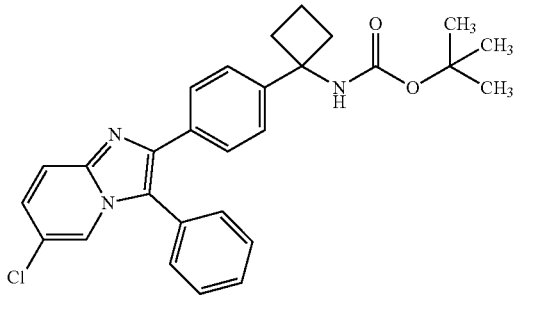 [SMILES: CC(C)(C)OC(=O)NC1(c2ccc(-c3nc4ccc(Cl)cn4c3-c3ccccc3)cc2)CCC1]<br>{1-[4-(6-Chloro-3-phenyl-imidazo[1,2-a]pyridin-2-yl)-phenyl]-cyclobutyl}-carbamic acid tert-butyl ester | Method 2: RT = 1.49 min; m/z (rel intensity) 474 (100, (M + H)$^+$), 947 (30, (2M + H)$^+$). |

| Example | Structure/Name | UPLC-MS |
|---|---|---|
| Int-4-34 | | Method 2: RT = 1.62 min; m/z (rel intensity) 468 (80, (M + H)$^+$). |

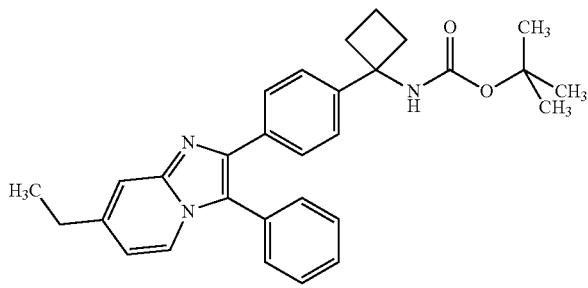 [SMILES: CCc1ccn2c(-c3ccccc3)c(-c3ccc(C4(NC(=O)OC(C)(C)C)CCC4)cc3)nc2c1]

{1-[4-(7-Ethyl-3-phenyl-imidazo[1,2-a]pyridin-2-yl)-phenyl]-cyclobutyl}-carbamic acid tert-butyl ester

| | | |
|---|---|---|
| Int-4-35 | | Method 2: RT = 1.61 min; m/z (rel intensity) 504 (100, (M + H)$^+$). |

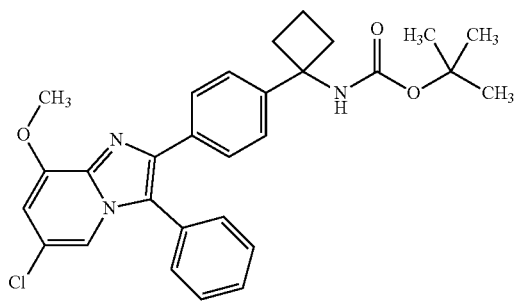 [SMILES: COc1cc(Cl)cn2c(-c3ccccc3)c(-c3ccc(C4(NC(=O)OC(C)(C)C)CCC4)cc3)nc12]

{1-[4-(6-Chloro-8-methoxy-3-phenyl-imidazo[1,2-a]pyridin-2-yl)-phenyl]-cyclobutyl}-carbamic acid tert-butyl ester

| | | |
|---|---|---|
| Int-4-36 | | Method 2: RT = 1.53 min; m/z (rel intensity) 500 (100, (M + H)$^+$), 999 (40, (2M + H)$^+$); ES− m/z (rel intensity) 498 (30, (M − H)$^-$), 997 (5, (2M − H)$^-$). |

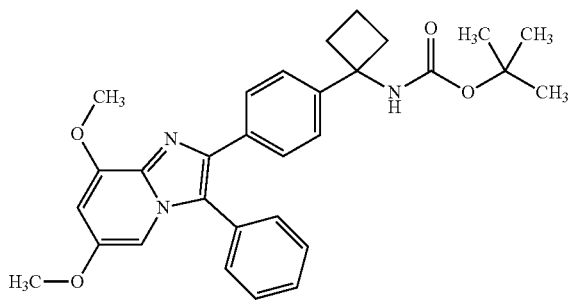 [SMILES: COc1cc(OC)c2nc(-c3ccc(C4(NC(=O)OC(C)(C)C)CCC4)cc3)c(-c3ccccc3)n2c1]

{1-[4-(6,8-Dimethoxy-3-phenyl-imidazo[1,2-a]pyridin-2-yl)-phenyl]-cyclobutyl}-carbamic acid tert-butyl ester

Intermediate Example Int-4-37

2-[4-(1-tert-butoxycarbonylamino-cyclobutyl)-phenyl]-3-phenyl-imidazo[1,2-a]pyridine-8-carboxylic acid ethyl ester

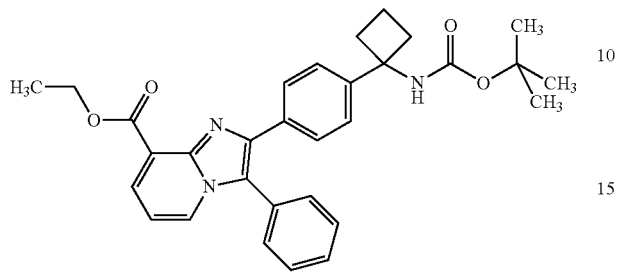

This intermediate example was obtained from the corresponding methyl ester in analogy to Intermediate Example Int-4-0, whereby an additional transesterification occurred.

UPLC-MS Method 2: RT=1.56 min; m/z=512.30 (M+H).

The following Intermediate Examples were prepared in analogy to the methods described above as indicated in the Table.

| Intermediate Example | Method | Structure/Name | UPLC-MS |
|---|---|---|---|
| Int-4-38 | Analogy to Int-4-0 | 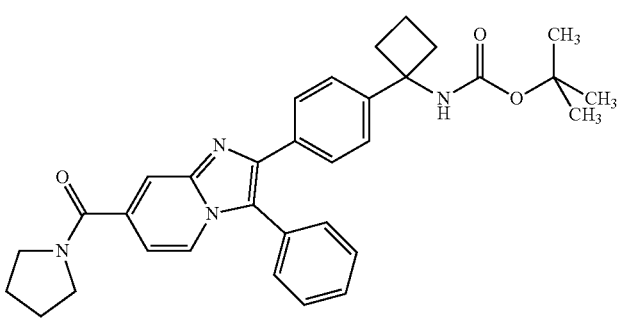 [SMILES: CC(C)(C)OC(=O)NC1(c2ccc(-c3nc4cc(C(=O)N5CCCC5)ccn4c3-c3ccccc3)cc2)CCC1]<br>(1-{4-[3-Phenyl-7-(pyrrolidine-1-carbonyl)-imidazo[1,2-a]pyridin-2-yl]-phenyl}-cyclobutyl)-carbamic acid tert-butyl ester | RT = 1.25 min; m/z = 537.36 (M + H) |
| Int-4-39 | Analogy to Int-4-0 | 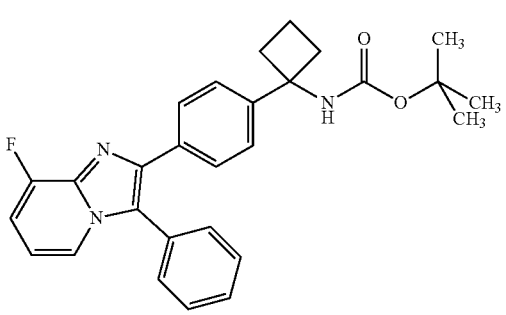 [SMILES: CC(C)(C)OC(=O)NC1(c2ccc(-c3nc4c(F)cccn4c3-c3ccccc3)cc2)CCC1]<br>{1-[4-(8-Fluoro-3-phenyl-imidazo[1,2-a]pyridin-2-yl)-phenyl]-cyclobutyl}-carbamic acid tert-butyl ester | RT = 1.64 min; m/z = 458.21 (M + H) |

-continued

| Intermediate Example | Method | Structure/Name | UPLC-MS |
|---|---|---|---|
| Int-4-40 | Analogy to Int-4-0 | 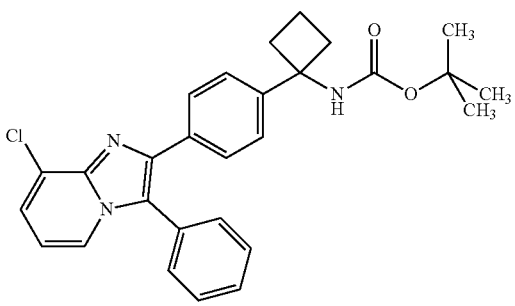 [SMILES: CC(C)(C)OC(=O)NC1(c2ccc(-c3nc4c(Cl)cccn4c3-c3ccccc3)cc2)CCC1]<br>{1-[4-(8-Chloro-3-phenyl-imidazo[1,2-a]pyridin-2-yl)-phenyl]-cyclobutyl}-carbamic acid tert-butyl ester | RT = 1.57 min; m/z = 474.22 (M + H) |
| Int-4-41 | Analogy to Int-4-0 | 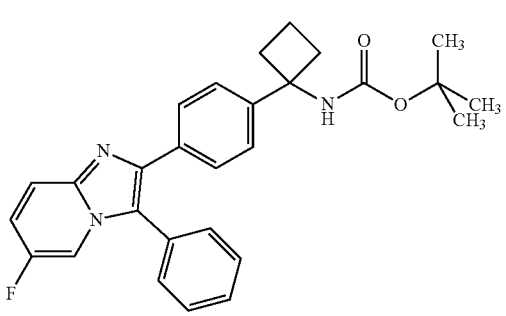 [SMILES: CC(C)(C)OC(=O)NC1(c2ccc(-c3nc4ccc(F)cn4c3-c3ccccc3)cc2)CCC1]<br>{1-[4-(6-Fluoro-3-phenyl-imidazo[1,2-a]pyridin-2-yl)-phenyl]-cyclobutyl}-carbamic acid tert-butyl ester | RT = 1.52 min; m/z =458.22 (M + H) |
| Int-4-42 | Analogy to Int-4-0 Steps 1 and 2 | 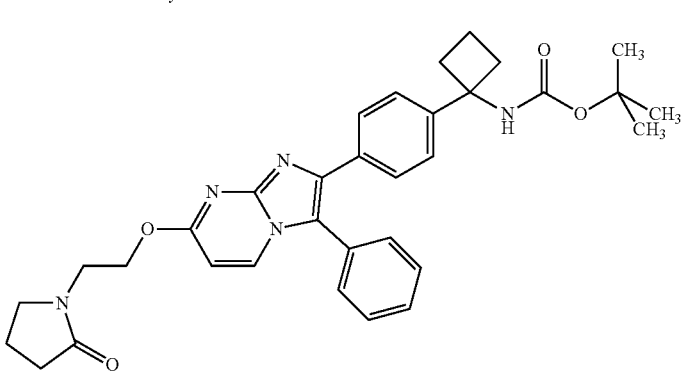<br>[1-(4-{7-[2-(2-Oxo-pyrrolidin-1-yl)-ethoxy]-3-phenyl-imidazo[1,2-a]pyrimidin-2-yl}-phenyl)-cyclobutyl]-carbamic acid tert-butyl ester | UPLC-MS Method 2: RT = 1.38 min; m/z = 568.33 (M + H) |
| Int-4-43 | Analogy to Int-4-0 Steps 1 and 2 | 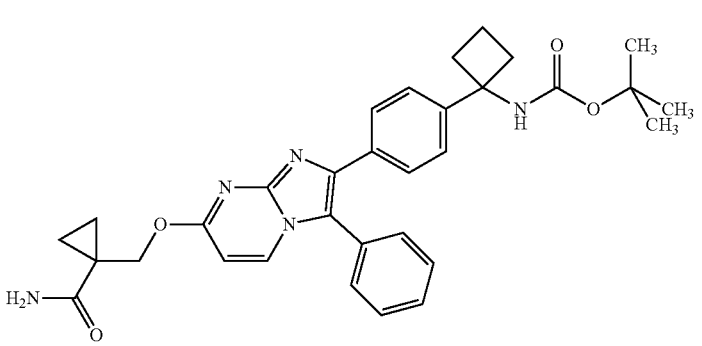 [SMILES: CC(C)(C)OC(=O)NC1(c2ccc(-c3nc4nc(OCC5(C(N)=O)CC5)ccn4c3-c3ccccc3)cc2)CCC1]<br>(1-{4-{7-(1-Carbamoyl-cyclopropylmethoxy)-3-phenyl-imidazo[1,2-a]pyrimidin-2-yl}-phenyl)-cyclobutyl]-carbamic acid tert-butyl ester | RT = 1.24 min; m/z = 554.32 (M + H) |

Intermediate Example Int-4-44

{1-[4-(6,8-dimethyl-3-phenyl-imidazo[1,2-a]pyridin-2-yl)-phenyl]-cyclobutyl}-carbamic acid tert-butyl ester

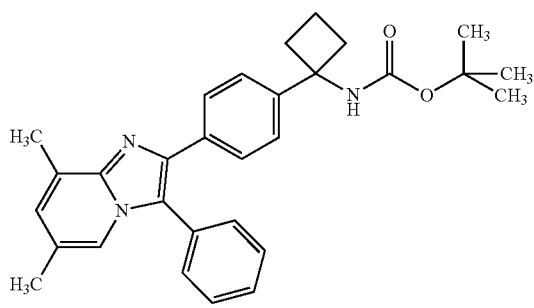 [SMILES: Cc1cc(C)c2nc(-c3ccc(C4(NC(=O)OC(C)(C)C)CCC4)cc3)c(-c3ccccc3)n2c1]

500 mg (1.13 mmol) {1-[4-(2-Bromo-2-phenyl-acetyl)phenyl]-cyclobutyl}-carbamic acid tert.-butyl ester, 137.5 mg (1.13 mmol) 3,5-dimethyl-pyridin-2-yl-amine and molecular sieves (4 Å, dried over night at 120° C. in a drying oven) were heated in 10 mL ethanol in a Dean-Stark apparatus for 23 hours. The reaction mixture had been sucked off via a glass fibre filter and evaporated to dryness. The residue was redissolved in dichloromethane, washed with an 1 M hydrochloric acid, saturated sodium bicarbonate and brine and dried (sodium sulfate). After filtration and removal of the solvent the residue was purified by chromatography on silicagel (eluents: hexane/ethyl acetate) yielding 142.6 mg (25.8%) of the pure title compound and 77.5 mg (14.7%) of the title compound which was slightly contaminated.

UPLC-MS (Method 2): RT=1.58 min; m/z=468 (ES+, M+1)

$^1$H-NMR (300 MHz, CD$_3$OD): δ 7.69 (1H), 7.20-7.62 (m, 9H), 7.03 (1H), 2.60 (s, 3H), 2.30-2.53 (m, 4H), 2.24 (s, 3H), 1.97-2.15 (m, 1H), 1.73-1.95 (m, 1H), 1.02-1.50 (m, 9H) ppm.

The following intermediate example had been prepared in analogy to intermediate example Int-4-44 by reacting {1-[4-(2-bromo-2-phenyl-acetyl)-phenyl]cyclobutyl}-carbamic acid tert.-butyl ester with the appropriately substituted 2-aminopyridine.

Intermediate Example Int-4-46

{1-[4-(6,8-difluoro-3-phenyl-imidazo[1,2-a]pyridin-2-yl)-phenyl]-cyclobutyl}-carbamic acid tert-butyl ester

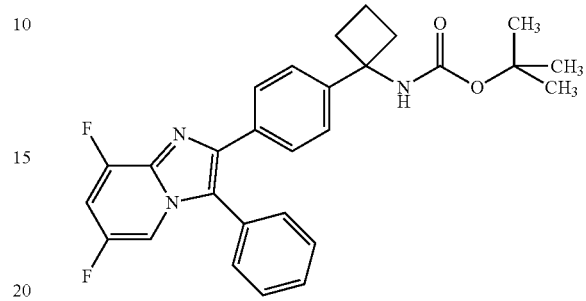

1 g (2.25 mmol) {1-[4-(2-Bromo-2-phenyl-acetyl)-phenyl]-cyclobutyl}-carbamic acid tert.-butyl ester, 292.8 mg (2.25 mmol) 3,5-difluoro-pyridin-2-yl-amine and 900 mg molecular sieves (3A, dried over night at 120° C. in a drying oven) in 20 mL ethanol were heated at reflux in a pressure pipe for 20 hours. The reaction mixture was sucked off via a glass fibre filter and evaporated to dryness. The residue was redissolved in dichloromethane, washed with hydrochloric acid (1 M), saturated sodium bicarbonate and brine and dried (sodium sulfate). After filtration and removal of the solvent the residue was purified by chromatography on silicagel (eluents: hexane/ethyl acetate) yielding 109.9 mg (9.8%) of the pure title compound.

UPLC-MS: RT=1.55 min; m/z=476 (ES+, M+1)

$^1$H-NMR (300 MHz, CDCl$_3$): δ 7.72 (br., 1H), 7.68 (d, 2H), 7.49-7.61 (m, 3H), 7.39-7.50 (m, 3H), 7.38 (d, 2H), 6.85-6.98 (m, 1H), 2.30-2.61 (m, 4H), 1.99-2.19 (m, 1H), 1.76-1.93 (m, 1H), 1.05-1.49 (m, 9H) ppm.

The following intermediate examples had been prepared in analogy to intermediate example Int-4-46 by reacting {1-[4-(2-bromo-2-phenyl-acetyl)-phenyl]-cyclobutyl}-carbamic acid tert.-butyl ester with the appropriately substituted 2-aminopyridines.

| Intermediate example | Structure/Name | 1H-NMR | UPLC-MS |
|---|---|---|---|
| Int-4-45 | 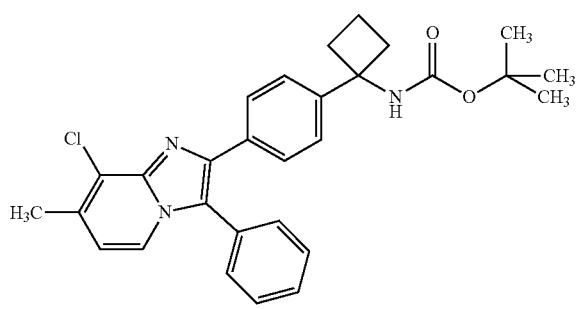 [SMILES: Cc1ccn2c(-c3ccccc3)c(-c3ccc(C4(NC(=O)OC(C)(C)C)CCC4)cc3)nc2c1Cl]<br>{1-[4-(8-Chloro-7-methyl-3-phenyl-imidazo[1,2-a]pyridin-2-yl)-phenyl]-cyclobutyl}-carbamic acid tert-butyl ester | | Method 2; RT = 1.54 min; m/z = 490 (ES+, M + 1) |

| Intermediate example | Structure/Name | 1H-NMR | UPLC-MS |
|---|---|---|---|
| Int-4-47 | {1-[4-(6-Chloro-8-methyl-3-phenyl-imidazo[1,2-a]pyridin-2-yl)-phenyl]-cyclobutyl}-carbamic acid tert-butyl ester | | RT = 1.55 min; m/z = 490 (ES+, M + 1) |
| Int-4-48 | 8-Bromo-2-[4-(1-tert-butoxycarbonyl-amino-cyclobutyl)-phenyl]-3-phenyl-imidazo[1,2-a]pyridine-6-carboxylic acid ethyl ester | | RT = 1.64 min; m/z = 592 (ES+, M + 1) |
| Int-4-49 | {1-[4-(6,8-Dichloro-3-phenyl-imidazo[1,2-a]pyridin-2-yl)-phenyl]-cyclobutyl}-carbamic acid tert-butyl ester | | RT = 1.64 min; m/z = 508 (ES+, M + 1) |
| Int-4-50 | {1-[4-(8-Cyano-7-methoxy-3-phenyl-imidazo[1,2-a]pyridin-2-yl)-phenyl]-cyclobutyl}-carbamic acid tert-butyl ester | (400 MHz, CD$_3$OD): δ 8.23 (d, 1H), 7.48-7.60 (m, 5H), 7.40-7.48 (m, 2H), 7.37 (d, 2H), 7.02 (d, 1H), 4.09 (s, 3H), 2.30-2.53 (m, 4H), 1.97-2.13 (m, 1H), 1.76-1.92 (m, 1H), 1.02-1.48 (m, 9H) ppm. | RT = 1.41 min; m/z = 495 (ES+, M + 1) |

| Intermediate example | Structure/Name | 1H-NMR | UPLC-MS |
|---|---|---|---|
| Int-4-51 | {1-[4-(6,7-Dichloro-3-phenyl-imidazo[1,2-a]pyridin-2-yl)-phenyl]-cyclobutyl}-carbamic acid tert-butyl ester | | RT = 1.64 min; m/z = 508 (ES+, M + 1) |
| Int-4-52 | {1-[4-(8-Bromo-6-chloro-7-methyl-3-phenyl-imidazo[1,2-a]pyridin-2-yl)-phenyl]-cyclobutyl}-carbamic acid tert-butyl ester | (300 MHz, dDMSO): δ 8.02 (br., 1H), 7.39-7.68 (m, 7H), 7.30 (d, 2H), 2.53 (s, 3H), 2.19-2.40 (m, 4H), 1.82-2.02 (m, 1H), 1.62-1.82 (m, 1H), 0.85-1.48 (m, 9H) ppm. | RT = 1.74 min; m/z = 570 (ES+, M + 1) |

Intermediate Example Int-4-53

{1-[4-(6-bromo-8-methyl-3-phenyl-imidazo[1,2-a]pyridin-2-yl)-phenyl]-cyclobutyl}-carbamic acid tert-butyl ester

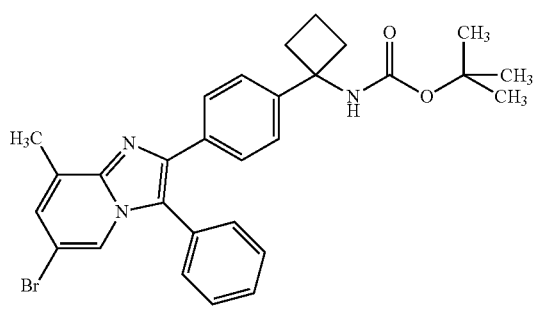

1.25 g (2.81 mmol) {1-[4-(2-Bromo-2-phenyl-acetyl)phenyl]-cyclobutyl}-carbamic acid tert.-butyl ester, 631.4 mg (3.38 mmol) 2-amino-5-bromo-3-methyl-pyridine, 2.15 g molecular sieves (4 Å, dried over night at 120° C. in a drying oven), 363.5 mg (2.81 mmol) N,N-diisopropylethylamine in 12 mL 2-propanol (degassed for 15') in a microwave vial, sealed with a microwave cap, were heated at 130° C. for 17 hours in a heating block. The reaction mixture was sucked off via a glass fibre filter and the filter was washed with dichloromethane. After evaporation to dryness, the residue was redissolved in dichloromethane (200 mL), washed with an 1 M hydrochloric acid (50 mL), saturated sodium bicarbonate (50 mL) and brine (100 mL) and dried (sodium sulfate). After filtration and removal of the solvent the residue was purified by chromatography on silicagel (eluents: hexane/ethyl acetate) yielding 256.7 mg (17.1%) of the title compound.

UPLC-MS: RT=1.73 min; m/z=534 (ES+, M+1)

The following intermediate examples had been prepared in analogy to intermediate example Int-4-53 by reacting {1-[4-(2-bromo-2-phenyl-acetyl)-phenyl]-cyclobutyl}-carbamic acid tert.-butyl ester with the appropriately substituted 2-aminopyridines.

| Intermediate example | Structure/Name | 1H-NMR | UPLC-MS |
|---|---|---|---|
| Int-4-54 | {1-[4-(8-Bromo-6-methyl-3-phenyl-imidazo[1,2-a]pyridin-2-yl)-phenyl]-cyclobutyl}-carbamic acid tert-butyl ester | (300 MHz, dDMSO): δ 7.78 (br., 1H), 7.40-7.68 (m, 9H), 7.26 (d, 2H), 2.23-2.40 (m, 4H), 2.22 (s, 3H), 1.82-2.01 (m, 1H), 1.62-1.82 (m, 1H), 0.96-1.42 (m, 9H) ppm. | RT = 1.64 min; m/z = 532 (ES+, M + 1) |
| Int-4-55 | {1-[4-(6-Bromo-7,8-dimethyl-3-phenyl-imidazo[1,2-a]pyridin-2-yl)-phenyl]-cyclobutyl}-carbamic acid tert-butyl ester | (400 MHz, dDMSO): δ 7.98 (br., 1H), 7.42-7.63 (m, 8H), 7.30 (d, 2H), 2.63 (s, 3H), 2.41 (s, 3H), 2.26-2.40 (m, 4H), 1.88-2.03 (m, 1H), 1.67-1.82 (m, 1H), 0.98-1.43 (m, 9H) ppm. | RT = 1.47 min; m/z = 546 (ES+, M + 1) |

Intermediate Example Int-4-56

{1-[4-(8-bromo-6-chloro-3-phenyl-imidazo[1,2-a]pyridin-2-yl)-phenyl]-cyclobutyl}-carbamic acid tert-butyl ester

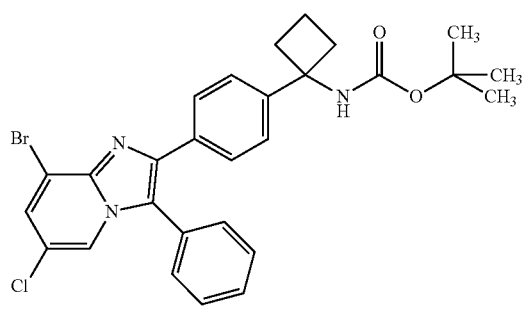 [SMILES: CC(C)(C)OC(=O)NC1(c2ccc(-c3nc4c(Cl)cc(Cl)cn4c3-c3ccccc3)cc2)CCC1]

2 g (4.50 mmol) {1-[4-(2-Bromo-2-phenyl-acetyl)-phenyl]-cyclobutyl}-carbamic acid tert.-butyl ester, 933.7 mg (4.50 mmol) 5-chloro-3-bromo-2-pyridin-2-yl-amine, 1.9 g molecular sieves (4A, dried over night at 120° C. in a drying oven), 581.7 mg (4.50 mmol) N,N-diisopropylethylamine in 40 mL 2-propanol (degassed for 15′) were heated in the microwave at 130° C. for 8 hours. The reaction mixture was sucked off via a glass fibre filter and the filtrate evaporated to dryness. The residue was purified by HPLC yielding 164 mg (6.3%) of the desired compound.

UPLC-MS: RT=1.69 min; m/z=552 (ES+, M+1)

¹H-NMR (300 MHz, dDMSO): δ 8.01 (br., 1H), 7.81 (1H), 7.40-7.65 (m, 8H), 7.29 (d, 2H), 2.20-2.42 (m, 4H), 1.82-2.02 (m, 1H), 1.62-1.82 (m, 1H), 0.98-1.42 (m, 9H) ppm.

The following intermediate examples had been prepared in analogy to intermediate example Int-4-56 by reacting {1-[4-(2-bromo-2-phenyl-acetyl)-phenyl]-cyclobutyl}-carbamic acid tert.-butyl ester with the appropriately substituted 2-aminopyridines.

| Intermediate example | Structure/Name | 1H-NMR | UPLC-MS |
|---|---|---|---|
| Int-4-57 | 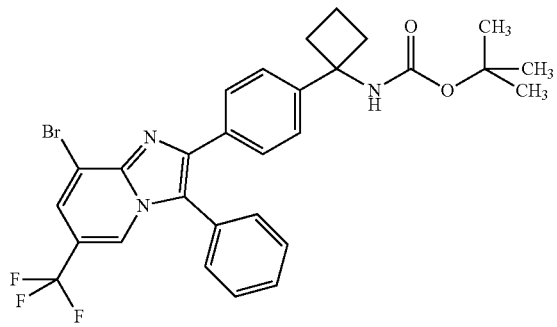 [SMILES: CC(C)(C)OC(=O)NC1(c2ccc(-c3nc4c(Br)cc(C(F)(F)F)cn4c3-c3ccccc3)cc2)CCC1]<br>{1-[4-(8-Bromo-3-phenyl-6-trifluoromethyl-imidazo[1,2-a]pyridin-2-yl)-phenyl]-cyclobutyl}-carbamic acid tert-butyl ester | | RT = 1.61 min; m/z = 588 (ES+, M + 1) |
| Int-4-58 | 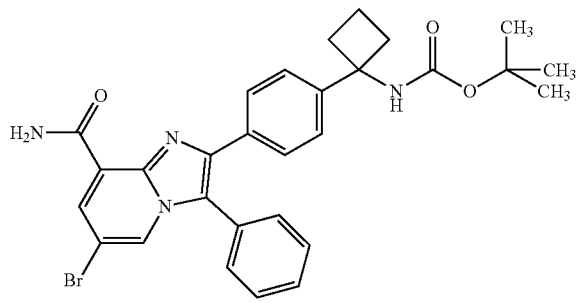 [SMILES: CC(C)(C)OC(=O)NC1(c2ccc(-c3nc4c(C(N)=O)cc(Br)cn4c3-c3ccccc3)cc2)CCC1]<br>{1-[4-(6-Bromo-8-carbamoyl-3-phenyl-imidazo[1,2-a]pyridin-2-yl)-phenyl]-cyclobutyl}-carbamic acid tert-butyl ester | | RT = 1.54 min; m/z = 561 (ES+, M + 1) |
| Int-4-59 | 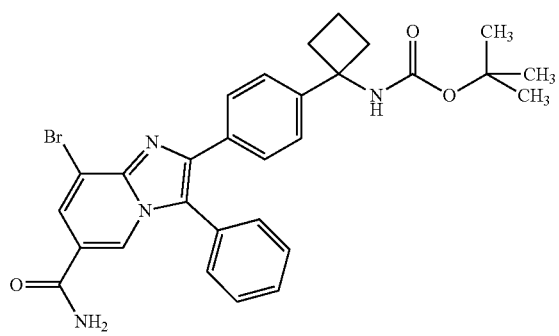<br>{1-[4-(8-Bromo-6-carbamoyl-3-phenyl-imidazo[1,2-a]pyridin-2-yl)-phenyl]-cyclobutyl}-carbamic acid tert-butyl ester | | RT = 1.31 min; m/z = 563 (ES+, M + 1) |

Intermediate Example Int-4-60

2-[4-(1-tert-butoxycarbonylamino-cyclobutyl)-phenyl]-3-phenyl-imidazo[1,2-a]pyridine-7-carboxylic acid methyl ester

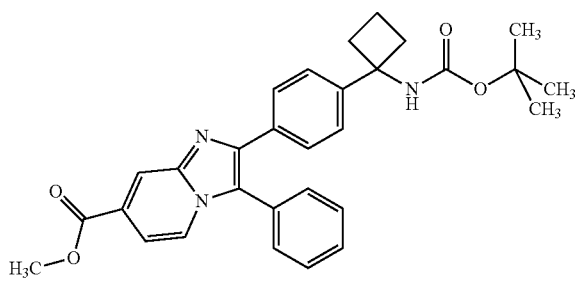 [SMILES: COC(=O)c1ccn2c(-c3ccccc3)c(-c3ccc(C4(NC(=O)OC(C)(C)C)CCC4)cc3)nc2c1]

A mixture of {1-[4-(2-bromo-2-phenyl-acetyl)-phenyl]-cyclobutyl}-carbamic acid tert-butyl ester [Int-1-A] (4.40 g, 9.91 mmol), methyl 2-aminopyridine-4-carboxylate (3.01 g, 19.8 mmol, 2 equiv) and powdered activated 3A sieves (10 g) in ethanol (37 mL) was heated for 4 h at the reflux temperature. The resulting solution was filtered through a pad of Celite with the aid of $CH_2Cl_2$. The resulting solution was separated between $CH_2Cl_2$ (50 mL) and a saturated aqueous $NaHCO_3$ solution 50 mL). The organic phase was washed with a saturated aqueous NaCl solution, dried ($Na_2SO_4$ anh), and concentrated under reduced pressure. The remaining material was purified using MPLC (Biotage Isolera; 100 g SNAP cartridge: 100% hexane for 1.0 min., gradient to 80% hexane/20% EtOAc over 1.0 min., 80% hexane/20% EtOAc for 2.0 min., gradient to 75% hexane/25% EtOAc over 1.0 min., 75% hexane/25% EtOAc for 2.0 min, gradient to 50% hexane/50% EtOAc over 4.0 min., 50% hexane/50% EtOAc for 5.0 min., gradient to 25% hexane/75% EtOAc over 9.5 min.) to give 2-[4-(1-tert-butoxycarbonylamino-cyclobutyl)-phenyl]-3-phenyl-imidazo[1,2-a]pyridine-7-carboxylic acid methyl ester (2.3 g, 47%):

UPLC-MS (Method 2): RT=1.48 min; m/z (rel intensity) 498 (70, $(M+H)^+$), 995 (100, $(2M+H)^+$); ES–: m/z (rel intensity) 496 (20, $(M-H)^-$), 993 (40, $(2M-H)^-$).

1H-NMR (d6-DMSO): δ 1.05 (br s, 3H), 1.29 (br s, 6H), 1.72 (br s, 1H), 1.88-1.97 (m, 1H), 2.27-2.35 (m, 4H), 3.88 (s, 3H), 7.26-7.30 (m, 3H), 7.49-7.61 (m, 8H), 8.07 (br d, J=6.3 Hz, 1H), 8.20 (s, 1H) ppm.

The following examples were prepared in a manner analogous to that described in Intermediate Example Int-4-60: substituting appropriate starting materials where necessary:

| Example | Structure/Name | UPLC-MS |
|---|---|---|
| Int-4-61 | 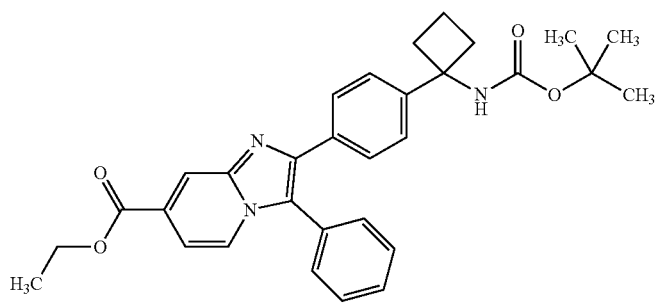 [SMILES: CCOC(=O)c1ccn2c(-c3ccccc3)c(-c3ccc(C4(NC(=O)OC(C)(C)C)CCC4)cc3)nc2c1]<br>2-[4-(1-tert-Butoxycarbonylamino-cyclobutyl)-phenyl]-3-phenyl-imidazo[1,2-a]pyridine-7-carboxylic acid ethyl ester | Method 2: RT = 1.53 min; m/z (rel intensity) 512 (100, $(M + H)^+$). |
| Int-4-62 | 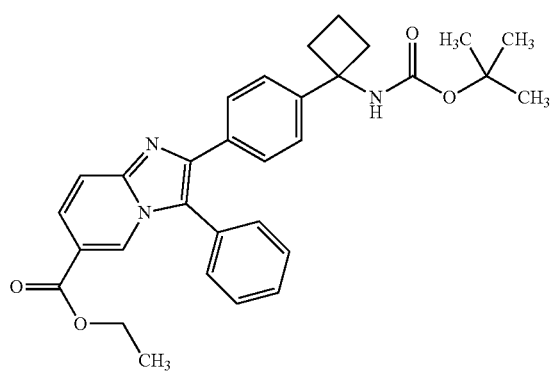 [SMILES: CCOC(=O)c1ccc2nc(-c3ccc(C4(NC(=O)OC(C)(C)C)CCC4)cc3)c(-c3ccccc3)n2c1]<br>2-[4-(1-tert-Butoxycarbonylamino-cyclobutyl)-phenyl]-3-phenyl-imidazo[1,2-a]pyridine-6-carboxylic acid ethyl ester | Method 2: RT = 1.56 min; m/z (rel intensity) 512 (100, $(M + H)^+$). |

Intermediate Example Int-4-63

2-[4-(1-tert-butoxycarbonylamino-cyclobutyl)-phenyl]-8-chloro-3-phenyl-imidazo[1,2-a]pyridine-6-carboxylic acid methyl ester

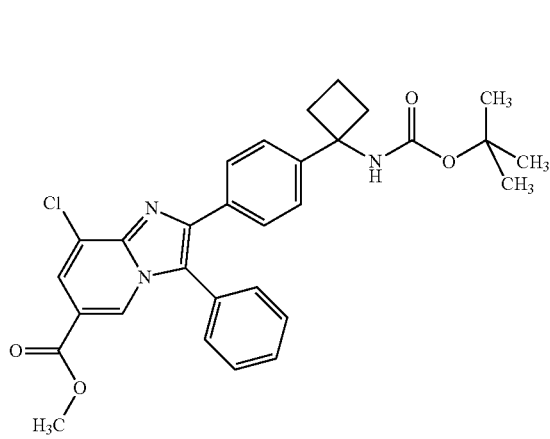 [SMILES: COC(=O)c1cc(Cl)c2nc(-c3ccc(C4(NC(=O)OC(C)(C)C)CCC4)cc3)c(-c3ccccc3)n2c1]

A mixture of 6-amino-5-chloronicotinic acid methyl ester (0.588 g, 3.15 mmol), {1-[4-(2-bromo-2-phenyl-acetyl)-phenyl]-cyclobutyl}-carbamic acid tert-butyl ester [Int-1-A] (2.00 g, 70% purity by UPLC-MS, 3.15 mmol) and powdered activated 3 Å molecular sieves in isopropanol (9.7 mL) was heated at reflux for 20 hours. On cooling, the mixture was diluted with DCM and water, filtered through Celite and the organic extract washed with brine, dried and concentrated in vacuo. Purification was achieved by chromatography on silica gel (gradient elution: hexane-hexane/ethyl acetate 1:1) to give the title compound contaminated with 6-amino-5-chloronicotinic acid methyl ester. Further purification was achieved by acid extraction of a solution of the crude product in ethyl acetate with dilute aqueous hydrochloric acid (1 M). The organic extract was washed with brine, dried and concentrated in vacuo to give the title compound;

UPLC-MS: RT=1.60 min; m/z=532.21 (M+H).

Intermediate Example Int-4-64

{1-[4-(7-cyano-3-phenyl-imidazo[1,2-a]pyridin-2-yl)-phenyl]-cyclobutyl}-carbamic acid tert-butyl ester

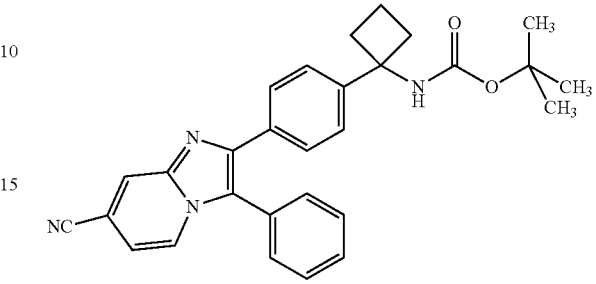

A mixture of {1-[4-(2-bromo-2-phenyl-acetyl)-phenyl]-cyclobutyl}-carbamic acid tert-butyl ester [Int-1-A] (2.65 g, 5.69 mmol), 2-amino-4-cyanopyridine (1.42 g, 11.9 mmol, 2 equiv) and powdered activated 3 Å molecular sieves (10 g) in ethanol (22 mL) was heated for 4 h at the reflux temperature. The reaction mixture was cooled to room temperature, additional 2-amino-4-cyanopyridine (0.71 g, 6.0 mmol, 1 equiv) was added, and the resulting mixture was heated at the reflux temperature for 5 h. The resulting solution was separated between EtOAc (75 mL) and an saturated aqueous NaHCO$_3$ solution (75 mL). The organic phase was washed with a saturated aqueous NaCl solution (25 mL), dried (Na$_2$SO$_4$ anh), and concentrated under reduced pressure. The remaining material was purified using MPLC (Biotage Isolera; 25 g SNAP cartridge: 80% hexane/20% EtOAc for 3.0 min., gradient to 70% hexane/30% EtOAc over 13.7 min.) to give {1-[4-(7-cyano-3-phenyl-imidazo[1,2-a]pyridin-2-yl)-phenyl]-cyclobutyl}-carbamic acid tert-butyl ester (0.57 g, 21%).

UPLC-MS (Method 2): RT=1.46 min; m/z (rel intensity) 465 (100, (M+H)$^+$), 929 (70, (2M+H)$^+$).

MS: m/z (rel intensity) 440 (100, (M+H)$^+$).

1H-NMR (d6-DMSO): δ 1.06 (br s, 3H), 1.28 (br s, 6H), 1.72 (br s, 1H), 1.85-1.97 (m, 1H), 2.25-2.36 (m, 4H), 7.12 (dd, J=7.2, 1.5, 1H), 7.28 (d, J=8.5, 2H), 7.47-7.60 (m, 7H), 8.09 (br d, J=6.8 Hz, 1H), 8.41 (s, 1H) ppm.

The following example was prepared in a manner analogous to that described in Example Int-4-64: substituting appropriate starting materials where necessary:

| Intermediate Example | Structure/Name | UPLC-MS |
|---|---|---|
| Int-4-65 | 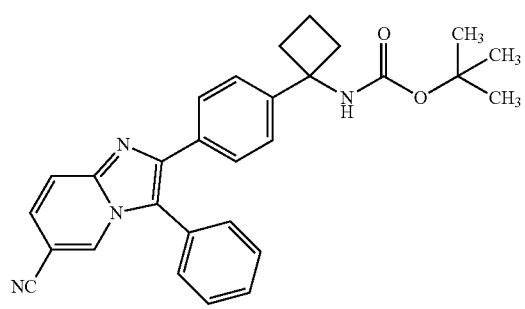 [SMILES: CC(C)(C)OC(=O)NC1(c2ccc(-c3nc4ccc(C#N)cn4c3-c3ccccc3)cc2)CCC1]<br>{1-[4-(6-Cyano-3-phenyl-imidazo[1,2-a]pyridin-2-yl)-phenyl]-cyclobutyl}-carbamic acid tert-butyl ester | Method 2: RT = 1.45 min; m/z (rel intensity) 465 (80, (M + H)$^+$), 929 (100, (2M + H)$^+$). |

Intermediate Example Int-4-66

{1-[4-(6-bromo-8-methoxy-3-phenyl-imidazo[1,2-a]pyridin-2-yl)-phenyl]-cyclobutyl}-carbamic acid tert-butyl ester

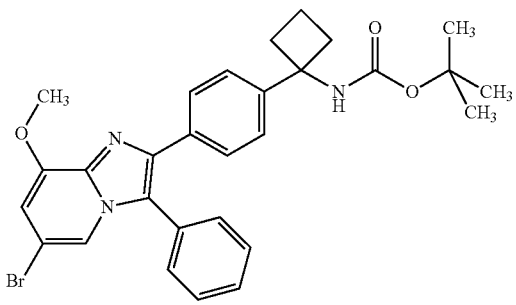

Step 1: 5-bromo-3-methoxy-pyridin-2-ylamine

The title compound is known in the literature. For methods of preparation, see WO2009/115572.

Step 2: {1-[4-(6-bromo-8-methoxy-3-phenyl-imidazo[1,2-a]pyridin-2-yl)-phenyl]-cyclobutyl}-carbamic acid tert-butyl ester This intermediate was prepared in analogy to 2-[4-(1-tert-butoxycarbonylamino-cyclobutyl)-phenyl]-8-chloro-3-phenyl-imidazo[1,2-a]pyridine-6-carboxylic acid methyl ester by using 5-bromo-3-methoxy-pyridin-2-ylamine from Step 1.

UPLC-MS: RT=1.55 min; m/z=550.18 (M+H; M=$C_{29}H_{30}{}^{81}BrN_3O_3$)

1H-NMR (300 MHz, d6-DMSO, uncorrected): δ 7.45-7.59 (m, 9H), 7.23 (d, 2H), 6.86 (m, 1H), 3.89 (s, 3H), 2.23-2.37 (m, 4H), 1.85-1.97 (m, 1H), 1.64-1.78 (m, 1H), 1.06 & 1.28 (2×s, 9H) ppm.

Intermediate Example Int-5-0

{1-[4-(6-methylcarbamoyl-3-phenyl-imidazo[1,2-a]pyridin-2-yl)-phenyl]-cyclobutyl}-carbamic acid tert-butyl ester

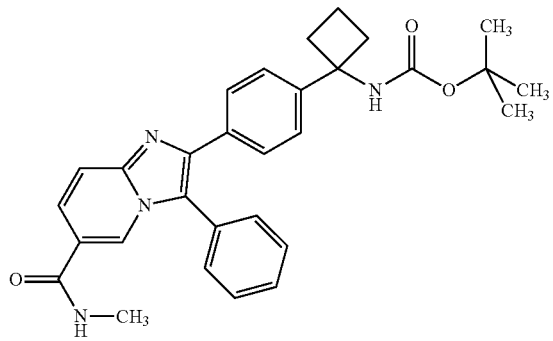 [SMILES: CNC(=O)c1ccc2nc(-c3ccc(C4(NC(=O)OC(C)(C)C)CCC4)cc3)c(-c3ccccc3)n2c1]

A mixture of 2-[4-(1-tert-butoxycarbonylamino-cyclobutyl)-phenyl]-3-phenyl-imidazo[1,2-a]pyridine-6-carboxylic acid methyl ester (100 mg) and a solution of methylamine in methanol (2M, 1.4 mL) was heated at 100° C. under microwave irradiation for 90 minutes followed by a further 90 minutes. On cooling, the reaction mixture was concentrated in vacuo to give the title compound which was used without further purification in the next step.

UPLC-MS (Method 2): RT=1.15 min; m/z=497.28 (M+H).

Intermediate Example Int-5-1

{1-[4-(6-carbamoyl-3-phenyl-imidazo[1,2-a]pyridin-2-yl)-phenyl]-cyclobutyl}-carbamic acid tert-butyl ester

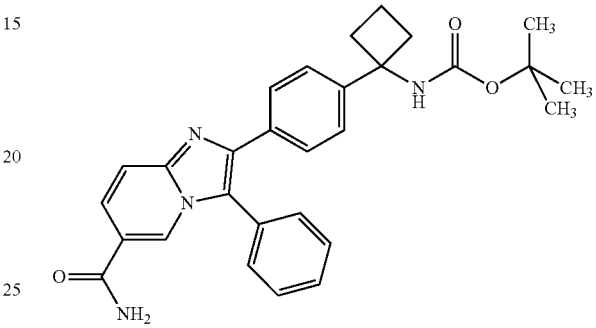

A mixture of 2-[4-(1-tert-butoxycarbonylamino-cyclobutyl)-phenyl]-3-phenyl-imidazo[1,2-a]pyridine-6-carboxylic acid methyl ester (100 mg) and a solution of ammonia in methanol (7M, 1.4 mL) was heated at 130° C. for 90 minutes under microwave irradiation. On cooling, the reaction mixture was concentrated in vacuo. Purification was achieved by chromatography on silica gel to give the title compound.

UPLC-MS (Method 2): RT=1.26 min; m/z=483.25 (M+H).

Intermediate Example Int-5-2

{1-[4-(7-carbamoyl-3-phenyl-imidazo[1,2-a]pyridin-2-yl)-phenyl]-cyclobutyl}-carbamic acid tert-butyl ester

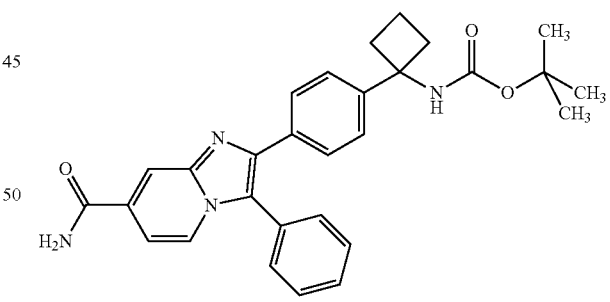

A mixture of 2-[4-(1-tert-butoxycarbonylamino-cyclobutyl)-phenyl]-3-phenyl-imidazo[1,2-a]pyridine-7-carboxylic acid methyl ester (150 mg) and a solution of ammonia in methanol (7M, 2.15 mL) was heated at 130° C. for 90 minutes under microwave irradiation. On cooling, the reaction mixture was concentrated in vacuo. Purification was achieved by chromatography on silica gel to give the title compound.

UPLC-MS (Method 2): RT=1.29 min; m/z=483.32 (M+H).

The following examples were prepared in a manner analogous to that described in Intermediate Example Int-5-2: substituting appropriate starting materials where necessary:

| Intermediate example | Structure/Name | 1H-NMR | UPLC-MS |
|---|---|---|---|
| Int-5-3 | {1-[4-(6-Carbamoyl-7,8-dimethyl-3-phenyl-imidazo[1,2-a]pyridin-2-yl)-phenyl]-cyclobutyl}-carbamic acid tert-butyl ester | (300 MHz, dDMSO): δ 7.78-7.96 (br., 2H), 7.32-7.65 (m, 9H), 7.29 (d, 2H), 2.55 (s, 3H), 2.20-2.42 (m, 7H), 1.82-2.02 (m, 1H), 1.62-1.82 (m, 1H), 0.95-1.45 (m, 9H) ppm. | RT = 1.00 min; m/z = 511 (ES+, M + 1) |
| Int-5-4 | {1-[4-(6-Carbamoyl-8-methyl-3-phenyl-imidazo[1,2-a]pyridin-2-yl)-phenyl]-cyclobutyl}-carbamic acid tert-butyl ester | (300 MHz, dDMSO): δ 8.35 (br. 1H), 8.08 (br., 1H), 7.30-7.68 (m, 10H), 7.29 (d, 2H), 2.58 (s, 3H), 2.20-2.42 (m, 4H), 1.82-2.01 (m, 1H), 1.63-1.82 (m, 1H), 0.95-1.45 (m, 9H) ppm. | RT = 1.14 min; m/z = 497 (ES+, M + 1) |
| Int-5-5 | {1-[4-(8-Carbamoyl-6-methyl-3-phenyl-imidazo[1,2-a]pyridin-2-yl)-phenyl]-cyclobutyl}-carbamic acid tert-butyl ester | (400 MHz, dDMSO): δ 9.61 (1H), 8.03 (1H), 7.96 (br., 1H), 7.91 (1H), 7.45-7.65 (m, 8H), 7.29 (d, 2H), 2.21-2.42 (m, 7H), 1.85-2.02 (m, 1H), 1.63-1.82 (m, 1H), 0.95-1.42 (m, 9H) ppm. | RT = 1.42 min; m/z = 497 (ES+, M + 1) |
| Int-5-6 | {1-[4-(7-Methylcarbamoyl-3-phenyl-imidazo[1,2-a]pyridin-2-yl)-phenyl]-cyclobutyl}-carbamic acid tert-butyl ester | | Method 2: RT = 1.31 min; m/z (rel intensity) 497 (70, (M + H)+), 993 (100, (2M + H)+). |

| Intermediate example | Structure/Name | 1H-NMR | UPLC-MS |
|---|---|---|---|
| 5-7 | 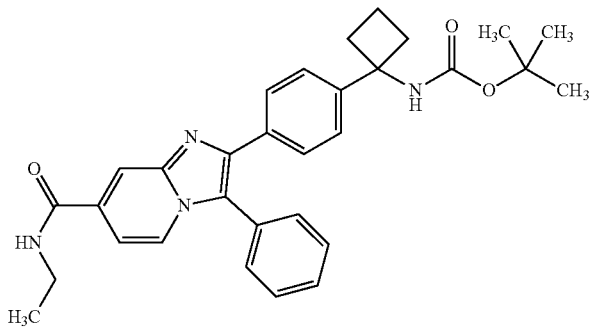 [SMILES: CCNC(=O)c1ccn2c(-c3ccccc3)c(-c3ccc(C4(NC(=O)OC(C)(C)C)CCC4)cc3)nc2c1]{1-[4-(7-Ethylcarbamoyl-3-phenyl-imidazo[1,2-a]pyridin-2-yl)-phenyl]-cyclobutyl}-carbamic acid tert-butyl ester | | Method 2:<br>RT = 1.37 min;<br>m/z (rel intensity) 511 (100,<br>m/z (rel intensity) 509 (900,<br>(M – H)⁻). |

Intermediate Example Int-5-8

{1-[4-(6-isopropylcarbamoyl-3-phenyl-imidazo[1,2-a]pyridin-2-yl)-phenyl]-cyclobutyl}-carbamic acid tert-butyl ester

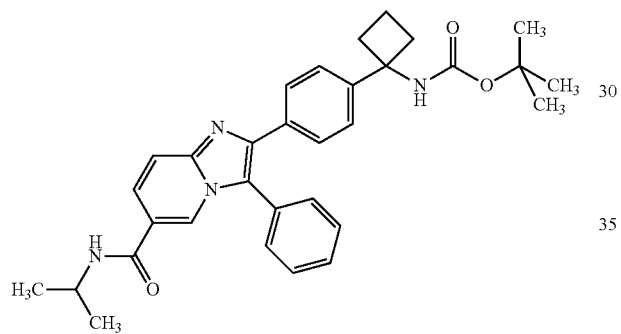

Step 1: 2-[4-(1-tert-butoxycarbonylamino-cyclobutyl)-phenyl]-3-phenyl-imidazo[1,2-a]pyridine-6-carboxylic acid 2-[4-(1-tert-butoxycarbonylamino-cyclobutyl)-phenyl]-3-phenyl-imidazo[1,2-a]pyridine-6-carboxylic acid methyl ester (0.76 g) was suspended in tert-butanol (19.2 mL) and treated with dilute aqueous sodium hydroxide solution (1M, 6.1 mL). The mixture was heated to 70° C. for 3.5 h. On cooling the reaction was diluted with water and the pH adjusted to 5 with dilute aqueous hydrochloric acid. The resulting emulsion was extracted with ethyl acetate and the organic extract washed with brine, dried and concentrated in vacuo to give the crude title compound which was used without further purification.

UPLC-MS: RT=1.19 min; m/z=484.23 (M+H).

Step 2: {1-[4-(6-isopropylcarbamoyl-3-phenyl-imidazo[1,2-a]pyridin-2-β-phenyl]-cyclobutyl}-carbamic acid tert-butyl ester A solution of 2-[4-(1-tert-butoxycarbonylamino-cyclobutyl)-phenyl]-3-phenyl-imidazo[1,2-a]pyridine-6-carboxylic acid from Step 1 (100 mg) in DMF (0.63 mL) was treated with 2-(7-aza-1H-benzotriazole-1-yl)-1,1,3,3-tetramethyluronium hexafluorophosphate [HATU] (102 mg), N,N-diisopropylamine (0.108 mL) and isopropylamine (0.025 mL) and stirred under argon at rt for 2.5 h. The mixture was allowed to stand overnight, diluted with water and the resulting precipitate filtered and dried to give the crude product which was used without further purification in the next step;

UPLC-MS: RT=1.29 min; m/z=525.30 (M+H).

The following intermediates were prepared in analogy by using the appropriate amine or amine hydrochloride starting material. In the case that the corresponding amine hydrochloride was used, an extra equivalent of tertiary amine base was employed.

| Intermediate Example | Structure/Name | UPLC-MS |
|---|---|---|
| Int-5-9 | 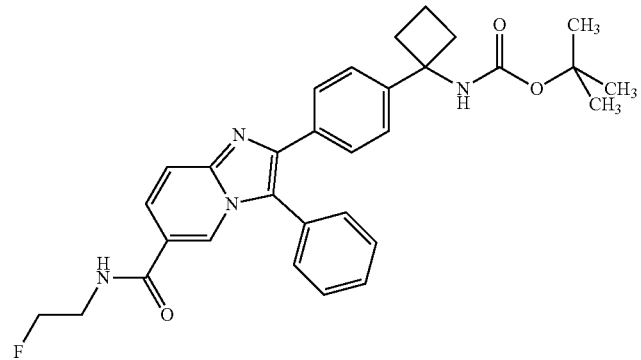 [SMILES: CC(C)(C)OC(=O)NC1(c2ccc(-c3nc4ccc(C(=O)NCCF)cn4c3-c3ccccc3)cc2)CCC1] | RT = 1.21 min;<br>m/z = 529.30<br>(M + H) |

| Intermediate Example | Structure/Name | UPLC-MS |
|---|---|---|
| | (1-{4-[6-(2-Fluoro-ethylcarbamoyl)-3-phenyl-imidazo[1,2-a]pyridin-2-yl]-phenyl}-cyclobutyl)-carbamic acid tert-butyl ester | |
| Int-5-10 | 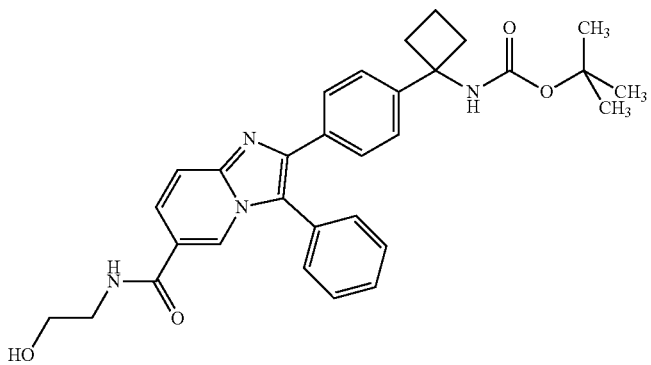 [SMILES: CC(C)(C)OC(=O)NC1(c2ccc(-c3nc4ccc(C(=O)NCCO)cn4c3-c3ccccc3)cc2)CCC1]<br>(1-{4-[6-(2-Hydroxy-ethylcarbamoyl)-3-phenyl-imidazo[1,2-a]pyridin-2-yl]-phenyl}-cyclobutyl)-carbamic acid tert-butyl ester | RT = 1.09 min;<br>m/z = 527.29<br>(M + H) |
| Int-5-11 | 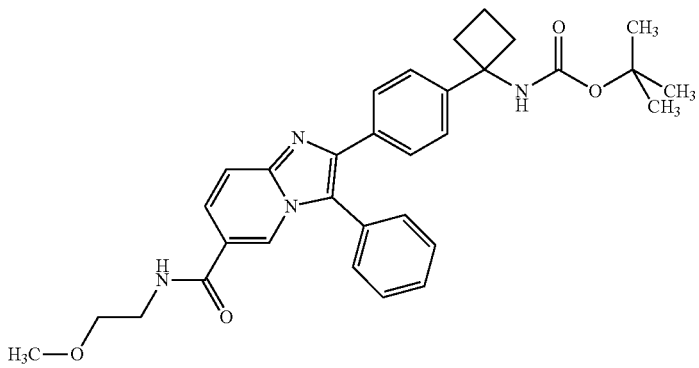 [SMILES: COCCNC(=O)c1ccc2nc(-c3ccc(C4(NC(=O)OC(C)(C)C)CCC4)cc3)c(-c3ccccc3)n2c1]<br>(1-{4-[6-(2-Methoxy-ethylcarbamoyl)-3-phenyl-imidazo[1,2-a]pyridin-2-yl]-phenyl}-cyclobutyl)-carbamic acid tert-butyl ester | RT = 1.18 min;<br>m/z = 541.30<br>(M + H) |
| Int-5-12 | 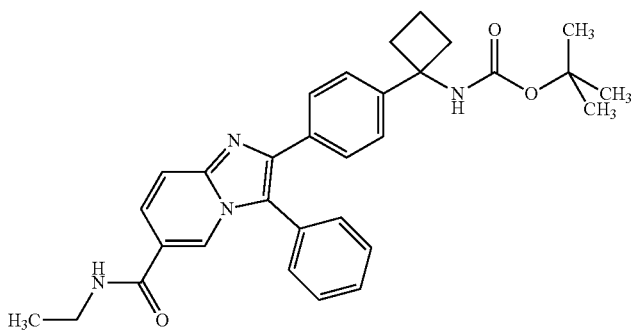 [SMILES: CCNC(=O)c1ccc2nc(-c3ccc(C4(NC(=O)OC(C)(C)C)CCC4)cc3)c(-c3ccccc3)n2c1]<br>{1-[4-(6-Ethylcarbamoyl-3-phenyl-imidazo[1,2-a]pyridin-2-yl)-phenyl]-cyclobutyl}-carbamic acid tert-butyl ester | RT = 1.21 min;<br>m/z = 511.30<br>(M + H) |

| Intermediate Example | Structure/Name | UPLC-MS |
|---|---|---|
| Int-5-13 | 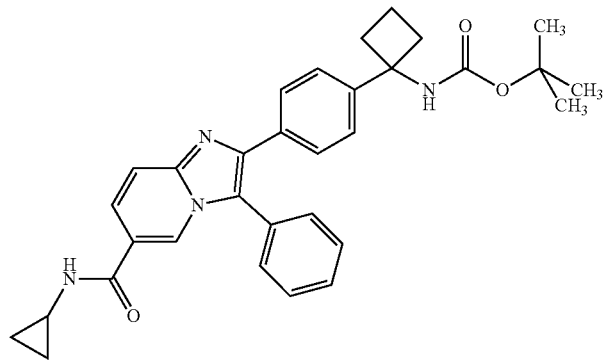 [SMILES: CC(C)(C)OC(=O)NC1(c2ccc(-c3nc4ccc(C(=O)NC5CC5)cn4c3-c3ccccc3)cc2)CCC1]<br>{1-[4-(6-Cyclopropylcarbamoyl-3-phenyl-imidazo[1,2-a]pyridin-2-yl)-phenyl]cyclobutyl}-carbamic acid tert-butyl ester | RT = 1.24 min;<br>m/z = 523.27<br>(M + H) |
| Int-5-14 | 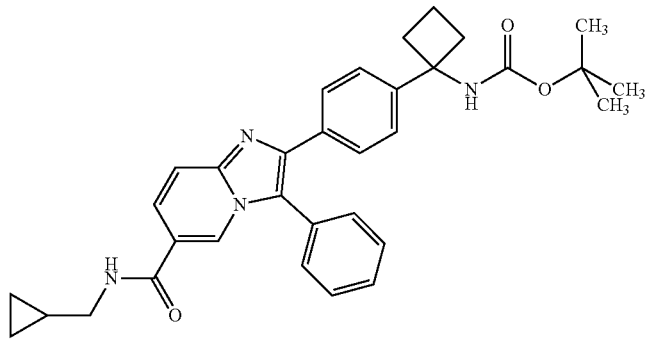 [SMILES: CC(C)(C)OC(=O)NC1(c2ccc(-c3nc4ccc(C(=O)NCC5CC5)cn4c3-c3ccccc3)cc2)CCC1]<br>(1-{4-[6-(Cyclopropylmethyl-carbamoyl)-3-phenyl-imidazo[1,2-a]pyridin-2-yl]-phenyl}-cyclobutyl)-carbamic acid tert-butyl ester | RT = 1.29 min;<br>m/z = 537.31<br>(M + H) |
| Int-5-15 | 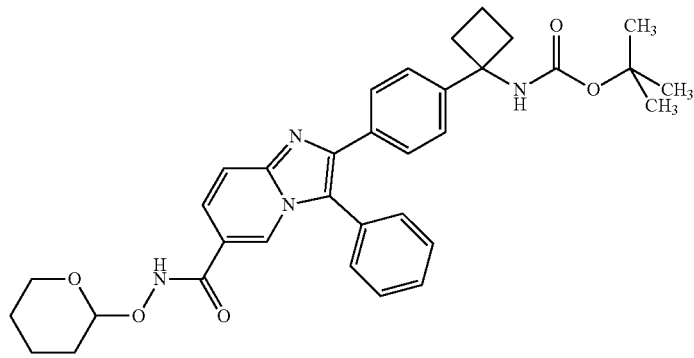 [SMILES: CC(C)(C)OC(=O)NC1(c2ccc(-c3nc4ccc(C(=O)NOC5CCCCO5)cn4c3-c3ccccc3)cc2)CCC1]<br>(1-{4-[3-Phenyl-6-(tetrahydro-pyran-2-yloxycarbamoyl)-imidazo[1,2-a]pyridin-2-yl]-phenyl}-cyclobutyl)-carbamic acid tert-butylester | RT = 1.29 min;<br>m/z = 583.31<br>(M + H) |

Intermediate Example Int-6-0

{1-[4-(6-methoxymethyl-3-phenyl-imidazo[1,2-a]pyridin-2-yl)-phenyl]-cyclobutyl}-carbamic acid tert-butyl ester

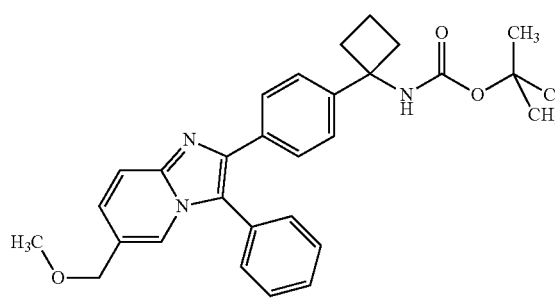

A solution of {1-[4-(6-hydroxymethyl-3-phenyl-imidazo[1,2-a]pyridin-2-yl)-phenyl]-cyclobutyl}-carbamic acid tert-butyl ester (67 mg) in DMF (0.6 mL) under argon at 0° C. was treated with sodium hydride (8.4 mg of a 60% dispersion in mineral oil) and stirred for 30 minutes. Methyl iodide (0.007 mL) was added dropwise, the mixture warmed to rt and stirred for 3 hours. The mixture was partitioned between ethyl acetate and water and the organic phase washed with brine, dried and concentrated in vacuo to give the crude title compound which was used in the next step without further purification.

UPLC-MS: RT=1.17 min; m/z=484.28 (M+H).

Intermediate Example Int-7-0

1-{4-[6-(1-hydroxy-ethyl)-3-phenyl-imidazo[1,2-a]pyridin-2-yl]-phenyl}-cyclobutyl)-carbamic acid tert-butyl ester

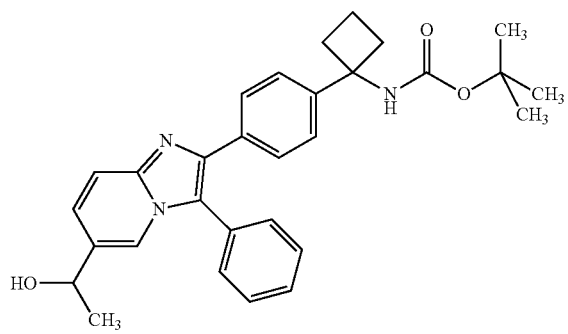 [SMILES: CC(O)c1ccc2nc(-c3ccc(C4(NC(=O)OC(C)(C)C)CCC4)cc3)c(-c3ccccc3)n2c1]

Step 1: {1-[4-(6-formyl-3-phenyl-imidazo[1,2-a]pyridin-2-yl)-phenyl]-cyclobutyl}-carbamic acid tert-butyl ester

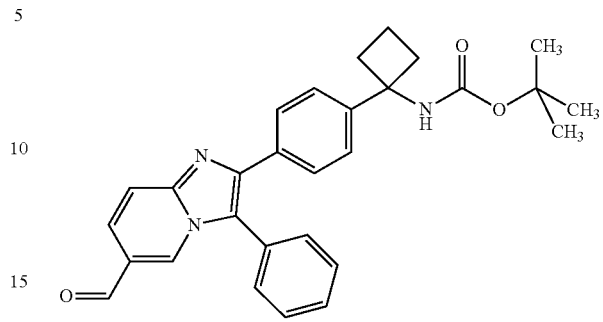

A solution of {1-[4-(6-hydroxymethyl-3-phenyl-imidazo[1,2-a]pyridin-2-yl)-phenyl]-cyclobutyl}-carbamic acid tert-butyl ester (200 mg) and triethylamine (0.125 mL) in DCM (1.9 mL) at 0° C. was treated with a solution of pyridine-sulfur trioxide complex (142 mg, 0.894 mmol) in DMSO (0.021 mL). The reaction mixture was warmed to rt and stirred for 2 hours. The mixture was partitioned between ethyl acetate and water and the organic phase washed with water, dried and concentrated in vacuo to give the crude title compound which was used in the next step without further purification.

UPLC-MS: RT=1.41 min; m/z=468.23 (M+H).

Step 2: 1-{4-[6-(1-hydroxy-ethyl)-3-phenyl-imidazo[1,2-a]pyridin-2-yl]-phenyl}-cyclobutyl)-carbamic acid tert-butyl ester A solution of the aldehyde from Step 1 (100 mg) in THF (1.7 mL) under argon at −30° C. was treated with a solution of methyl magnesium bromide in diethyl ether (3M, 0.21 mL, 3 Eq). The mixture was allowed to warm to −10° C., stirred for 2 hours and quenched with saturated aqueous ammonium chloride solution. The mixture was extracted with ethyl acetate and the organic phase washed with brine, dried and concentrated in vacuo to give the title compound which was used without further purification in the next step.

UPLC-MS: RT=1.10 min; m/z=484.31.

Intermediate Example Int-8-0

[1-(4-{6-[(2-methoxy-ethylamino)-methyl]-3-phenyl-imidazo[1,2-a]pyridin-2-yl}-phenyl)-cyclobutyl]-carbamic acid tert-butyl ester

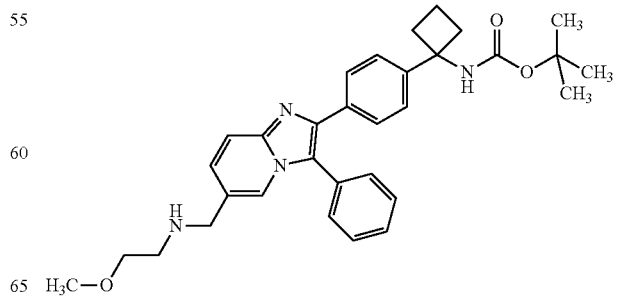

Step 1: {1-[4-(6-Chloromethyl-3-phenyl-imidazo[1,2-a]pyridin-2-yl)-phenyl]-cyclobutyl}-carbamic acid tert-butyl ester

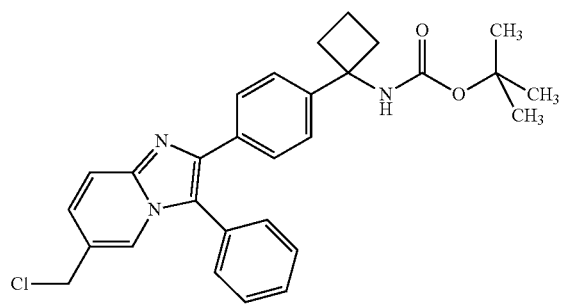 [SMILES: CC(C)(C)OC(=O)NC1(c2ccc(-c3nc4ccc(CCl)cn4c3-c3ccccc3)cc2)CCC1]

A solution of {1-[4-(6-hydroxymethyl-3-phenyl-imidazo[1,2-a]pyridin-2-yl)-phenyl]-cyclobutyl}-carbamic acid tert-butyl ester (200 mg) in DCM (1.9 mL), was treated with triethylamine (0.062 mL), cooled to 0° C. (ice bath), treated with methanesulfonyl chloride (0.028 mL, 0.358 mmol) and stirred for 2 hours at rt. The reaction mixture was partitioned between DCM and saturated aqueous sodium hydrogen-carbonate solution and the organic phase washed with brine, dried and concentrated in vacuo to give the crude title compound.
UPLC-MS: RT=1.28 min; m/z=488.24 (M+H).

Step 2: [1-(4-{6-[(2-methoxy-ethylamino)-methyl]-3-phenyl-imidazo[1,2-a]pyridin-2-yl}-phenyl)-cyclobutyl]-carbamic acid tert-butyl ester A mixture of {1-[4-(6-chloromethyl-3-phenyl-imidazo[1,2-a]pyridin-2-yl)-phenyl]-cyclobutyl}-carbamic acid tert-butyl ester (103 mg) and 2-methoxyethylamine (31 mg, 0.035 mL) in THF (1.1 mL) was heated at 110° C. under microwave irradiation for 1 hour. On cooling, the reaction mixture was concentrated in vacuo to give the crude title compound which was used in the next step without further purification.
UPLC-MS: RT=0.90 min; m/z=527.35 (M+H).

Intermediate Example Int-9-0

4-{2-[4-(1-tert-butoxycarbonylamino-cyclobutyl)-phenyl]-3-phenyl-imidazo[1,2-a]pyridin-7-yl}-pyrazole-1-carboxylic acid tert-butyl ester

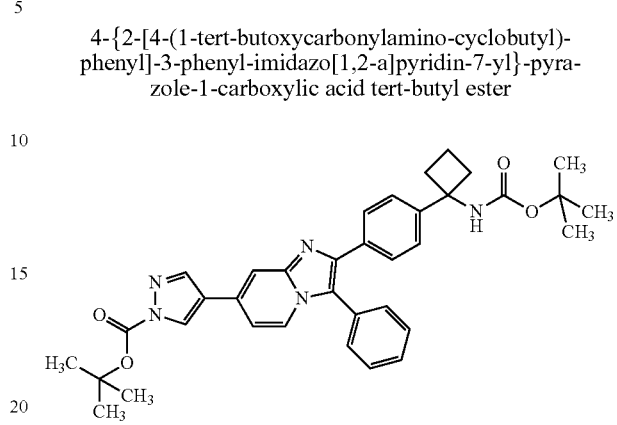

A mixture of {1-[4-(7-bromo-3-phenyl-imidazo[1,2-a]pyridin-2-yl)-phenyl]-cyclobutyl}-carbamic acid tert-butyl ester (150 mg), [1-(tert-butoxycarbonyl)-1H-pyrazol-4-yl]boronic acid (123 mg), 1,1'-bis(diphenylphosphino)ferrocene-dichloropalladium(II) (24 mg) and sodium carbonate (92 mg) in dioxane (3.1 mL) and water (0.4 mL) was degassed, placed under an argon atmosphere and heated at 105° C. under microwave irradiation for 30 minutes. On cooling, a further portion of catalyst was added (24 mg) and the mixture heated for a further 30 minutes under microwave irradiation. On cooling, the reaction was partitioned between aqueous ammonium chloride solution and DCM and the organic phase washed with brine, dried and concentrated in vacuo to give the crude title compound (183 mg) which was used in the next step (deprotection of both Boc groups under the standard conditions given in Example 1.0) without further purification.
UPLC-MS: RT=1.34 min; m/z=606.40 (M+H).

The following Intermediate Examples were prepared in analogy to Intermediate Example Int-9-0, using the appropriate bromo derivative and the appropriate boronic acid or boronic ester derivative.

| Intermediate Example | Structure/Name | 1H-NMR | UPLC-MS |
|---|---|---|---|
| Int-9-1 | 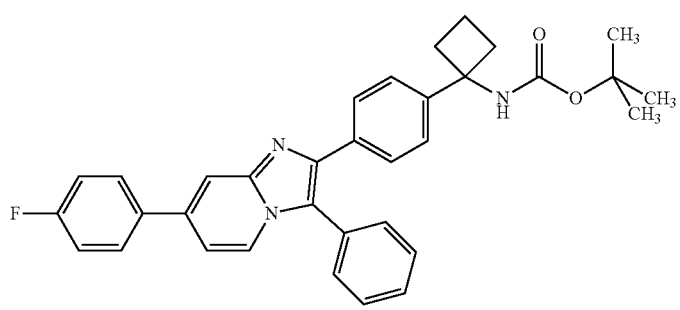 [SMILES: CC(C)(C)OC(=O)NC1(c2ccc(-c3nc4cc(-c5ccc(F)cc5)ccn4c3-c3ccccc3)cc2)CCC1]<br>(1-{4-[7-(4-Fluoro-phenyl)-3-phenyl-imidazo[1,2-a]pyridin-2-yl]-phenyl}-cyclobutyl)-carbamic acid tert-butyl ester | | RT = 1.34 min; m/z = 534.36 (M + 1) |

-continued

| Intermediate Example | Structure/Name | 1H-NMR | UPLC-MS |
|---|---|---|---|
| Int-9-2 | (1-{4-[3-Phenyl-8-(1H-pyrazol-4-yl)-imidazo[1,2-a]pyridin-2-yl]-phenyl}-cyclobutyl)-carbamic acid tert-butyl ester | | Method 2: RT = 1.49 min; m/z = 506.28 (M + 1) |
| Int-9-3 | {1-[4-(3-Phenyl-6-pyridin-3-yl-imidazo[1,2-a]pyridin-2-yl)-phenyl]-cyclobutyl}-carbamic acid tert-butyl ester (SOX 5277-1-1) | | Method 2: RT = 1.41 min; m/z (rel intensity) 517 (100, (M + H)⁺); ES– m/z (rel intensity) 515 (50, (M − H)⁻). |
| Int-9-4 | {1-[4-(3-Phenyl-6-pyridin-4-yl-imidazo[1,2-a]pyridin-2-yl)-phenyl]-cyclobutyl}-carbamic acid tert-butyl ester | | Method 2: RT = 1.40 min; m/z (rel intensity) 517 (100, (M + H)⁺). |
| Int-9-5 | {1-[4-(3-Phenyl-6-pyridin-2-yl-imidazo[1,2-a]pyridin-2-yl)-phenyl]-cyclobutyl}-carbamic acid tert-butyl ester | | Method 2: RT = 1.31 min; m/z (rel intensity) 517 (100, (M + H)⁺). |

-continued

| Intermediate Example | Structure/Name | 1H-NMR | UPLC-MS |
|---|---|---|---|
| Int-9-6 | {1-[4-(3-Phenyl-7-pyridin-4-yl-imidazo[1,2-a]pyridin-2-yl)-phenyl]-cyclobutyl}-carbamic acid tert-butyl ester | (d6-DMSO): δ 1.07 (br s, 3H), 1.29 (br s, 6H), 1.73 (br s, 1H), 1.87-1.97 (m, 1H), 2.28-2.36 (m, 4H), 7.27 (d, J = 8.6 Hz, 2H), 7.35 (dd, J = 7.3, 1.8 Hz, 1H), 7.50-7.61 (m, 7H), 7.85 (app d, J = 6.1 Hz, 2H), 8.07 (br s, 1H), 8.23 (d, J = 1.0 Hz, 1H), 8.65 (d, J = 6.1, 2H) ppm. | Method 2: RT = 1.67 min; m/z (rel intensity) 517 (100, (M + H)+). |
| Int-9-7 | {1-[4-(3-Phenyl-7-pyridin-3-yl-imidazo[1,2-a]pyridin-2-yl)-phenyl]-cyclobutyl}-carbamic acid tert-butyl ester | | Method 2: RT = 1.44 min; m/z (rel intensity) 517 (100, (M + H)+); ES− m/z (rel intensity) 515 (90,(M − H)−) |
| Int-9-8 | 4-{2-[4-(1-tert-Butoxycarbonylamino-cyclobutyl)-phenyl]-3-phenyl-imidazo[1,2-a]pyridin-7-yl}-pyrazole-1-carboxylic acid tert-butyl ester (SOX 5252-1-1) | | UPLC-MS (Method 2): RT = 1.35 min; m/z (rel intensity) 606 (100, (M + H)+); |
| Int-9-9 | (1-{4-[8-(4-Fluorophenyl)-3-phenyl-imidazo[1,2-a]pyridin-2-yl]-phenyl}-cyclobutyl)-carbamic acid tert.-butyl ester | (400 MHz, dDMSO): δ 8.20-8.32 (m, 2H), 7.99 (br., 1H), 7.43-7.68 (m, 9H), 7.31-7.42 (m, 2H), 7.29 (d, 2H), 6.92-7.02 (m, 1H), 2.20-2.42 (m, 4H), 1.82-2.02 (m, 1H), 1.61-1.82 (m, 1H), 0.93-1.43 (m, 9H) ppm. | RT = 1.63 min; m/z = 534 (ES+, M + 1) |

-continued

| Intermediate Example | Structure/Name | 1H-NMR | UPLC-MS |
|---|---|---|---|
| Int-9-10 | (1-{4-[8-(3-Fluorophenyl)-3-phenyl-imidazo[1,2-a]pyridin-2-yl]-phenyl}-cyclobutyl)-carbamic acid tert.-butyl ester | (400 MHz, dDMSO): δ 8.12-8.20 (m, 1H), 8.08 (1H), 8.00 (br., 1H), 7.45-7.68 (m, 10H), 7.20-7.32 (m, 3H), 6.93-7.01 (m, 1H), 2.20-2.42 (m, 4H), 1.82-2.02 (m, 1H), 1.62-1.82 (m, 1H), 0.92-1.42 (m, 9H) ppm. | RT = 1.66 min; m/z = 534 (ES+, M + 1) |
| Int-9-11 | (1-{4-[8-(5-Methoxypyridin-3-yl)-3-phenyl-imidazo[1,2-a]pyridin-2-yl]-phenyl}-cyclobutyl)-carbamic acid tert.-butyl ester | (300 MHz, dDMSO): δ 8.99 (1H), 8.38 (1H), 8.32 (1H), 8.00 (br, 1H), 7.70 (1H), 7.42-7.65 (m, 8H), 7.29 (d, 2H), 6.93-7.05 (m, 1H), 3.93 (s, 3H), 2.19-2.42 (m, 4H), 1.82-2.02 (m, 1H), 1.62-1.82 (m, 1H), 0.92-1.42 (m, 9H) ppm. | RT = 1.47 min; m/z = 547 (ES+, M + 1) |
| Int-9-12 | 5-{2-[4-(1-tert.-Butoxycarbonylamino-cyclobutyl)-phenyl]-3-phenyl-imidazo-[1,2-a]pyridin-8-yl}-pyrazole-1-carboxyl acid tert.-butyl ester | | RT = 1.23 min; m/z = 506 (ES+, M + 1-Boc residue) |
| Int-9-13 | 1-{4-[8-(1H-Indazol-6-yl)-3-phenyl-imidazo[1,2-a]pyridin-2-yl]-phenyl}-cyclobutyl)-carbamic acid tert-butyl ester | (300 MHz, dDMSO): δ 13.20 (1H), 8.68 (1H), 8.12 (1H), 8.00 (d, br., 1H), 7.89 (d, 1H), 7.79 (d, 1H), 7.42-7.70 (m, 9H), 7.28 (d, 2H), 6.93-7.06 (m, 1H), 2.20-2.42 (m, 4H), 1.82-2.02 (m, 1H), 1.60-1.82 (m, 1H), 0.92-1.42 (m, 9H) ppm. | RT = 1.33 min; m/z = 556 (ES+, M + 1) |

-continued

| Intermediate Example | Structure/Name | 1H-NMR | UPLC-MS |
|---|---|---|---|
| Int-9-14 | (1-{4-[6-Chloro-8-(4-fluorophenyl)-7-methyl-3-phenyl-imidazo[1,2-a]pyridin-2yl]-phenyl}-cyclobutyl)-carbamic acid tert.-butyl ester | | RT = 1.66 min; m/z = 582 (ES+, M + 1) |
| Int-9-15 | (1-{4-[6-Chloro-7-methyl-3-phenyl-8-(2H-pyrazol-3-yl)-imidazo[1,2-a]pyridin-2-yl]-phenyl}-cyclobutyl)-carbamic acid tert-butyl ester | | RT = 1.45 min; m/z = 554 (ES+, M + 1) |
| Int-9-16 | (1-{4-[7,8-Dimethyl-3-phenyl-6-(2H-pyrazol-3-yl)-imidazo[1,2-a]pyridin-2-yl]-phenyl}-cyclobutyl)-carbamic acid tert-butyl ester | | RT = 1.11 min; m/z = 532 (ES−, M − 1) |
| Int-9-17 | {1-[4-(6-Methyl-3-phenyl-8-pyridin-3-yl)-imidazo[1,2-a]pyridin-2-yl)-phenyl]-cyclobutyl}-carbamic acid tert-butyl ester | (400 MHz, dDMSO): δ 9.39 (1H), 8.57-8.68 (m, 2H), 7.80 (br., 1H), 7.40-7.65 (m, 10H), 7.25 (d, 2H), 2.20-2.41 (m, 7H), 1.82-2.00 (m, 1H), 1.62-1.80 (m, 1H), 0.92-1.42 (m, 9H) ppm. | Method 2: RT =1.61 min; m/z = 529 (ES−, M − 1) |

| Intermediate Example | Structure/Name | 1H-NMR | UPLC-MS |
|---|---|---|---|
| Int-9-18 | (1-{4-[8-(5-Methoxypyridin-3-yl)-6-methyl-3-phenyl-imidazo[1,2-a]pyridin-2-yl]-phenyl}-cyclobutyl)-carbamic acid tert-butyl ester | (400 MHz, dDMSO): δ 9.00 (1H), 8.35 (1H), 8.31 (1H), 7.80 (br., 1H), 7.40-7.65 (m, 9H), 7.29 (d, 2H), 3.93 (s, 3H), 2.20-2.40 (m, 7H), 1.82-2.00 (m, 1H), 1.65-1.80 (m, 1H), 0.92-1.40 (m, 9H) ppm. | Method 2: RT = 1.64 min; m/z = 559 (ES−, M − 1) |
| Int-9-19 | 5-{2-[4-(1-tert.-Butoxycarbonylamino-cyclobutyl)-phenyl]-6-methyl-3-phenyl-imidazo[1,2-a]pyridin-8-yl}-pyrazole-1-carboxylic acid tert-butyl ester | | Method 2: RT = 1.60 min; m/z = 518 (ES−, M − 1-Boc residue) |
| Int-9-20 | (1-{4-[6-Methyl-3-phenyl-8-(1H-pyrazol-4-yl)-imidazo[1,2-a]pyridin-2-yl]-phenyl}-cyclobutyl)-carbamic acid tert-butyl ester | (300 MHz, dDMSO): δ 13.07 (1H), 8.85 (br., 1H), 8.45 (br., 1H), 7.39-7.70 (m, 10H), 7.29 (d, 2H), 2.28-2.42 (m, 4H), 2.28 (s, 3H), 1.85-2.03 (m, 1H), 1.65-1.82 (m, 1H), 0.98-1.45 (m, 9H) ppm. | Method 2: RT = 1.57 min; m/z = 518 (ES−, M − 1) |
| Int-9-21 | (1-{4-[8-Carbamoyl-3-phenyl-6-(1H-pyrazol-4-yl)-imidazo[1,2-a]pyridin-2-yl]-phenyl}-cyclobutyl)-carbamic acid tert-butyl ester | | RT = 1.30 min; m/z = 549 (ES+, M + 1) |

| Intermediate Example | Structure/Name | 1H-NMR | UPLC-MS |
|---|---|---|---|
| Int-9-22 | 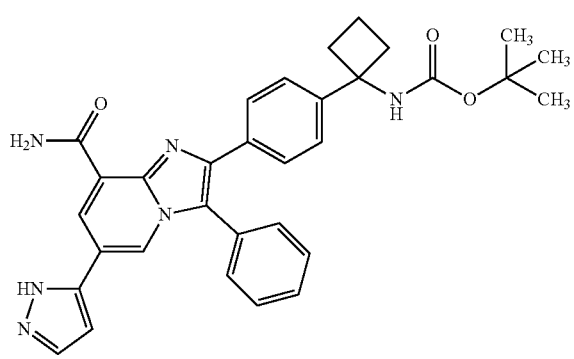 [SMILES: CC(C)(C)OC(=O)NC1(c2ccc(-c3nc4c(C(N)=O)cc(-c5ccn[nH]5)cn4c3-c3ccccc3)cc2)CCC1]<br>(1-{4-[8-Carbamoyl-3-phenyl-6-(2H-pyrazol-3-yl)-imidazo[1,2-a]pyridin-2-yl]-phenyl}-cyclobutyl)-carbamic acid tert-butyl ester | | RT = 1.34 min; m/z = 549 (ES+, M + 1) |
| Int-9-23 | 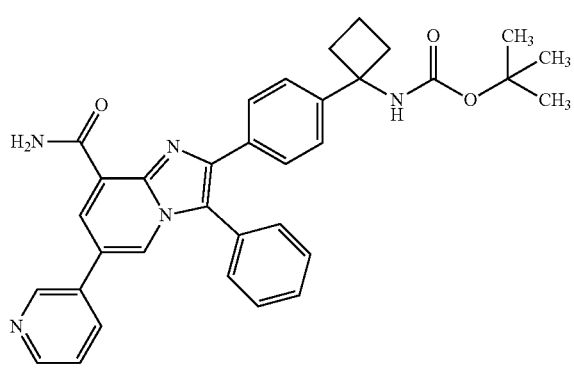 [SMILES: CC(C)(C)OC(=O)NC1(c2ccc(-c3nc4c(C(N)=O)cc(-c5cccnc5)cn4c3-c3ccccc3)cc2)CCC1]<br>{1-[4-(8-Carbamoyl-3-phenyl-6-pyridin-3-yl-imidazo[1,2-a]pyridin-2-yl)-phenyl]-cyclobutyl}-carbamic acid tert-butyl ester | | RT = 1.34 min; m/z = 560 (ES+, M + 1) |
| Int-9-24 | 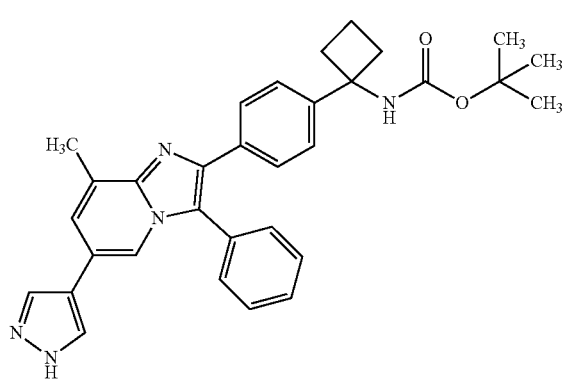 [SMILES: Cc1cc(-c2cn[nH]c2)cn2c(-c3ccccc3)c(-c3ccc(C4(NC(=O)OC(C)(C)C)CCC4)cc3)nc12]<br>(1-{4-[8-Methyl-3-phenyl-6-(1H-pyrazol-4-yl)-imidazo[1,2-a]pyridin-2-yl]-phenyl}-cyclobutyl)-carbamic acid tert-butyl ester | | RT = 1.04 min; m/z = 518 (ES−, M − 1) |

-continued

| Intermediate Example | Structure/Name | 1H-NMR | UPLC-MS |
|---|---|---|---|
| Int-9-25 | 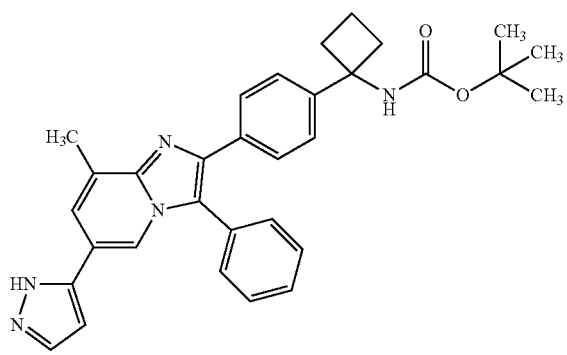 [SMILES: Cc1cc(-c2ccn[nH]2)cn2c(-c3ccccc3)c(-c3ccc(C4(NC(=O)OC(C)(C)C)CCC4)cc3)nc12]<br>(1-{4-[8-Methyl-3-phenyl-6-(2H-pyrazol-3-yl)-imidazo[1,2-a]pyridin-2-yl]-phenyl}-cyclobutyl)-carbamic acid tert-butyl ester | | RT = 1.10 min; m/z = 518 (ES−, M − 1) |
| Int-9-26 | 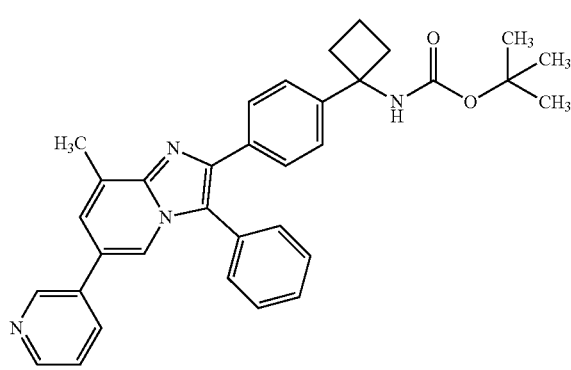 [SMILES: Cc1cc(-c2cccnc2)cn2c(-c3ccccc3)c(-c3ccc(C4(NC(=O)OC(C)(C)C)CCC4)cc3)nc12]<br>{1-[4-(8-Methyl-3-phenyl-6-pyridin-3-yl-imidazo[1,2-a]pyridin-2-yl)-phenyl]-cyclobutyl}-carbamic acid tert-butyl ester | | RT = 1.21 min; m/z = 531 (ES+, M + 1) |
| Int-9-27 | 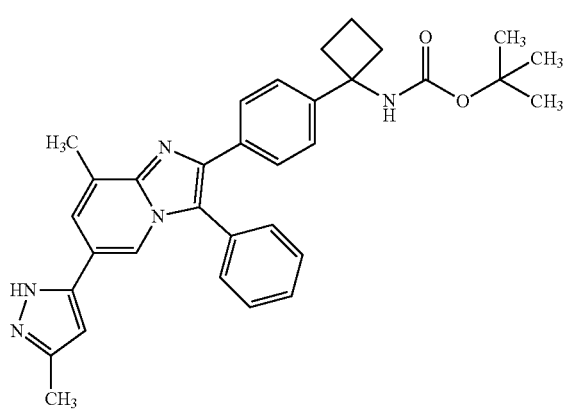 [SMILES: Cc1cc(-c2cc(C)c3nc(-c4ccc(C5(NC(=O)OC(C)(C)C)CCC5)cc4)c(-c4ccccc4)n3c2)[nH]n1]<br>(1-{4-[8-Methyl-6-(5-methyl-2H-pyrazol-3-yl)-3-phenyl-imidazo[1,2-a]pyridin-2-yl]phenyl}-cyclobutyl)-carbamic acid tert-butyl ester | | RT = 1.23 min; m/z = 532 (ES−, M − 1) |

Intermediate Example Int-9-28

(1-{4-[3-phenyl-7-(1H-pyrazol-3-yl)-imidazo[1,2-a]pyridin-2-yl]-phenyl}-cyclobutyl)-carbamic acid tert-butyl ester

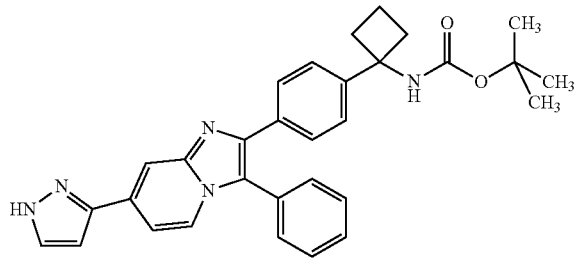 [SMILES: CC(C)(C)OC(=O)NC1(c2ccc(-c3nc4cc(-c5cc[nH]n5)ccn4c3-c3ccccc3)cc2)CCC1]

To a solution of {1-[4-(7-bromo-3-phenyl-imidazo[1,2-a]pyridin-2-yl)-phenyl]-cyclobutyl}-carbamic acid tert-butyl ester (200 mg, 0.38 mmol), and 1-(tert-butoxycarbonyl)pyrazole-5-boronic acid (164 mg, 0.77 mmol, 2 equiv) in dioxane (4 mL) under argon was added [1,1-bis(diphenylphosphino)ferrocene]dichloro-palladium(II) CH$_2$Cl$_2$ complex (63 mg, 0.77 mmol, 20 mol %), Na$_2$CO$_3$ (123 mg, 1.16 mmol, 3 equiv) and water (0.5 mL). The resulting mixture was heated at 105° C. for 8 h in a microwave apparatus. The reaction mixture was mixed with water (10 mL), a saturated aqueous NH$_4$Cl solution (10 mL) and CH$_2$Cl$_2$ (25 mL) with vigorous stirring at room temperature for 30 min. The organic phase was washed with a saturated aqueous NaCl solution (25 mL), dried (Na$_2$SO$_4$ anh), and concentrated under reduced pressure.

The resulting material was used in subsequent steps without further purification.

UPLC-MS (Method 2): RT=1.11 min; m/z (rel intensity) 506 (100, (M+H)$^+$).

The following examples were prepared in a manner analogous to that described in Intermediate Example Int-9-28: substituting appropriate starting materials where necessary:

| Intermediate Example | Structure/Name | UPLC-MS |
|---|---|---|
| Int-9-29 | 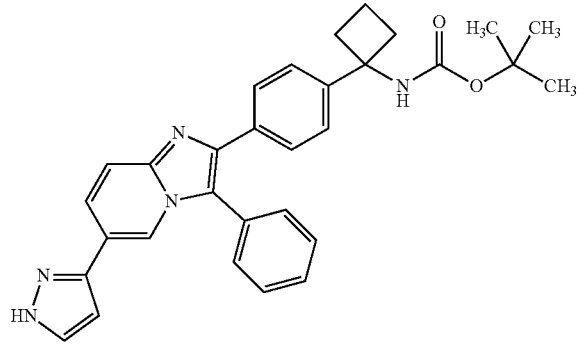 [SMILES: CC(C)(C)OC(=O)NC1(c2ccc(-c3nc4ccc(-c5cc[nH]n5)cn4c3-c3ccccc3)cc2)CCC1]<br>(1-{4-[3-Phenyl-6-(1H-pyrazol-3-yl)-imidazo[1,2-a]pyridin-2-yl]-phenyl}-cyclobutyl)-carbamic acid tert-butyl ester | Method 2: RT = 1.13 min; m/z (rel intensity) 506 (100, (M + H)$^+$). |
| Int-9-30 | 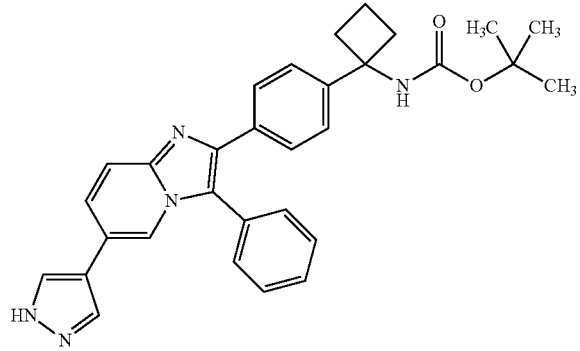 [SMILES: CC(C)(C)OC(=O)NC1(c2ccc(-c3nc4ccc(-c5cn[nH]c5)cn4c3-c3ccccc3)cc2)CCC1]<br>(1-{4-[3-Phenyl-6-(1H-pyrazol-4-yl)-imidazo[1,2-a]pyridin-2-yl]-phenyl}-cyclobutyl)-carbamic acid tert-butyl ester | Method 2: RT = 1.09 min; m/z (rel intensity) 506 (100, (M + H)$^+$). |

Intermediate Example Int-10-0

{1-[4-(7-cyclopropyl-3-phenyl-imidazo[1,2-a]pyridin-2-yl)-phenyl]-cyclobutyl}-carbamic acid tert-butyl ester

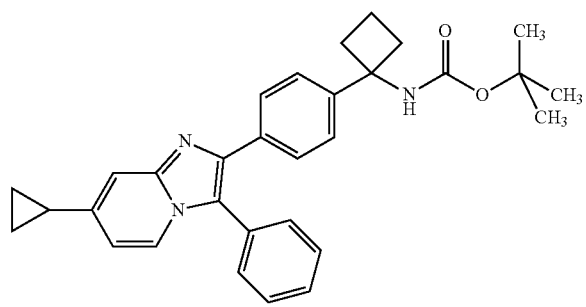 [SMILES: CC(C)(C)OC(=O)NC1(c2ccc(-c3nc4cc(C5CC5)ccn4c3-c3ccccc3)cc2)CCC1]

A mixture of {1-[4-(7-bromo-3-phenyl-imidazo[1,2-a]pyridin-2-yl)-phenyl]-cyclobutyl}-carbamic acid tert-butyl ester (200 mg, 0.38 mmol), cyclopropylboronic acid (166 mg, 1.93 mmol, 5.0 equiv), tetrakis(triphenylphosphine)palladium(0) (18 mg, 0.015 mmol, 4 mol %) and $K_3PO_4$ (164 mg, 0.77 mmol, 2.0 equiv), in toluene (4.5 mL) was heated at the reflux temperature for 16 h with monitoring by UPLC-MS. The resulting mixture was heated at 90° C. for 1 h in a microwave apparatus, then concentrated under reduced pressure. The remaining material was treated with water (25 mL), and was then extracted with EtOAc (2×25 mL). The combined organic phases were washed with water (25 mL), dried ($Na_2SO_4$ anh), and concentrated under reduced pressure. The remaining material (205 mg) was was purified using MPLC (Biotage Isolera Flash $NH_2$ Snap 10 reverse phase column; 100% $CH_2Cl_2$ for 1 min., gradient to 90% $CH_2Cl_2$/10% MeOH over 10 min.; 90% $CH_2Cl_2$/10% MeOH for 4 min.) to give {1-[4-(7-cyclopropyl-3-phenyl-imidazo[1,2-a]pyridin-2-yl)-phenyl]-cyclobutyl}-carbamic acid tert-butyl ester (162 mg, 87%):

UPLC-MS (Method 2): RT=1.21 min; m/z (rel intensity) 480 (100, $(M+H)^+$).

1H-NMR (d6-DMSO): δ 0.19 (s, 3H), 0.23 (s, 6H), 1.08 (br s, 3H), 1.28 (br s, 6H), 1.73 (br s, 1H), 1.85-1.99 (m, 1H), 2.25-2.37 (m, 4H), 6.82 (d, J=7.2 Hz, 1H), 7.25 (d, J=7.9 Hz, 2H), 7.44-7.60 (m, 7H), 7.75 (br s, 1H), 7.93 (br d, J=4.5 Hz, 1H) ppm.

The following Intermediate Example was prepared in analogy to Intermediate Example Int-10-0, using the appropriate bromide.

| Intermediate Example | Structure/Name | UPLC-MS |
|---|---|---|
| Int-10-1 | | RT = 1.31 min; m/z = 480.32 (M + H) |

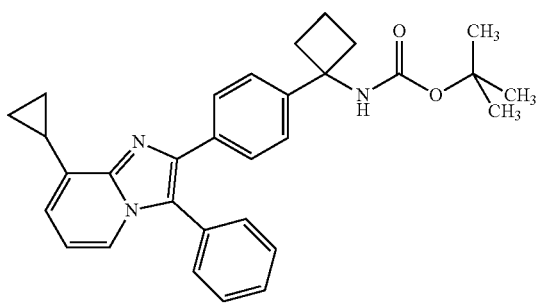 [SMILES: CC(C)(C)OC(=O)NC1(c2ccc(-c3nc4c(C5CC5)cccn4c3-c3ccccc3)cc2)CCC1]

{1-[4-(8-Cyclopropyl-3-phenyl-imidazo[1,2-a]pyridin-2-yl)-phenyl]-cyclobutyl}-carbamic acid tert-butyl ester

Intermediate Example Int-11-0

(1-{4-[3-phenyl-7-(4,4,5,5-tetramethyl-[1,3,2]dioxaborolan-2-yl)-imidazo[1,2-a]pyridin-2-yl]-phenyl}-cyclobutyl)-carbamic acid tert-butyl ester

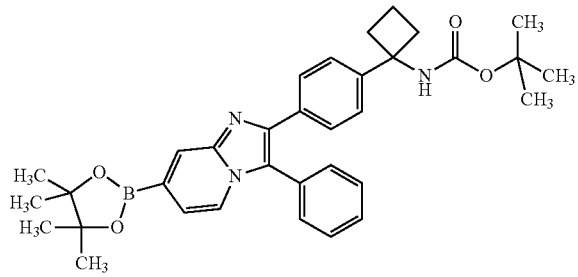 [SMILES: CC(C)(C)OC(=O)NC1(c2ccc(-c3nc4cc(B5OC(C)(C)C(C)(C)O5)ccn4c3-c3ccccc3)cc2)CCC1]

A mixture of {1-[4-(7-bromo-3-phenyl-imidazo[1,2-a]pyridin-2-yl)-phenyl]-cyclobutyl}-carbamic acid tert-butyl ester (300 mg, 0.57 mmol), bis(pinacolatoborane) (176 mg, 0.69 mmol, 1.2 equiv), [1,1-bis(diphenylphosphino)ferrocene]dichloropalladium(II) CH$_2$Cl$_2$ complex (47 mg, 0.06 mmol, 10 mol %) and potassium acetate (170 mg, 1.74 mmol, 3.0 equiv), in DMF (6 mL) under an atmosphere of argon was heated at 100° C. for 3.5 h. in a microwave apparatus. The resulting mixture was filtered and the resulting solution was used without further purification:

UPLC-MS (Method 2; in situ hydrolysis to the boronic acid was observed during UPLC analysis): RT=1.00 min; m/z (rel intensity) 484 (100, (M+H)$^+$); 967 (70, (2M+H)$^+$).

Intermediate Example Int-11-1

{1-[4-(3-Phenyl-7-pyridin-2-yl-imidazo[1,2-a]pyridin-2-yl)-phenyl]-cyclobutyl}-carbamic acid tert-butyl ester

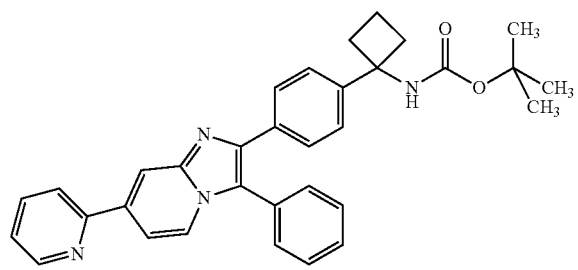 [SMILES: CC(C)(C)OC(=O)NC1(c2ccc(-c3nc4cc(-c5ccccn5)ccn4c3-c3ccccc3)cc2)CCC1]

To a solution of (1-{4-[3-phenyl-7-(4,4,5,5-tetramethyl-[1,3,2]dioxaborolan-2-yl)-imidazo[1,2-a]pyridin-2-yl]-phenyl}-cyclobutyl)-carbamic acid tert-butyl ester [prepared in a manner analogous to that described in Int 11-0; 100% yield assumed] (0.29 mmol) in DMF (3 mL) was added 2-bromopyridine (0.034 mL, 0.32 mmol, 1.1 equiv) and dioxane (1.2 mL). The resulting solution was placed under an argon atmosphere, then, [1,1-bis(diphenylphosphino)ferrocene]dichloro-palladium(II) CH$_2$Cl$_2$ complex (24 mg, 0.03 mmol, 10 mol %) and an aqueous 1 N NaOH solution (0.9 mL, 1.84 mmol, 6.3 equiv) were added. The resulting mixture was heated at 140° C. for 1 h in a microwave apparatus. The resulting mixture was added to water (15 mL). The resulting mixture was extracted with EtOAc (3×25 mL), dried (Na$_2$SO$_4$ anh), and concentrated under reduced pressure. The remaining material was purified using MPLC (Biotage Isolera; 10 g SNAP cartridge: 100% hexane for 2 min., gradient to 70% hexane/30% EtOAc over 1 min., 70% hexane/30% EtOAc for 3 min., gradient to 50% hexane/50% EtOAc over 1.5 min., 50% hexane/50% EtOAc for 2.5 min., gradient to 100% EtOAc over 1 min., 100% EtOAc for 9.6 min,) to give {1-[4-(3-phenyl-7-pyridin-2-yl-imidazo[1,2-a]pyridin-2-yl)-phenyl]-cyclobutyl}-carbamic acid tert-butyl ester (85 mg, 54% two steps):

UPLC-MS (Method 2): RT=1.53 min; m/z (rel intensity) 517 (100, (M+H)$^+$).

MS: m/z (rel intensity) 517 (100, (M+H)$^+$).

1H-NMR (d6-DMSO): δ 1.08 (br s, 3H), 1.29 (br s, 6H), 1.73 (br s, 1H), 1.87-2.00 (m, 1H), 2.26-2.38 (m, 4H), 7.27 (d, J=8.5 Hz, 2H), 7.37 (dd, J=7.4, 4.9 Hz, 1H), 7.49-7.62 (m, 7H), 7.69 (dd, J=7.2, 1.7 Hz, 2H), 7.90 (app td, 7.8, 1.7 Hz, 1H), 8.06 (br d, J=7.0 Hz, 1H), 8.16 (d, J=8.1 Hz, 1H), 8.38 (s, 1H) ppm.

The following examples were prepared in a manner analogous to that described in Intermediate Example Int-11-1: substituting appropriate starting materials where necessary:

| Example | Structure/Name | UPLC-MS |
|---|---|---|
| Int-11-2 | <br>(1-{4-[7-(1H-Imidazol-2-yl)-3-phenyl-imidazo[1,2-a]pyridin-2-yl]-phenyl}-cyclobutyl)-carbamic acid tert-butyl ester | Method 2: RT = 1.32 min;<br>m/z (rel intensity) 506 (100, (M + H)$^+$). |

| Example | Structure/Name | UPLC-MS |
| --- | --- | --- |
| Int-11-3 | (1-{4-[7-(3H-Imidazol-4-yl)-3-phenyl-imidazo[1,2-a]pyridin-2-yl]-phenyl}-cyclobutyl)-carbamic acid tert-butyl ester | Method 2: RT = 1.31 min;<br>m/z (rel intensity) 506 (100, (M + H)+); |
| Int-11-4 | (1-{4-[7-(3-Methyl-3H-imidazol-4-yl)-3-phenyl-imidazo[1,2-a]pyridin-2-yl]-phenyl}-cyclobutyl)-carbamic acid tert-butyl ester | Method 2: RT = 1.63 min;<br>m/z (rel intensity) 520 (100, (M + H)+) |
| Int-11-5 | (1-{4-[6-(3H-Imidazol-4-yl)-3-phenyl-imidazo[1,2-a]pyridin-2-yl]-phenyl}-cyclobutyl)-carbamic acid tert-butyl ester (SOX 5458-2-4) | Method 2: RT = 1.26 min;<br>m/z (rel intensity) 506 (100, (M + H)+); ES−<br>m/z (rel intensity) 504 (100, (M − H)−) |
| Int-11-6 | (1-{4-[6-(1H-Imidazol-2-yl)-3-phenyl-imidazo[1,2-a]pyridin-2-yl]-phenyl}-cyclobutyl)-carbamic acid tert-butyl ester (SOX 5417-1-1) | Method 2: RT = 1.18 min;<br>m/z (rel intensity) 506 (100, (M + H)+); ES−<br>m/z (rel intensity) 504 (100, (M − H)−) |

| Example | Structure/Name | UPLC-MS |
|---|---|---|
| Int-11-7 | 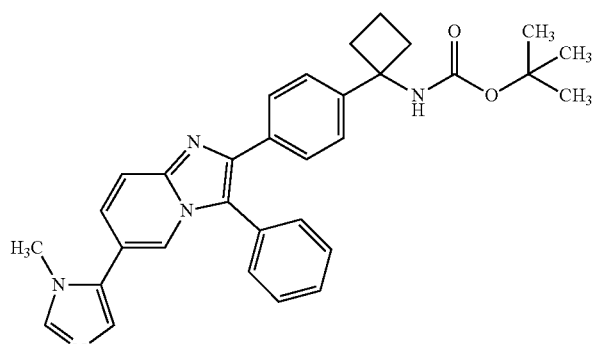<br>(1-{4-[6-(3-Methyl-3H-imidazol-4-yl)-3-phenyl-imidazo[1,2-a]pyridin-2-yl]-phenyl}-cyclobutyl)-carbamic acid tert-butyl ester | Method 2: RT = 1.03 min; m/z (rel intensity) 520 (40, (M + H)$^+$). |
| Int-11-8 | 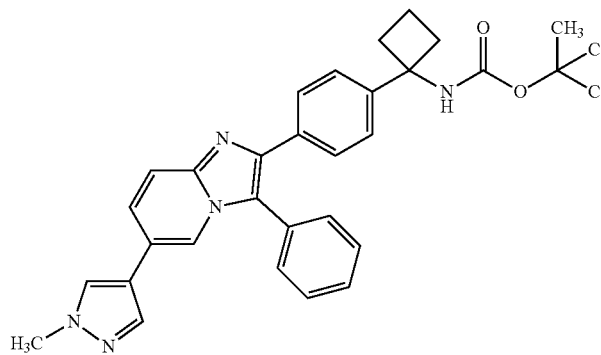<br>(1-{4-[6-(1-Methyl-1H-pyrazol-4-yl)-3-phenyl-imidazo[1,2-a]pyridin-2-yl]-phenyl}-cyclobutyl)-carbamic acid tert-butyl ester (SOX 5366-1-1) | Method 2: RT = 1.16 min; m/z (rel intensity) 520 (100, (M + H)$^+$). |
| Int-11-9 | 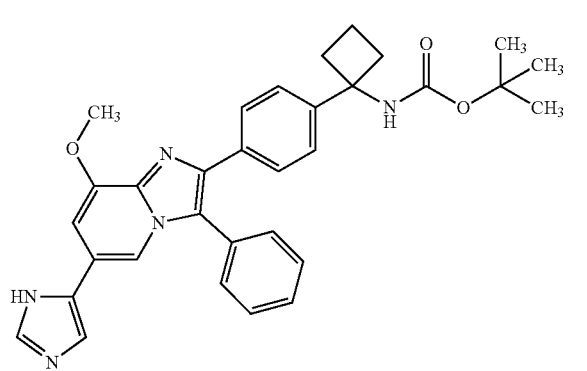 [SMILES: COc1cc(-c2cnc[nH]2)cn2c(-c3ccccc3)c(-c3ccc(C4(NC(=O)OC(C)(C)C)CCC4)cc3)nc12]<br>(1-{4-[6-(3H-Imidazol-4-yl)-8-methoxy-3-phenyl-imidazo[1,2-a]pyridin-2-yl]-phenyl}-cyclobutyl)-carbamic acid tert-butyl ester | Method 2: RT = 1.27 min; m/z (rel intensity) 536 (100, (M + H)$^+$); ES– m/z (rel intensity) 534 (100, (M – H)$^-$). |

| Example | Structure/Name | UPLC-MS |
|---|---|---|
| Int-11-10 | 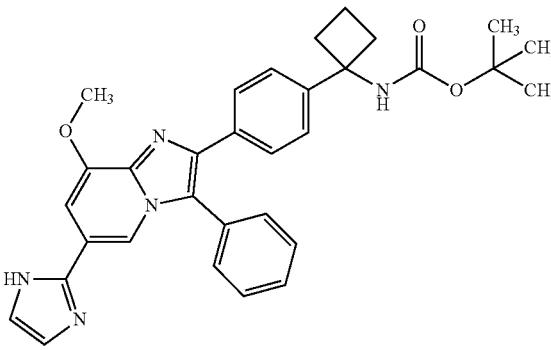 [SMILES: COc1cc(-c2ncc[nH]2)cn2c(-c3ccccc3)c(-c3ccc(C4(NC(=O)OC(C)(C)C)CCC4)cc3)nc12]<br>(1-{4-[6-(1H-Imidazol-2-yl)-8-methoxy-3-phenyl-imidazo[1,2-a]pyridin-2-yl]-phenyl}-cyclobutyl)-carbamic acid tert-butyl ester | Method 2: RT = 1.30 min; m/z (rel intensity) 536 (100, (M + H)$^+$); ES– m/z (rel intensity) 534 (100, (M – H)$^-$). |
| Int-11-11 | 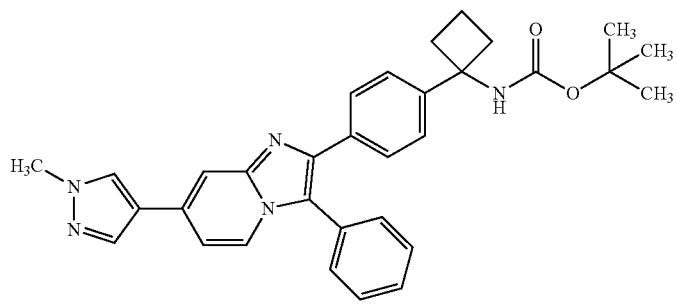 [SMILES: Cn1cc(-c2ccn3c(-c4ccccc4)c(-c4ccc(C5(NC(=O)OC(C)(C)C)CCC5)cc4)nc3c2)cn1]<br>(1-{4-[7-(1-Methyl-1H-pyrazol-4-yl)-3-phenyl-imidazo[1,2-a]pyridin-2-yl]-phenyl}-cyclobutyl)-carbamic acid tert-butyl ester | Method 2: RT = 1.66 min; m/z (rel intensity) 520 (100, (M + H)$^+$). |

Intermediate Example Int-12-0

[1-(4-{7-[2-(1,3-dioxo-1,3-dihydro-isoindol-2-yl)-ethoxy]-3-phenyl-imidazo[1,2-a]pyrimidin-2-yl}-phenyl)-cyclobutyl]-carbamic acid tert-butyl ester

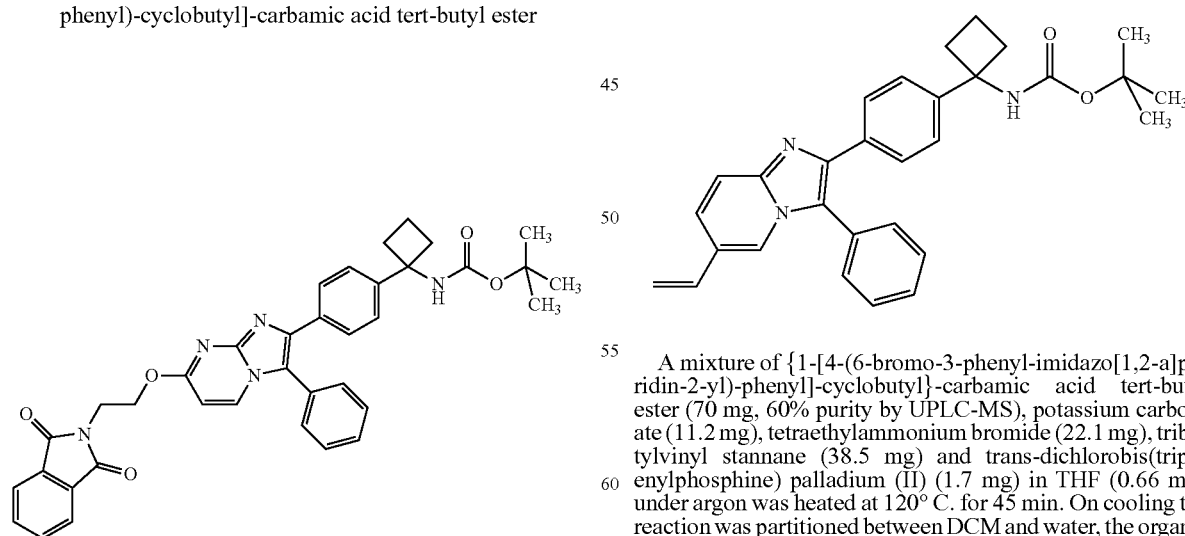

The Intermediate Example Int-12-0 was prepared in analogy to Intermediate Example Int-4-0.

UPLC-MS (Method 2): RT=1.53 min; m/z=630.33 (M+H)

Intermediate Example Int-13-0

{1-[4-(3-phenyl-6-vinyl-imidazo[1,2-a]pyridin-2-yl)-phenyl]-cyclobutyl}-carbamic acid tert-butyl ester

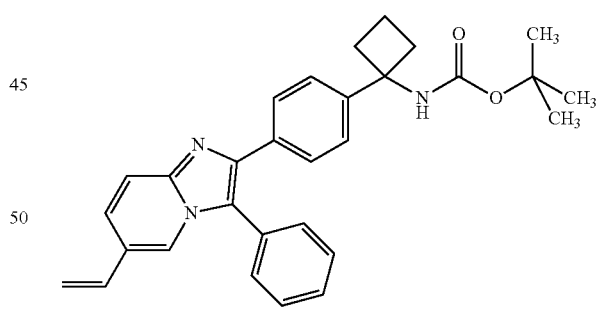

A mixture of {1-[4-(6-bromo-3-phenyl-imidazo[1,2-a]pyridin-2-yl)-phenyl]-cyclobutyl}-carbamic acid tert-butyl ester (70 mg, 60% purity by UPLC-MS), potassium carbonate (11.2 mg), tetraethylammonium bromide (22.1 mg), tributylvinyl stannane (38.5 mg) and trans-dichlorobis(triphenylphosphine) palladium (II) (1.7 mg) in THF (0.66 mL) under argon was heated at 120° C. for 45 min. On cooling the reaction was partitioned between DCM and water, the organic extract dried and concentrated to give the crude title compound which was used without further purification.

UPLC-MS: RT=1.38 min; m/z=466.38 (M+H).

The following Intermediate Example was prepared in analogy to Intermediate Example Int-13-0, using the appropriate bromide.

| Intermediate Example | Structure/Name | UPLC-MS |
|---|---|---|
| Int-13-1 | {1-[4-(3-Phenyl-8-vinyl-innidazo[1,2-a]pyridin-2-yl)-phenyl]-cyclobutyl}-carbamic acid tert-butyl ester | |

Intermediate Example Int-13-2

{1-[4-(3-phenyl-7-vinyl-imidazo[1,2-a]pyridin-2-yl)-phenyl]-cyclobutyl}-carbamic acid tert-butyl ester

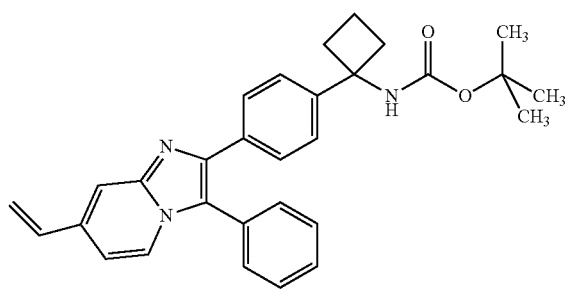 [SMILES: C=Cc1ccn2c(-c3ccccc3)c(-c3ccc(C4(NC(=O)OC(C)(C)C)CCC4)cc3)nc2c1]

A mixture of {1-[4-(7-bromo-3-phenyl-imidazo[1,2-a]pyridin-2-yl)-phenyl]-cyclobutyl}-carbamic acid tert-butyl ester (100 mg, 0.19 mmol) and tetrakis(triphenylphosphine)-palladium(0) (2.2 mg, 0.2 mmol, 1.0 mol %) in DME (1.5 mL) under an atmosphere of argon was stirred at room temperature for 10 min. To the resulting mixture was added $K_2CO_3$ (26.7 mg, 0.19 mmol, 1.0 equiv) and water (0.5 mL), followed by 2,4,6-trivinyl-cyclotriboroxane pyridine complex (46.4 mg, 0.19 mmol, 1 equiv). The resulting mixture was heated at the reflux temperature for 16 h with monitoring by UPLC-MS. The resulting mixture was concentrated under reduced pressure and treated with water (10 mL). The resulting mixture was extracted with EtOAc (2×10 mL). The combined organic phases were washed with water (10 mL), dried ($Na_2SO_4$ anh), and concentrated under reduced pressure. The remaining material was purified using MPLC (Biotage Isolera Flash $NH_2$ Snap 10 reverse phase column; 99% $CH_2Cl_2$/1% MeOH for 1 min., gradient to 90% $CH_2Cl_2$/10% MeOH over 10 min.; 90% $CH_2Cl_2$/10% MeOH over 5.2 min.) to give {1-[4-(3-phenyl-7-vinyl-imidazo[1,2-a]pyridin-2-yl)-phenyl]-cyclobutyl}-carbamic acid tert-butyl ester (77 mg, 85%),:

UPLC-MS (Method 2): RT=1.23 min; m/z (rel intensity) 466 (100, (M+H)$^+$).

The following examples were prepared in a manner analogous to that described in Intermediate Example Int-13-2: substituting appropriate starting materials where necessary:

| Intermediate Example | Structure/Name | UPLC-MS |
|---|---|---|
| Int-13-3 | {1-[4-(8-Methoxy-3-phenyl-6-vinyl-imidazo[1,2-a]pyridin-2-yl)-phenyl]-cyclobutyl}-carbamic acid tert-butyl ester | Method 2: RT = 1.56 min; m/z (rel intensity) 496 (100, (M + H)$^+$), 993 (80, (2M + H)$^+$); ES– m/z (rel intensity) 494 (80, (M – H)$^-$). |

Intermediate Example Int-13-4

{1-[4-(6-chloro-3-phenyl-8-vinyl-imidazo[1,2-a]pyridin-2-yl)-phenyl]-cyclobutyl}-carbamic acid tert-butyl ester

Intermediate Example Int-14-0

{1-[4-(3-phenyl-7-trimethylsilanylethynyl-imidazo[1,2-a]pyridin-2-yl)-phenyl]-cyclobutyl}-carbamic acid tert-butyl ester (SOX 5226-1-1)

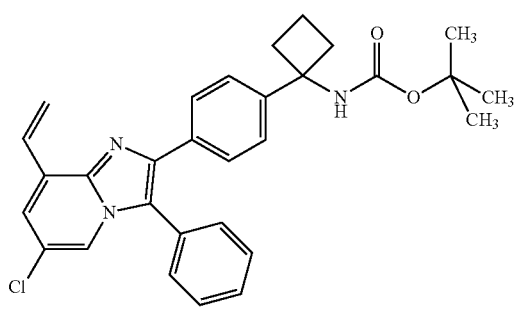 [SMILES: C=Cc1cc(Cl)cn2c(-c3ccccc3)c(-c3ccc(C4(NC(=O)OC(C)(C)C)CCC4)cc3)nc12]

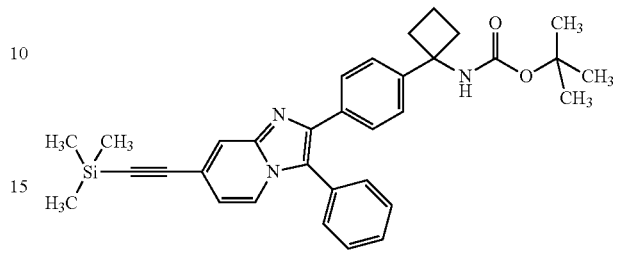

105 mg (0.19 mmol) {1-[4-(8-Bromo-6-chloro-3-phenyl-imidazo[1,2-a]pyridin-2-yl)-phenyl]-cyclobutyl}-carbamic acid tert-butyl ester, 45.7 mg (0.19 mmol) 2,4,6-trivinyl-cyclotriboroxane×pyridine, 21.9 mg (0.019 mmol) tetrakis triphenylphosphine palladium(0) and 26.2 mg (0.19 mmol) potassium carbonate in 1.48 mL dimethoxyethane and 0.52 mL water were heated in a microwave vial at 110° C. for 16 hours (heating block). The reaction mixture was poured on water/saturated ammonium chloride/dichloromethane and vigorously stirred for 30 minutes. The organic phase was separated and washed with brine, dried (sodium sulfate), filtrated and the solvent was removed. The crude product (120.9 mg) was used in the next step without further purification.

UPLC-MS: RT=1.75 min; m/z=500 (ES+, M+1)

The following intermediate example had been prepared in analogy according to intermediate example Int-13-4 by reacting {1-[4-(6-bromo-7,8-dimethyl-3-phenyl-imidazo[1,2-a]pyridin-2-yl)-phenyl]-cyclobutyl}-carbamic acid tert-butyl ester under the appropriate conditions.

To a mixture of {1-[4-(7-bromo-3-phenyl-imidazo[1,2-a]pyridin-2-yl)-phenyl]-cyclobutyl}-carbamic acid tert-butyl ester (100 mg, 0.19 mmol), [1,1-bis(diphenylphosphino)-ferrocene]dichloropalladium(II) $CH_2Cl_2$ complex (7.9 mg, 0.01 mmol, 5 mol %) and copper(I) iodide (3.7 mg, 0.019 mmol, 10 mol %) in DMF (2 mL) under an argon atmosphere was added trimethylsilylacetylene (0.08 mL, 0.58 mmol, 3.0 equiv) and triethylamine (0.13 mL, 0.96 mmol, 5.0 equiv). The resulting mixture was heated at 90° C. for 1 h in a microwave apparatus, then concentrated under reduced pressure. The remaining material was separated between water (50 mL) and EtOAc (50 mL). The aqueous phase was extracted with EtOAc (50 mL). The combined organic phases were washed with water (25 mL), dried ($Na_2SO_4$ anh), and concentrated under reduced pressure. The remaining material (112 mg) was purified using MPLC (Biotage Isolera Flash $NH_2$ Snap 10 reverse phase column; 99% $CH_2Cl_2$/1% MeOH for 1 min., gradient to 90% $CH_2Cl_2$/10% MeOH over 10 min.; 90% $CH_2Cl_2$/10% MeOH for 5.2 min.) to give {1-[4-(3-phenyl-7-trimethylsilanylethynyl-imidazo[1,2-a]pyridin-2-yl)-phenyl]-cyclobutyl}-carbamic acid tert-butyl ester (84 mg, 82%):

UPLC-MS (Method 2): RT=1.73 min; m/z (rel intensity) 536 (100, (M+H)$^+$).

1H-NMR (d6-DMSO): δ 0.19 (s, 3H), 0.23 (s, 6H), 1.08 (br s, 3H), 1.28 (br s, 6H), 1.73 (br s, 1H), 1.85-1.99 (m, 1H),

| Intermediate example | Structure/Name | 1H-NMR | UPLC-MS |
|---|---|---|---|
| Int-13-5 | 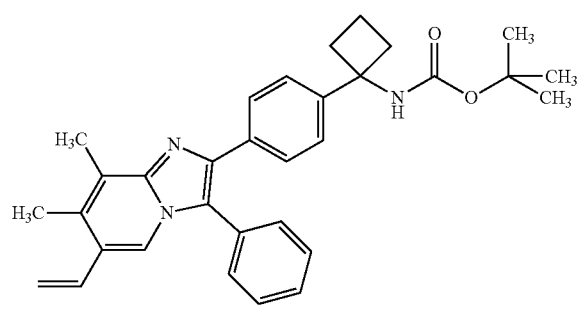 [SMILES: C=Cc1cn2c(-c3ccccc3)c(-c3ccc(C4(NC(=O)OC(C)(C)C)CCC4)cc3)nc2c(C)c1C]<br>{1-[4-(7,8-Dimethyl-3-phenyl-6-vinyl-imidazo[1,2-a]pyridin-2-yl)-phenyl]-cyclobutyl}-carbamic acid tert-butyl ester | | RT = 1.21 min; m/z = 494 (ES+, M + 1) |

2.25-2.37 (m, 4H), 6.82 (d, J=7.2 Hz, 1H), 7.25 (d, J=7.9 Hz, 2H), 7.44-7.60 (m, 7H), 7.75, br s, 1H), 7.93 (br d, J=4.5 Hz, 1H) ppm.

Intermediate Example 14-1

1-[4-(3-phenyl-7-trimethylsilanylethynyl-imidazo[1,2-a]pyridin-2-yl)-phenyl]-cyclobutylamine

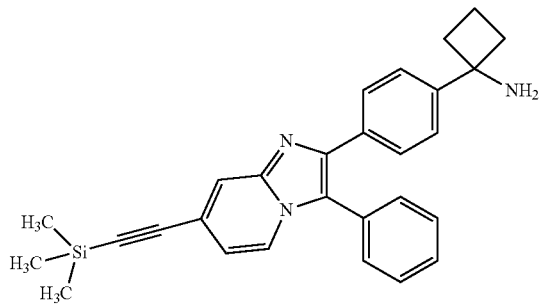 [SMILES: C[Si](C)(C)C#Cc1ccn2c(-c3ccccc3)c(-c3ccc(C4(N)CCC4)cc3)nc2c1]

To a solution of {1-[4-(3-phenyl-7-trimethylsilanylethynyl-imidazo[1,2-a]pyridin-2-yl)-phenyl]-cyclobutyl}-carbamic acid tert-butyl ester (84 mg, 0.16 mmol) in MeOH (0.8 mL) and CH$_2$Cl$_2$ (1.3 mL) was added a 4 molar solution of HCl in dioxane (0.8 mL, 3.1 mmol, 20 equiv) and the resulting solution was stirred at room temperature for 18 h with monitoring by UPLC-MS and the resulting solution was concentrated under reduced pressure. The remaining material (84 mg) was purified using MPLC (Biotage Isolera Flash NH$_2$ Snap 10 reverse phase column; 100% CH$_2$Cl$_2$ for 1 min., gradient to 95% CH$_2$Cl$_2$: 5% MeOH over 10 min.; 95% CH$_2$Cl$_2$: 5% MeOH for 5.2 min.). The resulting partially purified material (48 mg) was triturated with diisopropyl ether to give 1-[4-(3-phenyl-7-trimethylsilanylethynyl-imidazo[1,2-a]pyridin-2-yl)-phenyl]-cyclobutylamine (18 mg, 24%). The resulting diisopropyl ether solution was concentrated under reduced pressure. The remaining material was triturated with diisopropyl ether to give 1-[4-(3-phenyl-7-trimethylsilanylethynyl-imidazo[1,2-a]pyridin-2-yl)-phenyl]-cyclobutylamine (20 mg, 30%, 54% total):

UPLC-MS (Method 2): RT=1.67 min; m/z (rel intensity) 436 (10, (M+H)$^+$), 871 (50, (2M+H)$^+$).

1H-NMR (d6-DMSO): δ 0.04 (s, 9H), 1.35-1.43 (m, 1H), 1.70-1.77 (m, 1H), 1.79-1.84 (m, 2H), 2.09-2.15 (m, 2H), 6.61, (dd, J=7.2, 1.5 Hz, 1H), 7.15 (d, J=8.3 Hz, 2H), 7.28-7.40 (m, 7H), 7.55 (s, 1H), 7.72, (d, J=6.8, 1H) ppm.

Intermediate Example Int-15-0

(E)-3-{2-[4-(1-tert-butoxycarbonylamino-cyclobutyl)-phenyl]-3-phenyl-imidazo[1,2-a]pyridin-7-yl}-acrylic acid methyl ester

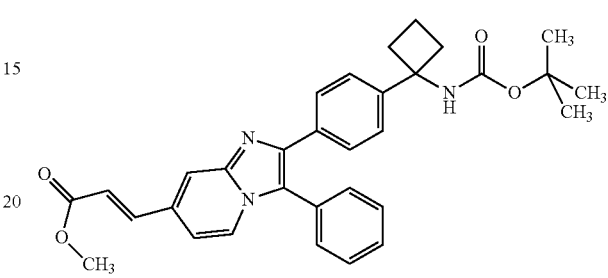

To a mixture of {1-[4-(7-bromo-3-phenyl-imidazo[1,2-a]pyridin-2-yl)-phenyl]-cyclobutyl}-carbamic acid tert-butyl ester (534 mg, 1.03 mmol), methyl acrylate (0.19 mL, 2.06 mmol, 2.0 equiv), triethylamine (0.16 mL, 1.17 mmol, 1.1 equiv), palladium(II) acetate (17 mg, 0.08 mmol, 7 mol %) and tri (2-tolyl)phosphine (53 mg, 0.18 mmol, 17 mol %) in acetonitrile (7 mL) was heated at 150° C. for 2 h. in a microwave apparatus. The reaction mixture was mixed with water (10 mL), a saturated aqueous NH$_4$Cl solution (10 mL) and CH$_2$Cl$_2$ (25 mL) with vigorous stirring at room temperature for 30 min. The resulting organic phase was washed with a saturated aqueous NaCl solution, dried (Na$_2$SO$_4$ anh), and concentrated under reduced pressure to give (E)-3-{2-[4-(1-tert-butoxycarbonylamino-cyclobutyl)-phenyl]-3-phenyl-imidazo[1,2-a]pyridin-7-yl}-acrylic acid methyl ester (452 mg, 75%):

UPLC-MS (Method 2): RT=1.52 min; m/z (rel intensity) 524 (100, (M+H)$^+$); ES–: m/z (rel intensity) 522 (10, (M–H)$^-$).

The following examples were prepared in a manner analogous to that described in Intermediate Example Int-15-0: substituting appropriate starting materials where necessary:

| Intermediate Example | Structure/Name | UPLC-MS |
|---|---|---|
| Int-15-1 | ![structure] (1-{4-[7-((E)-2-Carbamoyl-vinyl)-3-phenyl-imidazo[1,2-a]pyridin-2-yl]-phenyl}-cyclobutyl)-carbamic acid tert-butyl ester | Method 2: RT = 1.10 min; m/z (rel intensity) 509 (100, (M + H)$^+$). |

| Intermediate Example | Structure/Name | UPLC-MS |
|---|---|---|
| Int-15-2 | 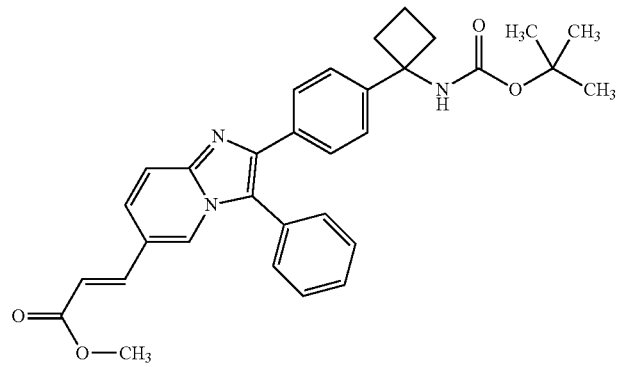 [SMILES: COC(=O)/C=C/c1ccc2nc(-c3ccc(C4(NC(=O)OC(C)(C)C)CCC4)cc3)c(-c3ccccc3)n2c1]<br>(E)-3-{2-[4-(1-tert-Butoxycarbonylamino-cyclobutyl)-phenyl]-3-phenyl-imidazo[1,2-a]pyridin-6-yl}-acrylic acid methyl ester | Method 2: RT = 1.40 min; m/z (rel intensity) 524 (30, (M + H)$^+$). |
| Int-15-3 | 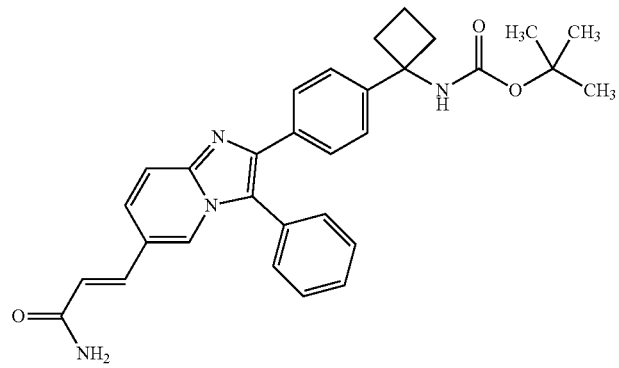 [SMILES: CC(C)(C)OC(=O)NC1(c2ccc(-c3nc4ccc(/C=C/C(N)=O)cn4c3-c3ccccc3)cc2)CCC1]<br>(1-{4-[6-((E)-2-Carbamoyl-vinyl)-3-phenyl-imidazo[1,2-a]pyridin-2-yl]-phenyl}-cyclobutyl)-carbamic acid tert-butyl ester | Method 2: RT = 1.07 min; m/z (rel intensity) 509 (100, (M + H)$^+$). |

Intermediate Example Int-16-0

(1-{4-[8-((E)-2-carbamoyl-vinyl)-6-methyl-3-phenyl-imidazo[1,2-a]pyridin-2-yl]-phenyl}-cyclobutyl)-carbamic acid tert.-butyl ester

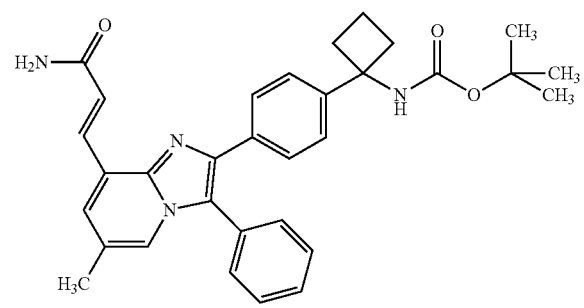 [SMILES: Cc1cc(/C=C/C(N)=O)c2nc(-c3ccc(C4(NC(=O)OC(C)(C)C)CCC4)cc3)c(-c3ccccc3)n2c1]

50 mg (0.09 mmol) {1-[4-(8-Bromo-6-methyl-3-phenyl-imidazo[1,2-a]pyridin-2-yl]-phenyl]-cyclobutyl}-carbamic acid tert-butyl ester, 13.4 mg (0.19 mmol) acryl amide, 4.86 mg (0.016 mmol) tri-2-tolylphosphane, 2.1 mg (0.009 mmol) palladium(II) acetate and 0.02 mL (0.1 mmol) triethylamine in 0.7 mL degassed acetonitrile were heated in the microwave at 110° C. for 60'. Due to an incomplete reaction additional 13.3 mg acrylamide and 4.2 mg palladium(II) acetate were added, and heating in the microwave was continued for two hours. The reaction mixture was poured on water/saturated ammonium chloride/dichloromethane and vigorously stirred for 30 minutes. The organic phase was separated and the aqueous phase was once more extracted with dichloromethane. The combined organic extracts were washed twice with brine, dried, and the solvent was removed. The crude product (76 mg) was purified by chromatography on silicagel (eluents: hexane/ethyl acetate) yielding 24.2 mg (49.3%) of the desired compound.

UPLC-MS (Method 2): RT=1.45 min; m/z=523 (ES+, M+1)

$^1$H-NMR (300 MHz, CDCl$_3$): δ 8.06 (d, 1H), 7.79 (d, 1H), 7.13-7.72 (m, 11H), 5.89 (very br., 1H), 5.59 (very br., 1H), 2.35-2.68 (m, 4H), 2.30 (s, 3H), 1.95-2.20 (m, 1H), 1.72-1.92 (m, 1H), 1.12-1.50 (m, 9H) ppm.

The following intermediate examples had been prepared in analogy according to intermediate example Int-16-0 by reacting the corresponding intermediates under the appropriate conditions.

| Intermediate example | Structure/Name | 1H-NMR | UPLC-MS |
|---|---|---|---|
| Int-16-1 | (1-{4-[8-((E)-2-Carbamoyl-vinyl)-6-chloro-7-methyl-3-phenyl-imidazo[1,2-a]pyridin-2-yl]-phenyl}-cyclobutyl)-carbamic acid tert.-butyl ester | | RT = 1.46 min; m/z = 557 (ES+, M + 1) |
| Int-16-2 | (1-{4-[6-((E)-2-Carbamoyl-vinyl)-7,8-dimethyl-3-phenyl-imidazo[1,2-a]pyridin-2-yl]-phenyl}-cyclobutyl)-carbamic acid tert.-butyl ester | | RT = 1.06 min; m/z = 537 (ES+, M + 1) |

Intermediate Example Int-17-0

2-[4-(1-tert-butoxycarbonylamino-cyclobutyl)-phenyl]-8-methoxy-3-phenyl-imidazo[1,2-a]pyridine-6-carboxylic acid methyl ester

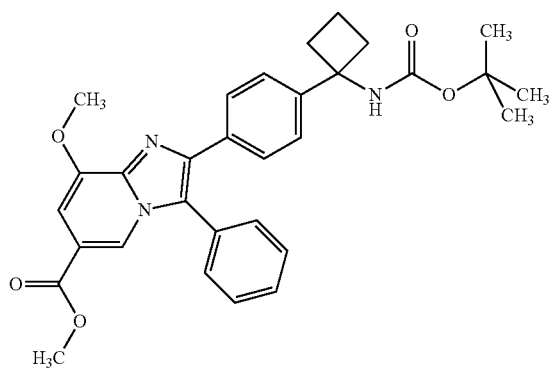 [SMILES: COC(=O)c1cc(OC)c2nc(-c3ccc(C4(NC(=O)OC(C)(C)C)CCC4)cc3)c(-c3ccccc3)n2c1]

The following reaction was carried out in a 50 mL autoclave reactor. {1-[4-(6-Bromo-8-methoxy-3-phenyl-imidazo[1,2-a]pyridin-2-yl)-phenyl]-cyclobutyl}-carbamic acid tert-butyl ester (700 mg, 1.28 mmol) was dissolved in methanol/THF (10:1, 20 mL) and Pd(dppf)Cl$_2$ (210 mg) and triethylamine (200 μL) were added. The mixture was purged with CO and stirred at rt under a CO pressure of 11 bar for 1 hour. The system was evacuated, placed under a CO pressure of 10 bar and the mixture heated at 100° C. at this pressure overnight. After a CO uptake of 2.8 bar the reaction was cooled, the pressure released and the mixture concentrated in vacuo. Purification by chromatography on silica gel (gradient elution: hexane to hexane:EtOAc 3:7) gave the product (480 mg, 70%).

UPLC-MS: RT=1.66 min; m/z=528.25 (M+H).

The following intermediate examples had been prepared in analogy according to intermediate example Int-17-0 by reacting the corresponding starting materials with carbon monoxide in an autoclave.

| Intermediate example | Structure/Name | 1H-NMR | UPLC-MS |
|---|---|---|---|
| Int-17-1 | 2-[4-[1-tert.-Butoxycarbonylamino-cyclobutyl)-phenyl]-6-methyl-3-phenyl-imidazo[1,2-a]pyridine-8-carboxylic acid methyl ester | (300 MHz, dDMSO): δ 7.98 (br., 1H), 7.75 (1H), 7.48-7.62 (m, 8H), 7.28 (d, 2H), 3.92 (s, 3H), 2.18-2.42 (m, 7H), 1.81-2.01 (m, 1H), 1.62-1.81 (m, 1H), 0.94-1.40 (m, 9H) ppm. | |
| Int-17-2 | 2-[4-[1-tert.-Butoxycarbonylamino-cyclobutyl)-phenyl]-6-chloro-7-methyl-3-phenyl-imidazo[1,2-a]pyridine-8-carboxylic acid methyl ester | | RT = 1.51 min; m/z = 546 (ES+, M + 1) |
| Int-17-3 | 2-[4-[1-tert.-Butoxycarbonylamino-cyclobutyl)-phenyl]-7,8-dimethyl-3-phenyl-imidazo[1,2-a]pyridine-6-carboxylic acid methyl ester | (300 MHz, dDMSO): δ 8.28 (s, 1H), 7.40-7.68 (m, 8H), 7.28 (d, 2H), 3.76 (s, 3H), 2.59 (s, 3H), 2.20-2.42 (m, 4H), 1.82-2.02 (m, 1H), 1.62-1.82 (m, 1H), 0.96-1.43 (m, 9H) ppm. | |
| Int-17-4 | 2-[4-[1-tert.-Butoxycarbonylamino-cyclobutyl)-phenyl]-8-methyl-3-phenyl-imidazo[1,2-a]pyridine-6-carboxylic acid methyl ester | (300 MHz, dDMSO): δ 8.31 (br., 1H), 7.45-7.68 (m, 9H), 7.28 (d, 2H), 3.81 (s, 3H), 2.61 (s, 3H), 2.22-2.42 (m, 4H), 1.82-2.02 (m, 1H), 1.62-1.82 (m, 1H), 0.98-1.42 (m, 9H) ppm. | |

| Intermediate example | Structure/Name | 1H-NMR | UPLC-MS |
|---|---|---|---|
| Int-17-5 | 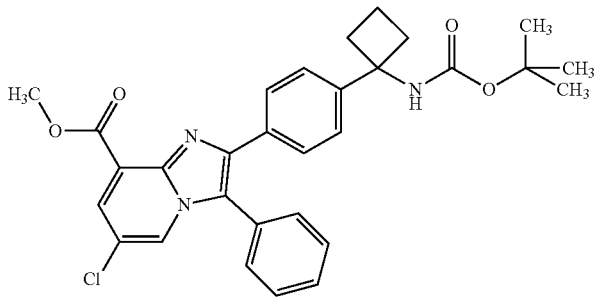 [SMILES: COC(=O)c1cc(Cl)cn2c(-c3ccccc3)c(-c3ccc(C4(NC(=O)OC(C)(C)C)CCC4)cc3)nc12]<br>2-[4-[1-tert.-Butoxycarbonylamino-cyclobutyl)-phenyl]-6-chloro-3-phenyl-imidazo[1,2-a]pyridine-8-carboxylic acid methyl ester | | RT = 1.43 min; m/z = 532 (ES+, M + 1) |

Intermediate Example Int-18-0

{1-[4-(6-carbamoyl-8-methoxy-3-phenylimidazo[1,2-a]pyridin-2-yl)-phenyl]-cyclobutyl}-carbamic acid tert-butyl ester

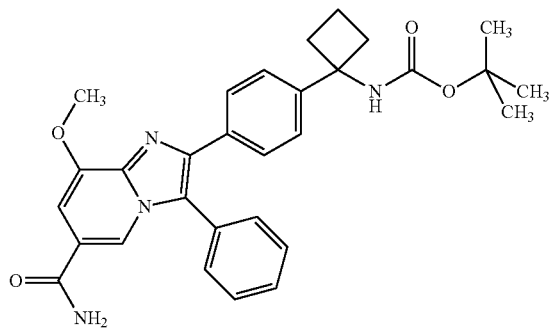 [SMILES: COc1cc(C(N)=O)cn2c(-c3ccccc3)c(-c3ccc(C4(NC(=O)OC(C)(C)C)CCC4)cc3)nc12]

A mixture of 2-[4-(1-tert-butoxycarbonylamino-cyclobutyl)-phenyl]-8-methoxy-3-phenyl-imidazo[1,2-a]pyridine-6-carboxylic acid methyl ester (200 mg) and a solution of ammonia in methanol (7M, 2.65 mL) was heated at 120° C. for 6 hours under microwave irradiation. On cooling, the reaction mixture was concentrated in vacuo. Purification was achieved by chromatography on silica gel to give the title compound.
UPLC-MS (Method 2): RT=1.26 min; m/z=513.25 (M+H).

Intermediate Example Int-19-0

3-{2-[4-(1-tert-butoxycarbonylamino-cyclobutyl)-phenyl]-3-phenyl-imidazo[1,2-a]pyridin-7-yl}-propionic acid methyl ester

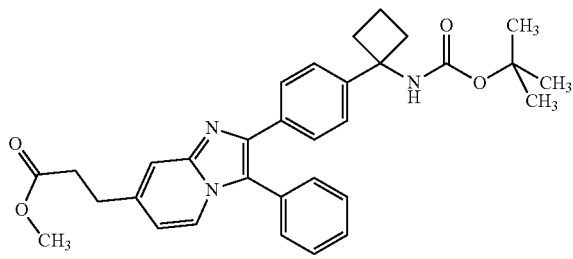 [SMILES: COC(=O)CCc1ccn2c(-c3ccccc3)c(-c3ccc(C4(NC(=O)OC(C)(C)C)CCC4)cc3)nc2c1]

A mixture of (E)-3-{2-[4-(1-tert-butoxycarbonylamino-cyclobutyl)-phenyl]-3-phenyl-imidazo[1,2-a]pyridin-7-yl}-acrylic acid methyl ester (450 mg, 0.86 mmol) and 10% palladium on carbon (0.2 g) in MeOH (20 mL) was stirred under a hydrogen atmosphere for 2 h, and the resulting mixture was filtered. The resulting solution was concentrated under reduced pressure. The remaining material was purified using MPLC (Biotage Isolera; 25 g SNAP cartridge: gradient from 100% hexane to 80% hexane/20% EtOAc over 1.0 min., 80% hexane/20% EtOAc for 3 min., gradient to 50% hexane/50% EtOAc over 3.5 min., 50% hexane/50% EtOAc for 14.6 min,) to give 3-{2-[4-(1-tert-butoxycarbonylamino-cyclobutyl)-phenyl]-3-phenyl-imidazo[1,2-a]pyridin-7-yl}-propionic acid methyl ester (208 mg, 46%):
UPLC-MS (Method 2): RT=1.50 min; m/z (rel intensity) 526 (100, (M+H)+); ES–: m/z (rel intensity) 524 (10, (M–H)−).
1H-NMR (d6-DMSO): δ 1.06 (br s, 3H), 1.29 (br s, 6H), 1.72 (br s, 1H), 1.85-1.96 (m, 1H), 2.25-2.36 (m, 4H), 2.69 (t, J=7.2 Hz, 2H), 2.89 (t; J=7.5 Hz, 2H), 3.57, (s, 3H), 6.77 (dd, J=7.2, 1.5 Hz, 1H), 7.23 (d, J=8.5 Hz, 2H), 7.42-7.58 (m, 9H), 7.85-7.90 (br m, 1H) ppm.

Intermediate Example Int-20-0

2-[4-(1-tert-butoxycarbonylamino-cyclobutyl)-phenyl]-3-phenyl-imidazo[1,2-a]pyridine-7-carboxylic acid

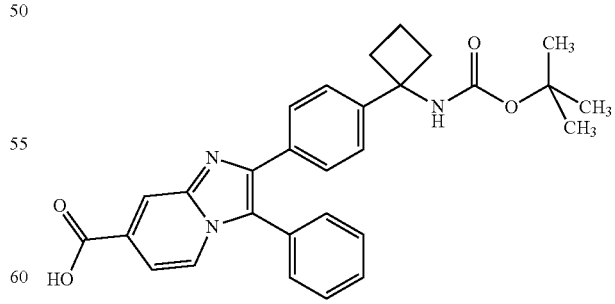

A solution of 2-[4-(1-tert-butoxycarbonylamino-cyclobutyl)-phenyl]-3-phenyl-imidazo[1,2-a]pyridine-7-carboxylic acid methyl ester (2.30 g, 4.60 mmol) in MeOH (77 mL) was added a solution of NaOH (3.7 g, 9.24 mmol, 2.0 equiv) in water (15 mL). The resulting mixture was stirred at room temperature for 12 h. The resulting clear solution was concentrated under pressure. The remaining material was treated with water (50 mL), made acidic with an aqueous 2N HCl solution, and extracted with a 4:1 $CH_2Cl_2$/isopropanol solution (4×25 mL). The combined organic phases were dried ($Na_2SO_4$ anh) and concentrated under reduced pressure to give 2-[4-(1-tert-butoxycarbonylamino-cyclobutyl)-phenyl]-3-phenyl-imidazo[1,2-a]pyridine-7-carboxylic acid (2.4 g, 107%):

UPLC-MS (Method 2): RT=0.85 min; m/z (rel intensity) 484 (100, $(M+H)^+$), 967 (30, $(2M+H)^+$); ES−: m/z (rel intensity) 482 (100, $(M-H)^−$), 965 (10, $(2M-H)^−$).

1H-NMR (d6-DMSO): δ 1.06 (br s, 3H), 1.29 (br s, 6H), 1.73 (br s, 1H), 1.85-2.10 (m, 1H), 2.25-2.37 (m, 4H), 7.31 (d, J=8.5 Hz, 2H), 7.39 (dd, J=7.3, 1.1 Hz, 1H) 7.48-7.62 (m, 7H), 8.03 (br d, J=7.0 Hz, 1H), 8.20 (s, 1H), 13.50 (br s, 0.5H) ppm.

The following examples was prepared in a manner analogous to that described in Intermediate Example Int-20-0: substituting appropriate starting materials where necessary:

| Example | Structure/Name | UPLC-MS |
|---|---|---|
| Int-20-1 | 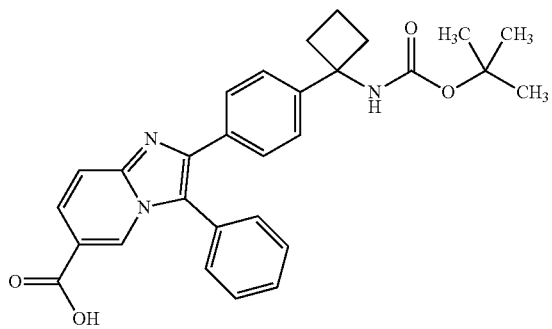 [SMILES: CC(C)(C)OC(=O)NC1(c2ccc(-c3nc4ccc(C(=O)O)cn4c3-c3ccccc3)cc2)CCC1]<br>2-[4-(1-tert-Butoxycarbonylamino-cyclobutyl)-phenyl]-3-phenyl-imidazo[1,2-a]pyridine-6-carboxylic acid | Method 2: RT = 0.78 min; m/z (rel intensity) 484 (100, $(M + H)^+$), 967 (80, $(M + H)^+$). |

Intermediate Example Int-21-0

{1-[4-(7-amino-3-phenyl-imidazo[1,2-a]pyridin-2-yl)-phenyl]-cyclobutyl}-carbamic acid tert-butyl ester

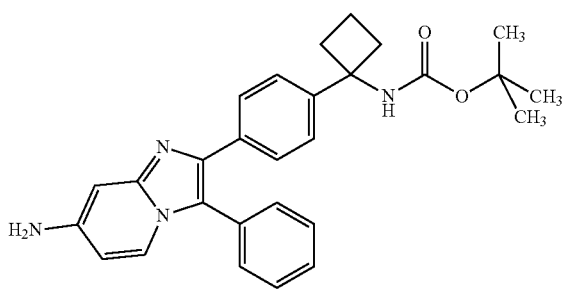 [SMILES: CC(C)(C)OC(=O)NC1(c2ccc(-c3nc4cc(N)ccn4c3-c3ccccc3)cc2)CCC1]

A solution of 2-[4-(1-tert-butoxycarbonylamino-cyclobutyl)-phenyl]-3-phenyl-imidazo[1,2-a]pyridine-7-carboxylic acid (1.20 g, 0.86 mmol) and 10% palladium on carbon (0.2 g) in MeOH (20 mL) in DMF (40 mL) and water (3.4 mL) was added triethylamine (0.38 mL, 2.73 mmol, 1.1 equiv) followed by diphenylphosphoryl azide (751 mg, 2.73 mmol, 1.1 equiv). The resulting mixture was stirred at room temperature 10 minutes, at 100° C. for 6 h, at room temperature for 12 h. To the resulting mixture was added triethylamine (0.38 mL, 2.73 mmol, 1.1 equiv) followed by diphenylphosphoryl azide (751 mg, 2.73 mmol, 1.1 equiv). The resulting mixture was heated at 100° C. for 12 h. The resulting mixture was separated between EtOAc (100 mL) and water (50 mL). The organic phase was dried ($Na_2SO_4$ anh) and concentrated under reduced pressure. The remaining material (1.4 g) was purified using MPLC (Biotage Isolera Flash $NH_2$ Snap 10 reverse phase column; 100% $CH_2Cl_2$ for 3.5 min., gradient to 90% $CH_2Cl_2$: 10% MeOH over 1 min.; 90% $CH_2Cl_2$: 10% MeOH for 5.5 min., gradient to 80% $CH_2Cl_2$: 20% MeOH over 6 min., 80% $CH_2Cl_2$: 20% MeOH for 10.2 min.) to give {1-[4-(7-amino-3-phenyl-imidazo[1,2-a]pyridin-2-yl)-phenyl]-cyclobutyl}-carbamic acid tert-butyl ester (508 mg, 45%):

UPLC-MS (Method 2): RT=1.36 min; m/z (rel intensity) 453 (100, $(M+H)^+$).

The following example was prepared in a manner analogous to that described in Intermediate Example Int-21-0: substituting appropriate starting materials where necessary:

| Intermediate Example | Structure/Name | UPLC-MS |
|---|---|---|
| Int-21-1 | {1-[4-(6-Amino-3-phenyl-imidazo[1,2-a]pyridin-2-yl)-phenyl]-cyclobutyl}-carbamic acid tert-butyl ester | Method 2: RT = 1.26 min; m/z (rel intensity) 455 (100, (M + H)+), 909 (60, (2M + H)+). |

Intermediate Example Int-22-0

{1-[4-(7-acetylamino-3-phenyl-imidazo[1,2-a]pyridin-2-yl)-phenyl]-cyclobutyl}-carbamic acid tert-butyl ester

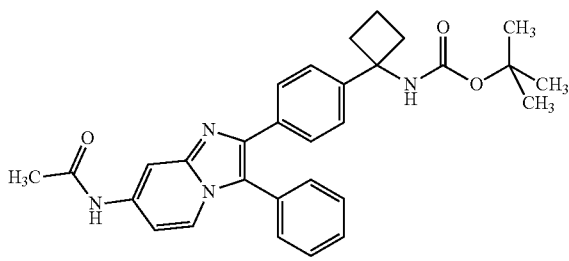 [SMILES: CC(=O)Nc1ccn2c(-c3ccccc3)c(-c3ccc(C4(NC(=O)OC(C)(C)C)CCC4)cc3)nc2c1]

A solution of {1-[4-(7-amino-3-phenyl-imidazo[1,2-a]pyridin-2-yl)-phenyl]-cyclobutyl}-carbamic acid tert-butyl ester [prepared in a manner analogous to that described in Int-21-0] (225 mg, 0.50 mmol), acetic anhydride (0.061 mL, 6.4 mmol, 1.3 equiv) and pyridine (0.10 mL, 1.24 mmol, 2.5 equiv) in $CH_2Cl_2$ (7 mL) was stirred at room temperature for 48 h. The resulting mixture was added to water (10 mL). The resulting mixture was extracted with $CH_2Cl_2$ (3×10 mL). The combined organic phases were dried ($Na_2SO_4$ anh) and concentrated under reduced pressure. The remaining material was purified using MPLC (Biotage Isolera Flash $NH_2$ Snap 10 reverse phase column; 100% $CH_2Cl_2$ for 2 min., gradient to 95% $CH_2Cl_2$: 5% MeOH over 1 min.; 95% $CH_2Cl_2$: 5% MeOH for 4.5 min., gradient to 90% $CH_2Cl_2$: 10% MeOH over 4 min., 90% $CH_2Cl_2$: 10% MeOH for 3 min., gradient to 80% $CH_2Cl_2$: 20% MeOH over 5 min., 80% $CH_2Cl_2$: 20% MeOH for 4.8 min.) to give {1-[4-(7-acetylamino-3-phenyl-imidazo[1,2-a]pyridin-2-yl)-phenyl]-cyclobutyl}-carbamic acid tert-butyl ester (151 mg, 61%):

UPLC-MS (Method 2): RT=1.28 min; m/z (rel intensity) 497 (300, (M+H)+).

The following examples were prepared in a manner analogous to that described in Intermediate Example Int-22-0: substituting appropriate starting materials where necessary:

| Intermediate Example | Structure/Name | UPLC-MS |
|---|---|---|
| Int-22-1 | {1-[4-(3-Phenyl-7-ureido-imidazo[1,2-a]pyridin-2-yl)-phenyl]-cyclobutyl}-carbamic acid tert-butyl ester | Method 2: RT = 1.21 min; m/z (rel intensity) 497 (100, (M + H)+), 994 (100, (2M + H)+); ES−: m/z (rel intensity) 495 (100, (M − H)−), 992 (30, (2M − H)−). |

-continued

| Intermediate Example | Structure/Name | UPLC-MS |
|---|---|---|
| Int-22-2 | 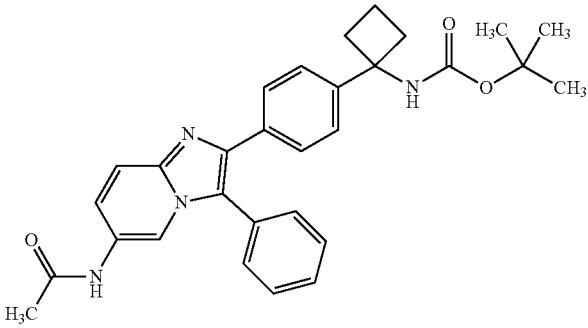 [SMILES: CC(C)(C)OC(=O)NC1(c2ccc(-c3nc4ccc(NC(N)=O)cn4c3-c3ccccc3)cc2)CCC1]<br>{1-[4-(6-Acetylamino-3-phenyl-imidazo[1,2-a]pyridin-2-yl)-phenyl]-cyclobutyl}-carbamic acid tert-butyl ester | Method 2: RT = 1.26 min;<br>m/z (rel intensity) 497 (70, (M + H)$^+$), 993 (100, (2M + H)$^+$). |
| Int-22-3 | 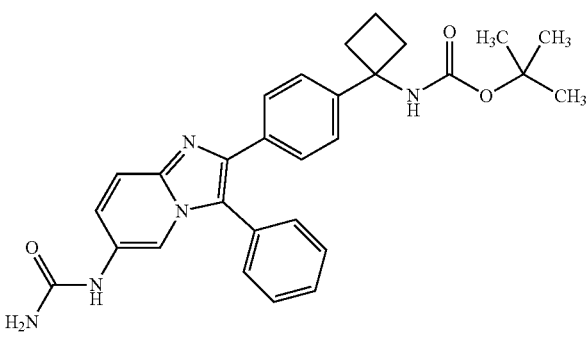<br>{1-[4-(3-Phenyl-6-ureido-imidazo[1,2-a]pyridin-2-yl)-phenyn-cyclobutyl}-carbamic acid tert-butyl ester | Method 2: RT = 1.26 min;<br>m/z (rel intensity) 497 (70, (M + H)$^+$), 993 (100, (2M + H)$^+$). |
| Int-22-4 | 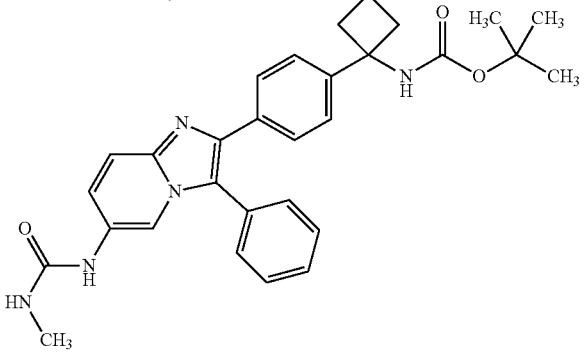<br>(1-{4-[6-(3-Methyl-ureido)-3-phenyl-imidazo[1,2-a]pyridin-2-yl]-phenyl}-cyclobutyl)-carbamic acid tert-butyl ester | Method 2: RT = 1.23 min; m/z (rel intensity) 512 (100, (M + H)$^+$), 993 (5, (2M + H)$^+$). |
| Int-22-5 | 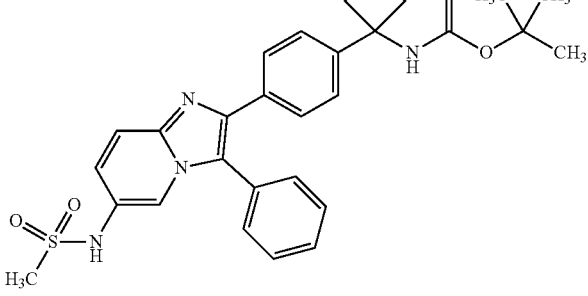<br>{1-[4-(6-Methanesulfonylamino-3-phenyl-imidazo[1,2-a]pyridin-2-yl)-phenyl]-cyclobutyl}-carbamic acid tert-butyl ester | Method 2: RT = 0.93 min; m/z (rel intensity) 533 (100, (M + H)$^+$); ES−: m/z (rel intensity) 531 (100, (M − H)$^−$). |

Intermediate Example Int-23-0

(1-{4-[7-(3-methyl-ureido)-3-phenyl-imidazo[1,2-a]pyridin-2-yl]-phenyl}-cyclobutyl)-carbamic acid tert-butyl ester

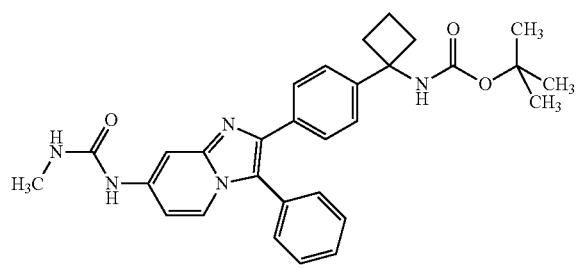 [SMILES: CNC(=O)Nc1ccn2c(-c3ccccc3)c(-c3ccc(C4(NC(=O)OC(C)(C)C)CCC4)cc3)nc2c1]

A mixture of {1-[4-(7-bromo-3-phenyl-imidazo[1,2-a]pyridin-2-yl)-phenyl]-cyclobutyl}-carbamic acid tert-butyl ester (100 mg, 0.193 mmol), Pd$_2$dba$_3$ (3.6 mg, 0.004 mmol), 4,5-bis(diphenylphosphino)-9,9-dimethylxanthene (7 mg, 0.012 mmol), cesium carbonate (75 mg, 0.231 mmol) and methylurea (74 mg, 1.0 mmol) in dioxane (2.3 mL) and DMF (0.8 mL) was degassed, placed under an argon atmosphere and heated at 110° C. for 5 hours. On cooling, the reaction was partitioned between aqueous sodium hydrogen carbonate solution and DCM and the organic phase washed with brine, dried and concentrated in vacuo to give the crude title compound (100 mg) which was used in the next step without further purification.

UPLC-MS: RT=1.16 min; m/z=512.28 (M+H).

Intermediate Example Int-24-0

(1-{4-[7-(methoxy-methyl-carbamoyl)-3-phenyl-imidazo[1,2-a]pyridin-2-yl]-phenyl}-cyclobutyl)-carbamic acid tert-butyl ester A mixture of 2-[4-(1-tert-butoxycarbonylamino-cyclobutyl)-phenyl]-3-phenyl-imidazo[1,2-a]pyridine-7-carboxylic acid [prepared in a manner analogous to that described in Int-20-0] (750 mg, 1.55 mmol), N-methyl-O-methyl-hydroxylyamine HCl salt (227 mg, 2.33 mmol, 1.5 equiv) N,N-diisopropylethylamine (1.6 mL, 9.30 mmol, 6.0 equiv) and PyBOP (1.01 g, 1.94 mmol, 1.25 equiv) in DMF (23 mL) was stirred at room temperature for 24 h. The resulting mixture was added to ice water (25 mL). The resulting mixture was extracted with EtOAc (4×25 mL). The combined organic phases were washed with water (2×50 mL), dried (Na$_2$SO$_4$ anh) and concentrated under reduced pressure. The remaining material was purified using MPLC (Biotage Isolera; 25 g SNAP cartridge: 100% hexane for 1 min., gradient to 75% hexane/25% EtOAc over 1 min., 75% hexane/25% EtOAc for 3 min., gradient to 50% hexane/50% EtOAc over 1 min., 50% hexane/50% EtOAc for 4.5 min, gradient to 25% hexane/75% EtOAc over 2.5 min., gradient to 100% EtOAc over 2 min., 100% EtOAc for 10.6 min.) to give (1-{4-[7-(methoxy-methyl-carbamoyl)-3-phenyl-imidazo[1,2-a]pyridin-2-yl]-phenyl}-cyclobutyl)-carbamic acid tert-butyl ester (679 mg, 76%):

UPLC-MS (Method 2): RT=1.42 min; m/z (rel intensity) 527 (100, (M+H)$^+$); ES−: m/z (rel intensity) 525 (40, (M−H)$^-$).

The following examples were prepared in a manner analogous to that described in Intermediate Example Int-24-0: substituting appropriate starting materials where necessary:

| Intermediate Example | Structure/Name | UPLC-MS |
|---|---|---|
| Int-24-1 | (1-{4-[3-Phenyl-7-(tetrahydro-pyran-2-yloxycarbamoyl)-imidazo[1,2-a]pyridin-2-yl]-phenyl}-cyclobutyl)-carbamic acid tert-butyl ester | Method 2: RT = 0.96 min; m/z (rel intensity) 583 (100, (M + H)$^+$); ES−: m/z (rel intensity) 581 (30, (M − H)$^-$). |

| Intermediate Example | Structure/Name | UPLC-MS |
|---|---|---|
| Int-24-2 | 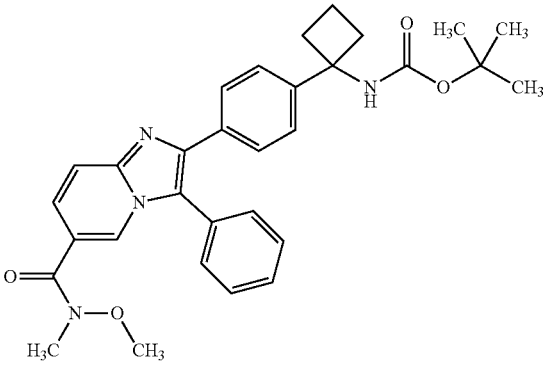 [SMILES: CON(C)C(=O)c1ccc2nc(-c3ccc(C4(NC(=O)OC(C)(C)C)CCC4)cc3)c(-c3ccccc3)n2c1]<br>(1-{4-[6-(Methoxy-methyl-carbamoyl)-3-phenyl-imidazo[1,2-a]pyridin-2-yl]-phenyl}-cyclobutyl)-carbamic acid tert-butyl ester | Method 2: RT = 1.36 min; m/z (rel intensity) 527 (100, (M + H)$^+$); ES−: m/z (rel intensity) 525 (5, (M − H)$^-$). |

Intermediate Example int-25-0

{1-[4-(7-acetyl-3-phenyl-imidazo[1,2-a]pyridin-2-yl)-phenyl]-cyclobutyl}-carbamic acid tert-butyl ester

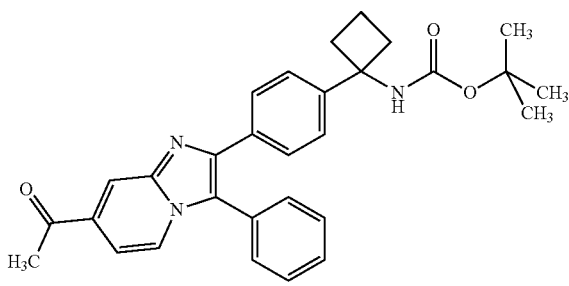 [SMILES: CC(=O)c1ccn2c(-c3ccccc3)c(-c3ccc(C4(NC(=O)OC(C)(C)C)CCC4)cc3)nc2c1]

To a solution of (1-{4-[7-(methoxy-methyl-carbamoyl)-3-phenyl-imidazo[1,2-a]pyridin-2-yl]-phenyl}-cyclobutyl)-carbamic acid tert-butyl ester [prepared in a manner analogous to that described in Int-24-0] (250 mg, 0.48 mmol) in THF (10 mL) under an atmosphere of argon at 0° C. was added a 3 M solution of methyl-magnesium chloride in THF (0.4 mL, 1.2 mmol, 2.5 equiv). The resulting was stirred for 1 h at 0° C., then for 5 h at room temperature. The resulting material was added to a saturated aqueous NH$_4$Cl solution (10 mL). The resulting mixture was extracted with EtOAc (3×20 mL). The combined organic phases were dried (Na$_2$SO$_4$ anh) and concentrated under reduced pressure. The remaining material was purified using MPLC (Biotage Isolera; 25 g SNAP cartridge: 100% hexane for 1 min., gradient to 75% hexane/25% EtOAc over 1 min., 75% hexane/25% EtOAc for 3 min., gradient to 50% hexane/50% EtOAc over 1 min., 50% hexane/50% EtOAc for 4.5 min, gradient to 25% hexane/75% EtOAc over 2.5 min., gradient to 100% EtOAc over 2 min., 100% EtOAc for 10.6 min.) to give {1-[4-(7-acetyl-3-phenyl-imidazo[1,2-a]pyridin-2-yl)-phenyl]-cyclobutyl}-carbamic acid tert-butyl ester (151 mg, 66%):

UPLC-MS (Method 2): RT=1.43 min; m/z (rel intensity) 482 (60, (M+H)$^+$), 964 (100, (M+H)$^+$),; ES−: m/z (rel intensity) 479 (10, (M−H)$^-$).

The following example was prepared in a manner analogous to that described in Intermediate Example Int-25-0: substituting appropriate starting materials where necessary:

| Intermediate Example | Structure/Name | UPLC-MS |
|---|---|---|
| Int-25-1 | 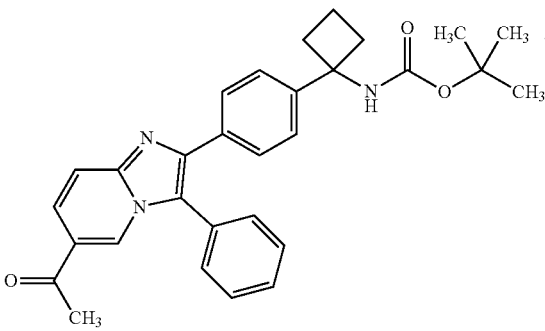 [SMILES: CC(=O)c1ccc2nc(-c3ccc(C4(NC(=O)OC(C)(C)C)CCC4)cc3)c(-c3ccccc3)n2c1]<br>{1-[4-(6-Acetyl-3-phenyl-imidazo[1,2-a]pyridin-2-yl)-phenyl]-cyclobutyl}-carbamic acid tert-butyl ester | Method 2: RT = 1.40 min; m/z (rel intensity) 482 (100, (M + H)$^+$), 963 (30, (M + H)$^+$). |

Intermediate Example Int-26-0

(1-{4-[3-phenyl-7-(2H-tetrazol-5-yl)-imidazo[1,2-a]pyridin-2-yl]-phenyl}-cyclobutyl)-carbamic acid tert-butyl ester

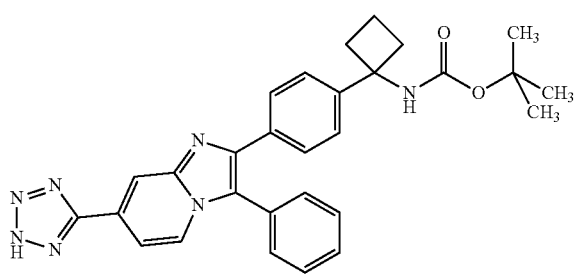 [SMILES: CC(C)(C)OC(=O)NC1(c2ccc(-c3nc4cc(-c5nn[nH]n5)ccn4c3-c3ccccc3)cc2)CCC1]

A mixture of {1-[4-(7-cyano-3-phenyl-imidazo[1,2-a]pyridin-2-yl)-phenyl]-cyclobutyl}-carbamic acid tert-butyl ester (200 mg, 0.43 mmol), sodium azide (336 mg, 5.16 mmol, 12 equiv), NH$_4$Cl (276 mg, 5.16 mmol, 12 equiv) and DMF (4.3 mL) was heated under an argon atmosphere for 3.5 h at 150° C. in a microwave apparatus. The reaction mixture was added to a saturated aqueous NaHCO$_3$ solution (10 mL). The resulting mixture was extracted with a 4:1 CH$_2$Cl$_2$/isopropanol mixture (25 mL). The combined organic phases were dried (Na$_2$SO$_4$ anh), and concentrated under reduced pressure. The remaining material was purified using MPLC (Biotage Isolera; 25 g SNAP cartridge: 80% hexane/20% EtOAc for 3.0 min., gradient to 70% hexane/30% EtOAc over 13.7 min.) to give (1-{4-[3-Phenyl-7-(2H-tetrazol-5-yl)-imidazo[1,2-a]pyridin-2-yl]-phenyl}-cyclobutyl)-carbamic acid tert-butyl ester (0.12 g, 52%):

UPLC-MS (Method 2): RT=0.90 min; m/z (rel intensity) 5.08 (100, (M+H)$^+$).

MS: m/z (rel intensity) 508 (100, (M+H)$^+$); ES− m/z (rel intensity) 506 (100, (M−H)$^−$). 1H-NMR (d6-DMSO): δ 1.07 (br s, 3H), 1.29 (br s, 6H), 1.73 (br s, 1H), 1.88-1.97 (m, 1H), 2.27-2.36 (m, 4H), 7.27 (d, J=8.3, 2H), 7.49-7.60 (m, 8H), 8.08 (br d, J=7.6 Hz, 1H), 8.13 (s, 1H) ppm.

The following example was prepared in a manner analogous to that described in Intermediate Example Int-26-0: substituting appropriate starting materials where necessary:

Intermediate Example Int-27-0

{1-[4-(3-phenyl-7-pyrazol-1-yl-imidazo[1,2-a]pyridin-2-yl)-phenyl]-cyclobutyl}-carbamic acid tert-butyl ester

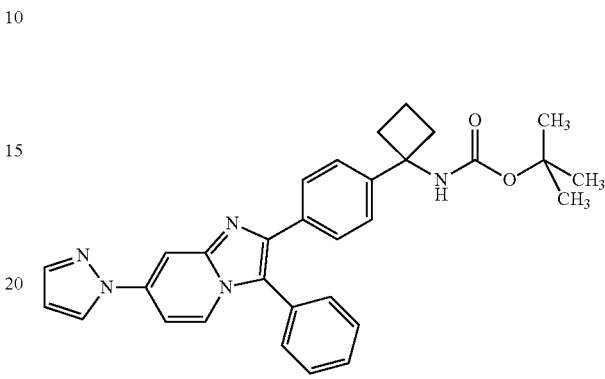

A mixture of {1-[4-(7-bromo-3-phenyl-imidazo[1,2-a]pyridin-2-yl)-phenyl]-cyclobutyl}-carbamic acid tert-butyl ester (230 mg, 0.44 mmol), pyrazole (39 mg, 0.58 mmol), copper (I) iodide (8.5 mg, 0.044 mmol), potassium phosphate (186 mg, 0.88 mmol) and ethylene diamine (3 µL, 0.044 mmol) in dioxane (2.4 mL) was degassed, placed under an argon atmosphere and heated at 110° C. for 5 hours. On cooling, the reaction was partitioned between aqueous sodium hydrogen carbonate solution and DCM and the organic phase was washed with brine, dried and concentrated in vacuo to give the crude title compound (100 mg). The reaction was repeated using a further 150 mg of the bromide intermediate to give a further batch of the crude title compound (140 mg). Purification by chromatagraphy gave the title compound (200 mg), which was used in the next step without further purification.

UPLC-MS: RT=1.48 min; m/z=506.23 (M+H).

The following intermediate example was prepared in analogy.

| Intermediate Example | Structure/Name | UPLC-MS |
|---|---|---|
| Int-26-1 | 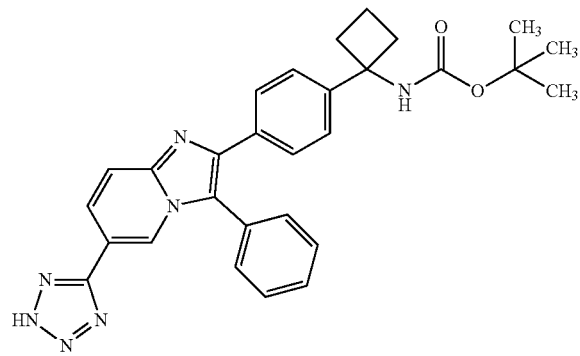 [SMILES: CC(C)(C)OC(=O)NC1(c2ccc(-c3nc4ccc(-c5nn[nH]n5)cn4c3-c3ccccc3)cc2)CCC1]<br>(1-{4-[3-Phenyl-6-(2H-tetrazol-5-yl)-imidazo[1,2-a]pyridin-2-yl]-phenyl}-cyclobutyl)-carbamic acid tert-butyl ester | Method 2: RT = 0.85 min; m/z (rel intensity) 508 (100, (M + H)$^+$). |

| Intermediate Example | Structure/Name | UPLC-MS |
|---|---|---|
| Int-27-1 | 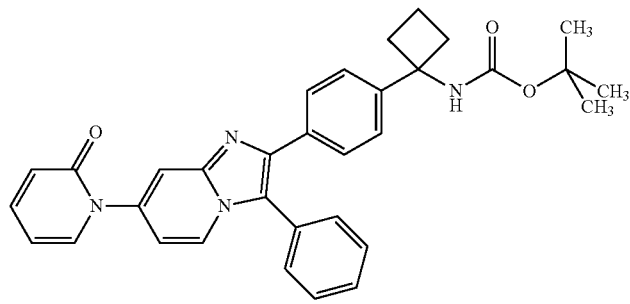<br>(1-{4-[7-(2-Oxo-2H-pyridin-1-yl)-3-phenyl-imidazo[1,2a]pyridin-2-yl]-phenyl}-cyclobutyl)carbamic acid tert-butyl ester | RT = 1.26 min; m/z 533.25 (M + H) |

Intermediate Example Int-28-0 tert-butyl (1-{4-[3-phenyl-6-(1H-pyrazol-1-yl)imidazo[1,2-a]pyridin-2-yl]phenyl}cyclobutyl)carbamate Intermediate Example Int-29-0

{1-[4-(6-chloro-8-cyano-3-phenyl-imidazo[1,2-a]pyridin-2-yl)-phenyl]-cyclobutyl}-carbamic acid tert-butyl ester

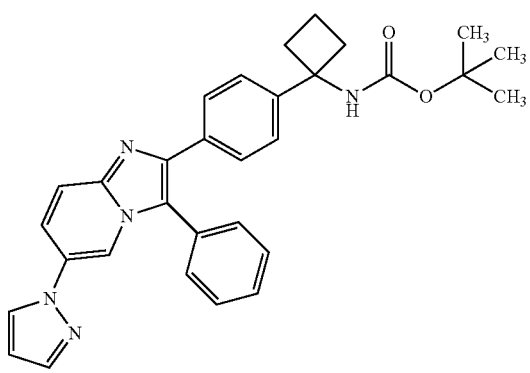 [SMILES: CC(C)(C)OC(=O)NC1(c2ccc(-c3nc4ccc(-n5cccn5)cn4c3-c3ccccc3)cc2)CCC1]

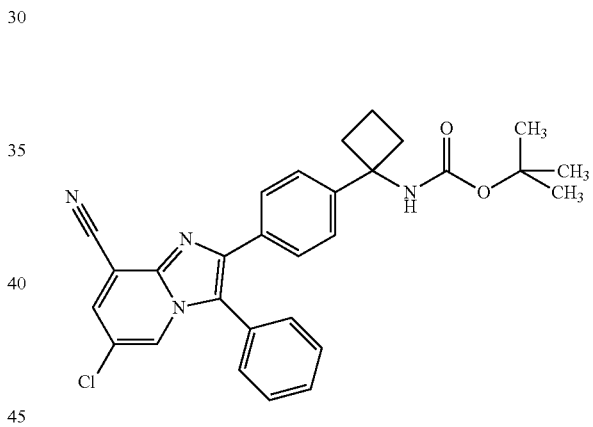

A mixture of tert-butyl {1-[4-(6-bromo-3-phenylimidazo[1,2-a]pyridin-2-yl)phenyl]cyclobutyl}carbamate (see Int 4-18, 230 mg, 0.443 mmol), copper(I) iodide (12.6 mg, 0.07 mmol), 1H-pyrazole (36.5 mg, 0.537 mmol), potassium carbonate (36.5 mg, 0.537 mmol) and quinolin-8-ol (9.73 mg, 0.007 mmol) in 0.6 ml DMSO was heated to 150° C. for 7 h under argon atmosphere. The mixture was triturated with 10% ammonium hydroxide solution and charcoal. After filtration through Celite the filter pad was washed with ethyl acetate. The combined solutions were washed with brine and filtered through a silicone filter. The volatile compounds were removed in vacuo. The crude material was purified by reverse phase HPLC chromatography (Chromatorex RP C-18 10_m; 125*30 mm, acetonitrile/water 30/70->acetonitrile/water 100/0) to give 20 mg of the title compound (9 ($Y_0$ overall yield).

UPLC-MS (Method 2): RT=1.25 min; m/z [ES$^+$]=506 (M+1)$^+$.

300 mg (0.54 mmol) {1-[4-(8-Bromo-6-chloro-3-phenyl-imidazo[1,2-a]pyridin-2-yl)-phenyl]-cyclobutyl}-carbamic acid tert-butyl ester, intermediate example Int-400-12, 3.5 mg (0.054 mmol) zinc, 44.3 mg (0.054 mmol) 1,1 bis(diphenylphosphino)-ferrocenedichloropalladium(II) and 127.4 mg (1.08 mmol) zinc cyanide in 4.5 mL N,N-dimethylacetamide (degassed) were heated in the microwave at 110° C. for three hours. Due to an incomplete reaction additional zinc, catalyst and zinc cyanide were added, and stirring was continued at 150° C. for one hour. The reaction mixture was diluted with ethyl acetate and washed with water/saturated ammonium chloride. The organic phase was separated, dried (sodium sulfate), filtrated and the solvent was removed. The crude product (530 mg >100%) was used in the next step without further purification.

UPLC-MS: RT=1.56 min; m/z=499 (ES+, M+1)

Example 1-0

1-[4-(3-phenyl-imidazo[1,2-a]pyrimidin-2-yl)-phenyl]-cyclobutylamine

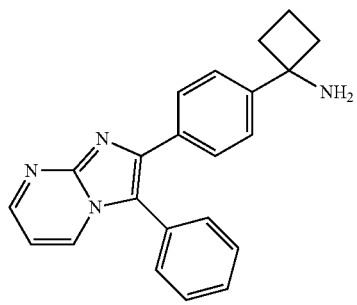 [SMILES: NC1(c2ccc(-c3nc4ncccn4c3-c3ccccc3)cc2)CCC1]

To a mixture of crude {1-[4-(3-phenyl-imidazo[1,2-a]pyrimidin-2-yl)-phenyl]-cyclobutyl}-carbamic acid tert-butyl ester (390 mg) in DCM (0.9 mL) and methanol (0.57 mL) was added a solution of 4 M hydrogen chloride in dioxane (1.77 mL) and the mixture was stirred overnight at rt. The mixture was poured onto ice, made alkaline with aqueous sodium hydroxide (2 N) and extracted three times with a mixture of DCM/methanol. The combined organic phases were washed with brine, dried and concentrated in vacuo to give the crude title compound as a yellow oil. Purification was achieved by chromatography [amino phase silica; gradient elution: hexane to EtOAc], followed by trituration with diisopropylether at 0° C. to give the title compound (21.9 mg).

UPLC-MS: RT=0.76 min; m/z=324.54 (M−NH$_2$);

MS (ESI): 324.17 (M−NH$_2$, 100%), 341.21 (M+1);

1H NMR (400 MHz, d6-DMSO): δ 8.59 (dd, 1H), 8.46 (dd, 1H), 7.55-7.64 (m, 7H), 7.41 (d, 2H), 7.04 (dd, 1H), 2.34-2.41 (m, 2H), 1.89-2.13 (m, 5H), 1.59-1.69 (m, 1H) ppm.

The following examples were prepared in analogy to Example 1-0. In some cases chromatography was not necessary; trituration with diisopropylether at 0° C. was sufficient to get the pure compounds.

| Example | Structure/Name | 1H-NMR | UPLC-MS |
|---|---|---|---|
| 1-1 | 1-[4-(7-methyl-3-phenyl-imidazo[1,2-a]pyrimidin-2-yl)-phenyl]-cyclobutylamine | (300 MHz, d6-DMSO): δ 8.29 (d, 1H), 7.46-7.56 (m, 7H), 7.35 (d, 2H), 6.98 (d, 1H), 2.52 (s, 3H), 2.32-2.41 (m, 2H), 2.07-2.16 (m, 2H), 1.86-2.04 (m, 1H), 1.54-1.68 (m, 1H) ppm. | RT = 0.79 min; m/z = 338.55 (M − NH$_2$) |
| 1-2 | 1-[4-(7-cyclopropyl-3-phenyl-imidazo[1,2-a]pyrimidin-2-yl)-phenyl]-cyclobutylamine | (300 MHz, d6-DMSO): δ 8.22 (d, 1H), 7.45-7.56 (m, 7H), 7.34 (d, 2H), 6.95 (d, 1H), 2.31-2.39 (m, 2H), 2.15-2.23 (m, 1H), 2.04-2.13 (m, 2H), 1.90-2.01 (m, 1H), 1.54-1.67 (m, 1H), 1.06-1.08 (m, 4H) ppm. | RT = 0.87 min; m/z = 364.53 (M − NH$_2$) |

| Example | Structure/Name | 1H-NMR | UPLC-MS |
|---|---|---|---|
| 1-3 | 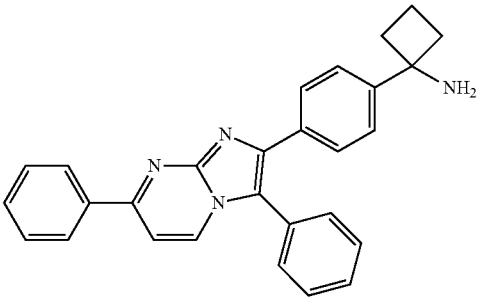
1-[4-(3,7-diphenyl-imidazo[1,2-a]pyrimidin-2-yl)-phenyl]-cyclobutylamine | (300 MHz, d6-DMSO): δ 8.49 (d, 1H), 8.24-8.26 (m, 2H), 7.57-7.67 (m, 11H), 7.40 (d, 2H), 2.34-2.41 (m, 2H), 1.92-2.10 (m, 3H), 1.59-1.69 (m, 1H) ppm. | RT = 0.97 min; m/z = 400.55 (M − NH$_2$) |
| 1-4 | 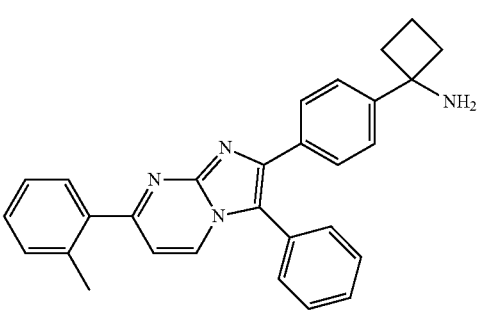
1-[4-(3-phenyl-7-o-tolyl-imidazo[1,2-a]pyrimidin-2-yl)-phenyl]-cyclobutylamine | (600 MHz, d6-DMSO): δ 8.47 (d, 1H), 7.55-7.64 (m, 8H), 7.36-7.43 (m, 5H), 7.21 (d, 1H), [s, 3H, obscured by solvent], 2.36-2.41 (m, 2H), 2.07-2.12 (m, 2H), 1.95-2.01 (m, 1H), 1.61-1.68 (m, 1H) ppm. | RT= 1.06 min; m/z = 414.17 (M − NH$_2$) |
| 1-5 | 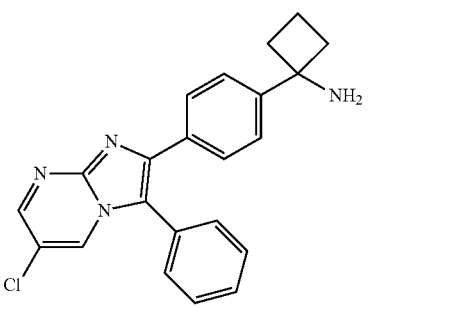
1-[4-(6-chloro-3-phenyl-imidazo[1,2-a]pyrimidin-2-yl)-phenyl]-cyclobutylamine | | RT = 0.92 min; m/z = 358.45 (M − NH$_2$) |
| 1-6 | 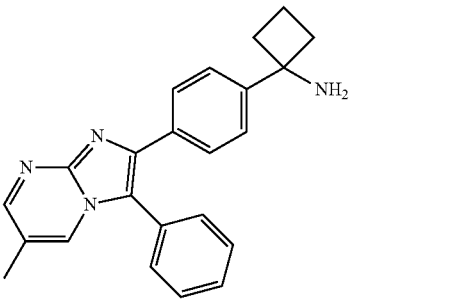
1-[4-(6-methyl-3-phenyl-imidazo[1,2-a]pyrimidin-2-yl)-phenyl]-cyclobutylamine | (300 MHz, d6-DMSO): δ 8.43 (d, 1H), 8.22 (m, 1H), 7.47-7.57 (m, 7H), 7.33 (d, 2H), 2.27-2.36 (m, 2H), 2.24 (s, 3H), 1.82-2.09 (m, 5H), 1.51-1.64 (m, 1H) ppm. | RT = 0.80 min; m/z = 338.54 (M − NH$_2$) |

-continued

| Example | Structure/Name | 1H-NMR | UPLC-MS |
|---|---|---|---|
| 1-7 | 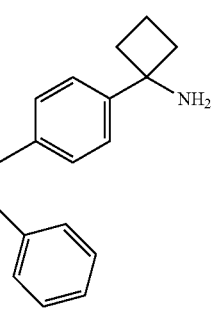<br>1-[4-(6-methoxy-3-phenyl-imidazo[1,2-a]pyrimidin-2-yl)-phenyl]-cyclobutylamine | | RT = 0.87 min;<br>m/z = 354.21<br>(M − NH$_2$) |
| 1-8 | 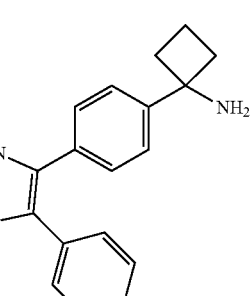<br>1-[4-(6-ethoxy-3-phenyl-imidazo[1,2-a]pyrimidin-2-yl)-phenyl]-cyclobutylamine | (400 MHz, d6-DMSO): δ 8.43 (d, 1H), 7.81 (d, 1H), 7.48-7.57 (m, 7H), 7.33 (d, 2H), 3.97 (q, 2H), 2.28-2.35 (m, 2H), 1.86-2.06 (m, 3H), 1.54-1.63 (m, 1H), 1.29 (t, 3H) ppm. | RT = 0.86 min<br>m/z = 368.53<br>(M − NH$_2$) |
| 1-9 | 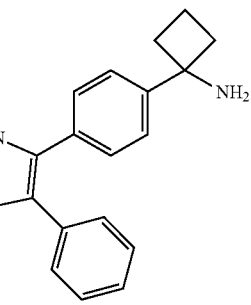<br>1-[4-(3,6-diphenyl-imidazo[1,2-a]pyrimidin-2-yl)-phenyl]-cyclobutylamine | (300 MHz, d6-DMSO): δ 8.94 (d, 1H), 8.48 (d, 1H), 7.72 (d, 2H), 7.39-7.63 (m, 12H), 2.33-2.41 (m, 2H, partially obscured by solvent), 1.92-2.11 (m, 3H), 1.56-1.69 (m, 1H) ppm. | RT = 1.05 min<br>m/z = 400.25<br>(M − NH$_2$) |
| 1-10 | 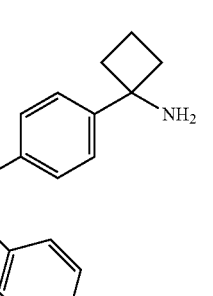<br>2-[4-(1-amino-cyclobutyl)-phenyl]-3-phenyl-imidazo[1,2-a]pyridine-6-carbonitrile | (300 MHz, d6-DMSO): δ 8.67 (m, 1H), 7.78 (d, 1H), 7.49-7.59 (m, 8H), 7.34 (d, 2H), 2.27.2.35 (m, 2H), 1.88.2.04 (m, 5H), 1.53-1.63 (m, 1H) ppm. | |

-continued

| Example | Structure/Name | 1H-NMR | UPLC-MS |
|---|---|---|---|
| 1-11 | 1-[4-(3-Phenyl-7-pyrazol-1-yl-imidazo[1,2-a]pyridin-2-yl)-phenyl]-cyclobutylamine | | Method 2: RT = 1.26 min; m/z = 406.16 (M + H) |
| 1-12 | 2-[4-(1-Amino-cyclobutyl)-phenyl]-8-methoxy-3-phenyl-imidazo[1,2-a]pyridine-6-carboxylic acid methyl ester | | Method 2: RT = 1.28 min; m/z 411.14 (ES+; (M − NH$_2$) |
| 1-13 | 2-[4-(1-Amino-cyclobutyl)-phenyl]-8-methoxy-3-phenyl-imidazo[1,2-a]pyridine-6-carboxylic acid amide | (400 MHz, d6-DMSO, uncorrected): δ 8.11 (br s, 1H), 8.08 (m, 1H), 7.47-7.62 (m, 8H), 7.32 (m, 2H), 7.13 (m, 1H), 4.00 (s, 3H), 2.28-2.34 (m, 2H), 2.19 (br s, NH$_2$), 1.88-2.04 (m, 3H), 1.53-1.63 (m, 1H) ppm. | Method 2: RT = 0.97 min; m/z 413.33 (ES+; M + H) |
| 1-14 | 1-{2-[4-(1-Amino-cyclobutyl)-phenyl]-3-phenyl-imidazo[1,2-a]pyridin-7-yl}-3-methyl-urea | | Method 2: RT = 1.06 min; m/z 412.16 (ES+; M + H) |

-continued

| Example | Structure/Name | 1H-NMR | UPLC-MS |
|---|---|---|---|
| 1-15 | 1-{2-[4-(1-Amino-cyclobutyl)-phenyl]-3-phenyl-imidazo[1,2-a]pyridin-7-yl}-1H-pyridin-2-one | | Method 2:<br>RT = 1.09 min;<br>m/z 433.18<br>(ES+; M + H) |
| 1-16 | 1-{4-[3-Phenyl-6-(1H-pyrazol-1-yl)imidazo[1,2-a]pyridin-2-yl]phenyl}cyclobutanamine | (400 MHz, d6-DMSO): δ 8.49 (d, 1H), 8.34 (m, 1H), 7.86 (dd, 1H), 7.80 (d, 1H), 7.69 (d, 1H), 7.50-7.63 (m, 7H), 7.34 (d,2H), 6.51 (t, 1H), 2.26-2.36 (m, 3H), 1.88-2.04 (m, 2H),1.59 (m, 1H) ppm, NH$_2$ is not assigned. | Method 2:<br>RT = 0.82 min;<br>m/z (ES+) = 389<br>(M − NH$_2$)$^+$; |

Example 2-0

1-[4-(7-methoxy-3-phenyl-imidazo[1,2-a]pyrimidin-2-yl)-phenyl]-cyclobutylamine

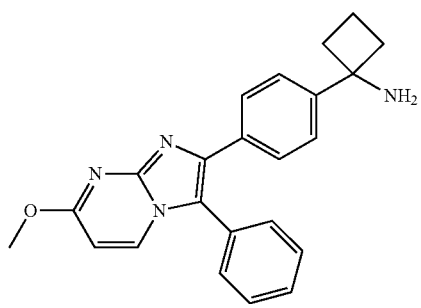 [SMILES: COc1ccn2c(-c3ccccc3)c(-c3ccc(C4(N)CCC4)cc3)nc2n1]

To a mixture of crude {1-[4-(7-methoxy-3-phenyl-imidazo[1,2-a]pyrimidin-2-yl)-phenyl]-cyclobutyl}-carbamic acid tert-butyl ester (550 mg) in DCM (3 mL) and methanol (1.9 mL) was added a solution of 4 M hydrogen chloride in dioxane (5.8 mL) and the mixture was stirred for 2 hours at rt. The mixture was poured onto ice, made alkaline with aqueous sodium hydroxide (2 N) and extracted three times with a mixture of DCM/methanol. The combined organic phases were washed with brine, dried and concentrated in vacuo. Purification was achieved by chromatography [silica; gradient elution: DCM to 8:2 DCM/ethanol] to give the title compound (220 mg).

UPLC-MS: RT=0.77 min; m/z=354.52 (M−NH$_2$);

MS (ESI): 353.99 (M−NH$_2$, 100%), 371.01 (M+1);

1H NMR (400 MHz, d6-DMSO): δ 8.21 (d, 1H), 7.49-7.60 (m, 7H), 7.36 (d, 2H), 6.54 (d, 1H), 3.99 (s, 3H), 2.32-2.38 (m, 2H), 2.42 (br s), 1.92-2.09 (m, 3H), 1.58-1.68 (m, 1H) ppm.

The following examples were prepared in analogy to Example 2-0, with the exception that the HCl acid salt examples were isolated from the reaction by filtration.

| Example | Structure/Name | 1H-NMR | UPLC-MS |
|---|---|---|---|
| 2-1 | 2-[4-(1-amino-cyclobutyl)-phenyl]-3-phenyl-imidazo[1,2-a]pyrimidin-7-ol | (500 MHz, d6-DMSO): δ 7.76 (d, 1H), 7.54-7.57 (m, 3H), 7.46-7.49 (m, 4H), 7.37 (d, 2H), 5.98 (d, 1H), 2.40-2.45 (m, 2H), 2.20-2.26 (m, 2H), 1.99-2.05 (m, 1H), 1.65-1.71 (m, 1H) ppm. | RT = 0.75 min; m/z = 340.55 (M − $NH_2$); m/z (ES−) 355.48 (M − 1) |
| 2-2 | 1-[4-(3-phenyl-7-propoxy-imidazo[1,2-a]pyrimidin-2-yl)-phenyl]-cyclobutylamine | (300 MHz, d6-DMSO, uncorrected): δ 8.16 (d, 1H), 7.44-7.57 (m, 7H), 7.31 (d, 2H), 6.49 (m, 1H), 4.32 (t, 2H), 2.27-2.35 (m, 2H), 1.87-2.04 (m, 3H + $NH_2$), 1.67-1.84 (m, 2H), 1.51-1.63 (m, 1H), 0.97 (t, 3H) ppm. | RT = 1.00 min; m/z = 382.14 (M − $NH_2$) |
| 2-3 | 2-[4-(1-amino-cyclobutyl)-phenyl]-3-phenyl-imidazo[1,2-a]pyridine-8-carbonitrile | (300 MHz, d6-DMSO, uncorrected): δ 8.24 (d, 1H), 7.99 (d, 1H), 7.49-7.59 (m, 7H), 6.99 (t, 1H), 2.27-2.36 (m, 2H), 2.15 (br s, $NH_2$), 1.87-2.06 (m, 3H), 1.52-1.64 (m, 1H) ppm. | RT = 0.96 min; m/z = 348.15 (M − $NH_2$); m/z (ES−) 409.05 (M − H + $HCO_2H$) |
| 2-4 | 1-[4-(7-methyl-3-phenyl-imidazo[1,2-a]pyridin-2-yl)-phenyl]-cyclobutylamine | | RT = 0.76 min; m/z = 354.19 (M + H) |

-continued

| Example | Structure/Name | 1H-NMR | UPLC-MS |
|---|---|---|---|
| 2-5 | 1-[4-(8-methyl-3-phenyl-imidazo[1,2-a]pyridin-2-yl)-phenyl]-cyclobutyl amine | (400 MHz, d6-DMSO, uncorrected): δ 7.80 (d, 1H), 7.44-7.56 (m, 5H), 7.44-7.46 (m, 2H), 7.32 (d, 2H), 7.08 (d, 1H), 6.76 (t, 1H), 2.54 (s, 3H), 2.28-2.34 (m, 2H), 1.86-2.04 (m, 3H + NH$_2$), 1.53-1.62 (m, 1H) ppm. | |
| 2-6 | 2-[4-(1-amino-cyclobutyl)-phenyl]-3-phenyl-imidazo[1,2-a]pyridine-7-carbonitrile | (400 MHz, d6-DMSO, uncorrected): δ 8.43 (m, 1H), 8.10 (d, 1H), 7.52-7.62 (m, 7H), 7.38 (d, 2H), 7.14 (dd, 1H), 2.30-2.37 (m, 2H), 1.91-2.08 (m, 3H + NH2), 1.56-1.65 (m, 1H) ppm. | |
| 2-7 | 1-[4-(6-methyl-3-phenyl-imidazo[1,2-a]pyridin-2-yl)-phenyl]-cyclobutyl amine | (300 MHz, d6-DMSO, uncorrected): δ 7.72 (m, 1H), 7.43-7.60 (m, 8H), 7.30 (d, 2H), 7.13 (dd, 1H), 2.23-2.35 (m, 2H), 2.20 (s, 3H), 1.84-2.04 (m, 3H + NH$_2$), 1.52-1.63 (m, 1H) ppm. | RT = 0.86 min; m/z = 354.17 (M + H), 337.16 (M − NH$_2$) |
| 2-8 | 1-[4-(7-methoxy-3-phenyl-imidazo[1,2-a]pyridin-2-yl)-phenyl]-cyclobutylamine | (300 MHz, d6-DMSO, uncorrected): δ 7.79 (d, 1H), 7.42-7.54 (m, 7H), 7.30 (d, 2H), 7.01 (d, 1H), 6.54 (dd, 1H), 3.83 (s, 3H), 2.23-2.35 (m, 2H). 1.84-2.04 (m, 3H + NH$_2$), 1.54-1.67 (m, 1H) ppm. | RT = 0.84 min; m/z = 370.17 (M + H), 353.12 (M − NH$_2$) |

-continued

| Example | Structure/Name | 1H-NMR | UPLC-MS |
|---|---|---|---|
| 2-9 | 2-[4-(1-amino-cyclobutyl)-phenyl]-3-phenyl-imidazo[1,2-a]pyridine-6-carboxylic acid methylamide | (400 MHz, d6-DMSO, uncorrected): δ 8.56 (q, NH), 8.42 (m, 1H), 7.68 (m, 2H), 7.50-7.63 (m, 7H), 7.33 (d, 2H), 2.72 (d, 3H), 2.28-2.34 (m, 2H), 2.09 (br s, NH$_2$), 1.88-2.03 (m, 3H) ppm. | RT = 0.72 min; m/z = 380.18 (M − NH$_2$); m/z (ES−) 441.21 (M − H + HCO$_2$H) |
| 2-10 | 1-[4-(6-methoxymethyl-3-phenyl-imidazo[1,2-a]pyridin-2-yl)-phenyl]-cyclobutylamine | (400 MHz, d6-DMSO, uncorrected): δ 7.87 (s, 1H), 7.46-7.63 (m, 8H), 7.32 (d, 2H), 7.22 (dd, 1H), 4.36 (s, 2H), 3.22 (s, 3H), 2.28-2.34 (m, 2H), 2.18 (br s, NH2), 1.86-2.05 (m, 3H), 1.53-1.63 (m, 1H) ppm. | RT = 0.76 min; m/z = 367.19 (M − NH$_2$) |
| 2-11 | 1-[4-(3-phenyl-imidazo[1,2-a]pyridin-2-yl)-phenyl]-cyclobutylamine |  | Method 2: RT = 1.23 min m/z = 340.22 (M + H) |
| 2-12 | 1-[4-(8-methoxy-3-phenyl-imidazo[1,2-a]pyridin-2-yl)-phenyl]-cyclobutylamine | (400 MHz, d6-DMSO, uncorrected): δ 7.44-7.59 (m, 8H), 7.31 (d, 2H), 6.76 (t, 1H), 6.69 (d, 1H), 3.95 (s, 3H), 2.27-2.34 (m, 2H), 1.86-2.03 (m, 3H + NH$_2$) ppm. | RT = 0.77 min; m/z = 353.17 (M − NH$_2$) |

-continued

| Example | Structure/Name | 1H-NMR | UPLC-MS |
|---|---|---|---|
| 2-13 | 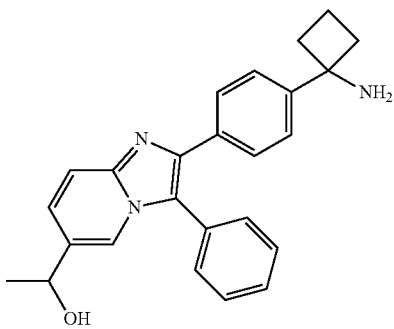<br>1-{2-[4-(1-amino-cyclobutyl)-phenyl]-3-phenyl-imidazo[1,2-a]pyridin-6-yl}-ethanol<br>[as racemic mixture] | (400 MHz, d6-DMSO, uncorrected): δ 7.85 (s, 1H), 7.45-7.60 (m, 8H), 7.31 (d, 2H), 7.25 (dd, 1H), 5.27 (d, 1H), 4.70 (m, 1H), 2.28-2.34 (m, 2H + NH2), 1.88-2.04 (m, 3H), 1.53-1.63 (m, 1H), 1.29 (d, 3H) ppm. | RT = 0.67 min; m/z = 376.19 (M − NH$_2$); m/z (ES−) 428.22 (M − H + HCO$_2$H) |
| 2-14 | 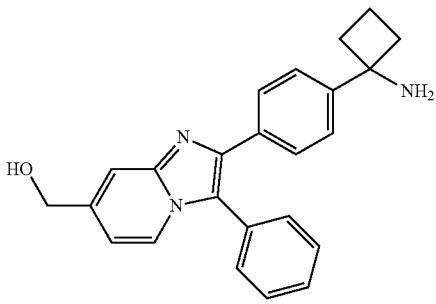<br>{2-[4-(1-amino-cyclobutyl)-phenyl]-3-phenyl-imidazo[1,2-a]pyridin-7-yl}-methanol | (300 MHz, d6-DMSO, uncorrected): δ 7.90 (d, 1H), 7.44-7.58 (m, 8H), 7.31 (d, 2H), 6.80 (d, 1H), 5.40 (m, 1H), 4.52 (m, 2H), 2.24-2.36 (m, 2H + NH$_2$), 1.87-2.06 (m, 3H), 1.51-1.64 (m, 1H) ppm. | RT = 0.63 min; m/z = 353.19 (M − NH$_2$); m/z (ES−) 414.13 (M − H + HCO$_2$H) |
| 2-15 | 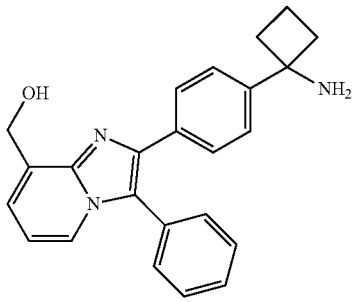<br>{2-[4-(1-amino-cyclobutyl)-phenyl]-3-phenyl-imidazo[1,2-a]pyridin-8-yl}-methanol | (XX MHz, d6-DMSO, uncorrected): δ 7.84 (d, 1H), 7.44-7.56 (m, 7H), 7.27-7.34 (m, 3H), 6.86 (t, 1H), 5.37 (m, 1H), 4.90 (m, 2H), 2.28-2.36 (m, 2H), 1.87-2.07 (m, 3H), 1.54-1.64 (m, 1H) ppm. | RT = 0.69 min; m/z = 353.18 (M − NH$_2$); m/z (ES−) 414.14 (M − H + HCO$_2$H) |
| 2-16 | 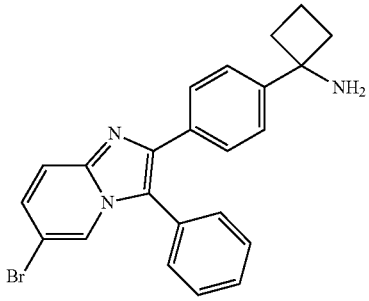<br>1-[4-(6-bromo-3-phenyl-imidazo[1,2-a]pyridin-2-yl)-phenyl]-cyclobutylamine | (400 MHz, d6-DMSO, uncorrected): δ 8.01 (s, 1H), 7.49-7.65 (m, 8H), 7.40 (dd, 1H), 7.33 (d, 2H), 2.27-2.34 (m, 2H), 2.14 (br s, NH$_2$), 1.90-2.03 (m, 3H), 1.53-1.62 (m, 1H) ppm. | |

-continued

| Example | Structure/Name | 1H-NMR | UPLC-MS |
|---|---|---|---|
| 2-17 | 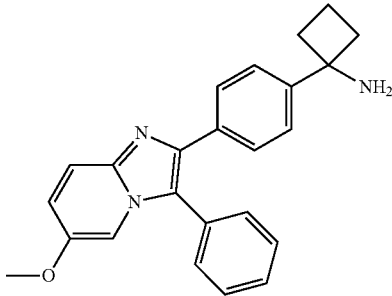<br>1-[4-(6-methoxy-3-phenyl-imidazo[1,2-a]pyridin-2-yl)-phenyl]-cyclobutylamine | | Method 2:<br>RT = 1.25 min;<br>m/z = 370.18<br>(M + H) |
| 2-18 | 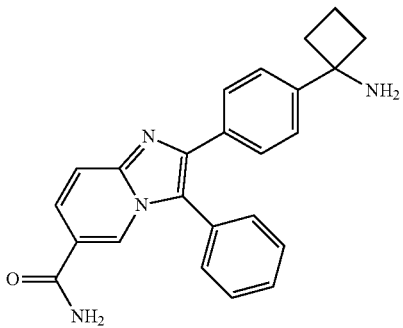<br>2-[4-(1-amino-cyclobutyl)-phenyl]-3-phenyl-imidazo[1,2-a]pyridine-6-carboxylic acid amide | | RT = 0.67 min;<br>m/z = 366.14<br>(M − NH2); 427.14<br>(M − H + HCO$_2$H,<br>ES−) |
| 2-19 | 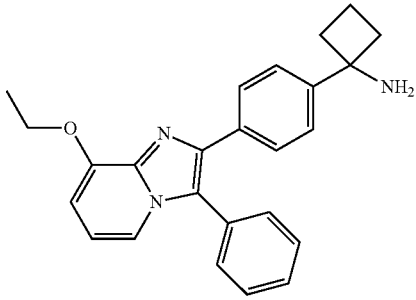<br>1-[4-(8-ethoxy-3-phenyl-imidazo[1,2-a]pyridin-2-yl)-phenyl]-cyclobutylamine | | RT = 0.83 min;<br>m/z = 367.17<br>(M − NH$_2$) |
| 2-20 | 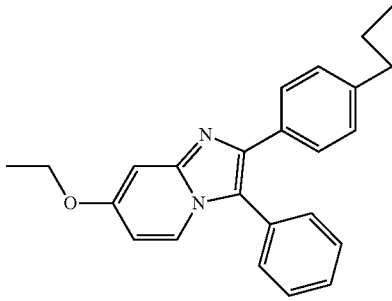<br>1-[4-(7-ethoxy-3-phenyl-imidazo[1,2-a]pyridin-2-yl)-phenyl]-cyclobutylamine | | UPLC-MS<br>Method 2:<br>RT = 1.34 min;<br>m/z = 384.26<br>(M + H) |

| Example | Structure/Name | 1H-NMR | UPLC-MS |
|---|---|---|---|
| 2-21 | 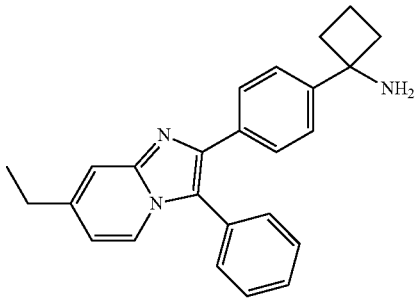<br>1-[4-(7-ethyl-3-phenyl-imidazo[1,2-a]pyridin-2-yl)-phenyl]-cyclobutylamine | | UPLC-MS<br>Method 2:<br>RT = 1.38 min;<br>m/z = 368.29<br>(M + H) |
| 2-22 | 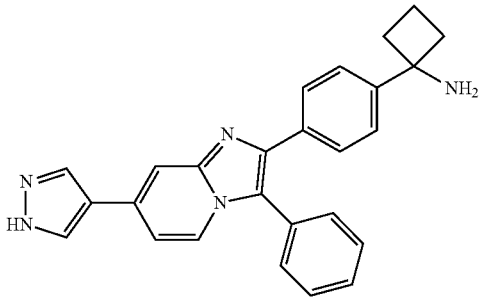<br>1-{4-[3-phenyl-7-(1H-pyrazol-4-yl)-imidazo[1,2-a]pyridin-2-yl]-phenyl}-cyclobutylamine | | UPLC-MS<br>Method 2:<br>RT = 1.12 min;<br>m/z = 406.30<br>(M + H) |
| 2-23 | 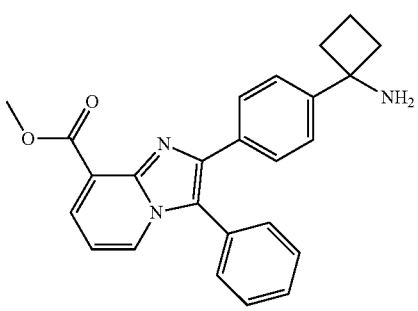<br>2-[4-(1-amino-cyclobutyl)-phenyl]-3-phenyl-imidazo[1,2-a]pyridine-8-carboxylic acid methyl ester | | Method 2:<br>RT = 1.20 min;<br>m/z = 398.16<br>(M + H) |
| 2-24 | 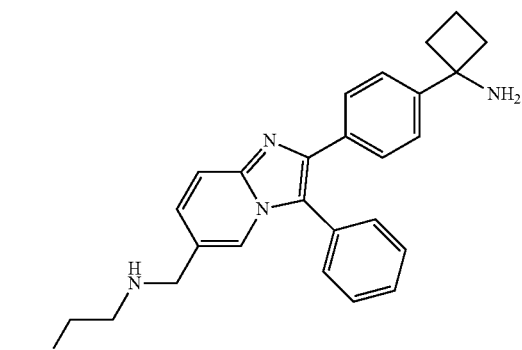<br>1-(4-{6-[(2-methoxy-ethylamino)-methyl]-3-phenyl-imidazo[1,2-a]pyridin-2-yl}-phenyl)-cyclobutylamine | | RT = 0.60 min;<br>m/z = 410.23<br>(M −NH$_2$); 471.20<br>(M − H + HCO$_2$H,<br>ES−) |

| Example | Structure/Name | 1H-NMR | UPLC-MS |
|---|---|---|---|
| 2-25 | 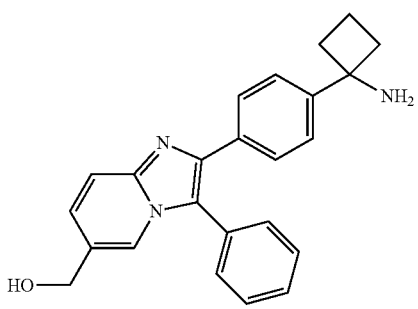<br>{2-[4-(1-amino-cyclobutyl)-phenyl]-3-phenyl-imidazo[1,2-a]pyridin-6-yl}-methanol | | Method 2:<br>RT = 1.04 min;<br>m/z = 370.18<br>(M + H) |
| 2-26 | 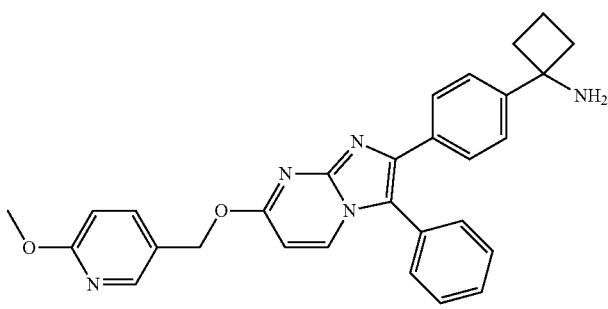<br>1-{4-[7-(6-methoxy-pyridin-3-ylmethoxy)-3-phenyl-imidazo[1,2-a]pyrimidin-2-yl]-phenyl}-cyclobutylamine | (400 MHz, d6-DMSO, uncorrected): δ 8.32 (m, 1H), 8.20 (m, 1H), 7.86 (m, 1H), 7.48-7.51 (m, 7H), 7.33 (m, 2H), 6.82-6.84 (m, 1H), 6.53 (m, 1H), 5.41 (s, 2H), 3.82 (s, 3H), 2.31 (m, 2H), 1.93-2.01 (m, 3H + NH$_2$), 1.59 (m, 1H) ppm | Method 2:<br>RT = 1.33 min;<br>m/z = 478.23<br>(M + H) |
| 2-27 | 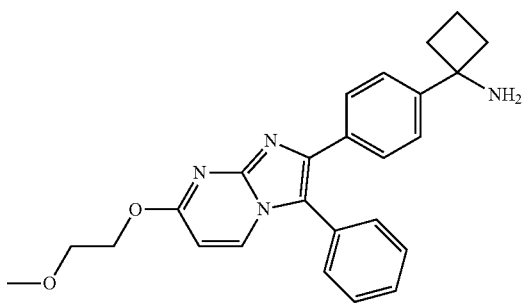<br>1-{4-[7-(2-methoxy-ethoxy)-3-phenyl-imidazo[1,2-a]pyrimidin-2-yl]-phenyl}-cyclobutylamine | (300 MHz, d6-DMS0, uncorrected): δ 8.17 (d, 1H), 7.45-7.56 (m, 7H), 7.31 (d, 2H), 6.52 (d, 1H), 4.48 (m, 2H), 3.69 (m, 2H), [3H obscured by solvent], 2.28-2.35 (m, 2H), 2.08 (br s, NH$_2$), 1.84-2.04 (m, 3H) 1.53-1.61 (m, 1H) ppm | Method 2:<br>RT = 1.22 min;<br>m/z = 415.19<br>(M + H) |
| 2-28 | 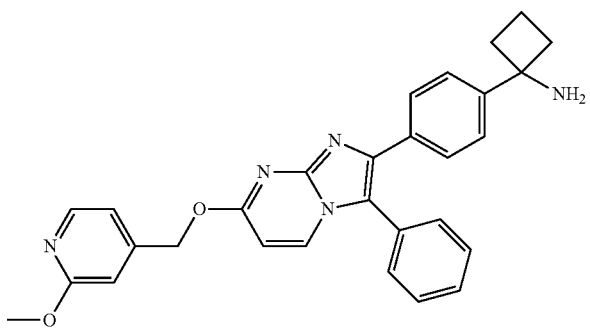<br>1-{4-[7-(2-methoxy-pyridin-4-ylmethoxy)-3-phenyl-imidazo[1,2-a]pyrimidin-2-yl]-phenyl}-cyclobutylamine | (400 MHz, d6-DMSO, uncorrected): δ 8.24 (d, 1H), 8.14 (d, 1H), 7.46-7.55 (m, 7H), 7.31 (d, 2H), 7.04 (d, 1H), 6.85 (s, 1H), 6.64 (d, 1H), 5.48 (s, 2H), 3.81 (s, 3H), 2.27-2.33 (m, 2H), 1.87-2.03 (m, 3H + NH$_2$), 1.52-1.62 (s, 1H) ppm | Method 2:<br>RT = 1.29 min;<br>m/z = 478.0<br>(M + H), 461.0<br>(M − NH$_2$) |

| Example | Structure/Name | 1H-NMR | UPLC-MS |
|---|---|---|---|
| 2-29 | 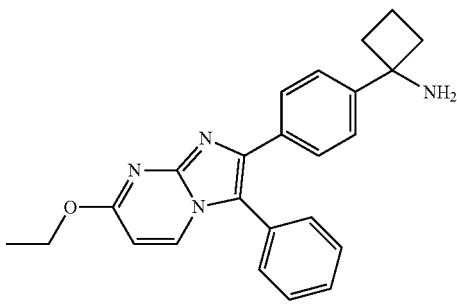<br>1-[4-(7-ethoxy-3-phenyl-imidazo[1,2-a]pyrimidin-2-yl)-phenyl]-cyclobutylamine | (300 MHz, d6-DMSO, uncorrected): δ 8.16 (d, 1H), 7.45-7.55 (m, 7H), 7.31 (d, 2H), 8.47 (d, 1H), 4.41 (q, 2H), 2.23-2.35 (m, 2H), 1.84-2.04 (m, 3H + NH$_2$), 1.35 (t, 3H) ppm | |
| 2-30 | 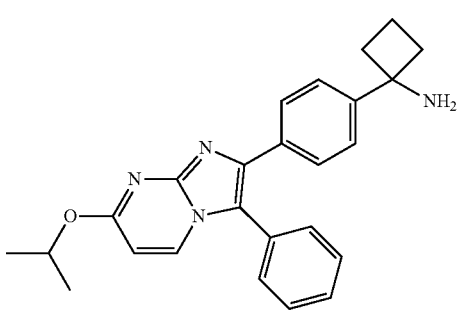<br>1-[4-(7-isopropoxy-3-phenyl-imidazo[1,2-a]pyrimidin-2-yl)-phenyl]-cyclobutylamine | (300 MHz, d6-DMSO, uncorrected): δ 8.14 (d, 1H), 7.45-7.57 (m, 7H), 7.31 (d, 2H), 6.42 (d, 1H), 5.35 (septet, 1H), 2.28-2.37 (m, 2H), 1.82-2.07 (m, 3H), 1.52-1.65 (m, 1H), 1.34 (d, 6H) ppm | RT = 0.99 min; m/z = 382.16 (M − NH$_2$) |
| 2-31 | 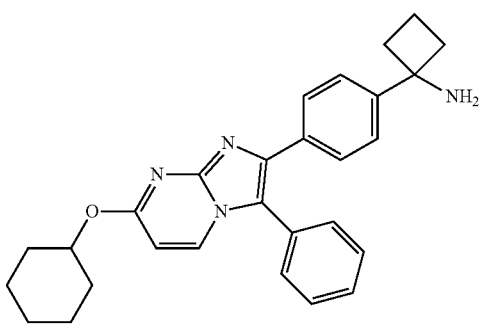<br>1-[4-(7-cyclohexyloxy-3-phenyl-imidazo[1,2-a]pyrimidin-2-yl)-phenyl]-cyclobutylamine | | RT = 1.14 min; m/z = 422.21 (M − NH$_2$) |
| 2-32 | 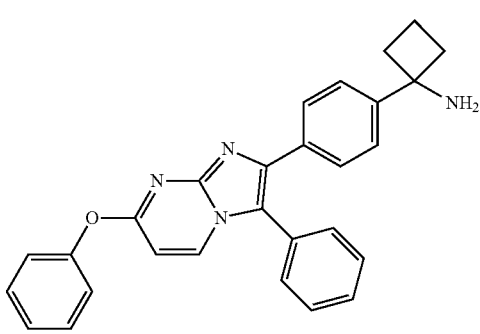<br>1-[4-(7-phenoxy-3-phenyl-imidazo[1,2-a]pyrimidin-2-yl)-phenyl]-cyclobutylamine | | RT = 1.00 min; m/z = 416.16 (M − NH$_2$) |

| Example | Structure/Name | 1H-NMR | UPLC-MS |
|---|---|---|---|
| 2-33 | 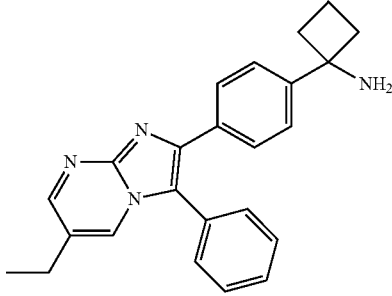<br>1-[4-(6-ethyl-3-phenyl-imidazo[1,2-a]pyrimidin-2-yl)-phenyl]-cyclobutylamine | (400 MHz, d6-DMSO, uncorrected): δ 8.50 (m, 1H), 8.19 (m, 1H), 7.49-7.57 (m, 7H), 7.34 (d, 2H), 2.61 (q, 2H), 2.29-2.35 (m, 2H), 2.25 (br s, NH$_2$), 1.88-2.05 (m, 3H), 1.53-1.63 (m, 1H), 1.15 (t, 3H) ppm. | RT = 0.92 min; m/z = 369.20 (M + H) |
| 2-34 | 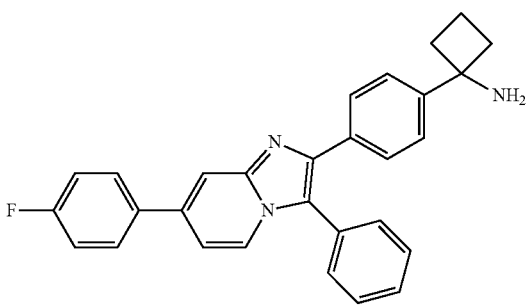<br>1-{4-[7-(4-fluoro-phenyl)-3-phenyl-imidazo[1,2-a]pyridin-2-yl]-phenyl}-cyclobutylamine | (d6-DMSO): δ 1.53-1.65 (m, 1H), 1.82-2.07 (m, 3H), 2.23 (br s, 1H), 2.28-2.37 (m, 2H), 7.22 (dd, J = 7.4, 1.9 Hz, 1H), 7.27-7.36 (m, 4H), 7.48-7.62 (m, 7H), 7.86 (ddm, J = 8.9, 3.4 Hz, 2H), 7.96 (d, J = 1.1 Hz, 1H), 8.00 (d, J = 7.4 Hz, 2H) ppm. | Method 2: RT = 1.47 min; m/z = 434.29 (M + H) |
| 2-35 | 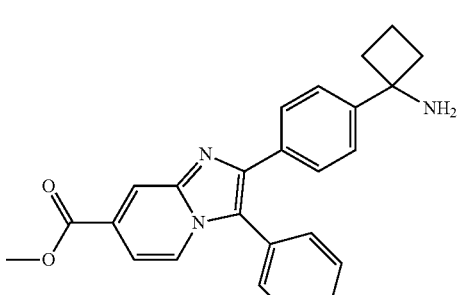<br>2-[4-(1-amino-cyclobutyl)-phenyl]-3-phenyl-imidazo[1,2-a]pyridine-7-carboxylic acid methyl ester | | Method 2: RT = 1.25 min; m/z = 398.32 (M + H) |
| 2-36 | 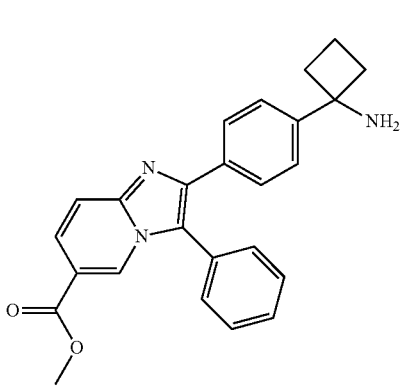<br>2-[4-(1-amino-cyclobutyl)-phenyl]-3-phenyl-imidazo[1,2-a]pyridine-6-carboxylic acid methyl ester | | RT = 0.90 min; m/z = 381.16 (M − NH$_2$); 442.27 (M − H + HCO$_2$H, ES−) |

| Example | Structure/Name | 1H-NMR | UPLC-MS |
|---|---|---|---|
| 2-37 | 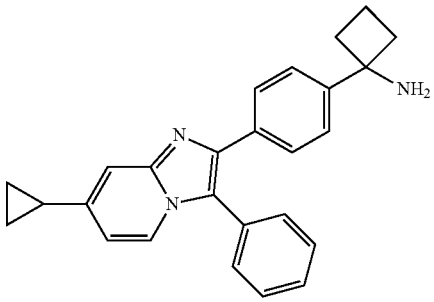<br>1-[4-(7-cyclopropyl-3-phenyl-imidazo[1,2-a]pyridin-2-yl)-phenyl]-cyclobutylamine | (CD$_3$OD): δ 0.79-0.85 (m, 2H), 1.04-1.11 (m, 2H), 1.68-1.79 (m, 1H), 1.97-2.10 (m, 2H), 2.19-2.30 (m, 2H), 2.49-2.58 (m, 2H), 2.58-2.64 (m, 2H), 6.63, (dd, J = 7.4, 1.7 Hz, 1H), 7.33 (br s, 1H), 7.33-7.39 (m, 2H), 7.40-7.45 (m, 2H), 7.51-7.59 (m, 5H), 7.92 (d, J = 7.2, 1H). ppm. | Method 2:<br>RT = 1.38 min;<br>m/z = 380.27<br>(M + H) |
| 2-38 | 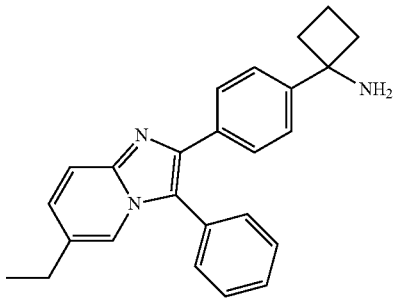<br>1-[4-(6-ethyl-3-phenyl-imidazo[1,2-a]pyridin-2-yl)-phenyl]-cyclobutylamine | | Method 2:<br>RT = 1.40 min;<br>m/z = 368.22<br>(M + H) |
| 2-39 | 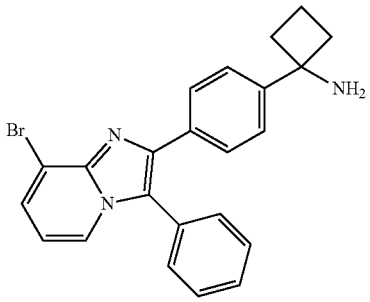<br>1-[4-(8-bromo-3-phenyl-imidazo[1,2-a]pyridin-2-yl)-phenyl]-cyclobutylamine | | RT = 0.98 min;<br>m/z = 404.05<br>(M − NH2) |
| 2-40 | 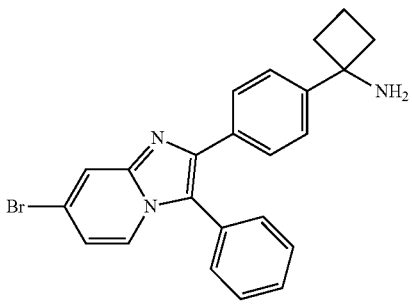<br>1-[4-(7-bromo-3-phenyl-imidazo[1,2-a]pyridin-2-yl)-phenyl]-cyclobutylamine | (300 MHz, d6-DMSO, uncorrected): δ 7.95 (m, 1H), 7.89 (d, 1H), 7.46-7.60 (m, 7H), 7.32 (d, 2H), 6.97-7.00 (m, 1H), 2.28-2.34 (m, 2H), 1.87-2.16 (m, 5H), 1.52-1.63 (m, 1H) ppm. | Method 2:<br>RT = 1.37 min;<br>m/z = 403.12 (M − NH$_2$), 837.25 (2M + H) |

| Example | Structure/Name | 1H-NMR | UPLC-MS |
|---|---|---|---|
| 2-41 | 2-[4-(1-amino-cyclobutyl)-phenyl]-3-phenyl-imidazo[1,2-a]pyridine-7-carboxylic acid amide | | Method 2: RT = 1.03 min; m/z = 366.23 (M − NH₂) |
| 2-42 | {2-[4-(1-Amino-cyclobutyl)-phenyl]-3-phenyl-imidazo[1,2-a]pyridin-7-yl}-pyrrolidin-1-yl-methanone | (300 MHz, d6-DMSO, uncorrected): δ 7.97 (d, 1H), 7.80 (s, 1H), 7.47-7.61 (m, 7H), 7.33 (d, 2H), 6.97 (dd, 1H), 3.52 (t, 2H), 3.46 (t, 2H), 2.27-2.35 (m, 2H), 1.79-2.05 (m, 9H), 1.53-1.63 (m, 1H) ppm | |
| 2-43 | 2-[4-(1-Amino-cyclobutyl)-phenyl]-3-phenyl-imidazo[1,2-a]pyridine-8-carboxylic acid ethyl ester | | Method 2: RT = 1.32 min m/z = 412.22 (M + H) |
| 2-44 | 1-[4-(8-Fluoro-3-phenyl-imidazo[1,2-a]pyridin-2-yl)-phenyl]-cyclobutylamine | (400 MHz, d6-DMSO, uncorrected): δ 7.79 (d, 1H), 7.49-7.58 (m, 7H), 7.34 (d, 2H), 7.18 (t, 1H), 6.82 (m, 1H), 2.29-2.35 (m, 2H), 1.89-2.05 (m, 3H), 1.55-1.63 (m, 1H) ppm | Method 2: RT = 1.26 min; m/z = 341.15 (M − NH₂) |

| Example | Structure/Name | 1H-NMR | UPLC-MS |
|---|---|---|---|
| 2-45 | 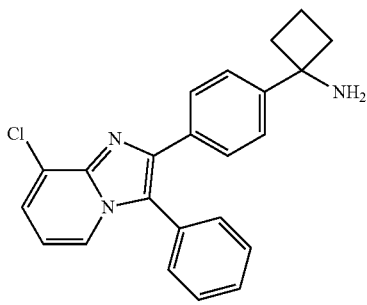<br>1-[4-(8-Chloro-3-phenyl-imidazo[1,2-a]pyridin-2-yl)-phenyl]-cyclobutylamine | (300 MHz, d6-DMSO, uncorrected): δ 7.93 (d, 1H), 7.46-7.61 (m, 8H), 7.34 (d, 2H), 6.84 (t, 1H), 2.27-2.35 (m, 2H), 1.84-2.05 (m, 5H), 1.51-1.63 (m, 1H) ppm | Method 2:<br>RT = 1.33 min;<br>m/z = 357.11<br>(M − NH$_2$) |
| 2-46 | 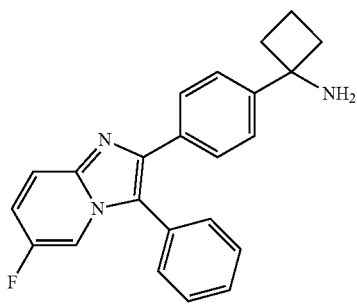<br>1-[4-(6-Fluoro-3-phenyl-imidazo[1,2-a]pyridin-2-yl)-phenyl]-cyclobutylamine | (400 MHz, d6-DMSO, uncorrected): δ 8.04 (dd, 1H), 7.73 (dd, 1H), 7.49-7.62 (m, 7H), 7.34-7.40 (m, 3H), 2.30-2.37 (m, 2H), 1.89-2.06 (m, 5H), 1.55-1.65 (m, 1H) ppm | Method 2:<br>RT = 1.27 min;<br>m/z = 341.15<br>(M − NH$_2$) |
| 2-47 | 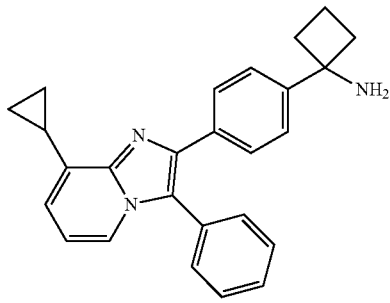<br>1-[4-(8-Cyclopropyl-3-phenyl-imidazo[1,2-a]pyridin-2-yl)-phenyl]-cyclobutylamine | | Method 2:<br>RT = 1.45 min;<br>m/z = 380.19<br>(M + H) |
| 2-48 | 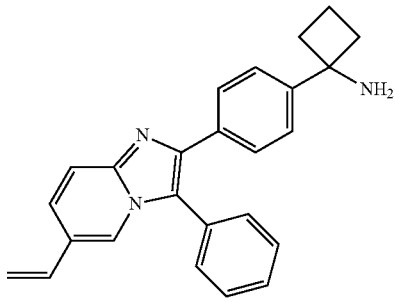<br>1-[4-(3-Phenyl-6-vinyl-imidazo[1,2-a]pyridin-2-yl)-phenyl]-cyclobutylamine | | Method 2:<br>RT = 1.35 min;<br>m/z = 366.20<br>(M + H) |

| Example | Structure/Name | 1H-NMR | UPLC-MS |
|---|---|---|---|
| 2-49 | 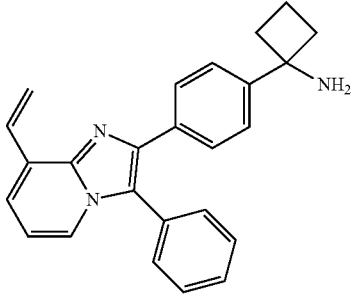<br>1-[4-(3-Phenyl-8-vinyl-imidazo[1,2-a]pyridin-2-yl)-phenyl]-cyclobutylamine | | Method 2:<br>RT = 1.45 min;<br>m/z = 349.16<br>(M − NH$_2$) |
| 2-50 | 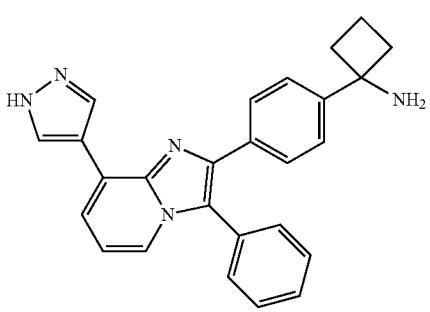<br>1-{4-[3-Phenyl-8-(1H-pyrazol-4-yl)-imidazo[1,2-a]pyridin-2-yl]-phenyl}-cyclobutylamine | | Method 2:<br>RT = 1.26 min;<br>m/z = 389.16 (M − NH$_2$); 404.18 (M − H, ES−) |
| 2-51 | 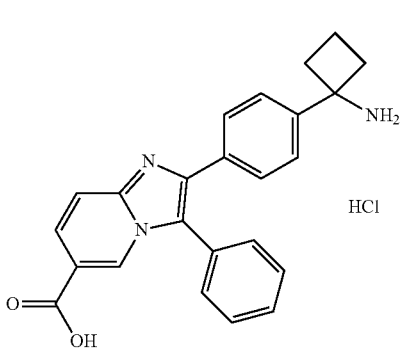<br>2-[4-(1-Amino-cyclobutyl)-phenyl]-3-phenyl-imidazo[1,2-a]pyridine-6-carboxylic acid hydrochloride salt | (300 MHz, d6-DMSO, uncorrected): δ 8.68 (br s), 8.43 (m, 1H), 7.83-7.90 (m, 2H), 7.56-7.67 (m, 7H), 7.50 (d, 2H), 2.52 (4H partially obscured by solvent), 2.05-2.19 (m, 1H), 1.67-1.82 (m, 1H) ppm | |
| 2-52 | 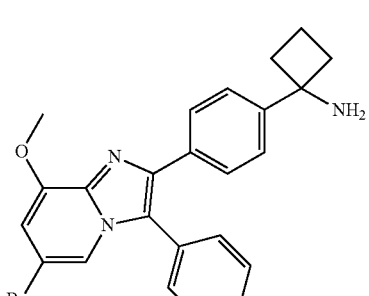<br>1-[4-(6-Bromo-8-methoxy-3-phenyl-imidazo[1,2-a]pyridin-2-yl)-phenyl]-cyclobutylamine | (300 MHz, d6-DMSO, uncorrected): δ 7.45-7.61 (m. 8H), 7.31 (d, 2H), 6.86 (d, 1H), 3.98 (s, 3H), 2.71 (br s), 2.27-2.36 (m, 2H), 1.85-2.07 (m, 3H), 1.51-1.64 (m, 1H) ppm | |

| Example | Structure/Name | 1H-NMR | UPLC-MS |
|---|---|---|---|
| 2-53 | 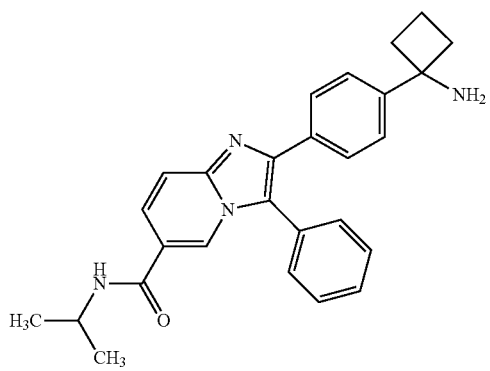<br>2-[4-(1-Amino-cyclobutyl)-phenyl]-3-phenyl-imidazo[1,2-a]pyridine-6-carboxylic acid isopropylamide | | Method 2:<br>RT = 1.18 min;<br>m/z = 408.19 (M − NH$_2$); 423.17 (M − H, ES−) |
| 2-54 | 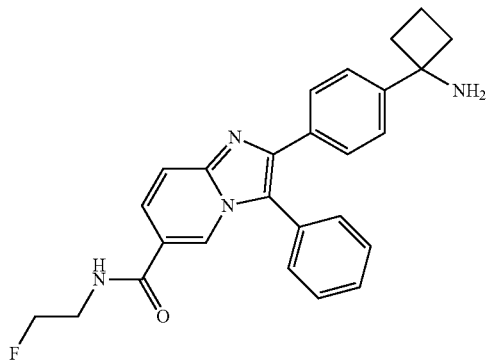<br>2-[4-(1-Amino-cyclobutyl)-phenyl]-3-phenyl-imidazo[1,2-a]pyridine-6-carboxylic acid (2-fluoro-ethyl)-amide | | Method 2:<br>RT = 1.08 min;<br>m/z = 412.16 (M − NH$_2$); 427.19 (M − H, ES−) |
| 2-55 | 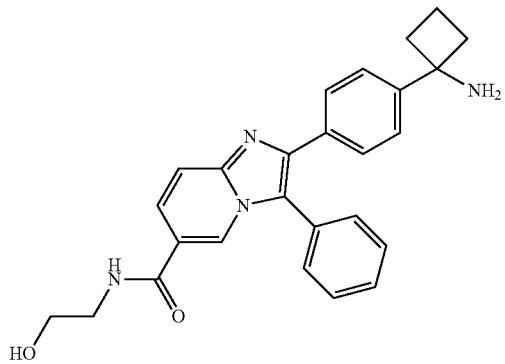<br>2-[4-(1-Amino-cyclobutyl)-phenyl]-3-phenyl-imidazo[1,2-a]pyridine-6-carboxylic acid (2-hydroxy-ethyl)-amide | | Method 2:<br>RT = 0.96 min;<br>m/z = 425.18<br>(M − H, ES−) |

| Example | Structure/Name | 1H-NMR | UPLC-MS |
|---|---|---|---|
| 2-56 | 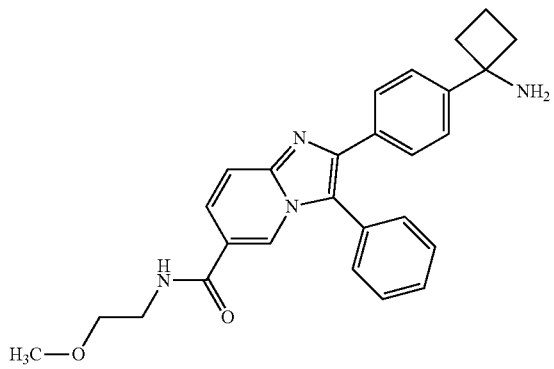<br>2-[4-(1-Amino-cyclobutyl)-phenyl]-3-phenyl-imidazo[1,2-a]pyridine-6-carboxylic acid (2-methoxy-ethyl)-amide | | Method 2:<br>RT = 1.07 min;<br>m/z = 439.19<br>(M − H, ES−) |
| 2-57 | 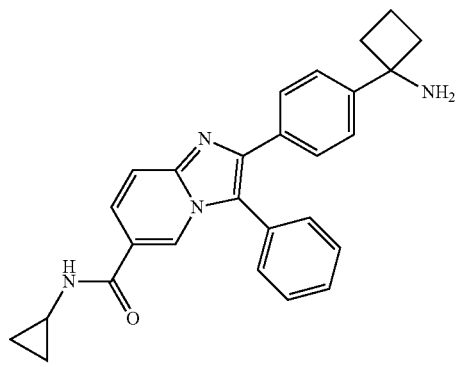<br>2-[4-(1-Amino-cyclobutyl)-phenyl]-3-phenyl-imidazo[1,2-a]pyridine-6-carboxylic acid cyclopropylamide | | Method 2:<br>RT = 1.11 min;<br>m/z = 421.16<br>(M − H, ES−) |
| 2-58 | 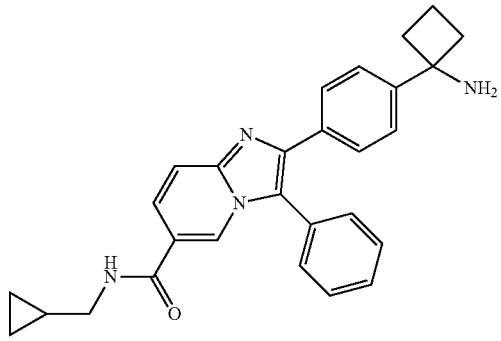<br>2-[4-(1-Amino-cyclobutyl)-phenyl]-3-phenyl-imidazo[1,2-a]pyridine-6-carboxylic acid cyclopropylmethyl-amide | | Method 2:<br>RT = 1.19 min;<br>m/z = 435.17<br>(M − H, ES−) |

| Example | Structure/Name | 1H-NMR | UPLC-MS |
|---|---|---|---|
| 2-59 | 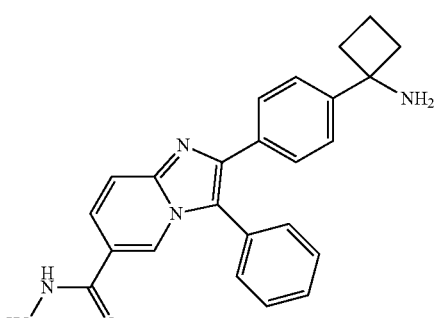<br>2-[4-(1-Amino-cyclobutyl)-phenyl]-3-phenyl-imidazo[1,2-a]pyridine-6-carboxylic acid hydroxyamide | | RT = 0.64 min;<br>m/z = 397.15<br>(M − H, ES−) |
| 2-60 | 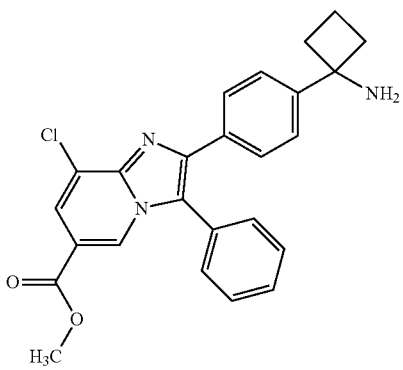<br>2-[4-(1-Amino-cyclobutyl)-phenyl]-8-chloro-3-phenyl-imidazo[1,2-a]pyridine-6-carboxylic acid methyl ester | (300 MHz, d6-DMSO, uncorrected): δ 8.33 (d, 1H), 7.79 (d, 1H), 7.53-7.67 (m, 7H), 7.38 (d, 2H), 3.80 (s, 3H), 3.70 (br s), 2.31-2.20 (m, 2H), 2.05-2.14 (m, 2H), 1.87-2.01 (m, 1H), 1.54-1.68 (m, 1H) ppm. | |
| 2-61 | 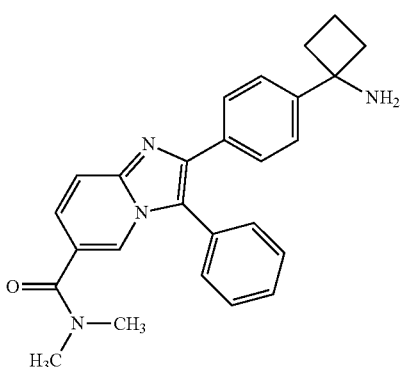<br>2-[4-(1-Amino-cyclobutyl)-phenyl]-3-phenyl-imidazo[1,2-a]pyridine-6-carboxylic acid dimethylamide | | Method 2:<br>RT = 1.08 min;<br>m/z = 409.15<br>(M − H, ES−) |

| Example | Structure/Name | 1H-NMR | UPLC-MS |
|---|---|---|---|
| 2-62 | 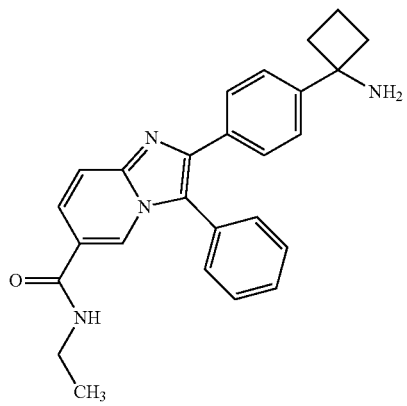<br>2-[4-(1-Amino-cyclobutyl)-phenyl]-3-phenyl-imidazo[1,2-a]pyridine-6-carboxylic acid ethylamide | | Method 2:<br>RT = 1.11 min;<br>m/z = 409.14<br>(M − H, ES−) |
| 2-63 | 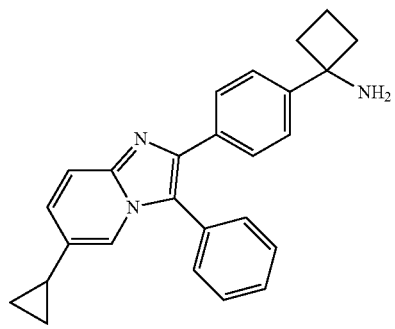<br>1-[4-(6-Cyclopropyl-3-phenyl-imidazo[1,2-a]pyridin-2-yl)-phenyl]-cyclobutylamine | | Method 2:<br>RT = 1.39 min;<br>m/z = 380.18<br>(M + H) |
| 2-64 | 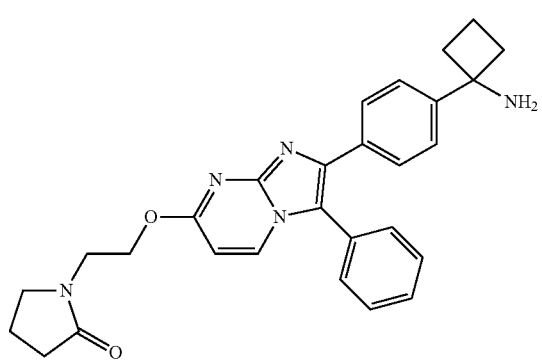<br>1-(2-{2-[4-(1-Amino-cyclobutyl)-phenyl]-3-phenyl-imidazo[1,2-a]pyrimidin-7-yloxy}-ethyl)-pyrrolidin-2-one | | Method 4:<br>RT = 1.09 min;<br>m/z = 468.0<br>(M + H) |

| Example | Structure/Name | 1H-NMR | UPLC-MS |
|---|---|---|---|
| 2-65 | 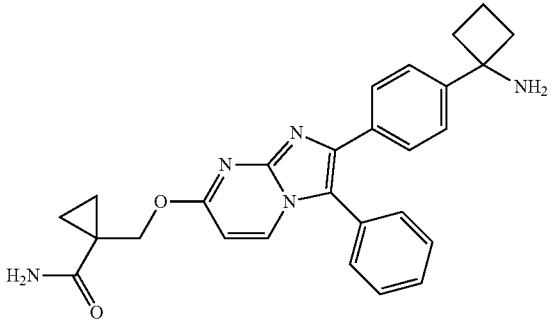<br>1-{2-[4-(1-Amino-cyclobutyl)-phenyl]-3-phenyl-imidazo[1,2-a]pyrimidin-7-yloxymethyl}-cyclopropanecarboxylic acid amide | | Method 2:<br>RT = 1.16 min;<br>m/z = 454.22<br>(M + H) |
| 2-66 | 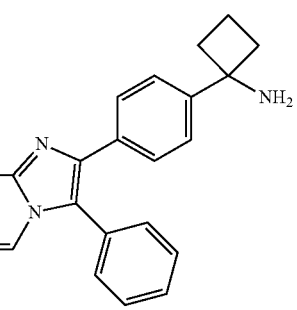<br>1-[4-(7-Chloro-3-phenyl-imidazo[1,2-a]pyridin-2-yl)-phenyl]-cyclobutylamine | | Method 2: RT = 1.35 min; m/z (rel intensity) 747 (30, (2M + H)+). |
| 2-67 | 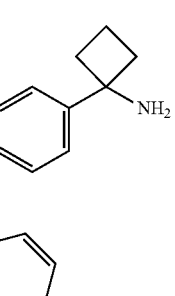<br>1-[4-(7-Fluoro-3-phenyl-imidazo[1,2-a]pyridin-2-yl)-phenyl]-cyclobutylamine | | Method 2: RT = 1.26 min; m/z (rel intensity) 358 (50, (M + H)+),. 715 (30, (2M + H)+). |

Example 2-68

1-{4-[8-(4-fluorophenyl)-3-phenyl-imidazo[1,2-a]pyridin-2-yl]-phenyl}-cyclobutylamine

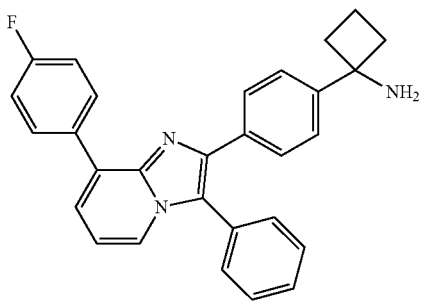 [SMILES: NC1(c2ccc(-c3nc4c(-c5ccc(F)cc5)cccn4c3-c3ccccc3)cc2)CCC1]

81 mg (0.15 mmol) (1-{4-[8-(4-Fluorophenyl)-3-phenyl-imidazo[1,2-a]pyridin-2-yl]-phenyl}-cyclobutyl)-carbamic acid tert.-butyl ester, intermediate example Int-300-0, were dissolved in 7 mL 4 M hydrogen chloride in dioxane. The reaction mixture was stirred over night at room temperature. After evaporation of the solvent the residue was dissolved in methanol and purified by chromatography on silicagel (amine phase, eluents: methanol/ammonia) followed by an additional chromatography (amine phase, eluents: ethyl acetate/hexane) yielding 38.2 mg (55.2%) of the title compound.

UPLC-MS: RT=1.13 min; m/z=434 (ES+, M+1)
$^1$H-NMR (300 MHz, dDMSO): δ 8.22-8.35 (m, 2H), 7.99 (d, 1H), 7.42-7.70 (m, 8H), 7.25-7.42 (m, 4H), 6.91-7.03 (m, 1H), 2.21-2.41 (m, 2H), 1.82-2.19 (m, 5H), 1.48-1.70 (m, 1H) ppm.

In some cases the work-up procedure was different from that described in the aforementioned example. Two alternative methods were used.

In example 2-73 for example the solvent was evaporated and the residue was treated with saturated sodium bicarbonate solution (pH 9). After stirring for one hour dichloromethane were added and stirring was continued for one hour. The organic phase was separated and the aqueous phase was extracted once more with dichloromethane. The combined organic extracts were washed with water and brine, dried, filtrated and the solvent was evaporated. The crude product was purified by HPLC to yield the title compound.

In example 2-75 for example the solvent was evaporated. The residue was dissolved in methanol and given on a Pora-Pak Rxn CX column. The column was washed with 100 mL methanol and the product was eluted with methanol/NH$_3$ yielding the title compound.

The following examples had been prepared in analogy according to example 2-68 by cleaving the protecting group in the corresponding intermediate examples, using an adequate work-up and subsequent purification if necessary.

| Example | Structure/Name | 1H-NMR | UPLC-MS |
|---|---|---|---|
| 2-69 | 1-{4-[8-(3-Fluorophenyl)-3-phenyl-imidazo[1,2-a]pyridin-2-yl]-phenyl}-cyclobutylamine | (300 MHz, dDMSO): δ 8.19 (1H), 8.09 (d, 1H), 8.00 (d, 1H), 7.43-7.71 (m, 9H), 7.48 (d, 2H), 7.19-7.32 (m, 1H), 6.93-7.03 (m, 1H), 2.25-2.41 (m, 2H), 1.81-2.18 (m, 5H), 1.50-1.70 (m, 1H) ppm. | RT = 1.11 min; m/z = 434 (ES+, M + 1) |
| 2-70 | 1-{4-[8-(5-Methoxypyridin-3-yl)-3-phenyl-imidazo[1,2-a]pyridin-2-yl]-phenyl}-cyclobutylcarbamine | (300 MHz, dDMSO): δ 8.98 (1H), 8.28-8.40 (m, 2H), 8.00 (d, 1H), 7.72 (d, 1H), 7.45-7.67 (m, 7H), 7.35 (d, 2H), 6.92-7.05 (m, 1H), 3.93 (s, 3H), 2.25-2.40 (m, 2H), 1.82-2.18 (m, 5H), 1.49-1.65 (m, 1H) ppm. | RT = 0.92 min; m/z = 430 (ES+, M − NH$_2$) |

-continued

| Example | Structure/Name | 1H-NMR | UPLC-MS |
|---|---|---|---|
| 2-71 | 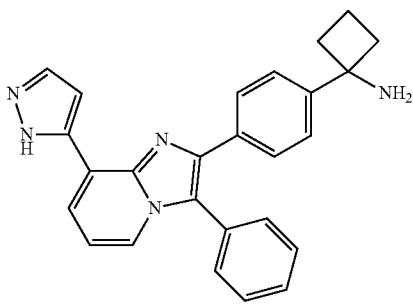<br>1-{4-[3-Phenyl-8-(2H-pyrazol-3-yl)-imidazo[1,2-a]pyridin-2-yl]-phenyl}-cyclobutylamine | (300 MHz, dDMSO): δ 13.09 and 13.48 (br., 1H), 7.43-8.01 (m, 11H), 7.40 (d, 2H), 6.88-7.02 (m, 1H), 2.10-2.40 (m, 4H), 1.82-2.10 (m, 3H), 1.50-1.69 (m, 1H) ppm. | |
| 2-72 | 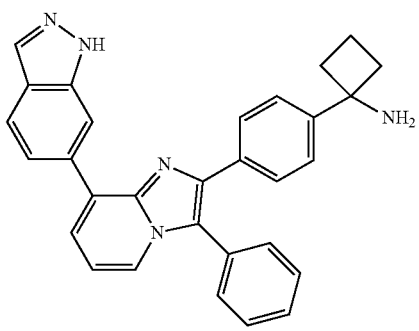<br>1-{4-[8-(1H-Indazol-6-yl)-3-phenyl-imidazo[1,2-a]pyridin-2-yl]-phenyl}-cyclobutylamine | (400 MHz, dDMSO): δ 13.21 (s, 1H), 8.68 (1H), 8.12 (1H), 7.99 (d, 1H), 7.90 (d, 1H), 7.80 (d, 1H), 7.49-7.67 (m, 8H), 7.38 (d, 2H), 6.95-7.02 (m, 1H), 2.27-2.39 (m, 2H), 1.87-2.09 (m, 5H), 1.51-1.65 (m, 1H) ppm. | RT = 0.89 min; m/z = 456 (ES+, M + 1) |
| 2-73 | 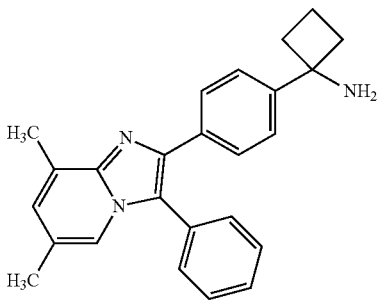<br>1-[4-(6,8-Dimethyl-3-phenyl-imidazo[1,2-a]pyridin-2-yl]-phenyl]-cyclobutylamine | (300 MHz, CD$_3$OD): δ 7.69 (1H), 7.42-7.60 (m, 4H), 7.25-7.42 (m, 5H), 7.02 (1H), 2.60 (s, 3H), 2.43-2.60 (m, 2H), 2.12-2.32 (m, 5H), 1.95-2.12 (m, 1H), 1.62-1.81 (m, 1H) ppm. | RT = 0.70 min; m/z = 351 (ES+, M − NH$_2$) |
| 2-74 | 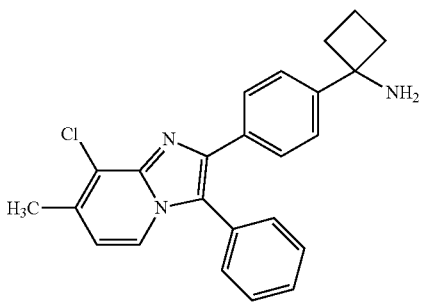<br>1-[4-(8-Chloro-7-methyl-3-phenyl-imidazo[1,2-a]pyridin-2-yl]-phenyl]-cyclobutylamine | (300 MHz, CD$_3$OD): δ 7.92 (d, 1H), 7.45-7.63 (m, 5H), 7.30-7.45 (m, 4H), 6.83 (d, 1H), 2.38-2.62 (m, 5H), 2.12-2.32 (m, 2H), 1.92-2.12 (m, 1H), 1.62-1.82 (m, 1H) ppm. | RT = 0.93 min; m/z = 371 (ES+, M − NH$_2$) |

-continued

| Example | Structure/Name | 1H-NMR | UPLC-MS |
|---|---|---|---|
| 2-75 | <br>1-[4-(7,8-Difluoro-3-phenyl-imidazo[1,2-a]pyridin-2-yl]-phenyl]-cyclobutylamine | (300 MHz, dDMSO): δ 7.92-8.02 (m, 1H), 7.43-7.68 (m, 8H), 7.35 (d, 2H), 2.22-2.39 (m, 2H), 1.85-2.15 (m, 5H), 1.50-1.65 (m, 1H) ppm. | RT = 0.93 min; m/z = 376 (ES+, M + 1) |
| 2-76 | <br>1-[4-(6-Chloro-8-methyl-3-phenyl-imidazo[1,2-a]pyridin-2-yl]-phenyl]-cyclobutylamine | (300 MHz, CD$_3$OD): δ 7.93 (1H), 7.50-7.70 (m, 5H), 7.32-7.50 (m, 4H), 2.55-2.75 (m, 5H), 2.30-2.50 (m, 2H), 2.02-2.22 (m, 1H), 1.75-1.94 (m, 1H) ppm. | RT = 1.01 min; m/z = 371 (ES+, M – NH$_2$) |
| 2-77 | 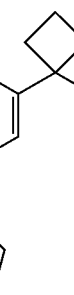<br>2-[4-(1-Amino-cyclobutyl)-phenyl]-8-bromo-3-phenyl-imidazo[1,2-a]pyridine-6-carboxylic acid ethyl ester | | RT = 1.08 min; m/z = 475 (ES–, M – NH$_2$) |
| 2-78 | <br>1-[4-(6,8-Dichloro-3-phenyl-imidazo[1,2-a]pyridin-2-yl]-phenyl]-cyclobutylamine | | RT = 1.03 min; m/z = 391 (ES+, M – NH$_2$) |

| Example | Structure/Name | 1H-NMR | UPLC-MS |
|---|---|---|---|
| 2-79 | 2-[4-(1-Amino-cyclobutyl)-phenyl]-7-methoxy-3-phenyl-imidazo[1,2-a]pyridine-8-carbonitrile | (300 MHz, CD₃OD): δ 8.22 (d, 1H), 7.49-7.65 (m, 5H), 7.40-7.49 (m, 2H), 7.39 (d, 2H), 7.01 (d, 1H), 4.12 (s, 3H), 2.50-2.68 (m, 2H), 2.22-2.38 (m, 2H), 1.98-2.18 (m, 1H), 1.68-1.86 (m, 1H) ppm. | RT = 0.91 min; m/z = 378 (ES+, M − NH₂) |
| 2-80 | 1-[4-(6,7-Dichloro-3-phenyl-imidazo[1,2-a]pyridin-2-yl]-phenyl]-cyclobutylamine | | RT = 1.02 min; m/z = 391 (ES+, M − NH₂) |
| 2-81 | 1-[4-(8-Bromo-6-chloro-7-methyl-3-phenyl-imidazo[1,2-a]pyridin-2-yl]-phenyl]-cyclobutylamine | (400 MHz, dDMSO): δ 8.01 (s, 1H), 7.43-7.68 (m, 7H), 7.38 (d, 2H), 2.54 (s, 3H), 2.25-2.40 (m, 2H), 1.85-2.12 (m, 5H), 1.51-1.65 (m, 1H) ppm. | RT = 1.11 min; m/z = 469 (ES+, M + 1) |
| 2-82 | 1-[4-(6-Bromo-8-methyl-3-phenyl-imidazo[1,2-a]pyridin-2-yl]-phenyl]-cyclobutylamine | (300 MHz, CD₃OD): δ 7.98 (1H), 7.49-7.62 (m, 4H), 7.29-7.48 (m, 5H), 7.26 (1H), 2.64 (s, 3H), 2.43-2.59 (m, 2H), 2.11-2.31 (m, 2H), 1.96-2.11 (m, 1H), 1.62-1.80 (m, 1H) ppm. | RT = 0.93 min; m/z = 417 (ES+, M − NH₂) |

| Example | Structure/Name | 1H-NMR | UPLC-MS |
|---|---|---|---|
| 2-83 | 1-[4-(8-Bromo-6-methyl-3-phenyl-imidazo[1,2-a]pyridin-2-yl]-phenyl]-cyclobutylamine | (300 MHz, CD$_3$OD): δ 7.81 (1H), 7.48-7.62 (m, 6H), 7.30-7.48 (m, 4H), 2.40-2.62 (m, 2H), 2.15-2.35 (m, 5H), 1.98-2.15 (m, 1H), 1.62-1.82 (m, 1H) ppm. | RT = 0.95 min; m/z = 417 (ES+, M − NH$_2$) |
| 2-84 | 1-[4-(6-Bromo-7,8-dimethyl-3-phenyl-imidazo[1,2-a]pyridin-2-yl]-phenyl]-cyclobutylamine | (300 MHz, CD$_3$OD): δ 8.07 (1H), 7.48-7.62 (m, 5H), 7.30-7.48 (m, 4H), 2.69 (s, 3H), 2.40-2.60 (m, 5H), 2.13-2.30 (m, 2H), 1.94-2.12 (m, 1H), 1.62-1.80 (m, 1H) ppm. | RT = 1.03 min; m/z = 431 (ES+, M − NH$_2$) |
| 2-85 | 1-[4-(8-Bromo-6-chloro-3-phenyl-imidazo[1,2-a]pyridin-2-yl]-phenyl]-cyclobutylamine | (300 MHz, dDMSO): δ 8.00 (1H), 7.81 (1H), 7.45-7.67 (m, 7H), 7.38 (d, 2H), 2.22-2.49 (m, 2H), 1.85-2.15 (m, 5H), 1.50-1.68 (m, 1H) ppm. | RT = 1.00 min; m/z = 454 (ES+, M + 1) |
| 2-86 | 1-[4-(8-Bromo-3-phenyl-6-trifluoromethyl-imidazo[1,2-a]pyridin-2-yl]-phenyl}-cyclobutylamine | (300 MHz, CD$_3$OD): δ 8.29 (1H), 7.88 (1H), 7.55-7.70 (m, 5H), 7.45-7.55 (m, 2H), 7.42 (d, 2H), 2.49-2.65 (m, 2H), 2.20-2.38 (m, 2H), 1.98-2.19 (m, 1H), 1.70-1.85 (m, 1H) ppm. | RT = 1.15 min; m/z = 471 (ES+, M − NH$_2$) |

| Example | Structure/Name | 1H-NMR | UPLC-MS |
|---|---|---|---|
| 2-87 | 1-{4-[6-Chloro-8-(4-fluorophenyl)-7-methyl-3-phenyl-imidazo[1,2-a]pyridin-2-yl]-phenyl}-cyclobutylamine | (300 MHz, CD₃OD): δ 8.02 (s, 1H), 7.45-7.66 (m, 6H), 7.20-7.42 (m, 7H), 2.20-2.38 (m, 2H), 2.20 (s, 3H), 1.80-2.10 (m, 3H), 1.49-1.62 (m, 1H) ppm. | RT = 1.15 min; m/z = 465 (ES+, M − NH₂) |
| 2-88 | 1-{4-[6-Chloro-7-methyl-3-phenyl-8-(2H-pyrazol-3-yl)-imidazo[1,2-a]pyridin-2-yl]-phenyl}-cyclobutylamine | (400 MHz, CD₃OD): δ 8.09 (s, 1H), 7.82 (1H), 7.49-7.65 (m, 5H), 7.41-7.51 (m, 2H), 7.38 (d, 2H), 6.75 (1H), 2.52-2.68 (m, 2H), 2.45 (s, 3H), 2.25-2.49 (m, 2H), 2.01-2.18 (m, 1H), 1.72-1.88 (m, 1H) ppm. | RT = 0.91 min; m/z = 454 (ES+, M + 1) |
| 2-89 | 1-{4-[7,8-Dimethyl-3-phenyl-6-(2H-pyrazol-3-yl)-imidazo[1,2-a]pyridin-2-yl]-phenyl}-cyclobutylamine | (400 MHz, dDMSO): δ 7.92 (s, 1H), 7.41-7.62 (m, 9H), 7.33 (d, 2H), 2.61 (s, 3H), 2.39 (s, 3H), 2.25-2.59 (m, 2H), 1.83-2.15 (m, 3H), 1.52-1.65 (m, 1H) ppm. | RT = 0.73 min; m/z = 434 (ES+, M + 1) |
| 2-90 | 1-{4-[6-Methyl-3-phenyl-8-pyridin-3-yl-imidazo[1,2-a]pyridin-2-yl]-phenyl}-cyclobutylamine | (400 MHz, dDMSO): δ 9.39 (d, 1H), 8.58-8.65 (m, 2H), 7.80 (1H), 7.45-7.63 (m, 9H), 7.37 (d, 2H), 2.22-2.39 (m, 5H), 1.98-2.10 (m, 2H), 1.85-1.98 (m, 1H), 1.51-1.65 (m, 1H) ppm. | Method 2: RT = 1.42 min; m/z = 414 (ES+, M − NH₂) |

| Example | Structure/Name | 1H-NMR | UPLC-MS |
|---|---|---|---|
| 2-91 | 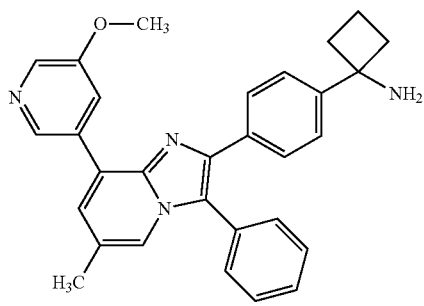<br>1-{4-[8-(5-Methoxy-pyridin-3-yl)-6-methyl-3-phenyl-imidazo[1,2-a]pyridin-2-yl]-phenyl}-cyclobutylamine | (300 MHz, dDMSO): δ 9.00 (d, 1H), 8.28-8.39 (m, 2H), 7.80 (1H), 7.45-7.68 (m, 8H), 7.37 (d, 2H), 3.92 (s, 3H), 2.22-2.42 (m, 5H), 2.01-2.15 (m, 2H), 1.85-2.01 (m, 1H), 1.51-1.69 (m, 1H) ppm. | Method 2:<br>RT = 1.45 min;<br>m/z = 444 (ES+,<br>M − $NH_2$) |
| 2-92 | 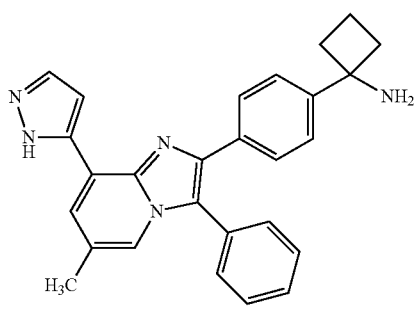<br>1-{4-[6-Methyl-3-phenyl-8-(2H-pyrazol-2-yl)-imidazo[1,2-a]pyridin-2-yl]-phenyl}-cyclobutylamine | (300 MHz, dDMSO): δ 13.09 and 13.43 (br., 1H), 7.43-7.92 (m, 11H), 7.38 (d, 2H), 2.20-2.41 (m, 5H), 1.82-2.19 (m, 5H), 1.50-1.68 (m, 1H) ppm. | |
| 2-93 | 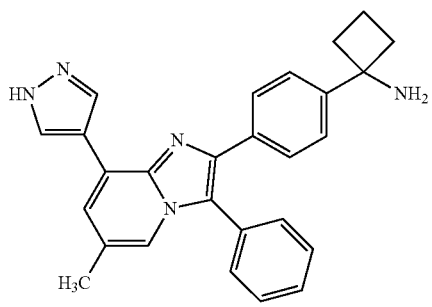<br>1-{4-[6-Methyl-3-phenyl-8-(1H-pyrazol-4-yl)-imidazo[1,2-a]pyridin-2-yl]-phenyl}-cyclobutylamine | (300 MHz, dDMSO): δ 13.08 (br., 1H), 8.82 (br., 1H), 8.48 (br., 1H), 7.40-7.65 (m, 9H), 7.38 (d, 2H), 2.29-2.41 (m, 2H), 2.28 (s, 3H), 2.00-2.12 (m, 2H), 1.86-2.00 (m, 1H), 1.51-1.69 (m, 1H) ppm. | Method 2:<br>RT = 1.32 min;<br>m/z = 403 (ES+,<br>M − $NH_2$) |
| 2-94 | 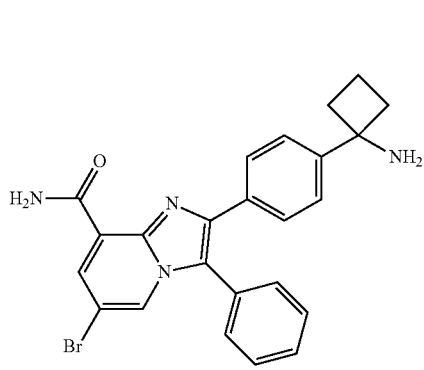<br>2-[4-(1-Amino-cyclobutyl)-phenyl]-6-bromo-3-phenyl-imidazo[1,2-a]pyridine-8-carboxylic acid amide | (400 MHz, $CD_3OD$): δ 8.45 (br., 2H), 8.25 (1H), 8.19 (1H), 7.79 (d, 2H), 7.55-7.68 (m, 3H), 7.48-7.55 (m, 2H), 7.47 (d, 2H), 2.68-2.81 (m, 2H), 2.49-2.62 (m, 2H), 2.12-2.28 (m, 1H), 1.85-2.01 (m, 1H) ppm. | RT = 0.88 min;<br>m/z = 446 (ES+,<br>M − $NH_2$) |

| Example | Structure/Name | 1H-NMR | UPLC-MS |
| --- | --- | --- | --- |
| 2-95 | 2-[4-(1-Amino-cyclobutyl)-phenyl]-8-bromo-3-phenyl-imidazo[1,2-a]pyridine-6-carboxylic acid amide | (400 MHz, CD$_3$OD): δ 8.63 (1H), 8.09 (1H), 7.52-7.66 (m, 5H), 7.45-7.53 (m, 2H), 7.40 (d, 2H), 2.45-2.59 (m, 2H), 2.15-2.29 (m, 2H), 1.98-2.11 (m, 1H), 1.65-1.80 (m, 1H) ppm. | RT = 0.75 min; m/z = 463 (ES+, M + 1) |
| 2-96 | 2-[4-(1-Amino-cyclobutyl)-phenyl]-6-methyl-3-phenyl-imidazo[1,2-a]pyridine-8-carboxylic acid amide | (400 MHz, dDMSO): δ 9.65 (1H), 8.03 (1H), 7.94 (d, 2H), 7.46-7.68 (m, 7H), 7.39 (d, 2H), 2.21-2.40 (m, 5H), 1.82-2.21 (m, 5H), 1.51-1.68 (m, 1H) ppm. | RT = 0.88 min; m/z = 397 (ES+, M + 1) |
| 2-97 | 2-[4-(1-Amino-cyclobutyl)-phenyl]-3-phenyl-6-(1H-pyrazol-4-yl)-imidazo[1,2-a]pyridine-8-carboxylic acid amide | (300 MHz, dDMSO): δ 13.02 (br., 1H), 9.68 (1H), 8.28 (1H), 8.20 (1H), 8.11 (1H), 7.42-7.68 (m, 8H), 7.38 (d, 2H), 2.25-2.40 (m, 2H), 1.82-2.20 (m, 5H), 1.49-1.69 (m, 1H) ppm. | RT = 0.79 min; m/z = 449 (ES+, M + 1) |

| Example | Structure/Name | 1H-NMR | UPLC-MS |
|---|---|---|---|
| 2-98 | 2-[4-(1-Amino-cyclobutyl)-phenyl]-3-phenyl-6-(2H-pyrazol-3-yl)-imidazo[1,2-a]pyridine-8-carboxylic acid amide | (400 MHz, dDMSO): δ 13.00 (br., 1H), 9.65 (1H), 8.48 (1H), 8.41 (1H), 8.13 (1H), 7.78 (br., 1H), 7.49-7.69 (m, 7H), 7.39 (d, 2H), 6.72 (1H), 2.22-2.39 (m, 2H), 1.85-2.20 (m, 5H), 1.51-1.68 (m, 1H) ppm. | RT = 0.82 min; m/z = 449 (ES+, M + 1) |
| 2-99 | 2-[4-(1-Amino-cyclobutyl)-phenyl]-3-phenyl-6-pyridin-3-yl-imidazo[1,2-a]pyridine-8-carboxylic acid amide | (300 MHz, dDMSO): δ 9.62 (1H), 8.85 (1H), 8.59 (1H), 8.33 (1H), 8.30 (1H), 8.19 (1H), 7.99-8.12 (m, 1H), 7.49-7.69 (m, 7H), 7.42-7.49 (m, 1H), 7.39 (d, 2H), 2.25-2.39 (m, 2H), 1.82-2.15 (m, 5H), 1.49-1.68 (m, 1H) ppm. | RT = 0.78 min m/z = 460 (ES+, M + 1) |
| 2-100 | 2-[4-(1-Amino-cyclobutyl)-phenyl]-7,8-dimethyl-3-phenyl-imidazo[1,2-a]pyridine-6-carboxylic acid amide | (300 MHz, dDMSO): δ 7.88 (br., 1H), 7.83 (1H), 7.45-7.65 (m, 7H), 7.42 (br., 1H), 7.35 (d, 2H), 2.57 (s, 3H), 2.25-2.40 (m, 5H), 1.85-2.12 (m, 5H), 1.49-1.69 (m, 1H) ppm. | RT = 0.65 min m/z = 411 (ES+, M + 1) |

| Example | Structure/Name | 1H-NMR | UPLC-MS |
|---|---|---|---|
| 2-101 | 2-[4-(1-Amino-cyclobutyl)-phenyl]-8-methyl-3-phenyl-imidazo[1,2-a]pyridine-6-carboxylic acid amide | (300 MHz, dDMSO): δ 8.32 (1H), 8.08 (br., 1H), 7.45-7.68 (m, 8H), 7.43 (br., 1H), 7.39 (d, 2H), 2.59 (s, 3H), 2.27-2.40 (m, 2H), 1.83-2.12 (m, 5H), 1.49-1.68 (m, 1H) ppm. | RT = 0.74 min; m/z = 397 (ES+, M + 1) |
| 2-102 | 1-{4-[8-Methyl-3-phenyl-6-(1H-pyrazol-4-yl)-imidazo[1,2-a]pyridin-2-yl]-phenyl}-cyclobutylamine | (300 MHz, dDMSO): δ 12.95 (br., 1H), 7.93 (1H), 7.70-8.20 (very br., 2H), 7.43-7.63 (m, 7H), 7.43 (1H), 7.34 (d, 2H), 2.59 (s, 3H), 2.24-2.41 (m, 2H), 1.81-2.18 (m, 5H), 1.49-1.67 (m, 1H) ppm. | RT = 0.65 min; m/z = 418 (ES-, M - 1) |
| 2-103 | 1-{4-[8-Methyl-3-phenyl-6-(2H-pyrazol-3-yl)-imidazo[1,2-a]pyridin-2-yl]-phenyl}-cyclobutylamine | (400 MHz, dDMSO): δ 12.89 (br., 1H), 8.18 (1H), 7.72 (br., 1H), 7.48-7.65 (m, 8H), 7.38 (d, 2H), 6.66 (1H), 2.61 (s, 3H), 2.28-2.39 (m, 2H), 2.12 (br., 2H), 1.85-2.08 (m, 3H), 1.51-1.65 (m, 1H) ppm. | RT = 0.70 min; m/z = 418 (ES-, M - 1) |

-continued

| Example | Structure/Name | 1H-NMR | UPLC-MS |
|---|---|---|---|
| 2-104 | 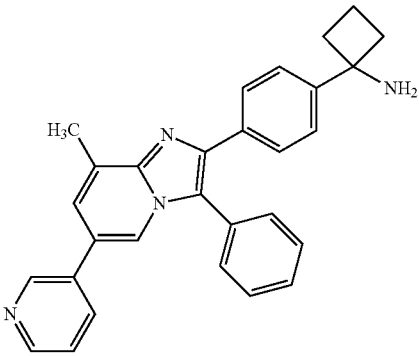<br>1-{4-[8-Methyl-3-phenyl-6-pyridin-3-yl-imidazo[1,2-a]pyridin-2-yl]-phenyl}-cyclobutylamine | (300 MHz, dDMSO): δ 8.81 (1H), 8.52 (1H), 7.94-8.08 (m, 2H), 7.48-7.62 (m, 8H), 7.39-7.48 (m, 1H), 7.35 (d, 2H), 2.63 (s, 3H), 2.26-2.39 (m, 2H), 1.85-2.15 (m, 5H), 1.49-1.69 (m, 1H) ppm. | RT = 0.83 min; m/z = 431 (ES+, M + 1) |
| 2-105 | 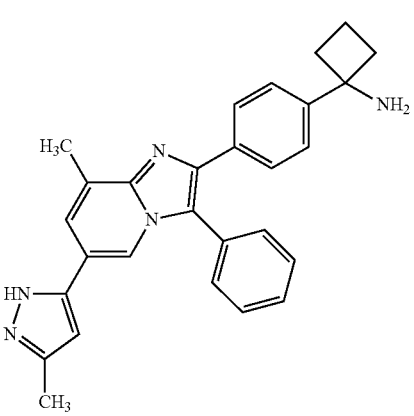<br>1-{4-[8-Methyl-3-phenyl-6-(5-methyl-2H-pyrazol-3-yl)-imidazo[1,2-a]pyridin-2-yl]-phenyl}-cyclobutylamine | (300 MHz, CD$_3$OD): δ 8.28 (1H), 7.40-7.62 (m, 8H), 7.40 (d, 2H), 6.35 (1H), 2.70 (s, 3H), 2.45-2.62 (m, 2H), 2.31 (s, 3H), 2.14-2.40 (m, 2H), 1.97-2.14 (m, 1H), 1.63-1.72 (m, 1H) ppm. | RT = 0.78 min; m/z = 432 (ES−, M − 1) |

Example 2-106

1-[4-(3-phenyl-imidazo[1,2-a]pyridin-2-yl)-phenyl]-cyclobutylamine

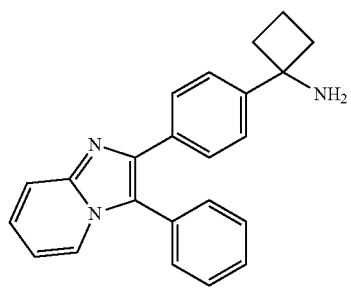 [SMILES: NC1(c2ccc(-c3nc4ccccn4c3-c3ccccc3)cc2)CCC1]

To a solution of {1-[4-(3-phenyl-imidazo[1,2-a]pyridin-2-yl)-phenyl]-cyclobutyl}-carbamic acid tert-butyl ester (50 mg, 0.11 mmol) in MeOH (0.45 mL) and CH$_2$Cl$_2$ (0.75 mL) was added a 4 molar solution of HCl in dioxane (0.57 mL, 2.2 mmol, 20 5equiv). The resulting solution was stirred at room temperature for 12 h, then was concentrated under reduced pressure. The remaining material was purified using MPLC (Biotage Isolera; 10 g SNAP cartridge: 100% CH$_2$Cl$_2$ 4.0 min., gradient to 95% CH$_2$Cl$_2$/5% MeOH 9.5 min., gradient to 90% CH$_2$Cl$_2$/10% MeOH 6.1 min.) to give 1-[4-(3-phenyl-imidazo[1,2-a]pyridin-2-yl)-phenyl]-cyclobutylamine (18 mg, 47%):

UPLC-MS (Method 2): RT=1.23 min; m/z (rel intensity) 340 (100, (M+H)$^+$).

MS: m/z (rel intensity) 340 (15, (M+H)$^+$).

1H-NMR (d6-DMSO): δ 1.59-1.67 (m, 1H), 1.93-2.00 (m, 1H), 2.23-2.28 (m, 2H), 2.25 (br s 1.5 H), 2.34-2.40 (m, 2H), 6.90, (td, J=6.8, 1.1 Hz, 1H), 7.32 (ddd, J=7.9, 6.8, 1.1 Hz, 1H), 7.37 (d, J=8.3 Hz, 2H), 7.51-7.53 (m, 2H), 7.55-7.58 (m, 3H), 7.62 (app t, J=7.2, 2H), 7.67, (d, J=9.0, 1H), 8.00 (d, J=7.2, 1H) ppm.

Example 2-107

1-[4-(6-ethoxy-3-phenyl-imidazo[1,2-a]pyridin-2-yl)-phenyl]-cyclobutylamine

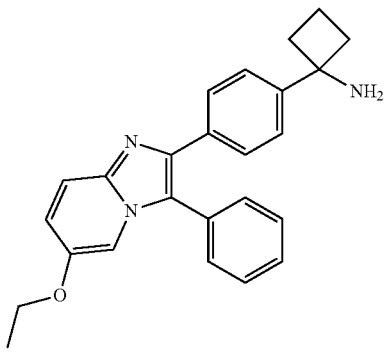 [SMILES: CCOc1ccc2nc(-c3ccc(C4(N)CCC4)cc3)c(-c3ccccc3)n2c1]

To a solution of {1-[4-(6-ethoxy-3-phenyl-imidazo[1,2-a]pyridin-2-yl)-phenyl]-cyclobutyl}-carbamic acid tert-butyl ester (255 mg, 0.53 mmol) in MeOH (2.1 mL) and CH$_2$Cl$_2$ (3.4 mL) was added a 4 molar solution of HCl in dioxane (2.6 mL, 10.5 mmol, 20 equiv). The resulting solution was stirred at room temperature for 12 h, then was concentrated under reduced pressure. The remaining material was purified using MPLC (Isolute Flash NH$_2$ reverse phase column; 100% CH$_2$Cl$_2$ for 5 min., gradient to 95% CH$_2$Cl$_2$: 5% MeOH over 15 minutes; gradient to 90% CH$_2$Cl$_2$: 10% MeOH over 15 min.; gradient to 80% CH$_2$Cl$_2$: 20% MeOH over 15 min.; and gradient to 75% CH$_2$Cl$_2$: 25% MeOH over 15 min.) to give 1-[4-(6-ethoxy-3-phenyl-imidazo[1,2-a]pyridin-2-yl)-phenyl]-cyclobutylamine (38 mg, 19%):

UPLC-MS (Method 2): RT=1.34 min; m/z (rel intensity) 384 (100, (M+H)$^+$).

1H-NMR (d6-DMSO): δ 1.34 (t, J=7.2, 3H), 1.52-1.63 (m, 1H), 1.85-2.50 (m, 5H), 2.26-2.35 (m, 2H), 4.10 (q, J=7.0 Hz, 2H), 6.53 (dd, J=7.5, 2.5 Hz, 1H), 6.99 (d, J=2.5 Hz, 1H), 7.30 (d, J=8.3, Hz, 2H), 7.41-7.58 (m, 7H), 7.78 (d, J=7.5, 1H) ppm.

Example 2-108

1-[4-(3-phenyl-7-vinyl-imidazo[1,2-a]pyridin-2-yl)-phenyl]-cyclobutylamine

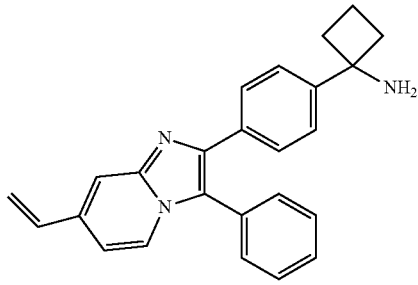 [SMILES: C=Cc1ccn2c(-c3ccccc3)c(-c3ccc(C4(N)CCC4)cc3)nc2c1]

To a solution of {1-[4-(3-phenyl-7-vinyl-imidazo[1,2-a]pyridin-2-yl)-phenyl]-cyclobutyl}-carbamic acid tert-butyl ester (77 mg, 0.17 mmol) in MeOH (0.7 mL) and CH$_2$Cl$_2$ (1.1 mL) was added a 4 molar solution of HCl in dioxane (0.8 mL, 3.3 mmol, 20 equiv) and the resulting solution was stirred at room temperature for 18 h with monitoring by UPLC-MS. The resulting material was concentrated under reduced pressure. The remaining material (82 mg) was purified using MPLC (Isolute Flash NH$_2$ reverse phase column; 100% CH$_2$Cl$_2$ for 1 min., gradient to 95% CH$_2$Cl$_2$: 5% MeOH over 10 min.; 95% CH$_2$Cl$_2$: 5% MeOH for 5.2 min.) to give partially purified material, which was further purified using preparative HPLC (Waters Autopurification System equipped with pump 254, Sample Manager 2767, CFO, DAD 2996, ELSD 2424 and SQD 3001 using a XBridge C18 5 uM 100×30 mm column; 70% water with 0.2% NH$_3$/30% acetonitrile 1 min., gradient to 30% water with 0.2% NH$_3$/70% acetonitrile over 7 min.) to give 1-[4-(3-phenyl-7-vinyl-imidazo[1,2-a]pyridin-2-yl)-phenyl]-cyclobutylamine (7 mg, 11%):

UPLC-MS (Method 2): RT=1.32 min; m/z (rel intensity) 366 (100, (M+H)$^+$).

Example 2-109

1-[4-(3-phenyl-7-pyridin-4-yl-imidazo[1,2-a]pyridin-2-yl)-phenyl]-cyclobutylamine

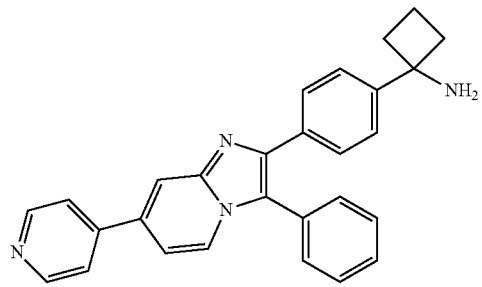 [SMILES: NC1(c2ccc(-c3nc4cc(-c5ccncc5)ccn4c3-c3ccccc3)cc2)CCC1]

To a solution of {1-[4-(3-phenyl-7-pyridin-4-yl-imidazo[1,2-a]pyridin-2-yl)-phenyl]-cyclobutyl}-carbamic acid tert-butyl ester (60 mg, 0.12 mmol) in MeOH (0.5 mL) and CH$_2$Cl$_2$ (0.7 mL) was added a 4 molar solution of HCl in dioxane (0.6 mL, 2.3 mmol, 20 equiv) and the resulting solution was stirred at room temperature for 12 h. The resulting solution was added to ice water, and the resulting mixture was extracted with CH$_2$Cl$_2$ (3×25 mL). The combined organic phases were dried (Na$_2$SO$_4$ anh), and concentrated under reduced pressure. The remaining material was purified using MPLC (Biotage Isolera Flash NH$_2$ Snap 10 reverse phase column; 100% CH$_2$Cl$_2$ for 4 min., gradient to 95% CH$_2$Cl$_2$: 5% MeOH over 1 min.; 95% CH$_2$Cl$_2$: 5% MeOH for 2.5 min., gradient to 90% CH$_2$Cl$_2$: 10% MeOH over 1 min., 90% CH$_2$Cl$_2$: 10% MeOH for 2.5 min., gradient to 80% CH$_2$Cl$_2$: 20% MeOH over 1.5 min., 80% CH$_2$Cl$_2$: 20% MeOH for 0.8 min., gradient to 74% CH$_2$Cl$_2$: 26% MeOH over 2.2 min., gradient to 70% CH$_2$Cl$_2$: 30% MeOH over 1.8 min., 70% CH$_2$Cl$_2$: 30% MeOH for 7.4 min.) to give 1-[4-(3-phenyl-7-pyridin-4-yl-imidazo[1,2-a]pyridin-2-yl)-phenyl]-cyclobutylamine (40 mg, 83%): UPLC-MS (Method 2): RT=1.22 min; m/z (rel intensity) 417 (700, (M+H)$^+$), 833 (40, (2M+H)$^+$).

MS: m/z (rel intensity) 417 (8, (M+H)$^+$).

1H-NMR (d6-DMSO): δ 1.56-1.67 (m, 1H), 1.91-2.00 (m, 1H), 2.03-2.12 (m, 2H), 2.31-2.39 (m, 2H), 7.33-7.38 (m, 3H), 7.50-7.62 (m, 7H), 7.85 (d, J=6.6 Hz, 2H), 8.06 (d, J=7.3 Hz, 1H), 8.23 (s, 1H), 8.65 (d, J=6.1 Hz, 2H) ppm.

The following examples were prepared in a manner analogous to that described in Example 2-109: substituting appropriate starting materials where necessary:

| Example | Structure/Name | 1H-NMR | UPLC-MS |
|---|---|---|---|
| 2-110 | 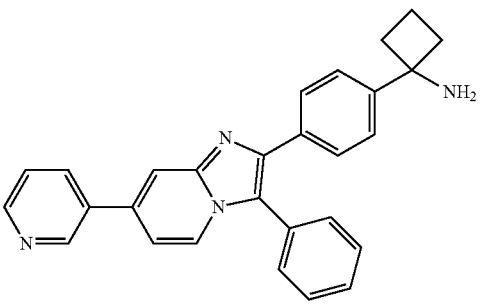<br>1-[4-(3-Phenyl-7-pyridin-3-yl-imidazo[1,2-a]pyridin-2-yl)-phenyl]-cyclobutylamine | (d6-DMSO): δ 1.5-1.65 (m, 1H), 1.86-2.07 (m, 5H), 2.27-2.37 (m, 2H), 7.30 (dd, J = 7.4, 1.7 Hz, 1H), 7.34 (d, J = 8.5 Hz, 2H), 7.47-7.63 (m, 8H), 8.04 (d, J = 7.4 Hz, 1H), 8.10 (s, 1H), 8.22 (app dt, J = 8.1, 1.8 Hz, 1H), 8.58 (dd, J = 4.1, 1.3 Hz, 1H), 9.04 (d, J = 2.1 Hz, 1H) ppm. | Method 2: RT = 1.20 min; m/z (rel intensity) 417 (100, (M + H)$^+$). |
| 2-111 | 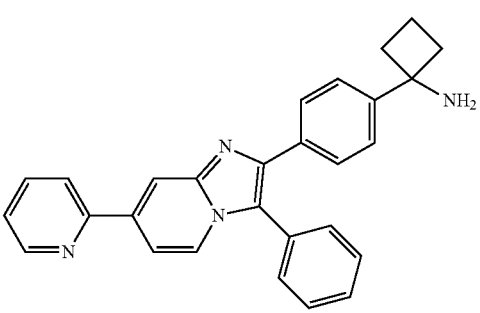<br>1-[4-(3-Phenyl-7-pyridin-2-yl-imidazo[1,2-a]pyridin-2-yl)-phenyl]-cyclobutylamine | (d6-DMSO): δ 1.58-1.68 (m, 1H), 1.90-2.01 (m, 1H), 2.06-2.14 (m, 2H), 2.33-2.41 (m, 2H), 7.35-7.40 (m, 3H), 7.51-7.62 (m, 7H), 7.69 (dd, J = 7.3, 1.8 Hz, 1H), 7.91 (app dt, J = 7.8, 1.8 Hz, 1H), 8.06 (dd, J = 7.3, 0.8 Hz, 1H), 8.17 (d, J = 8.1 Hz, 1H), 8.39 (s, 1H), 8.68 (dm, J = 4.8, 1H) ppm. | Method 2: RT = 1.33 min; m/z (rel intensity) 417 (40, (M + H)$^+$). MS: m/z (rel intensity) 417 (16, (M + H)$^+$). |
| 2-112 | 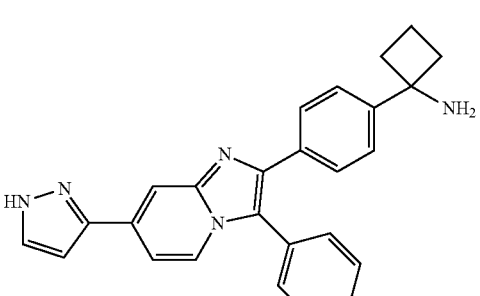<br>1-{4-[3-Phenyl-7-(1H-pyrazol-3-yl)-imidazo[1,2-a]pyridin-2-yl]-phenyl}-cyclobutylamine | (d6-DMSO): δ 1.55-1.63 (m, 1H), 1.87-1.97 (m, 1H), 1.97-2.05 (m, 2H), 2.28-2.35 (m, 2H), 3.13 (d, J = 5.1 Hz, 1H), 3.28 (d, J = 5.1 Hz, 1H), 5.72 (s, 1H), 6.91 (s, 1H), 7.33 (d, J = 8.6 Hz, 2H), 7.40 (brs, 1H), 7.48-7.60 (m, 7H), 7.80 (br s, 1H), 7.98 (d, J = 7.3 Hz, 1H), 8.02 (s, 1H) ppm. | Method 2: RT = 1.16 min; m/z (rel intensity) 406 (90, (M + H)$^+$). |
| 2-113 | 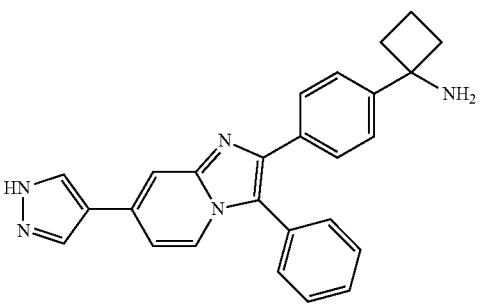<br>1-{4-[3-Phenyl-7-(1H-pyrazol-4-yl)-imidazo[1,2-a]pyridin-2-yl]-phenyl}-cyclobutylamine | (d6-DMSO): δ 1.51-1.65 (m, 1H), 1.85-2.06 (m, 3H), 2.27-2.37 (m, 2H), 7.16 (dd, J = 7.4, 1.7 Hz, 1H), 7.32 (d, J = 8.5 Hz, 2H), 7.46-7.60 (m, 7H), 7.89 (br s, 1H), 7.91 (d, J = 7.4 Hz, 1H), 8.11 (br s, 1H), 8.32, br s, 1H) ppm. | Method 2: RT = 1.12 min; m/z (rel intensity) 406 (100, (M + H)$^+$), 811 (20, (2M + H)$^+$). |

| Example | Structure/Name | 1H-NMR | UPLC-MS |
|---|---|---|---|
| 2-114 | 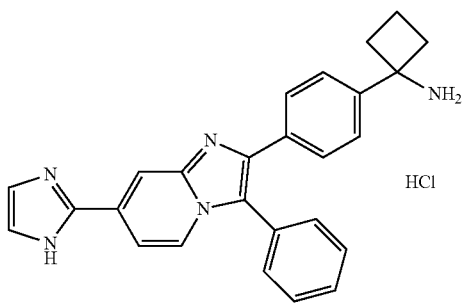<br>1-{4-[7-(1H-Imidazol-2-yl)-3-phenyl-imidazo[1,2-a]pyridin-2-yl]-phenyl}-cyclobutylamine HCl salt | (d6-DMSO): δ 1.72-1.84 (m, 1H), 2.09-2.19 (m, 1H), 2.51-2.61 (m, 4H), 7.52 (d, J = 8.5 Hz, 2H), 7.56-7.59 (m, 2H), 7.62-7.70 (m, 6H), 7.83 (s, 2H), 8.31 (d, J = 7.3 Hz, 1H), 8.60 (s, 1H), 8.62-8.71 (br m, 3H) ppm. | Method 2: RT = 1.08 min; m/z (rel intensity) 406 (100, (M + H)+).<br>MS: m/z (rel intensity) 406 (3, (M + H)+). |
| 2-115 | 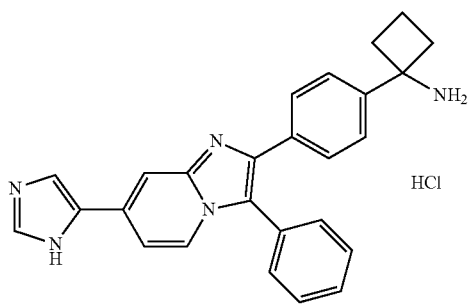<br>1-{4-[7-(3H-Imidazol-4-yl)-3-phenyl-imidazo[1,2-a]pyridin-2-yl]-phenyl}-cyclobutylamineHCl salt | (d6-DMSO): δ 1.68-1.81 (m, 1H), 2.08-2.21 (m, 1H), 2.49-2.56 (m, 4H), 7.52-7.67 (m, 11H), 8.26 (d, J = 7.2 Hz, 1H), 8.42 (d, J = 6.6 Hz, 2H), 8.76 (br s, 3H), 9.03 (br s, 1H) ppm. | Method 2: RT = 1.08 min; m/z (rel intensity) 406 (100, (M + H)+). |
| 2-116 | 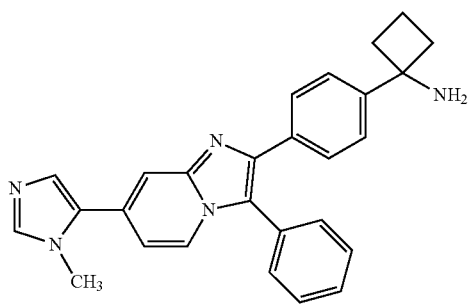<br>1-{4-[7-(3-Methyl-3H-imidazol-4-yl)-3-phenyl-imidazo[1,2-a]-pyridin-2-yl]-phenyl}-cyclobutylamine | (d6-DMSO): δ 1.54-1.65 (m, 1H), 1.89-1.98 (m, 1H), 2.01-2.09 (m, 2H), 2.30-2.37 (m, 2H), 3.80 (s, 3H), 7.04 (dd, J = 7.3, 1.8 Hz, 1H), 7.25 (d, J = 1.3 Hz, 1H), 7.34 (d, J = 8.3 Hz, 2H), 7.49-7.61 (m, 7H), 7.75 (s, 1H), 7.77 (br s, 1H), 7.96, (d, J = 6.3 Hz, 1H) ppm. | Method 2: RT = 1.13 min; m/z (rel intensity) 420 (100, (M + H)+), 839 (50, (2M + H)+). |
| 2-117 | 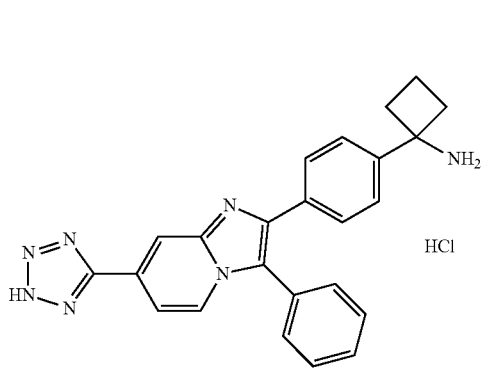<br>1-{4-[3-Phenyl-7-(2H-tetrazol-5-yl)-imidazo[1,2-a]pyridin-2-yl]-phenyl}-cyclobutylamine HCl salt | (d6-DMSO): δ 1.69-1.82 (m, 1H), 2.07-2.19 (m, 1H), 2.49-2.57 (m, 4H), 7.53 (d, J = 8.6 Hz, 2H), 7.57-7.60 (m, 2H), 7.61-7.68 (m, 5H), 7.73 (d, J = 7.3 Hz, 1H), 8.31 (d, J = 7.1 Hz, 1H), 8.53 (s, 1H), 8.72 (br s, 3H) ppm. | Method 2: RT = 0.75 min; m/z (rel intensity) 408 (40, (M + H)+), 815 (10, (2M + H)+).<br>MS (ES−): m/z (rel intensity) 442 (5, (M − H)−). |

-continued

| Example | Structure/Name | 1H-NMR | UPLC-MS |
|---|---|---|---|
| 2-118 | 2-[4-(1-Amino-cyclobutyl)-phenyl]-3-phenyl-imidazo[1,2-a]-pyridine-7-carboxylic acid methyl ester | (d6-DMSO): δ 1.55-1.64 (m, 1H), 1.88-2.05 (m, 3H), 2.28-2.34 (m, 2H), 3.88 (s, 3H), 7.29 (dd, J = 7.53 (d, J = 7.1, 1.8 Hz, 1H), 7.35 (d, J = 8.3 Hz, 2H), 7.49-7.62 (m, 7H), 8.06 (d, J = 7.8 Hz, 1H), 8.20 (s, 1H) ppm. | Method 2: RT = 1.25 min; m/z (rel intensity) 398 (100, (M + H)$^+$). MS: m/z (rel intensity) 398 (19, (M + H)$^+$). |
| 2-119 | 2-[4-(1-Amino-cyclobutyl)-phenyl]-3-phenyl-imidazo[1,2-a]-pyridine-7-carboxylic acid ethyl ester | (d6-DMSO): δ 1.33 (t, J = 7.2 Hz, 3H), 1.53-1.64 (m, 1H), 1.85-2.10 (m, 5H), 2.26-2.34 (m, 2H), 4.33 (q, J = 7.0 Hz, 2H), 7.28 (dd, J = 7.2, 1.7 Hz, 1H) 7.35 (d, J = 8.5 Hz, 2H), 7.48-7.63 (m, 7H), 8.06 (d, J = 7.4 Hz, 1H), 8.20 (s, 1H) ppm. | Method 2: RT = 1.36 min; m/z (rel intensity) 412 (20, (M + H)$^+$). MS: m/z (rel intensity) 412 (10, (M + H)$^+$). |
| 2-120 | 2-[4-(1-Amino-cyclobutyl)-phenyl]-3-phenyl-imidazo[1,2-a]-pyridine-7-carboxylic acid HCl salt | | Method 2: RT = 0.75 min; m/z (rel intensity) 384 (100, (M + H)$^+$), 767 (40, (2M + H)$^+$); ES−: m/z (rel intensity) 382 (100, (M − H)$^-$), 765 (10, (2M − H)$^-$). MS: m/z (rel intensity) 384 (20, (M + H)$^+$); ES−: m/z (rel intensity) 382 (100, (M − H)$^-$) |
| 2-121 | 2-[4-(1-Amino-cyclobutyl)-phenyl]-3-phenyl-imidazo[1,2-a]-pyridine-7-carboxylic acid amide | (d6-DMSO): δ 1.53-1.64 (m, 1H), 1.86-2.06 (m, 3H), 2.25-2.36 (m, 2H), 7.29 (dd, J = 7.2, 1.7 Hz, 1H) 7.34 (d, J = 8.5 Hz, 2H), 7.47-7.62 (m, 8H), 8.00 (br d, J = 7.0 Hz, 1H), 8.15 (br s, 1H), 8.21 (s, 1H) ppm. | Method 2: RT = 1.03 min; m/z (rel intensity) 383 (70, (M + H)$^+$). |

| Example | Structure/Name | 1H-NMR | UPLC-MS |
|---|---|---|---|
| 2-122 | 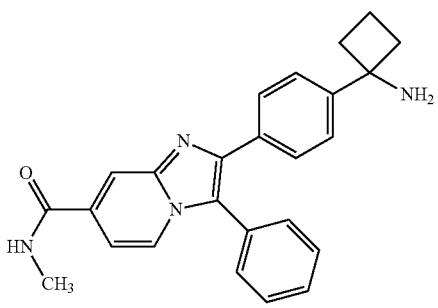<br>2-[4-(1-Amino-cyclobutyl)-phenyl]-3-phenyl-imidazo[1,2-a]-pyridine-7-carboxylic acid methylamide | | Method 2: RT = 1.09 min; m/z (rel intensity) 397 (100, (M + H)$^+$), 793 (40, (2M + H)$^+$). |
| 2-123 | 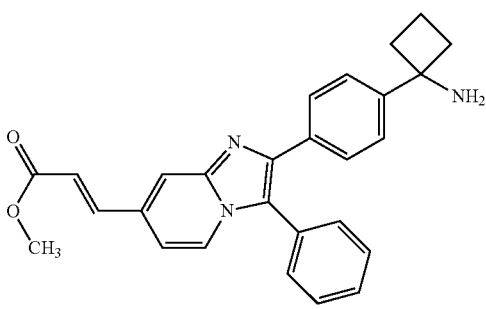<br>(E)-3-{2-[4-(1-Amino-cyclobutyl)-phenyl]-3-phenyl-imidazo[1,2-a]-pyridin-7-yl}-acrylic acid methyl ester | (d6-DMSO): δ 1.53-1.63 (m, 1H), 1.88-2.05 (m, 3H), 2.08 (br s, 2H), 2.28-2.35 (m, 2H), 3.73 (s, 3H), 6.69 (d, J = 15.9 Hz, 1H), 7.29 (dd, J = 7.3, 1.8 Hz, 1H) 7.34 (d, J = 8.6 Hz, 2H), 7.47-7.60 (m, 7H), 7.73 (d, J = 15.9 Hz, 1H), 7.91 (d, J = 7.3 Hz, 1H), 8.01 (s, 1H) ppm. | Method 2: RT = 1.31 min; m/z (rel intensity) 423 (30, (M + H)$^+$); 847 (60, (2M + H)$^+$). |
| 2-124 | 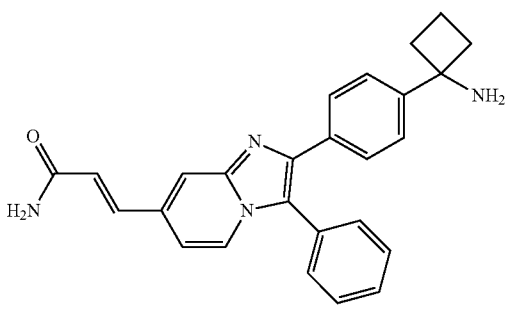<br>(E)-3-{2-[4-(1-Amino-cyclobutyl)-phenyl]-3-phenyl-imidazo[1,2-a]-pyridin-7-yl}-acrylamide | (d6-DMSO): δ 1.76-1.82 (m, 1H), 2.05-2.21 (m, 1H), 2.49-2.59 (m, 4H), 6.83 (d, J = 16.0 Hz, 1H), 7.24-7.30 (m, 1H) 7.37 (d, J = 5.8 Hz, 1H), 7.52-7.72 (m, 11H), 8.02 (s, 1H), 8.17 (d, J = 7.4 Hz, 1H), 8.73 (br s, 2H) ppm. | Method 2: RT = 1.06 min; m/z (rel intensity) 408 (60, (M + H)$^+$), 877 (30, (2M + H)$^+$). |
| 2-125 | 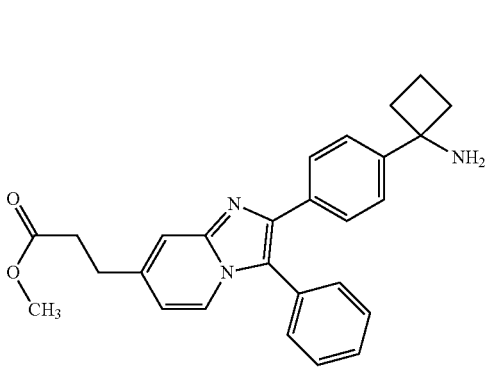<br>3-{2-[4-(1-Amino-cyclobutyl)-phenyl]-3-phenyl-imidazo[1,2-a]-pyridin-7-yl}-propionic acid methyl ester | | Method 2: RT = 1.30 min; m/z (rel intensity) 426 (100, (M + H)$^+$); 851 (20, (2M + H)$^+$). |

-continued

| Example | Structure/Name | 1H-NMR | UPLC-MS |
|---|---|---|---|
| 2-126 | 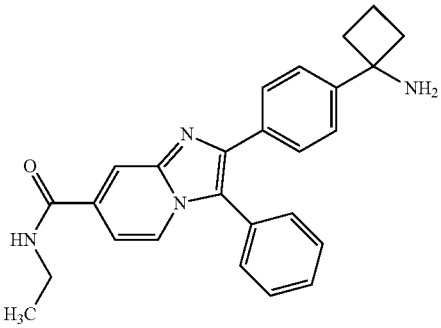<br>2-[4-(1-Amino-cyclobutyl)-phenyl]-3-phenyl-imidazo[1,2-a]-pyridine-7-carboxylic acid ethyl-amide | | Method 2: RT = 1.13 min m/z (rel intensity) 411 (100, (M + H)$^+$); 821 (5, (2M + H)$^+$); ES−: m/z (rel intensity) 409 (100, (M − H)$^−$), 819 (50, (M − H)$^−$). |
| 2-127 | 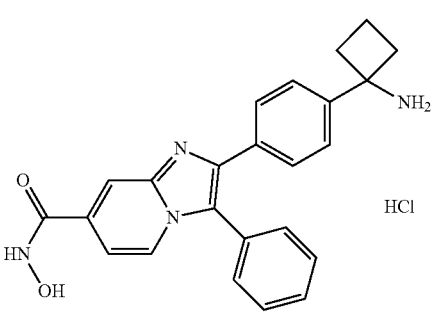<br>2-[4-(1-Amino-cyclobutyl)-phenyl]-3-phenyl-imidazo[1,2-a]-pyridine-7-carboxylic acid hydroxyamide | | |
| 2-128 | 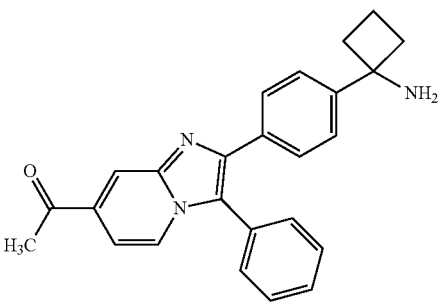<br>1-{2-[4-(1-Amino-cyclobutyl)-phenyl]-3-phenyl-imidazo[1,2-a]-pyridin-7-yl}-ethanone | | Method 2: RT = 1.02 min; m/z (rel intensity) 382 (100, (M + H)$^+$); 763 (70, (2M + H)$^+$). |
| 2-129 | 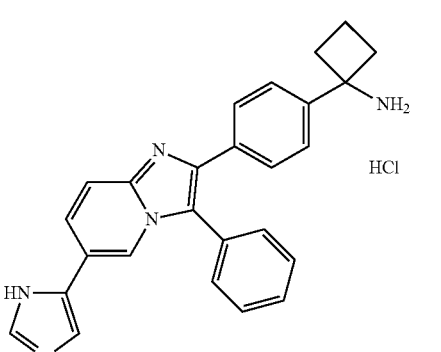<br>1-{4-[6-(3H-Imidazol-4-yl)-3-phenyl-imidazo[1,2-a]pyridin-2-yl]-phenyl}-cyclobutylamine HCl salt | | Method 2: RT = 1.17 min; m/z (rel intensity) 406 (70, (M + H)$^+$); 811 (20, (2M + H)$^+$); ES−: m/z (rel intensity) 404 (100, (M − H)$^−$), 809 (80, (M − H)$^−$). |

| Example | Structure/Name | 1H-NMR | UPLC-MS |
|---|---|---|---|
| 2-130 | 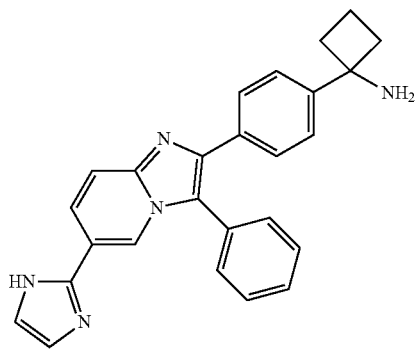<br>1-{4-[6-(1H-Imidazol-2-yl)-3-phenyl-imidazo[1,2a]pyridin-2-yl]-phenyl}-cyclobutylamine | | Method 2: RT = 1.01 min; m/z (rel intensity) 406 (70, (M + H)$^+$); 811 (30, (2M + H)$^+$); ES−: m/z (rel intensity) 404 (100, (M − H)$^-$), 809 (10, (M − H)$^-$). |
| 2-131 | 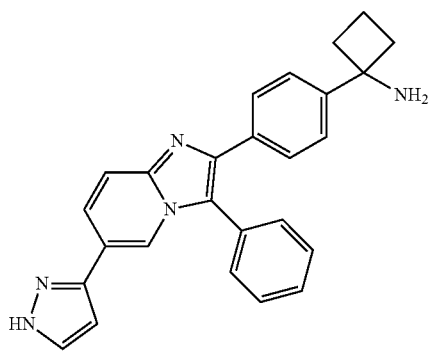<br>1-{4-[3-Phenyl-6-(1H-pyrazol-3-yl)-imidazo[1,2-a]pyridin-2-yl]-phenyl}-cyclobutylamine | | Method 2: RT = 1.12 min; m/z (rel intensity) 406 (100, (M + H)$^+$); 811 (70, (2M + H)$^+$). |
| 2-132 | 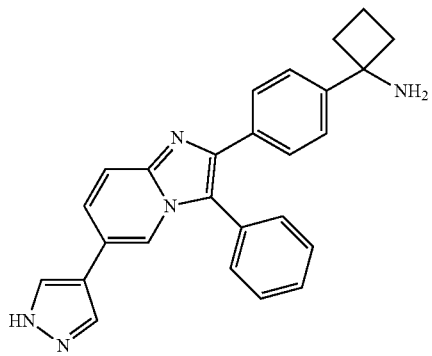<br>1-{4-[3-Phenyl-6-(1H-pyrazol-4-yl)-imidazo[1,2-a]pyridin-2-yl]-phenyl}-cyclobutylamine | | Method 2: RT = 1.05 min; m/z (rel intensity) 406 (100, (M + H)$^+$); 811 (20, (2M + H)$^+$). |

| Example | Structure/Name | 1H-NMR | UPLC-MS |
|---|---|---|---|
| 2-133 | 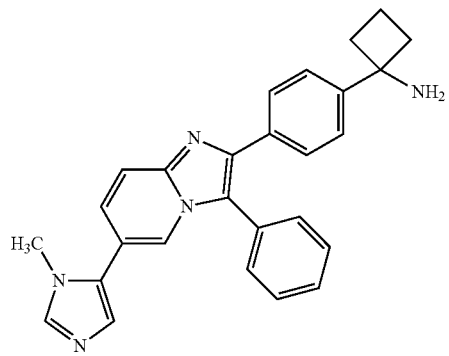<br>1-{4-[6-(3-Methyl-3H-imidazol-4-yl)-3-phenyl-imidazo[1,2-a]-pyridin-2-yl]-phenyl}-cyclobutylamine | | Method 2: RT = 1.07 min; m/z (rel intensity) 420 (100, (M + H)$^+$); 839 (5, (2M + H)$^+$). |
| 2-134 | 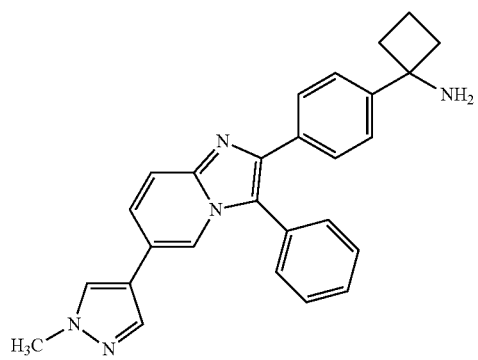<br>1-{4-[6-(1-Methyl-1H-pyrazol-4-yl)-3-phenyl-imidazo[1,2-a]-pyridin-2-yl]-phenyl}-cyclobutylamine | | Method 2: RT = 1.15 min; m/z (rel intensity) 420 (100, (M + H)$^+$); 839 (20, (2M + H)$^+$). |
| 2-135 | 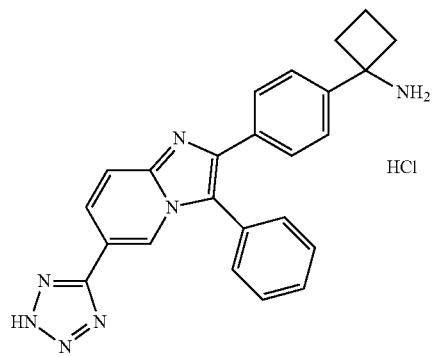<br>1-{4-[3-Phenyl-6-(2H-tetrazol-5-yl)-imidazo[1,2-a]pyridin-2-yl]-phenyl}-cyclobutylamine HCl salt | | Method 2: RT = 0.71 min; m/z (rel intensity) 408 (70, (M + H)$^+$); 815 (30, (2M + H)$^+$). |

| Example | Structure/Name | 1H-NMR | UPLC-MS |
|---|---|---|---|
| 2-136 | 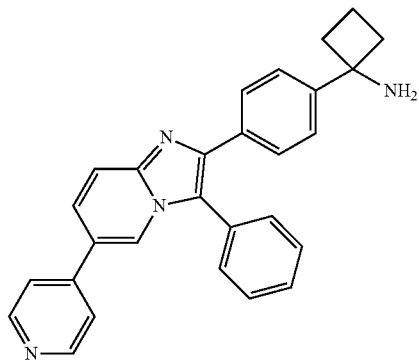<br>1-[4-(3-Phenyl-6-pyridin-4-yl-imidazo[1,2-a]pyridin-2-yl)-phenyl]-cyclobutylamine | | Method 2: RT = 1.15 min; m/z (rel intensity) 417 (100, (M + H)$^+$); 833 (20, (2M + H)$^+$). |
| 2-137 | 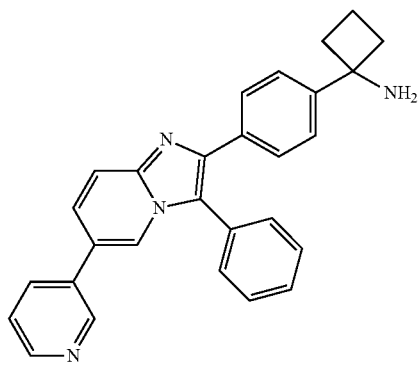<br>1-[4-(3-Phenyl-6-pyridin-3-yl-imidazo[1,2-a]pyridin-2-yl)-phenyl]-cyclobutylamine | | Method 2: RT = 1.19 min; m/z (rel intensity) 417 (90, (M + H)$^+$); 833 (100, (2M + H)$^+$). |
| 2-138 | 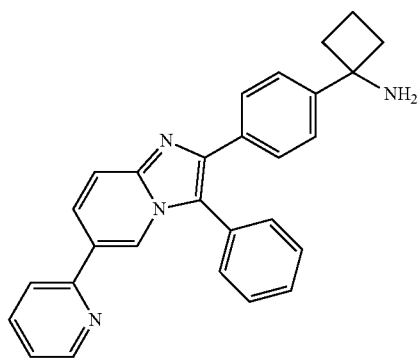<br>1-[4-(3-Phenyl-6-pyridin-3-yl-imidazo[1,2-a]pyridin-2-yl)-phenyl]-cyclobutylamine | | Method 2: RT = 1.19 min; m/z (rel intensity) 417 (20, (M + H)$^+$); 833 (100, (2M + H)$^+$). |

| Example | Structure/Name | 1H-NMR | UPLC-MS |
|---|---|---|---|
| 2-139 | 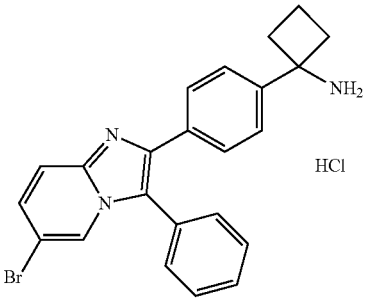<br>1-[4-(6-Bromo-3-phenyl-imidazo[1,2-a]pyridin-2-yl)-phenyl]-cyclobutylamine | | Method 2: RT = 1.36 min; m/z (rel intensity) 418 (100, (M + H)$^+$); 835 (20, (2M + H)$^+$). |
| 2-140 | 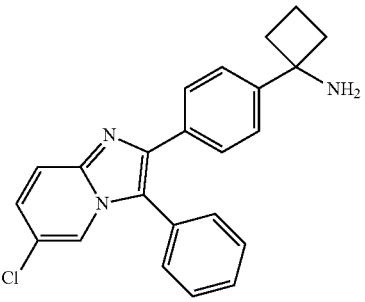<br>1-[4-(6-Chloro-3-phenyl-imidazo[1,2-a]pyridin-2-yl)-phenyl]-cyclobutylamine | | Method 2: RT = 1.36 min; m/z (rel intensity) 373 (10, (M + H)$^+$); 747 (30, (2M + H)$^+$). |
| 2-141 | 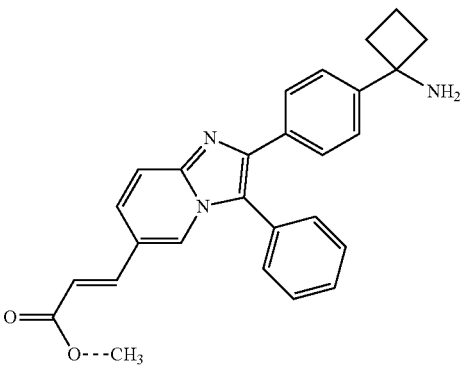<br>(E)-3-{2-[4-(1-Amino-cyclobutyl)-phenyl]-3-phenyl-imidazo[1,2-a]pyridin-6-yl}-acrylic acid methyl ester | | Method 2: RT = 1.29 min; m/z (rel intensity) 424 (30, (M + H)$^+$); 847 (30, (2M + H)$^+$). |
| 2-142 | 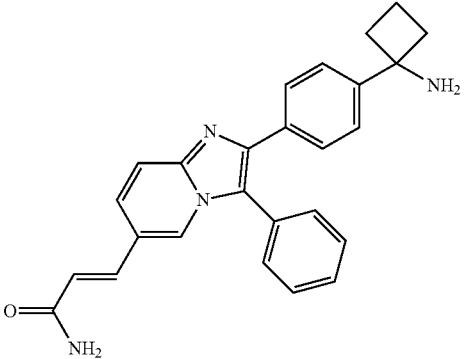<br>(E)-3-{2-[4-(1-Amino-cyclobutyl)-phenyl]-3-phenyl-imidazo[1,2-a]pyridin-6-yl}-acrylamide | | Method 2: RT = 1.00 min; m/z (rel intensity) 409 (70, (M + H)$^+$); 817 (30, (2M + H)$^+$). |

-continued

| Example | Structure/Name | 1H-NMR | UPLC-MS |
|---|---|---|---|
| 2-143 | 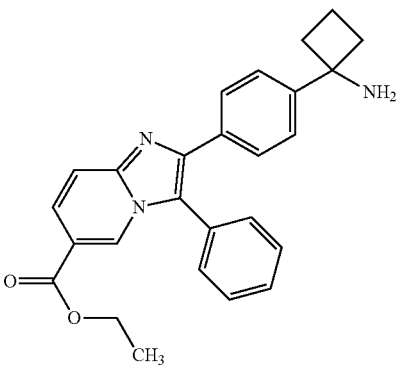<br>2-[4-(1-Amino-cyclobutyl)-3-phenyl-imidazo[1,2-a]pyridine-6-carboxylic acid ethyl ester | | Method 2: RT = 1.34 min; m/z (rel intensity) 412 (100, (M + H)$^+$); 823 (10, (2M + H)$^+$). |
| 2-144 | 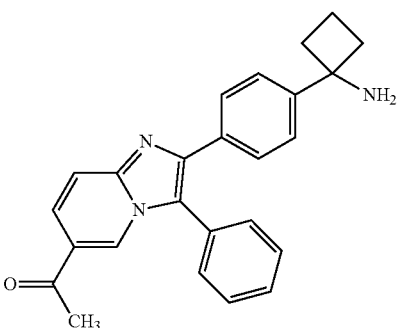<br>1-{2-[4-(1-Amino-cyclobutyl)-phenyl]-3-phenyl-imidazo[1,2-a]pyridin-6-yl}-ethanone | | Method 2: RT = 1.14 min; m/z (rel intensity) 382 (100, (M + H)$^+$); 763 (40, (2M + H)$^+$). |
| 2-145 | 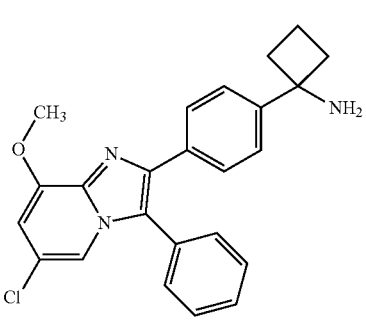<br>1-[4-(6-Chloro-8-methoxy-3-phenyl-imidazo[1,2-a]pyridin-2-yl)-phenyl]-cyclobutylamine | | Method 2: RT = 1.39 min; m/z (rel intensity) 404 (50, (M + H)$^+$); 807 (30, (2M + H)$^+$). |
| 2-146 | 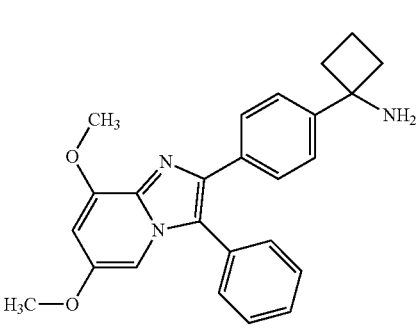<br>1-[4-(6,8-Dimethoxy-3-phenyl-imidazo[1,2-a]pyridin-2-yl)-phenyl]-cyclobutylamine | | Method 2: RT = 1.25 min; m/z (rel intensity) 400 (70, (M + H)$^+$); 799 (60, (2M + H)$^+$). |

-continued

| Example | Structure/Name | 1H-NMR | UPLC-MS |
|---|---|---|---|
| 2-147 | 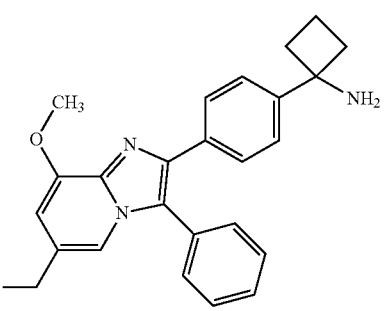<br>1-[4-(6-Ethyl-8-methoxy-3-phenyl-imidazo[1,2-a]pyridin-2-yl)-phenyl]-cyclobutylamine | | Method 2: RT = 1.40 min; m/z (rel intensity) 398 (100, (M + H)$^+$); 795 (20, (2M + H)$^+$). |
| 2-148 | 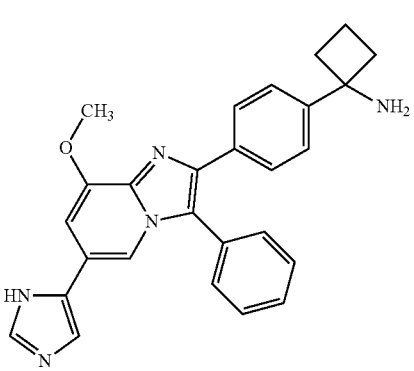<br>1-{4-[6-(3H-Imidazol-4-yl)-8-methoxy-3-phenyl-imidazo[1,2-a]pyridin-2-yl]-phenyl}-cyclobutylamine | | Method 2: RT = 1.03 min; m/z (rel intensity) 436 (100, (M + H)$^+$); 871 (5, (2M + H)$^+$); ES−: m/z (rel intensity) 434 (100, (M − H)$^-$), 869 (40, (2M − H)$^-$). |
| 2-149 | 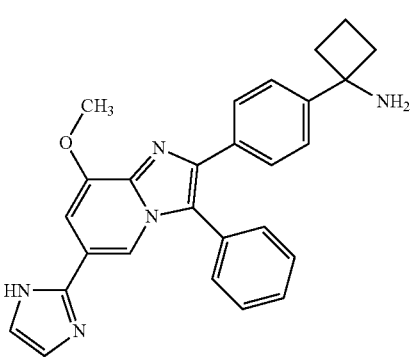<br>1-{4-[6-(1H-Imidazol-2-yl)-8-methoxy-3-phenyl-imidazo[1,2-a]pyridin-2-yl]-phenyl}-cyclobutylamine | | Method 2: RT = 1.06 min; m/z (rel intensity) 436 (100, (M + H)$^+$); 871 (5, (2M + H)$^+$); ES−: m/z (rel intensity) 434 (100, (M − H)$^-$), 869 (40, (2M − H)$^-$). |
| 2-150 | 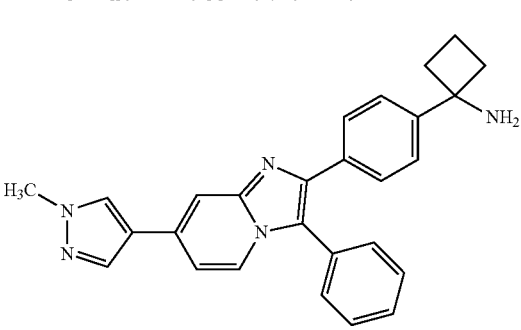<br>1-{4-[7-(1-Methyl-1H-pyrazol-4-yl)-3-phenyl-imidazo[1,2-a]pyridin-2-yl]-phenyl}-cyclobutylamine | | Method 2: RT = 1.19 min; m/z (rel intensity) 420 (100, (M + H)$^+$); 839 (60, (2M + H)$^+$). |

The following examples were prepared in a manner analogous to that described in Example 2-109: using trifluoromethanesulfonic acid in dioxane in place of HCl in dioxane, and substituting appropriate starting materials where necessary:

| Example | Structure/Name | UPLC-MS |
|---|---|---|
| 2-151 | 2-[4-(1-Amino-cyclobutyl)-phenyl]-3-phenyl-imidazo[1,2-a]pyridin-7-ylamine | Method 2: RT = 1.07 min; m/z (rel intensity) 355 (100, (M + H)$^+$). |
| 2-152 | N-{2-[4-(1-Amino-cyclobutyl)-phenyl]-3-phenyl-imidazo[1,2-a]pyridin-7-yl}-acetamide | Method 2: RT = 1.03 min; m/z (rel intensity) 397 (70, (M + H)$^+$). |
| 2-153 | {2-[4-(1-Amino-cyclobutyl)-phenyl]-3-phenyl-imidazo[1,2-a]pyridin-7-yl}-urea | Method 2: RT = 0.97 min; m/z (rel intensity) 398 (100, (M + H)$^+$), 795 (60, (2M + H)$^+$); ES−: m/z (rel intensity) 396 (100, (M − H)$^-$), 793 (30, (2M − H)$^-$). |
| 2-154 | 2-[4-(1-Amino-cyclobutyl)-phenyl]-3-phenyl-imidazo[1,2-a]pyridine-7-carboxylic acid methoxy-methyl-amide | Method 2: RT = 1.11 min; m/z (rel intensity) 427 (50, (M + H)$^+$). |

| Example | Structure/Name | UPLC-MS |
|---|---|---|
| 2-155 | 2-[4-(1-Amino-cyclobutyl)-phenyl]-3-phenyl-imidazo[1,2-a]pyridin-6-ylamine | Method 2: RT = 1.02 min; m/z (rel intensity) 355 (100, (M + H)$^+$). |
| 2-156 | N-{2-[4-(1-Amino-cyclobutyl)-phenyl]-3-phenyl-imidazo[1,2-a]pyridin-6-yl}-acetamide | Method 2: RT = 1.04 min; m/z (rel intensity) 397 (100, (M + H)$^+$). |
| 2-157 | {2-[4-(1-Amino-cyclobutyl)-phenyl]-3-phenyl-imidazo[1,2-a]pyridin-6-yl}-urea | Method 2: RT = 0.94 min; m/z (rel intensity) 398 (100, (M + H)$^+$). |
| 2-158 | 1-{2-[4-(1-Amino-cyclobutyl)-phenyl]-3-phenyl-imidazo[1,2-a]pyridin-6-yl}-3-methyl-urea | Method 2: RT = 1.00 min; m/z (rel intensity) 412 (100, (M + H)$^+$), 823 (5, (M + H)$^+$). |

| Example | Structure/Name | UPLC-MS |
|---|---|---|
| 2-159 | 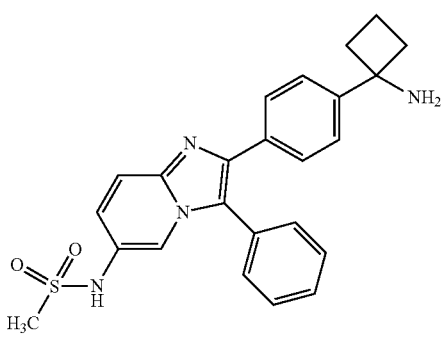<br>N-{2-[4-(1-Amino-cyclobutyl)-phenyl]-3-phenyl-imidazo[1,2-a]pyridin-6-yl}-methanesulfonamide | Method 2: RT = 0.70 min; m/z (rel intensity) 433 (100, (M + H)+). |
| 2-160 | 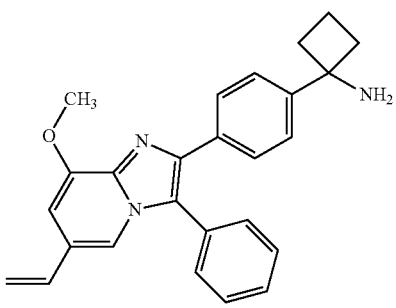<br>1-[4-(8-Methoxy-3-phenyl-6-vinyl-imidazo[1,2-a]pyridin-2-yl)-phenyl]-cyclobutylamine | Method 2: RT = 1.35 min; m/z (rel intensity) 396 (20, (M + H)+), 791 (30, (2M + H)+). |

Example 3-0

2-[4-(cis-1-amino-3-hydroxy-cyclobutyl)-phenyl]-3-phenyl-imidazo[1,2-a]pyrimidin-7-ol

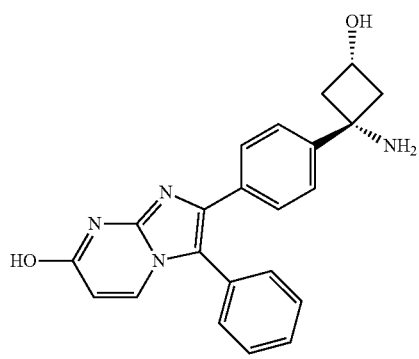 [SMILES: N[C@]1(c2ccc(-c3nc4nc(O)ccn4c3-c3ccccc3)cc2)C[C@H](O)C1]

A mixture of 5-[4-(7-methoxy-3-phenyl-imidazo[1,2-a]pyrimidin-2-yl)-phenyl]-2-oxa-4-aza-bicyclo[3.1.1]heptan-3-one (54 mg), aqueous potassium hydroxide (4M, 1.95 mL) and isopropanol (1.95 mL) was heated overnight at 100° C. On cooling the reaction was concentrated, taken up in water and extracted with DCM. The aqueous phase was concentrated, the residue extracted with hot THF, filtered and the filtrate concentrated to give the crude title compound. Purification was achieved by preparative reverse phase HPLC to give the title compound.

UPLC-MS: RT=0.66 min; m/z=356.10 (M−NH$_2$), 373.32 (M+1)

1H NMR (300 MHz, d6-DMSO): δ 7.71 (d, 1H), 7.43-7.53 (m, 5H), 7.38 (d, 2H), 7.31 (d, 2H), 5.93 (d, 1H), 3.73 (m, 1H), 2.65-2.71 (m, 2H), 1.99-2.05 (m, 2H) ppm.

Example 4-0

1-{4-[7-(2-amino-ethoxy)-3-phenyl-imidazo[1,2-a]pyrimidin-2-yl]-phenyl}-cyclobutylamine Step 1: 2-(2-{2-[4-(1-Amino-cyclobutyl)-phenyl]-3-phenyl-imidazo[1,2-a]pyrimidin-7-yloxy}-ethyl)-isoindole-1,3-dione

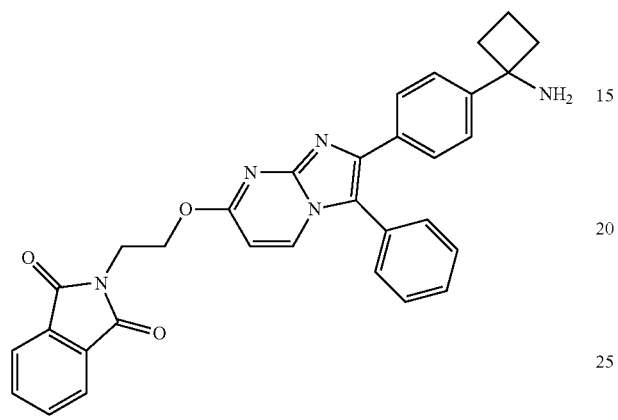

[1-(4-{7-[2-(1,3-dioxo-1,3-dihydro-isoindol-2-yl)-ethoxy]-3-phenyl-imidazo[1,2-a]pyrimidin-2-yl}-phenyl)-cyclobutyl]-carbamic acid tert-butyl ester (530 mg) was dissolved in methanol/DCM (1.3 mL/2.1 mL), treated with HCl in dioxane (4.08 mL of a 4M solution) and the mixture stirred overnight at rt. The reaction mixture was poured onto ice, made alkaline with 2N aqueous sodium hydroxide and extracted with EtOAc. The combined organic phases were washed with saturated aqueous sodium chloride, dried and concentrated in vacuo to give the crude title product as a yellow oil. Purification was achieved by trituration at 0° C. with diisopropyl ether. The resulting precipitate was filtered and dried to give the title compound as a solid (390 mg).

UPLC-MS (Method 2): RT=1.32 min; m/z=530.30 (M+H).

1H NMR (300 MHz, d6-DMSO, uncorrected): δ 8.14 (d, 1H), 7.76-7.86 (m, 4H), 7.43-7.54 (m, 7H), 7.31 (d, 2H), 6.39 (d, 1H), 4.62 (t, 2H), 4.03 (t, 2H), 2.27-2.35 (m, 2H), 1.84-2.04 (m, 3H+NH$_2$), 1.53-1.63 (m, 1H) ppm.

Step 2: 1-{4-[7-(2-amino-ethoxy)-3-phenyl-imidazo[1,2-a]pyrimidin-2-yl]-phenyl}-cyclobutylamine

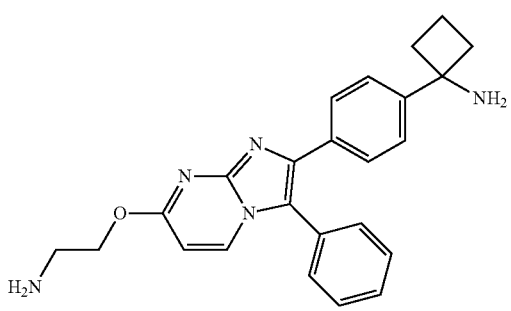 [SMILES: NCCOc1ccn2c(-c3ccccc3)c(-c3ccc(C4(N)CCC4)cc3)nc2n1]

2-(2-{2-[4-(1-Amino-cyclobutyl)-phenyl]-3-phenyl-imidazo[1,2-a]pyrimidin-7-yloxy}-ethyl)-isoindole-1,3-dione (340 mg from Step 1) was dissolved in ethanol (6.8 mL), treated with hydrazine hydrate (98%, 0.045 mL) and heated at 80° C. for 22 h. On cooling, the reaction mixture was diluted with diisopropyl ether and filtered. The filtrate was concentrated in vacuo to give the title compound (225 mg).

UPLC-MS (Method 2): RT=1.01 min; m/z=400.21 (M+H); m/z (ES−) 398.15 (M−H).

Example 5-0

2-[4-(1-amino-cyclobutyl)-phenyl]-3-phenyl-imidazo[1,2-a]pyridin-6-ol

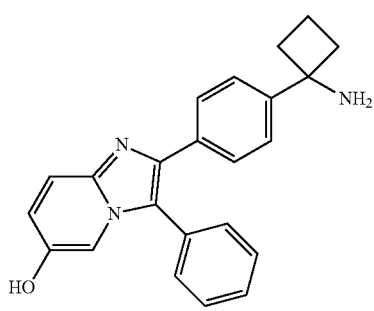 [SMILES: NC1(c2ccc(-c3nc4ccc(O)cn4c3-c3ccccc3)cc2)CCC1]

A solution of Example 2-17, 180 mg in N-methyl-pyrrolidinone (6.9 mL) under argon was heated to 100° C. and treated with sodium sulfide (0.211 g). The reaction mixture was heated at 160° C. for a further 30 minutes. On cooling the reaction mixture was concentrated in vacuo. Purification was achieved by chromatography on silica gel, followed by trituration with diisopropyl ether at 0° C., to give the title compound as a beige solid.

UPLC-MS (Method 2): RT=0.91 min; m/z=356.18 (M+H).

Example 5-1

2-[4-(1-amino-cyclobutyl)-phenyl]-3-phenyl-imidazo[1,2-a]pyridin-8-ol

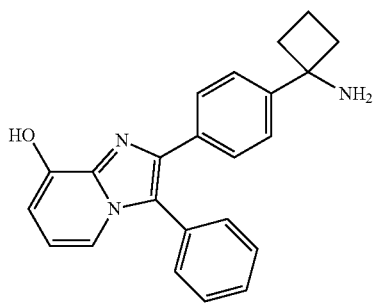 [SMILES: NC1(c2ccc(-c3nc4c(O)cccn4c3-c3ccccc3)cc2)CCC1]

The compound was prepared in analogy to Example 5-0, except that {1-[4-(8-methoxy-3-phenyl-imidazo[1,2-a]pyridin-2-yl)-phenyl]-cyclobutyl}-carbamic acid tert-butyl ester was used as starting material. The Boc protecting group cleaved under the reaction conditions.

UPLC-MS (Method 3): RT=0.68 min; m/z=356.0 (M+H).

Example 6-0

2-[4-(1-amino-cyclobutyl)-phenyl]-3-phenyl-imidazo[1,2-a]pyridine-8-carboxylic acid amide

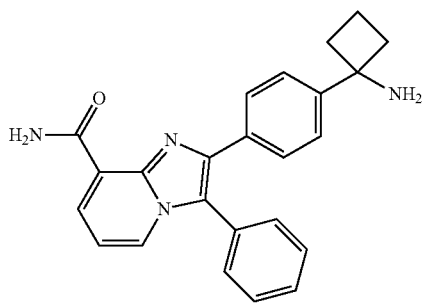 [SMILES: NC(=O)c1cccn2c(-c3ccccc3)c(-c3ccc(C4(N)CCC4)cc3)nc12]

A mixture of 2-[4-(1-amino-cyclobutyl)-phenyl]-3-phenyl-imidazo[1,2-a]pyridine-8-carboxylic acid methyl ester (Example 2-23, 128 mg) and ammonia (2.23 mL of a 7M aqueous solution) was heated at 130° C. under microwave irradiation for 90 minutes. On cooling, the reaction mixture was concentrated to give the title compound.

UPLC-MS (Method 2): RT=1.18 min; m/z=366.15 (M–NH$_2$).

Example 6-1

2-[4-(1-amino-cyclobutyl)-phenyl]-8-chloro-3-phenyl-imidazo[1,2-a]pyridine-6-carboxylic acid amide

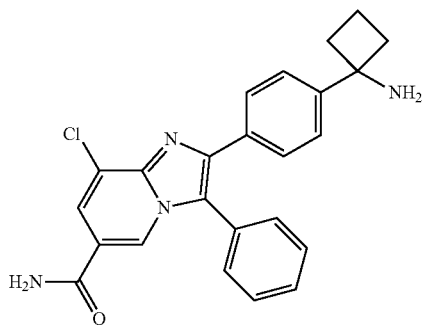 [SMILES: NC(=O)c1cc(Cl)c2nc(-c3ccc(C4(N)CCC4)cc3)c(-c3ccccc3)n2c1]

The title compound was prepared in analogy to Example 6-0 from 2-[4-(1-tert-butoxycarbonylamino-cyclobutyl)-phenyl]-8-chloro-3-phenyl-imidazo[1,2-a]pyridine-6-carboxylic acid methyl ester.

RT=0.75 min; m/z=400.10 (M–NH$_2$);

1H-NMR (400 MHz, d6-DMSO, uncorrected): δ 8.40 (d, 1H), 8.18 (br s), 7.94 (d, 1H), 7.52-7.64 (m, 7H), 7.36 (d, 2H), 2.29-2.35 (m, 2H), 1.87-2.06 (m, 3H), 1.54-1.64 (m, 1H) ppm.

Example 7-0

1-[4-(7-ethynyl-3-phenyl-imidazo[1,2-a]pyridin-2-yl)-phenyl]-cyclobutylamine

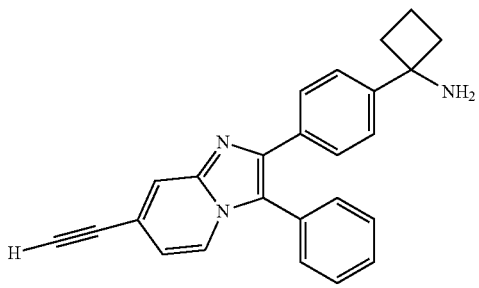 [SMILES: C#Cc1ccn2c(-c3ccccc3)c(-c3ccc(C4(N)CCC4)cc3)nc2c1]

To a solution of 1-[4-(3-phenyl-7-trimethylsilanylethynyl-imidazo[1,2-a]pyridin-2-yl)-phenyl]-cyclobutylamine (31 mg, 0.07 mmol) in THF (0.5 mL) was added a 1 M solution of tetra-n-butylammonium fluoride in THF (0.2 mL, 0.2 mmol, 3.0 equiv). The resulting solution was stirred at room temperature for 18 h, then was separated between water (15 mL) and EtOAc (15 mL). The aqueous layer was extracted with EtOAc (2×15 mL). The combined organic phases were washed with water (15 mL), dried (Na$_2$SO$_4$ anh) and concentrated under reduced pressure. The remaining material was treated with triethylamine (0.03 mL, 0.21 mmol, 3.0 equiv) and the resulting material was purified using MPLC (Biotage Isolera Flash NH$_2$ Snap 10 reverse phase column; 100% CH$_2$Cl$_2$ for 8.5 min., gradient to 95% CH$_2$Cl$_2$: 5% MeOH over 7 min.; 95% CH$_2$Cl$_2$: 5% MeOH for 9 min.) to give 1-[4-(7-ethynyl-3-phenyl-imidazo[1,2-a]pyridin-2-yl)-phenyl]-cyclobutylamine (12 mg, 39%).

UPLC-MS (Method 2): RT=1.32 min; m/z (rel intensity) 364 (25, (M+H)$^+$), 727 (40, (2M+H)$^+$).

1H-NMR (d6-DMSO): δ 1.18-1.33 (m, 1H), 1.48-1.63 (m, 1H), 1.87-2.05 (m, 2H), 2.26-2.39 (m, 2H), 4.41 (s, 1H), 6.84, (dd, J=7.2, 1.5 Hz, 1H), 7.33 (d, J=8.3 Hz, 2H), 7.24-7.61 (m, 7H), 7.80 (s, 1H), 7.93 (d, J=7.0 Hz, 1H) ppm.

Example 8-0

3-{2-[4-(1-amino-cyclobutyl)-phenyl]-3-phenyl-imidazo[1,2-a]pyridin-7-yl}-propionamide

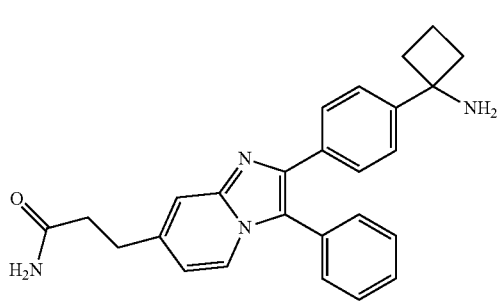 [SMILES: NC(=O)CCc1ccn2c(-c3ccccc3)c(-c3ccc(C4(N)CCC4)cc3)nc2c1]

A mixture of (E)-3-{2-[4-(1-amino-cyclobutyl)-phenyl]-3-phenyl-imidazo[1,2-a]pyridin-7-yl}-acrylamide (111 mg, 0.27 mmol) and 10% palladium on carbon (14 mg) in MeOH (10 mL) was stirred under a hydrogen atmosphere for 23 h, additional palladium on carbon (14 mg) was added and the reaction was stirred under a hydrogen atmosphere for 6 h. The resulting mixture was filtered. The resulting solution was concentrated under reduced pressure. The remaining material was purified using MPLC (Biotage Isolera Flash NH$_2$ Snap 10 reverse phase column; 100% CH$_2$Cl$_2$ for 8 min., gradient to 95% CH$_2$Cl$_2$: 5% MeOH over 5 min.; 95% CH$_2$Cl$_2$: 5% MeOH for 4 min., gradient to 80% CH$_2$Cl$_2$: 20% MeOH over 5 min., 80% CH$_2$Cl$_2$: 20% MeOH for 6.2 min.) to give 3-{2-[4-(1-amino-cyclobutyl)-phenyl]-3-phenyl-imidazo[1,2-a]pyridin-7-yl}-propionamide (24 mg, 17%):

UPLC-MS (Method 2): RT=1.02 min; m/z (rel intensity) 411 (100, (M+H)$^+$), 821 (10, (2M+H)$^+$); ES−: m/z (rel intensity) 409 (100, (M−H)$^−$), 819 (30, (2M−H)$^−$).

The following example was prepared in a manner analogous to that described in Example 8-0: substituting appropriate starting materials where necessary:

Example 9-0

{2-[4-(1-amino-cyclobutyl)-phenyl]-3-phenyl-imidazo[1,2-a]pyridin-7-yloxy}-acetic acid methyl ester

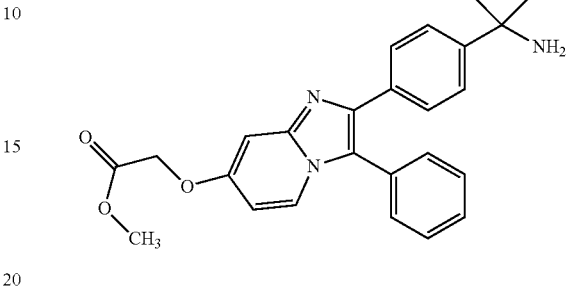

To a solution of 2-[4-(1-amino-cyclobutyl)-phenyl]-3-phenyl-imidazo[1,2-a]pyridin-7-ol (75 mg, 0.21 mmol), methyl bromoacetate (0.02 mL, 0.21 mmol, 1.0 equiv) and Cs$_2$CO$_3$ (138 mg, 0.422 mmol, 2 equiv) in DMF (2.5 mL) was stirred at room temperature for 12 h. The resulting mixture added to water (10 mL). The resulting mixture was extracted with EtOAc (3×10 mL). The combined organic phases were dried (Na$_2$SO$_4$ anh), and concentrated under reduced pressure. The remaining material was purified using MPLC (Biotage Isolera Flash NH$_2$ Snap 10 reverse phase column; 100% CH$_2$Cl$_2$ for 8 min., gradient to 95% CH$_2$Cl$_2$: 5% MeOH over 5 min.; 95% CH$_2$Cl$_2$: 5% MeOH for 4 min., gradient to 80% CH$_2$Cl$_2$: 20% MeOH over 5 min., 80% CH$_2$Cl$_2$: 20% MeOH for 6.2 min., gradient to 75% CH$_2$Cl$_2$: 25% MeOH over 2.0 min., 75% CH$_2$Cl$_2$: 25% MeOH for 18.2 min.) to give {2-[4-(1-amino-cyclobutyl)-phenyl]-3-phenyl-imidazo[1,2-a]pyridin-7-yloxy}-acetic acid methyl ester (31 mg, 34%):

UPLC-MS (Method 2): RT=01.21 min; m/z (rel intensity) 428 (100, (M+H)$^+$), 855 (50, (2M+H)$^+$).

The following examples were prepared in a manner analogous to that described in Example 9-0: substituting appropriate starting materials where necessary:

| Example | Structure/Name | 1H-NMR | UPLC-MS |
|---|---|---|---|
| 8-1 | 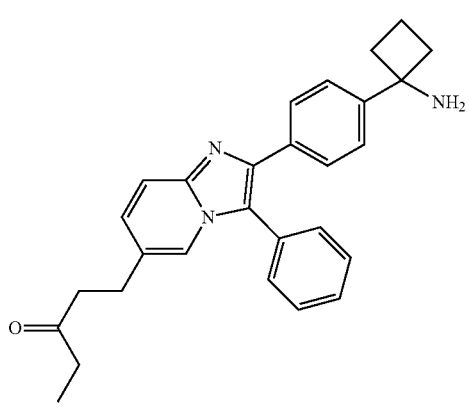<br>3 3-{2-[4-(1-Amino-cyclobutyl)-phenyl]-3-phenyl-imidazo[1,2-a]pyridin-6-yl}-propionic acid methyl ester | | RT = 1.25 min; m/z (rel intensity) 425 (100, (M + H)$^+$); 851 (30, (M + H)$^+$). |

| Example | Structure/Name | UPLC-MS |
|---|---|---|
| 9-1 | 2-{2-[4-(1-Amino-cyclobutyl)-phenyl]-3-phenyl-imidazo[1,2-a]pyridin-7-yloxy}-acetamide | Method 2: RT = 1.06 min; m/z (rel intensity) 413 (100, (M + H)+), 825 (20, (2M + H)+). |
| 9-2 | 2-{2-[4-(1-Amino-cyclobutyl)-phenyl]-3-phenyl-imidazo[1,2-a]pyridin-7-yloxy}-N,N-dimethyl-acetamide | Method 2: RT = 1.12 min; m/z (rel intensity) 441 (100, (M + H)+), 881 (10, (2M + H)+). |
| 9-3 | {2-[4-(1-Amino-cyclobutyl)-phenyl]-3-phenyl-imidazo[1,2-a]pyridin-7-yloxy}-acetonitrile | Method 2: RT = 1.27 min; m/z (rel intensity) 434 (100, (M + H)+), 867 (60, (2M + H)+). |
| 9-4 | {2-[4-(1-Amino-cyclobutyl)-phenyl]-3-phenyl-imidazo[1,2-a]pyridin-6-yloxy}-acetic acid methyl ester | Method 2: RT = 1.19 min; m/z (rel intensity) 428 (100, (M + H)+), 855 (90, (2M + H)+). |

| Example | Structure/Name | UPLC-MS |
|---|---|---|
| 9-5 | 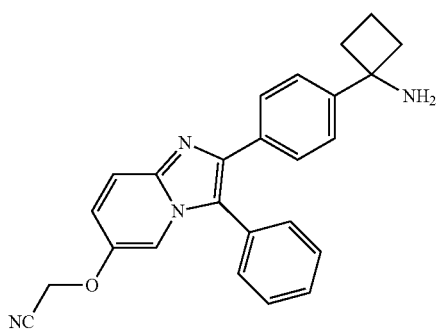<br>{2-[4-(1-Amino-cyclobutyl)-phenyl]-3-phenyl-imidazo[1,2-a]pyridin-6-yloxy}-acetonitrile | Method 2: RT = 1.46 min; m/z (rel intensity) 395 (100, (M + H)⁺), 789 (100, (2M + H)⁺). |

Example 10-0

2-[4-(1-amino-cyclobutyl)-phenyl]-3-phenyl-imidazo[1,2-a]pyridin-7-ol

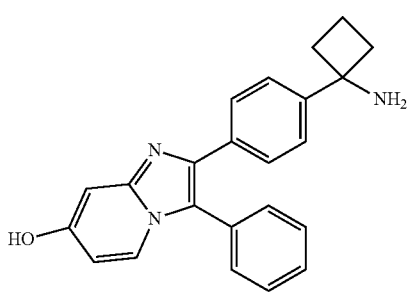 [SMILES: NC1(c2ccc(-c3nc4cc(O)ccn4c3-c3ccccc3)cc2)CCC1]

To a solution of 1-[4-(7-methoxy-3-phenyl-imidazo[1,2-a]pyridin-2-yl)-phenyl]-cyclobutylamine (408 mg, 1.10 mmol) in N-methylpyrrolidone (16 mL) at 100° C. was added $Na_2S$ (431 mg, 5.52 mmol, 5 equiv) in portions. The resulting mixture was heated at 160° C. for 30 min., cooled to room temperature, and concentrated under reduced pressure. The remaining material was purified using MPLC (Biotage Isolera Flash NH₂ Snap 10 reverse phase column; 100% $CH_2Cl_2$ for 8 min., gradient to 95% $CH_2Cl_2$: 5% MeOH over 5 min.; 95% $CH_2Cl_2$: 5% MeOH for 4 min., gradient to 80% $CH_2Cl_2$: 20% MeOH over 5 min., 80% $CH_2Cl_2$: 20% MeOH for 6.2 min., gradient to 75% $CH_2Cl_2$: 25% MeOH over 2.0 min., 75% $CH_2Cl_2$: 25% MeOH for 18.2 min.) to give 2-[4-(1-amino-cyclobutyl)-phenyl]-3-phenyl-imidazo[1,2-a]pyridin-7-ol (315 mg, 81%):

UPLC-MS (Method 2): RT=0.97 min; m/z (rel intensity) 356 (100, (M+H)⁺), 711 (20, (2M+H)⁺).

Example 11-0

3-{2-[4-(1-amino-cyclobutyl)-phenyl]-3-phenyl-imidazo[1,2-a]pyridin-6-yl}-pyridin-2-ol

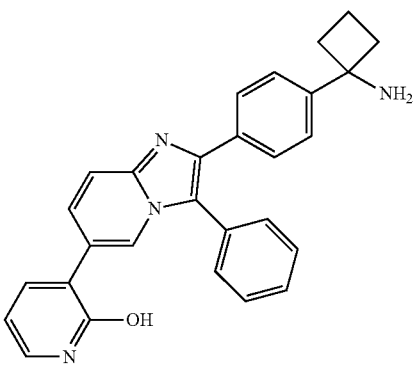 [SMILES: NC1(c2ccc(-c3nc4ccc(-c5cccnc5O)cn4c3-c3ccccc3)cc2)CCC1]

Step 1: (1-{4-[3-phenyl-6-(4,4,5,5-tetramethyl-[1,3,2]dioxaborolan-2-yl)-imidazo[1,2-a]pyridin-2-yl]-phenyl}-cyclobutyl)-carbamic acid tert-butyl ester

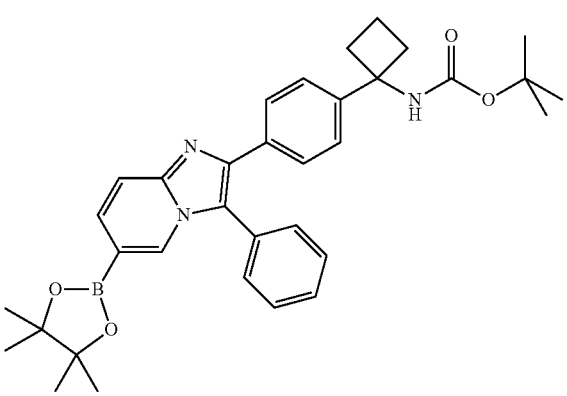 [SMILES: CC(C)(C)OC(=O)NC1(c2ccc(-c3nc4ccc(B5OC(C)(C)C(C)(C)O5)cn4c3-c3ccccc3)cc2)CCC1]

A mixture of {1-[4-(6-bromo-3-phenyl-imidazo[1,2-a]pyridin-2-yl)-phenyl]-cyclobutyl}-carbamic acid tert-butyl ester (0.89 g), bis-pinacolatodiborane (0.52 g), potassium acetate (0.505 g) and [1,1-bis-(diphenylphosphino)-ferrocene]-dichloropalladium-dichlormethane-complex (0.14 g) in DMF (18 mL) under argon was heated for 3.5 h at 100° C. under microwave irradiation. The crude reaction mixture was filtered over Celite and the solution split in two portions, one of which was used in the next reaction.

Step 2: (1-{4-[6-(2-benzyloxy-pyridin-3-yl)-3-phenyl-imidazo[1,2-a]pyridin-2-yl]-phenyl}-cyclobutyl)-carbamic acid tert-butyl ester

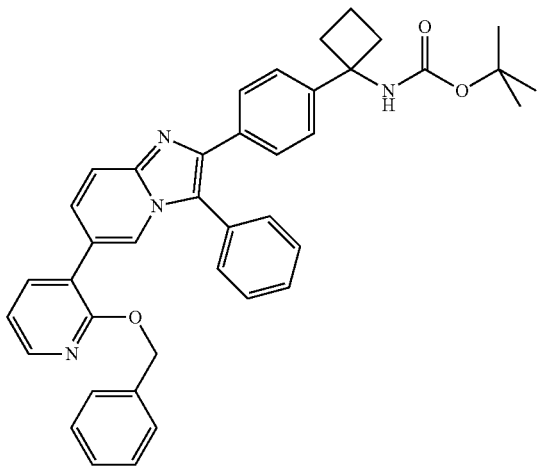 [SMILES: CC(C)(C)OC(=O)NC1(c2ccc(-c3nc4ccc(-c5cccnc5OCc5ccccc5)cn4c3-c3ccccc3)cc2)CCC1]

To the crude DMF solution of the boronate from Step 1 was added 2-benzyloxy-3-bromopyridine (0.25 g), aqueous sodium carbonate solution (2M, 2.8 mL) and dioxane (4 mL) and the mixture placed under argon. [1,1-bis-(diphenylphosphino)-ferrocene]-dichloropalladium-dichlormethane-complex (0.070 mg) was added and the mixture heated at 110° C. under microwave irradiation for 30 minutes. On cooling the mixture was partitioned between DCM and water and extracted. The organic portion was washed with brine, dried and concentrated in vacuo. Purification was achieved by chromatography on silica gel to give the title compound (138 mg).

UPLC-MS (Method 1): RT=1.53 min; m/z=623.27 (ES+; M+H).

Step 3: 1-{4-[6-(2-benzyloxy-pyridin-3-yl)-3-phenyl-imidazo[1,2-a]pyridin-2-yl]-phenyl}-cyclobutylamine

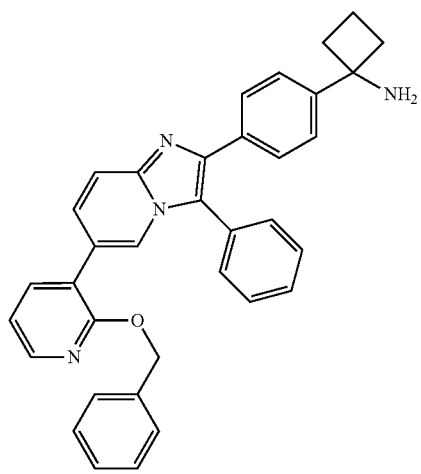 [SMILES: NC1(c2ccc(-c3nc4ccc(-c5cccnc5OCc5ccccc5)cn4c3-c3ccccc3)cc2)CCC1]

The crude product from Step 2 (240 mg) was dissolved in DCM/MeOH (1.2 mL/0.76 mL), cooled to 0° C. and treated with HCl (4 M soln in dioxane, 0.94 mL). The reaction was warmed to rt and stirred for 2 hours. The reaction was poured onto ice and extracted with DCM (3×). The organic phase was washed with brine, dried and concentrated in vacuo to give the crude title compound.

UPLC-MS (Method 2): RT=1.62 min; m/z=523.26 (ES+; M+H)

Step 4: 3-{2-[4-(1-amino-cyclobutyl)-phenyl]-3-phenyl-imidazo[1,2-a]pyridin-6-yl}-pyridin-2-ol

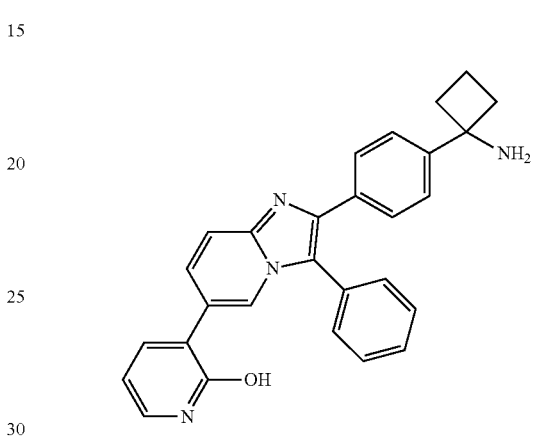

The crude product from Step 3 (167 mg) was dissolved in EtOH (7 mL) whereupon a precipitate formed which was filtered. The filtrate was hydrogenated using an H-Cube flow reactor (Pd/C cartridge, oven temperature 50° C.). The eluant was collected from the flow reactor in two fractions. The second fraction was concentrated in vacuo and triturated with DCM to give a solid which was filtered and dried to give a further portion of title compound (16 mg).

UPLC-MS (Method 1): RT=0.66 min; m/z=431.13 (ES−; M−H).

Example 12-0

1-{4-[6(5-methyl-2H-pyrazol-3-yl)-3-phenyl-imidazo[1,2-a]pyridin-2-yl]-phenyl}-cyclobutylamine

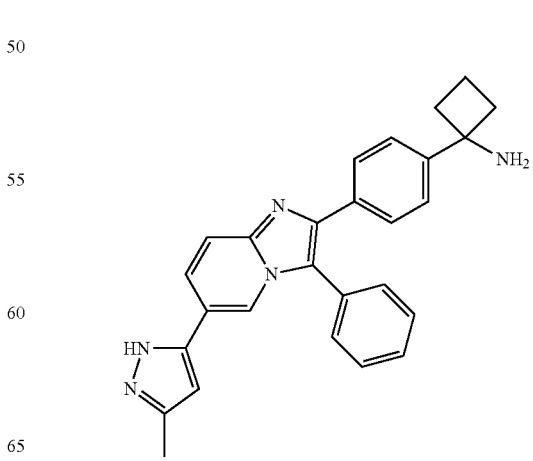

Step 1: 5-{2-[4-(1-tert-butoxycarbonylamino-cyclobutyl)-phenyl]-3-phenyl-imidazo[1,2-a]pyridin-6-yl}-3-methyl-pyrazole-1-carboxylic acid tert-butyl ester

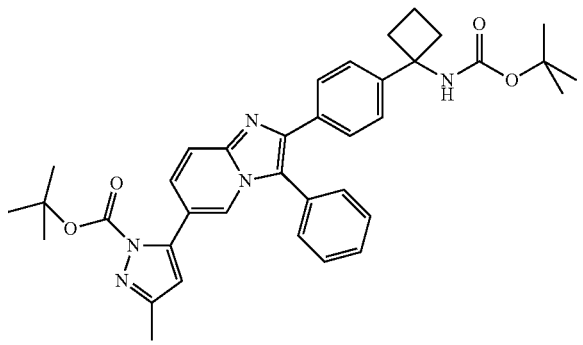 [SMILES: Cc1cc(-c2ccc3nc(-c4ccc(C5(NC(=O)OC(C)(C)C)CCC5)cc4)c(-c4ccccc4)n3c2)n(C(=O)OC(C)(C)C)n1]

A mixture of {1-[4-(6-bromo-3-phenyl-imidazo[1,2-a]pyridin-2-yl)-phenyl]-cyclobutyl}-carbamic acid tert-butyl ester (50 mg) and 1-tert-butoxycarbonyl-3-methylpyrazole-5-boronic acid (44 mg) in dioxane (1 mL) and water (0.43 mL) was placed under argon and [1,1-bis-(diphenylphosphino)-ferrocene]-dichloropalladium-dichlormethane-complex (7.9 mg) added. The mixture was heated at 110° C. under microwave irradiation for 60 minutes. On cooling the mixture was partitioned between DCM and water and extracted. The organic portion was dried and concentrated in vacuo to give the crude title compound which was used in the next step without further purification.

Step 2: 1-{4-[6-(5-methyl-2H-pyrazol-3-yl)-3-phenyl-imidazo[1,2-a]pyridin-2-yl]-phenyl}-cyclobutylamine

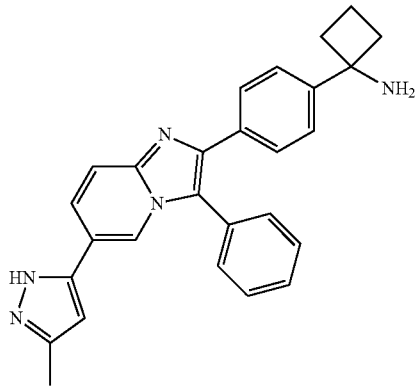 [SMILES: Cc1cc(-c2ccc3nc(-c4ccc(C5(N)CCC5)cc4)c(-c4ccccc4)n3c2)[nH]n1]

The crude product from Step 1 (79 mg) was dissolved in DCM/MeOH (2 mL/1 mL) and treated with HCl (4 M soln in dioxane, 0.96 mL). The reaction was stirred for 2 hours before it was poured onto ice, made alkaline with dilute aqueous sodium hydroxide solution (2M) and extracted with DCM. The organic phase was washed with brine, dried and concentrated in vacuo. Purification was achieved by chromatography on silica gel to give the title compound (10 mg).

UPLC-MS (Method 2): RT=1.16 min; m/z=420.38 (ES+; M+H).

Example 13-0

1-{4-[8-methoxy-3-phenyl-6-(1H-pyrazol-4-yl)-imidazo[1,2-a]pyridin-2-yl]-phenyl}-cyclobutylamine

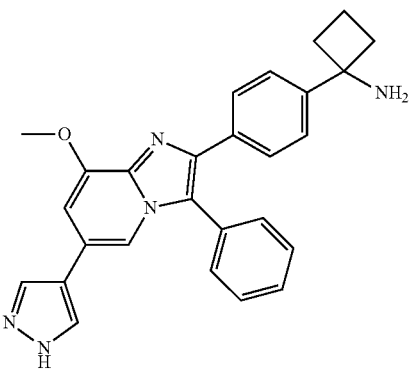 [SMILES: COc1cc(-c2cn[nH]c2)cn2c(-c3ccccc3)c(-c3ccc(C4(N)CCC4)cc3)nc12]

Step 1: 4-{2-[4-(1-amino-cyclobutyl)-phenyl]-8-methoxy-3-phenyl-imidazo[1,2-a]pyridin-6-yl}-pyrazole-1-carboxylic acid tert-butyl ester

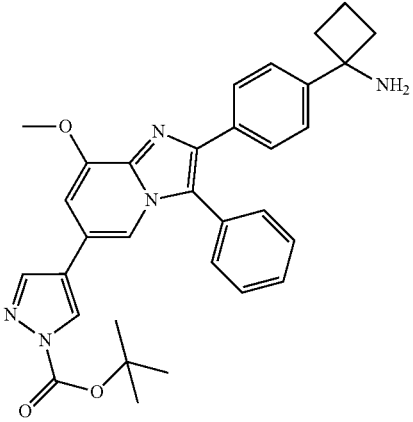 [SMILES: COc1cc(-c2cnn(C(=O)OC(C)(C)C)c2)cn2c(-c3ccccc3)c(-c3ccc(C4(N)CCC4)cc3)nc12]

A mixture of 1-[4-(6-bromo-8-methoxy-3-phenyl-imidazo[1,2-a]pyridin-2-yl)-phenyl]-cyclobutylamine (120 mg), [1-(tert-butoxycarbonyl)-1H-pyrazol-4-yl]boronic acid (170 mg) and potassium phosphate (170 mg) in toluene (0.9 mL), EtOH (1.86 mL) and water (0.93 mL) was placed under argon and bis(tri-tert-butyl phosphine)palladium(0) (13.7 mg) was added. The mixture was heated at 120° C. under microwave irradiation for 30 minutes. On cooling the mixture was partitioned between DCM and water and the phases separated. The organic portion was concentrated in vacuo to give the crude title compound which was used in the next step without further purification.

UPLC-MS (Method 2): RT=1.32 min; m/z=536.27 (ES+; M+H).

Step 2: 1-{4-[8-methoxy-3-phenyl-6-(1H-pyrazol-4-yl)-imidazo[1,2-a]pyridin-2-yl]-phenyl}-cyclobutylamine

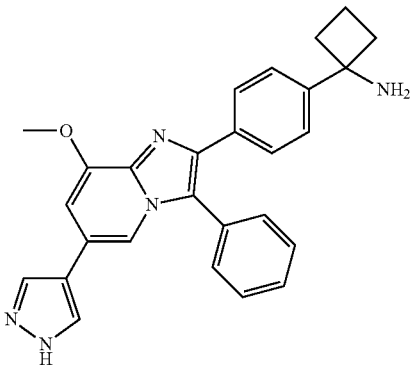 [SMILES: COc1cc(-c2cn[nH]c2)cn2c(-c3ccccc3)c(-c3ccc(C4(N)CCC4)cc3)nc12]

The crude product from Step 1 was dissolved in DCM/MeOH (1.2 mL/0.74 mL) and treated with HCl (4M solution in dioxane, 0.9 mL). The reaction was stirred at rt overnight before it was poured onto ice, made alkaline with dilute aqueous sodium hydroxide solution (2M) and extracted with DCM. The organic phase was washed with brine, dried and concentrated in vacuo. Purification was achieved by chromatography on silica gel to give the title compound (18 mg).

UPLC-MS (Method 2): RT=1.08 min; m/z=436.19 (ES+; M+H).

1H-NMR (300 MHz, d6-DMSO, uncorrected): δ 12.97 (br s, 1H), 7.97 (br s, 2H), 7.66 (m, 1H), 7.46-7.61 (m, 7H), 7.31 (d, 2H), 6.96 (m, 1H), 4.03 (s, 3H), 2.30-2.39 (m, 2H), 1.86-2.11 (m, 3H), 1.53-1.66 (m, 1H) ppm.

EXAMPLE

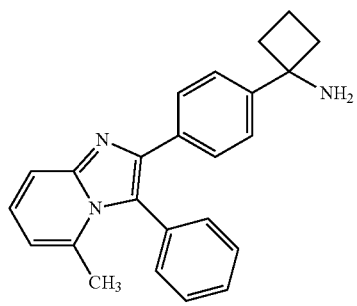 [SMILES: Cc1cccc2nc(-c3ccc(C4(N)CCC4)cc3)c(-c3ccccc3)n12]

Step 1: 2-chloro-N-(6-methylpyridin-2-yl)-2-phenylacetamide

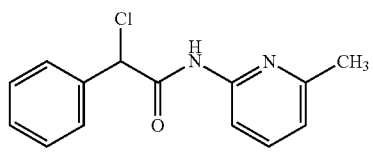 [SMILES: Cc1cccc(NC(=O)C(Cl)c2ccccc2)n1]

To an ice-cooled solution of 6-methylpyridin-2-amine [CAS 1824-81-3] (5.22 g, 44.08 mmol) in 350 mL anhydrous THF was added diisopropylethylamine (15.36 mL, 88.16 mmol). Chloro(phenyl)acetyl chloride [CAS 2912-62-1] (10.0 g, 52.9 mmol) was added dropwise and the resulting mixture was stirred for 1 h while cooling was maintained. The mixture was partitioned between ethyl acetate and water and the organic phase was washed with brine. The organic phase was filtered through a Whatman filter and the volatile components were removed by the use of a rotary evaporator to give title compound (14.3 g) in ~80% purity (LC-MS). The crude material was forwarded directly to the next step.

UPLC-MS: RT=1.26 min; m/z [ES−]=261 (M−1)−.

Step 2: 5-methyl-3-phenylimidazo[1,2-a]pyridin-2-ol

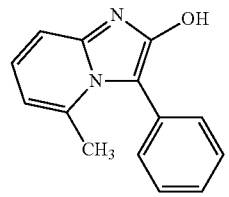 [SMILES: Cc1cccc2nc(O)c(-c3ccccc3)n12]

2-Chloro-N-(6-methylpyridin-2-yl)-2-phenylacetamide (11.5 g, ~80%, see step 1) was dissolved in 167 mL anhydrous THF. After addition of tetra-n-butyl ammonium iodide (700 mg, 1.90 mmol) the reaction mixture was cooled with ice-water. 2.5 Equivalents potassium bis(trimethylsilyl)amide as a 0.5M solution in THF (95 mL, 47.4 mmol) were added dropwise. The reaction mixture was stirred for 10 min at room temperature and for additional 2h at reflux. The reaction mixture was cooled to room temperature and partitioned between ethyl acetate and an 1M aqueous solution of citric acid. The organic phase was washed with brine and dried with sodium sulphate. LC-MS analysis showed that the predominant portion of the title compound was still remaining in the aqueous phase. The aqueous phase was therefore neutralized with 1M sodium hydroxide solution. After extraction with dichloromethane (2×) the combined organic phases were washed with brine and dried with sodium sulphate. The residue was triturated with hot ethyl acetate and was filtered while being hot. The filtrate was concentrated in vacuo. After drying under high vacuum 2.70 g (26%) of the title compound were observed.

UPLC.MS: RT=0.56 min; m/z [ES−]=223 (M−1)−.

Step 3: 2-bromo-5-methyl-3-phenylimidazo[1,2-a]pyridine

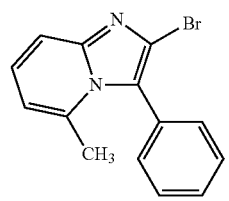 [SMILES: Cc1cccc2nc(Br)c(-c3ccccc3)n12]

5-Methyl-3-phenylimidazo[1,2-a]pyridin-2-ol from step 2 (1.30 g, 5.22 mmol) were dissolved in 41 mL 1,2-dichloroethane under argon atmosphere. 5 Equivalents of phosphoryl bromide (7.48 g, 26.1 mmol) were added and the reaction mixture was stirred at reflux temperature overnight. LC/MS analysis showed incomplete conversion, therefore another 5 equivalents phosphoryl bromide were added. After stirring for 4 h at reflux temperature LC/MS analysis again showed incomplete conversion, so 5 equivalents were added again. After stirring at reflux temperature overnight the reaction mixture was allowed to cool to room temperature. The reaction mixture was neutralized with aqueous sodium bicarbonate-solution followed by extraction with dichloromethane. The organic phase was washed with brine and filtered through a Whatman-filter. Drying under high vacuum gave 801 mg (44%) of the title compound in 83% purity (LC/MS, area-%).

UPLC-MS: RT=1.19 min; m/z [ES$^+$]=287 (M)$^+$.

Step 4: tert-butyl {1-[4-(4,4,5,5-tetramethyl-1,3,2-dioxaborolan-2-yl)phenyl]cyclobutyl}carbamate

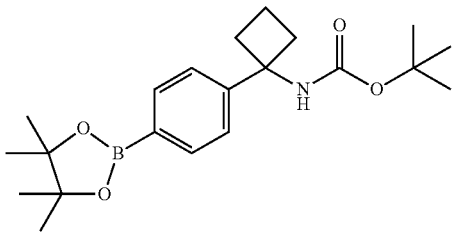 [SMILES: CC(C)(C)OC(=O)NC1(c2ccc(B3OC(C)(C)C(C)(C)O3)cc2)CCC1]

27.75 g (55 mmol) [1-(4-Bromo-phenyl)-cyclobutyl]-carbamic acid tert-butyl ester, 23.76 mmol (93.6 mmol) bis-(pinacolato)diboron, 25 g (255 mmol) potassium acetate and 2.08 g (2.55 mmol) 1,1'-bis(diphenylphosphino)ferrocene-dichloro-palladium(II) in 500 mL degassed THF were heated for three hours at reflux. The colour of the reaction mixture turned from dark red to black. Due to an incomplete reaction heating was continued for another two hours. The reaction mixture was poured on water (400 mL) and diluted with ethyl acetate (700 mL). After stirring for 30' the organic phase was separated and the aqueous phase was reextracted twice with ethyl acetate (400 and 200 mL). The combined organic extracts were washed with brine (200 mL) and dried (sodium sulfate). After evaporation of the solvent the residue was purified by chromatography (Biotage) yielding 28.99 g (91.3%) of the title compound.

1H NMR (400 MHz, d6-DMSO): δ 7.51-7.67 (m, 3H), 7.38 (d, 2H), 2.22-2.42 (m, 4H), 1.88-2.02 (m, 1H), 1.63-1.80 (m, 1H), 1.00-1.38 (m, 21H) ppm.

Step 5: tert-butyl {1-[4-(5-methyl-3-phenylimidazo[1,2-a]pyridin-2-yl)phenyl]cyclobutyl}carbamate

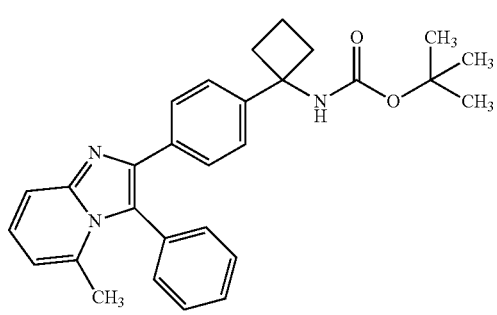 [SMILES: Cc1cccc2nc(-c3ccc(C4(NC(=O)OC(C)(C)C)CCC4)cc3)c(-c3ccccc3)n12]

A mixture of 2-bromo-5-methyl-3-phenylimidazo[1,2-a]pyridine (38 mg, 0.13 mmol), tert-butyl {1-[4-(4,4,5,5-tetramethyl-1,3,2-dioxaborolan-2-yl)phenyl]cyclobutyl}carbamate (see step 4, 64 mg, 0.17 mmol) and potassium phosphate (84.3 mg, 0.40 mmol) in 1.2 ml toluene/ethanol/water (1/2/1) was heated to 120° C. in a single mode microwave reactor (Biotage). This experiment was repeated employing the same protocol. Both reaction mixtures were combined and partitioned between dichloromethane and water. The mixture was filtered through a phase separator and concentrated in vacuo. The crude material was purified by column chromatography (Snap cartridge, hexane/ethyl acetate 95/5->hexane/ethyl acetate 1/1) to give 49 mg of the title compound (34% overall yield).

UPLC-MS: RT=1.12 min; m/z [ES$^+$]=454 (M+1)$^+$.

Step 6: 1-[4-(5-methyl-3-phenylimidazo[1,2-a]pyridin-2-yl)phenyl]cyclobutanamine

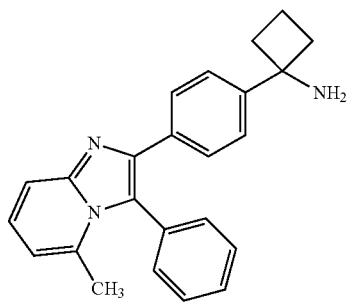 [SMILES: Cc1cccc2nc(-c3ccc(C4(N)CCC4)cc3)c(-c3ccccc3)n12]

To a mixture of crude tert-butyl {1-[4-(5-methyl-3-phenylimidazo[1,2-a]pyridin-2-yl)phenyl]cyclobutyl}carbamate (49 mg) in DCM (0.42 mL) and methanol (0.26 mL) was added a solution of 4 M hydrogen chloride in dioxane (0.54 mL) and the mixture was stirred overnight at rt. The mixture was poured onto ice, made alkaline with aqueous sodium hydroxide (2 N) and extracted three times with a mixture of DCM. The combined organic phases were washed with brine, dried and concentrated in vacuo to give 16 mg of the title compound in 42% overall yield.

LC-MS: RT=0.70 min; m/z (ES$^+$)=354 (M+1)$^+$;

1H NMR (400 MHz, d6-DMSO): δ 7.43-7.56 (m, 6H), 7.38 (d, 2H), 7.24 (d, 2H), 7.15 (dd, 1H), 6.58 (d, 1H), 2.23-2.33 (m, 2H), 2.05 (br s, 2H) 1.85-2.01 (m, 6H), 1.55 (m, 1H) ppm.

Example 15-0

2-[4-(1-aminocyclobutyl)phenyl]-8-chloro-3-phenylimidazo[1,2-a]pyridine-6-carbonitrile

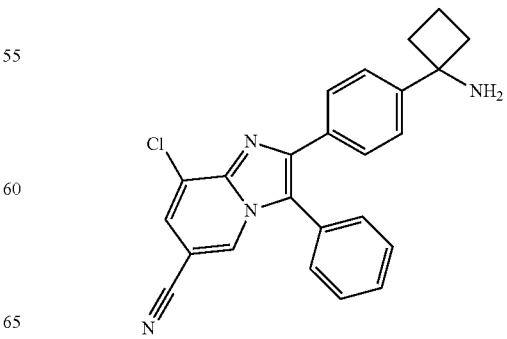

A mixture of 2-[4-(1-aminocyclobutyl)phenyl]-8-chloro-3-phenylimidazo[1,2-a]pyridine-6-carboxamide (see example 6-1, 100 mg, 0.17 mmol, 72% purity) and 1-propylphosphonic acid cyclic anhydride as 50%-solution in ethyl acetate (0.21 ml, 0.35 mmol) in 1.35 ml ethyl acetate were stirred at room temperature overnight. The reaction mixture was hydrolysed with water and extracted with ethyl acetate. The organic phase was filtered through a Whatman filter and the volatile components were removed by rotary evaporation. The crude material was purified by column chromatography (Snap cartridge, dichloromethane/ethanol 95/5->dichloromethane/ethanol 7/3) to give 11 mg of the title compound (16% overall yield).

LC-MS (Method 2): RT=0.97 min; m/z (ES$^+$)=382 (M–NH$_2$)$^+$.

Biological Investigations

The following assays can be used to illustrate the commercial utility of the compounds according to the present invention.

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Biological Assay 1.0: Akt1 Kinase Assay

Akt1 inhibitory activity of compounds of the present invention was quantified employing the Akt1 TR-FRET assay as described in the following paragraphs.

His-tagged human recombinant kinase full-length Akt1 expressed in insect cells was purchased form Invitrogen (part number PV 3599). As substrate for the kinase reaction the biotinylated peptide biotin-Ahx-KKLNRTLSFAEPG (C-terminus in amide form) was used which can be purchased e.g. from the company Biosynthan GmbH (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of Akt1 in assay buffer [50 mM TRIS/HCl pH 7.5, 5 mM MgCl$_2$, 1 mM dithiothreitol, 0.02% (v/v) Triton X-100 (Sigma)] were added and the mixture was incubated for 15 min at 22° C. to allow prebinding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 60 min at 22° C. The concentration of Akt1 in the assay was adjusted depending of the activity of the enzyme lot and was chosen appropriate to have the assay in the linear range, typical enzyme concentrations were in the range of about 0.05 ng/µl (final conc. in the 5 µl assay volume).

The reaction was stopped by the addition of 5 µl of a solution of HTRF detection reagents (200 nM streptavidine-XL665 [Cisbio] and 1.5 nM anti-phosho-Serine antibody [Millipore, cat. #35-001] and 0.75 nM LANCE Eu—W 1024 labeled anti-mouse IgG antibody [Perkin Elmer]) in an aqueous EDTA-solution (100 mM EDTA, 0.1% (w/v) bovine serum albumin in 50 mM HEPES/NaOH pH 7.5).

The resulting mixture was incubated 1 h at 22° C. to allow the binding of the biotinylated phosphorylated peptide to the streptavidine-XL665 and the antibodies. Subsequently the amount of phosphorylated substrate was evaluated by measurement of the resonance energy transfer from the anti-mouse-IgG-Eu-Chelate to the streptavidine-XL665. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and IC$_{50}$ values were calculated by a 4 parameter fit using an inhouse software.

Biological Assay 2.0: Akt2 Kinase Assay

Akt2 inhibitory activity of compounds of the present invention was quantified employing the Akt2 TR-FRET assay as described in the following paragraphs. His-tagged human recombinant kinase full-length Akt2 expressed in insect cells and activated by PDK1 was purchased form Invitrogen (part number PV 3975). As substrate for the kinase reaction the biotinylated peptide biotin-Ahx-KKLNRTLSFAEPG (C-terminus in amide form) was used which can be purchased e.g. from the company Biosynthan GmbH (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of Akt2 in assay buffer [50 mM TRIS/HCl pH 7.5, 5 mM MgCl$_2$, 1 mM dithiothreitol, 0.02% (v/v) Triton X-100 (Sigma)] were added and the mixture was incubated for 15 min at 22° C. to allow prebinding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 60 min at 22° C. The concentration of Akt2 in the assay was adjusted depending of the activity of the enzyme lot and was chosen appropriate to have the assay in the linear range, typical enzyme concentrations were in the range of about 0.2 ng/µl (final conc. in the 5 µl assay volume).

The reaction was stopped by the addition of 5 µl of a solution of HTRF detection reagents (200 nM streptavidine-XL665 [Cisbio] and 1.5 nM anti-phosho-Serine antibody [Millipore, cat. #35-001] and 0.75 nM LANCE Eu—W 1024 labeled anti-mouse IgG antibody [Perkin Elmer]) in an aqueous EDTA-solution (100 mM EDTA, 0.1% (w/v) bovine serum albumin in 50 mM HEPES/NaOH pH 7.5).

The resulting mixture was incubated 1 h at 22° C. to allow the binding of the biotinylated phosphorylated peptide to the streptavidine-XL665 and the antibodies. Subsequently the amount of phosphorylated substrate was evaluated by measurement of the resonance energy transfer from the anti-mouse-IgG-Eu-Chelate to the streptavidine-XL665. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an inhouse software.

Preferred compounds of the present invention show in either the Akt1 or Akt2 kinase assay: median $IC_{50}$<5 μM, more preferably, median $IC_{50}$<0.5 μM, even more preferably, median $IC_{50}$≤0.1 μM.

The following Table gives selected data for selected Examples of the present invention.

| Example | Akt1, median $IC_{50}$, μM | Akt1, median $IC_{50}$, μM |
|---|---|---|
| 1-0 | 0.348 | 0.563 |
| 1-1 | 1.157 | 0.153 |
| 1-2 | 1.009 | 0.054 |
| 1-3 | 0.176 | 0.033 |
| 1-4 | 4.695 | 0.094 |
| 1-6 | 0.388 | 0.293 |
| 1-7 | 0.109 | 0.291 |
| 1-8 | 0.233 | 0.328 |
| 1-9 | 0.685 | 0.550 |
| 1-10 | 0.287 | 0.426 |
| 1-11 | 0.102 | 0.013 |
| 1-12 | 0.053 | 0.038 |
| 1-13 | 0.024 | 0.009 |
| 1-14 | 0.588 | 0.146 |
| 1-15 | 2.268 | 0.402 |
| 1-16 | 0.228 | 0.193 |
| 2-0 | 0.142 | 0.120 |
| 2-1 | 0.544 | 0.564 |
| 2-2 | 0.230 | 0.148 |
| 2-3 | 0.064 | 0.313 |
| 2-4 | 0.829 | 0.241 |
| 2-5 | 0.100 | 0.274 |
| 2-6 | 0.145 | 0.052 |
| 2-7 | 0.203 | 0.229 |
| 2-8 | 0.096 | 0.047 |
| 2-9 | 0.144 | 0.116 |
| 2-10 | 0.723 | 0.419 |
| 2-12 | 0.173 | 0.124 |
| 2-13 | 0.171 | 0.769 |
| 2-14 | 1.771 | 0.357 |
| 2-15 | 0.168 | 0.263 |
| 2-16 | not tested | not tested |
| 2-17 | 0.036 | 0.163 |
| 2-18 | 0.067 | 0.066 |
| 2-19 | 0.130 | 0.106 |
| 2-21 | 1.657 | 0.053 |
| 2-22 | 0.188 | 0.022 |
| 2-23 | 0.047 | 0.204 |
| 2-24 | 5.643 | 1.958 |
| 2-25 | 0.504 | 0.385 |
| 2-26 | 0.221 | 0.038 |
| 2-27 | 1.186 | 0.416 |
| 2-28 | 0.179 | 0.165 |
| 2-29 | 0.190 | not tested |
| 2-30 | 1.225 | 0.139 |
| 2-31 | 1.315 | 0.138 |
| 2-32 | 1.385 | 0.085 |
| 2-33 | 0.379 | 0.161 |
| 2-34 | 0.989 | 0.050 |
| 2-35 | 0.226 | 0.064 |
| 2-36 | 0.061 | 0.198 |
| 2-37 | 1.636 | 0.101 |
| 2-38 | 0.260 | 0.192 |
| 2-39 | 0.033 | 0.162 |
| 2-40 | not tested | 0.046 |
| 2-41 | 0.204 | 0.050 |
| 2-42 | 19.417 | 0.519 |
| 2-43 | 0.062 | 0.233 |
| 2-44 | 0.142 | 0.277 |
| 2-45 | 0.043 | 0.216 |
| 2-46 | 0.101 | 0.385 |
| 2-47 | 0.140 | 0.253 |
| 2-48 | 0.300 | 0.422 |
| 2-49 | 0.180 | 1.592 |
| 2-50 | 0.099 | 0.231 |
| 2-51 | 0.091 | 0.067 |
| 2-52 | 0.019 | 0.017 |
| 2-53 | 1.708 | 0.279 |
| 2-54 | 0.423 | 0.144 |
| 2-55 | 1.136 | 0.482 |
| 2-56 | 0.452 | 0.515 |
| 2-57 | 0.493 | 0.295 |
| 2-58 | 0.342 | 0.239 |
| 2-59 | 0.257 | 0.118 |
| 2-60 | 0.031 | 0.116 |
| 2-61 | 1.904 | 1.483 |
| 2-62 | 0.376 | 0.154 |
| 2-63 | 0.734 | 0.154 |
| 2-64 | 1.659 | 0.777 |
| 2-65 | 1.066 | 0.338 |
| 2-66 | 0.113 | 0.060 |
| 2-67 | 0.064 | 0.079 |
| 2-68 | 0.308 | 0.521 |
| 2-69 | 0.208 | 0.480 |
| 2-70 | 0.106 | 0.267 |
| 2-71 | 0.064 | 0.170 |
| 2-72 | 0.390 | 0.749 |
| 2-73 | 0.058 | 0.056 |
| 2-74 | 0.170 | 0.210 |
| 2-75 | 0.052 | 0.073 |
| 2-76 | 0.025 | 0.160 |
| 2-77 | 0.017 | 0.102 |
| 2-78 | 0.007 | 0.062 |
| 2-79 | 0.247 | 0.108 |
| 2-80 | 0.150 | 0.093 |
| 2-81 | 0.018 | 0.015 |
| 2-82 | not tested | not tested |
| 2-83 | 0.017 | 0.109 |
| 2-84 | not tested | not tested |
| 2-85 | 0.005 | not tested |
| 2-86 | not tested | not tested |
| 2-87 | 1.368 | 0.516 |
| 2-88 | 0.187 | 0.392 |
| 2-89 | 0.330 | 0.055 |
| 2-90 | 0.150 | 0.410 |
| 2-91 | 0.371 | not tested |
| 2-92 | 0.229 | 0.736 |
| 2-93 | 0.081 | 0.203 |
| 2-94 | not tested | 0.041 |
| 2-95 | 0.011 | 0.024 |
| 2-96 | 0.893 | 1.375 |
| 2-97 | 0.067 | 0.050 |
| 2-98 | 0.069 | 0.119 |
| 2-99 | 0.177 | 0.112 |
| 2-100 | 0.201 | 0.091 |
| 2-101 | 0.014 | 0.036 |
| 2-102 | 0.106 | 0.100 |
| 2-103 | 0.099 | 0.190 |
| 2-104 | 0.175 | 0.129 |
| 2-105 | 0.217 | 0.475 |
| 2-106 | 0.151 | 0.435 |
| 2-107 | 0.204 | 0.070 |

-continued

| Example | Akt1, median IC$_{50}$, μM | Akt1, median IC$_{50}$, μM |
|---|---|---|
| 2-108 | 1.951 | 0.621 |
| 2-109 | 0.181 | 0.008 |
| 2-110 | 0.129 | 0.007 |
| 2-111 | 0.204 | 0.019 |
| 2-112 | 0.153 | 0.023 |
| 2-114 | 0.071 | 0.008 |
| 2-115 | 0.212 | 0.022 |
| 2-116 | 0.236 | 0.013 |
| 2-117 | 0.026 | 0.009 |
| 2-119 | 0.086 | 0.022 |
| 2-120 | 0.550 | 0.029 |
| 2-122 | 0.409 | 0.053 |
| 2-123 | 0.345 | 0.052 |
| 2-124 | 0.174 | 0.044 |
| 2-125 | 3.436 | 0.075 |
| 2-126 | 0.601 | 0.046 |
| 2-127 | 0.132 | 0.048 |
| 2-128 | 0.175 | 0.055 |
| 2-129 | 0.195 | 0.369 |
| 2-130 | 0.321 | 0.504 |
| 2-131 | 0.171 | 0.596 |
| 2-132 | 0.219 | 0.115 |
| 2-133 | 2.320 | 0.097 |
| 2-134 | 0.691 | 0.210 |
| 2-135 | 0.074 | 0.056 |
| 2-136 | 0.533 | 0.288 |
| 2-137 | 0.541 | 0.159 |
| 2-138 | 0.530 | 0.462 |
| 2-139 | 0.044 | 0.101 |
| 2-140 | 0.036 | 0.088 |
| 2-141 | 0.196 | 0.203 |
| 2-142 | 0.347 | 0.134 |
| 2-143 | 0.093 | 0.142 |
| 2-144 | 0.055 | 0.069 |
| 2-145 | 0.024 | 0.051 |
| 2-146 | 0.023 | 0.064 |
| 2-147 | 0.148 | 0.050 |
| 2-148 | 0.139 | 0.049 |
| 2-149 | 0.198 | 0.051 |
| 2-150 | 0.558 | 0.035 |
| 2-151 | 0.514 | 0.711 |
| 2-152 | 0.554 | 0.095 |
| 2-153 | 0.457 | 0.092 |
| 2-154 | 2.145 | 0.305 |
| 2-155 | 0.854 | 0.586 |
| 2-156 | 0.062 | 0.092 |
| 2-157 | 0.256 | 0.221 |
| 2-158 | 0.327 | 0.308 |
| 2-159 | 2.988 | 0.313 |
| 2-160 | 0.191 | 0.076 |
| 3-0 | 0.384 | 0.871 |
| 4-0 | 0.548 | not tested |
| 5-0 | 0.303 | 0.459 |
| 5-1 | 0.590 | 0.704 |
| 6-0 | 0.058 | 0.154 |
| 6-1 | 0.012 | 0.028 |
| 7-0 | 1.658 | 0.703 |
| 7-1 | 0.772 | 0.188 |
| 8-0 | 12.688 | 0.417 |
| 8-1 | not tested | 1.318 |
| 9-0 | 0.158 | 0.082 |
| 9-1 | 0.397 | 0.132 |
| 9-2 | 0.258 | 0.097 |
| 9-3 | 0.655 | 0.135 |
| 9-4 | 0.179 | 0.486 |
| 9-5 | 0.096 | 0.134 |
| 10-0 | 1.273 | 2.026 |
| 11-0 | 1.510 | 0.616 |
| 12-0 | 0.688 | 0.686 |
| 13-0 | 0.081 | 0.030 |
| 14-0 | 1.505 | 1.093 |
| 15-0 | 0.141 | 0.397 |

Cellular Assays 3.0: p-AKT1/2/3-S473, -T308, and p-4E-BP1-T70 Assays

The molecular mechanism of action was investigated in a set of experiments to assess the inhibition of the PI3K-AKT-mTOR pathway in responsive cell lines such as KPL4 breast tumour cell line (PIK3CAH1047R, HER20/E and hormone independent). The phospho-substrates of PI3K-AKT-mTOR axis were used as the read-outs to reflect pathway inhibition. Cells were seeded at 60-80% confluency per well in 96-well cell culture plates. After overnight incubation at 37° C. 5% CO2, cells were treated with compounds and vehicle at 37° C. for 2 hours. Thereafter, cells were lysed in 150 μl lysis buffer and the levels of phospho-AKT at T308 and S473 and p-4E-BP1 at T70 sites were determined with the corresponding AlphaScreen® SureFire® assay kits (Perkin Elmer: 4E-BP1 Assay Kit Cat # TRG4E2S10K; Akt 1/2/3 p-Ser 473 #TGRA4S500 and Akt 1/2/3 p-Thr 308 #TGRA3S500 as well as IgG detection Kit #6760617M) as described in the manuals. All measurements where at least done in duplicates and confirmed by independent repetition.

Alternatively pAKT-S473 was measured using the "Akt Duplex" of the MULTI-SPOT® Assay System (Fa. Meso Scale Discovery, Cat# N41100B-1) following manufacturers instructions. Each assay used 20 μg of protein extract and measured total AKT and p-AKT content simultaneously in one well. All measurements where at least done in duplicates and confirmed by independent repetition. Values for P-AKT are expressed as percentage of P-AKT level compared to total-AKT content of the extracts.

| Example | pAKT-S743 median IC$_{50}$, μM | P4EBP1-T70 median IC$_{50}$, μM |
|---|---|---|
| 1-0 | not tested | not tested |
| 1-1 | not tested | not tested |
| 1-2 | not tested | not tested |
| 1-3 | not tested | not tested |
| 1-4 | not tested | not tested |
| 1-6 | not tested | not tested |
| 1-7 | 0.038 | not tested |
| 1-8 | not tested | not tested |
| 1-9 | 0.770 | not tested |
| 1-10 | 0.138 | 2.031 |
| 1-11 | 0.037 | not tested |
| 1-12 | 0.276 | not tested |
| 1-13 | 0.035 | 1.018 |
| 1-14 | 1.173 | not tested |
| 1-15 | 1.647 | not tested |
| 1-16 | 0.359 | not tested |
| 2-0 | 0.030 | not tested |
| 2-1 | not tested | not tested |
| 2-2 | 0.250 | not tested |
| 2-3 | 0.032 | not tested |
| 2-4 | 0.292 | not tested |
| 2-5 | 0.209 | not tested |
| 2-6 | 0.333 | not tested |
| 2-7 | 0.487 | 3.960 |
| 2-8 | 0.237 | not tested |
| 2-9 | 0.062 | not tested |
| 2-10 | 0.428 | not tested |
| 2-12 | 0.159 | not tested |
| 2-13 | 0.758 | not tested |
| 2-14 | 0.510 | not tested |
| 2-15 | 0.163 | not tested |
| 2-16 | 0.477 | not tested |
| 2-17 | 0.035 | not tested |
| 2-18 | 0.033 | not tested |
| 2-19 | 0.093 | not tested |
| 2-21 | 0.537 | not tested |
| 2-22 | 0.142 | not tested |
| 2-23 | 1.006 | not tested |
| 2-24 | 3.317 | not tested |
| 2-25 | 0.213 | not tested |
| 2-26 | 0.090 | not tested |
| 2-27 | 0.111 | not tested |
| 2-28 | 0.114 | not tested |
| 2-29 | not tested | not tested |
| 2-30 | 0.464 | not tested |

| Example | pAKT-S743 median IC$_{50}$, μM | P4EBP1-T70 median IC$_{50}$, μM |
|---|---|---|
| 2-31 | not tested | not tested |
| 2-32 | not tested | not tested |
| 2-33 | 0.187 | not tested |
| 2-34 | 1.945 | not tested |
| 2-35 | 0.975 | not tested |
| 2-36 | 1.018 | not tested |
| 2-37 | 0.441 | not tested |
| 2-38 | 0.467 | not tested |
| 2-39 | 0.032 | not tested |
| 2-40 | 0.237 | not tested |
| 2-41 | 0.033 | not tested |
| 2-42 | 1.236 | not tested |
| 2-43 | 1.344 | not tested |
| 2-44 | 0.048 | not tested |
| 2-45 | 0.028 | not tested |
| 2-46 | 0.059 | not tested |
| 2-47 | 0.339 | not tested |
| 2-48 | 1.029 | not tested |
| 2-49 | 0.303 | not tested |
| 2-50 | 0.297 | not tested |
| 2-51 | 4.749 | not tested |
| 2-52 | 0.049 | not tested |
| 2-53 | 0.276 | not tested |
| 2-54 | 0.083 | not tested |
| 2-55 | 0.308 | not tested |
| 2-56 | 0.200 | not tested |
| 2-57 | 0.147 | not tested |
| 2-58 | 0.193 | not tested |
| 2-59 | 0.236 | not tested |
| 2-60 | 0.655 | not tested |
| 2-61 | 0.781 | not tested |
| 2-62 | 0.093 | not tested |
| 2-63 | 0.256 | not tested |
| 2-64 | 0.203 | not tested |
| 2-65 | 3.835 | not tested |
| 2-66 | 0.134 | not tested |
| 2-67 | 0.195 | 1.998 |
| 2-68 | 0.748 | not tested |
| 2-69 | 0.796 | not tested |
| 2-70 | 0.298 | not tested |
| 2-71 | 0.153 | not tested |
| 2-72 | 0.814 | not tested |
| 2-73 | 0.235 | 3.979 |
| 2-74 | 0.251 | 1.397 |
| 2-75 | 0.079 | 1.600 |
| 2-76 | 0.582 | 1.962 |
| 2-77 | 0.474 | 1.715 |
| 2-78 | 0.100 | 1.581 |
| 2-79 | 0.048 | 0.370 |
| 2-80 | 0.912 | 1.855 |
| 2-81 | 1.103 | 3.481 |
| 2-82 | 1.017 | 3.279 |
| 2-83 | 0.189 | 0.615 |
| 2-84 | 1.337 | 3.140 |
| 2-85 | 0.161 | 1.803 |
| 2-86 | 1.199 | 2.508 |
| 2-87 | 7.527 | 10.000 |
| 2-88 | 2.566 | 8.517 |
| 2-89 | 0.380 | 1.403 |
| 2-90 | 0.337 | 1.560 |
| 2-91 | 0.678 | 1.614 |
| 2-92 | 1.399 | 1.566 |
| 2-93 | 0.528 | 1.416 |
| 2-94 | 0.058 | 0.292 |
| 2-95 | 0.003 | 0.013 |
| 2-96 | 1.611 | 1.840 |
| 2-97 | 0.377 | 1.590 |
| 2-98 | 0.225 | 1.124 |
| 2-99 | 0.093 | 0.090 |
| 2-100 | 0.067 | 0.054 |
| 2-101 | 0.019 | 0.089 |
| 2-102 | 0.033 | 0.158 |
| 2-103 | 0.230 | 0.719 |
| 2-104 | 0.112 | 0.348 |
| 2-105 | 0.669 | 0.573 |
| 2-106 | 0.202 | not tested |
| 2-107 | 0.253 | not tested |
| 2-108 | 3.100 | not tested |
| 2-109 | 0.028 | not tested |
| 2-110 | 0.041 | not tested |
| 2-111 | 0.140 | not tested |
| 2-112 | 0.066 | not tested |
| 2-114 | 0.025 | not tested |
| 2-115 | 0.192 | not tested |
| 2-116 | 0.063 | not tested |
| 2-117 | 10.000 | not tested |
| 2-119 | 0.725 | not tested |
| 2-120 | 8.116 | not tested |
| 2-122 | 0.046 | not tested |
| 2-123 | 0.268 | not tested |
| 2-124 | 0.101 | not tested |
| 2-125 | 3.070 | not tested |
| 2-126 | 0.125 | not tested |
| 2-127 | 1.679 | 4.867 |
| 2-128 | 0.471 | not tested |
| 2-129 | 0.180 | 2.182 |
| 2-130 | 0.731 | not tested |
| 2-131 | 0.088 | not tested |
| 2-132 | 0.040 | not tested |
| 2-133 | 0.244 | not tested |
| 2-134 | 0.132 | not tested |
| 2-135 | 9.814 | not tested |
| 2-136 | 0.150 | not tested |
| 2-137 | 0.149 | not tested |
| 2-138 | 0.541 | not tested |
| 2-139 | 0.181 | not tested |
| 2-140 | 0.115 | 2.660 |
| 2-141 | 0.361 | not tested |
| 2-142 | 0.114 | not tested |
| 2-143 | 0.901 | 1.212 |
| 2-144 | 0.091 | 1.314 |
| 2-145 | 0.105 | 1.208 |
| 2-146 | 0.043 | 0.636 |
| 2-147 | 0.248 | 1.343 |
| 2-148 | 0.397 | 1.814 |
| 2-149 | 0.576 | 1.961 |
| 2-150 | 0.066 | not tested |
| 2-151 | 0.482 | 4.810 |
| 2-152 | 0.185 | not tested |
| 2-153 | 1.640 | not tested |
| 2-154 | 0.720 | not tested |
| 2-155 | 0.374 | 2.218 |
| 2-156 | 0.190 | 1.206 |
| 2-157 | 0.965 | not tested |
| 2-158 | 0.384 | not tested |
| 2-159 | 0.907 | 3.285 |
| 2-160 | 0.349 | 1.376 |
| 3-0 | not tested | not tested |
| 4-0 | 1.460 | not tested |
| 5-0 | 0.103 | not tested |
| 5-1 | 3.482 | not tested |
| 6-0 | 0.016 | 0.620 |
| 6-1 | 0.005 | not tested |
| 7-0 | 1.769 | not tested |
| 7-1 | 0.493 | not tested |
| 8-0 | 1.270 | not tested |
| 8-1 | 3.352 | not tested |
| 9-0 | 0.923 | not tested |
| 9-1 | 0.090 | not tested |
| 9-2 | 0.025 | not tested |
| 9-3 | 0.141 | not tested |
| 9-4 | 6.467 | not tested |
| 9-5 | 0.051 | not tested |
| 10-0 | 0.308 | not tested |
| 11-0 | 0.588 | not tested |
| 12-0 | 0.339 | not tested |
| 13-0 | 0.089 | not tested |
| 14-0 | 1.121 | 8.152 |
| 15-0 | 0.030 | not tested |

Biological Assay 4.0: Tumor Cell Proliferation Assays

Compounds were tested in a cell-based assay that measures the capacity of the compounds to inhibit tumour cell proliferation following a 72h drug exposure. Cell viability is determined using CellTiter-Glow® (CTG, Promega, cat# G7571/2/3). The CellTiter-Glo® Luminescent Cell Viability Assay is a homogeneous method to determine the number of viable cells in culture. Detection is based on using the luciferase reaction to measure the amount of ATP from viable cells. The amount of ATP in cells correlates with cell viability. Within minutes after a loss of membrane integrity, cells lose the ability to synthesize ATP, and endogenous ATPases destroy any remaining ATP; thus the levels of ATP fall precipitously.

Cells were plated at 3000-5000 cells/well (depending on the cell lines) in 90 µL growth medium on MTPs (Corning; #3603, black plate, clear flat bottom). For each cell line assayed, cells were plated onto a separate plate for determination of fluorescence at t=0 hour and t=72 hour time points. Following overnight incubation at 37° C., chemiluminescence values for the t=0 samples were determined after adding 10 µl medium and 100 µl CTG solution according to manufacture protocol. Plates for the t=72 hour time points were treated with compounds diluted into growth medium at ten times final concentration added in 10 µL to the cell culture plate. Cells were then incubated for 72 hours at 37° C. Chemiluminescence values for the t=72 hour samples were determined. For data analysis, briefly, data from 24h plate where used to reflect 100% inhibition of growth ("Ci") and DMSO control for uninhibited growth ("CO") and analyzed using MTS software package for $IC_{50}$ and Hill coefficient. Experiments were controlled using a reference compound as standard.

Preferred compounds of the present invention show in this assay an inhibition of cell growth of cell lines such as the KPL-4 breast cancer cell line with a median $IC_{50}$ of <10 µM, more preferably, median $IC_{50} \leq 1$ µM.

The following Table gives selected data for selected Examples of the present invention.

| Example | KPL-4 proliferation $IC_{50}$, µM | LnCAP proliferation $IC_{50}$, µM | MCF7 proliferation $IC_{50}$, µM |
| --- | --- | --- | --- |
| 1-0 | 1.5 | not tested | not tested |
| 1-1 | 2.0 | not tested | not tested |
| 1-2 | 1.8 | not tested | not tested |
| 1-3 | 1.7 | not tested | not tested |
| 1-4 | not tested | not tested | not tested |
| 1-6 | 1.0 | not tested | not tested |
| 1-7 | 1.0 | not tested | not tested |
| 1-8 | 2.3 | not tested | not tested |
| 1-9 | 2.0 | not tested | not tested |
| 1-10 | 1.6 | not tested | not tested |
| 1-11 | 1.5 | not tested | not tested |
| 1-12 | 8.3 | not tested | 0.8 |
| 1-13 | 0.9 | 1.1 | 0.4 |
| 1-14 | 9.8 | not tested | not tested |
| 1-15 | 10.0 | not tested | not tested |
| 1-16 | 2.0 | not tested | 1.8 |
| 2-0 | 0.8 | not tested | not tested |
| 2-1 | 5.4 | not tested | not tested |
| 2-2 | 1.7 | not tested | not tested |
| 2-3 | 2.4 | not tested | not tested |
| 2-4 | 2.0 | not tested | not tested |
| 2-5 | 4.3 | not tested | not tested |
| 2-6 | 1.6 | not tested | not tested |
| 2-7 | 1.9 | not tested | not tested |
| 2-8 | 1.8 | not tested | |
| 2-9 | 0.9 | not tested | |
| 2-10 | 1.9 | not tested | not tested |
| 2-12 | 1.3 | not tested | not tested |
| 2-13 | 2.2 | not tested | not tested |
| 2-14 | 3.0 | not tested | not tested |
| 2-15 | 3.2 | not tested | not tested |
| 2-16 | 1.9 | not tested | not tested |
| 2-17 | 1.5 | not tested | not tested |
| 2-18 | 0.5 | not tested | not tested |
| 2-19 | 1.6 | not tested | not tested |
| 2-21 | 2.0 | 1.9 | 2.0 |
| 2-22 | 1.5 | not tested | not tested |
| 2-23 | 9.8 | not tested | not tested |
| 2-24 | 4.5 | not tested | not tested |
| 2-25 | 2.3 | not tested | not tested |
| 2-26 | 1.9 | not tested | not tested |
| 2-27 | 1.9 | not tested | not tested |
| 2-28 | 1.8 | not tested | not tested |
| 2-29 | 1.8 | not tested | not tested |
| 2-30 | 2.3 | not tested | not tested |
| 2-31 | 1.9 | not tested | not tested |
| 2-32 | 1.8 | not tested | not tested |
| 2-33 | 1.0 | not tested | not tested |
| 2-34 | 2.2 | not tested | not tested |
| 2-35 | 5.0 | not tested | not tested |
| 2-36 | 10.0 | not tested | not tested |
| 2-37 | 1.9 | not tested | not tested |
| 2-38 | 1.9 | not tested | not tested |
| 2-39 | 1.6 | not tested | not tested |
| 2-40 | 1.9 | not tested | not tested |
| 2-41 | 0.6 | not tested | not tested |
| 2-42 | 9.2 | not tested | not tested |
| 2-43 | 9.2 | | not tested |
| 2-44 | 1.5 | | not tested |
| 2-45 | 1.8 | | not tested |
| 2-46 | 1.8 | | not tested |
| 2-47 | 2.0 | not tested | not tested |
| 2-48 | 2.5 | not tested | not tested |
| 2-49 | 8.7 | not tested | not tested |
| 2-50 | 1.9 | not tested | not tested |
| 2-51 | 10.0 | not tested | not tested |
| 2-52 | 1.5 | not tested | 1.1 |
| 2-53 | 2.0 | not tested | not tested |
| 2-54 | 1.3 | not tested | not tested |
| 2-55 | 5.5 | not tested | not tested |
| 2-56 | 3.4 | not tested | not tested |
| 2-57 | 3.1 | not tested | not tested |
| 2-58 | 1.9 | not tested | not tested |
| 2-59 | 3.8 | not tested | not tested |
| 2-60 | 7.7 | not tested | not tested |
| 2-61 | 9.4 | not tested | not tested |
| 2-62 | 1.7 | not tested | not tested |
| 2-63 | 2.0 | not tested | not tested |
| 2-64 | 3.2 | not tested | not tested |
| 2-65 | 10.0 | not tested | not tested |
| 2-66 | 1.8 | not tested | not tested |
| 2-67 | 1.7 | not tested | 1.3 |
| 2-68 | 3.1 | not tested | 1.9 |
| 2-69 | 2.9 | not tested | 1.8 |
| 2-70 | 2.0 | not tested | 1.6 |
| 2-71 | 1.9 | not tested | 1.6 |
| 2-72 | 2.1 | not tested | 1.7 |
| 2-73 | 1.8 | not tested | 1.7 |
| 2-74 | 1.4 | not tested | 1.6 |
| 2-75 | 1.1 | not tested | 0.6 |
| 2-76 | 2.1 | not tested | 1.7 |
| 2-77 | 8.1 | not tested | 1.7 |
| 2-78 | 1.9 | not tested | 1.1 |
| 2-79 | 0.9 | not tested | 0.5 |
| 2-80 | 2.0 | not tested | 1.8 |
| 2-81 | 1.8 | not tested | 1.7 |
| 2-82 | 2.1 | not tested | 1.7 |
| 2-83 | 1.8 | not tested | 2.0 |
| 2-84 | 2.2 | not tested | 1.6 |
| 2-85 | 1.9 | not tested | 1.4 |
| 2-86 | 2.0 | not tested | 1.8 |
| 2-87 | 3.7 | not tested | 2.1 |
| 2-88 | 2.5 | not tested | 2.1 |

| Example | KPL-4 proliferation IC$_{50}$, µM | LnCAP proliferation IC$_{50}$, µM | MCF7 proliferation IC$_{50}$, µM |
|---|---|---|---|
| 2-89 | 1.9 | not tested | 1.7 |
| 2-90 | 1.9 | not tested | 1.7 |
| 2-91 | 2.0 | not tested | 1.8 |
| 2-92 | 4.3 | not tested | 4.3 |
| 2-93 | 2.0 | not tested | 1.8 |
| 2-94 | 1.8 | not tested | 1.7 |
| 2-95 | 0.4 | not tested | 0.4 |
| 2-96 | 10.0 | not tested | 10.0 |
| 2-97 | 1.9 | not tested | 1.8 |
| 2-98 | 1.9 | not tested | 1.9 |
| 2-99 | 1.8 | not tested | 1.8 |
| 2-100 | 0.9 | not tested | 1.2 |
| 2-101 | 0.3 | not tested | 0.3 |
| 2-102 | 1.9 | not tested | 1.9 |
| 2-103 | 0.2 | not tested | 0.2 |
| 2-104 | 0.3 | not tested | 0.2 |
| 2-105 | 2.2 | not tested | 1.8 |
| 2-106 | 2.1 | not tested | not tested |
| 2-107 | 1.7 | not tested | not tested |
| 2-108 | 10.0 | not tested | not tested |
| 2-109 | 1.5 | not tested | not tested |
| 2-110 | 1.7 | 0.5 | 0.7 |
| 2-111 | 1.8 | not tested | not tested |
| 2-112 | 1.7 | not tested | not tested |
| 2-114 | 0.8 | not tested | 0.7 |
| 2-115 | 1.8 | 1.7 | not tested |
| 2-116 | 1.6 | not tested | not tested |
| 2-117 | 10.0 | not tested | |
| 2-119 | 4.2 | not tested | not tested |
| 2-120 | 10.0 | not tested | not tested |
| 2-122 | 1.2 | not tested | not tested |
| 2-123 | 2.4 | not tested | not tested |
| 2-124 | 2.3 | not tested | not tested |
| 2-125 | 3.1 | 9.9 | not tested |
| 2-126 | 1.6 | 1.0 | not tested |
| 2-127 | 5.4 | 1.2 | not tested |
| 2-128 | 4.4 | not tested | 1.7 |
| 2-129 | 1.8 | not tested | 0.3 |
| 2-130 | 8.4 | not tested | 1.8 |
| 2-131 | 1.7 | not tested | not tested |
| 2-132 | 1.7 | not tested | not tested |
| 2-133 | 2.0 | 1.7 | not tested |
| 2-134 | 2.1 | 1.8 | not tested |
| 2-135 | 10.0 | not tested | not tested |
| 2-136 | 1.9 | not tested | not tested |
| 2-137 | 1.7 | not tested | not tested |
| 2-138 | 2.4 | not tested | not tested |
| 2-139 | 2.0 | not tested | not tested |
| 2-140 | 1.9 | not tested | 0.5 |
| 2-141 | 5.3 | not tested | not tested |
| 2-142 | 2.6 | not tested | not tested |
| 2-143 | 9.5 | 1.8 | not tested |
| 2-144 | 1.7 | not tested | 1.3 |
| 2-145 | 1.0 | not tested | 0.3 |
| 2-146 | 0.7 | not tested | 0.6 |
| 2-147 | 1.7 | not tested | 0.5 |
| 2-148 | 1.9 | not tested | 1.5 |
| 2-149 | 2.9 | not tested | 1.8 |
| 2-150 | 1.7 | not tested | |
| 2-151 | 1.7 | not tested | 0.2 |
| 2-152 | 1.8 | not tested | 1.7 |
| 2-153 | 10.0 | not tested | 0.4 |
| 2-154 | 7.5 | not tested | 1.7 |
| 2-155 | 5.5 | not tested | 1.7 |
| 2-156 | 0.9 | not tested | 0.5 |
| 2-157 | 10.0 | not tested | 1.1 |
| 2-158 | 4.7 | not tested | 1.7 |
| 2-159 | 4.7 | not tested | 2.8 |
| 2-160 | 1.6 | not tested | 0.8 |
| 3-0 | not tested | not tested | not tested |
| 4-0 | 4.6 | not tested | not tested |
| 5-0 | 3.2 | not tested | not tested |
| 5-1 | 10.0 | not tested | not tested |
| 6-0 | 0.8 | not tested | 0.4 |
| 6-1 | 0.3 | 0.4 | 0.3 |
| 7-0 | 2.4 | not tested | not tested |
| 7-1 | 2.1 | not tested | not tested |
| 8-0 | 10.0 | not tested | not tested |
| 8-1 | 10.0 | not tested | not tested |
| 9-0 | 2.5 | not tested | not tested |
| 9-1 | 1.7 | not tested | not tested |
| 9-2 | 0.9 | not tested | not tested |
| 9-3 | 1.8 | not tested | 0.5 |
| 9-4 | 3.1 | not tested | not tested |
| 9-5 | 2.2 | not tested | not tested |
| 10-0 | 7.9 | not tested | not tested |
| 11-0 | 2.2 | 2.0 | not tested |
| 12-0 | 1.9 | 1.7 | not tested |
| 13-0 | 1.7 | not tested | 0.9 |
| 14-0 | 3.1 | not tested | 1.8 |
| 15-0 | 1.3 | not tested | 0.6 |

The following Table gives selected data for selected Examples of the present invention.

| Cell Line for proliferation assay | Tumor type | Example 1-3 median IC$_{50}$, µM | Example 2-0 median IC$_{50}$, µM |
|---|---|---|---|
| A2058 | melanoma | 2.2 | 2.1 |
| A375 | melanoma | 2.2 | 8.6 |
| H1993 | NSCLC | 0.6 | 0.5 |
| HMCB | melanoma | 2.6 | 8.5 |
| HT-144 | melanoma | 2.3 | 2.1 |
| Malme-3M | melanoma | 1.9 | 2.4 |
| MeWo | melanoma | 2.0 | 5.2 |
| SK-Mel-28 | melanoma | 2.0 | 3.7 |
| U87 | brain | 4.9 | 10.0 |
| UACC-257 | melanoma | 1.1 | 2.0 |
| UACC-62 | melanoma | 2.2 | 8.9 |

Example 5.0

Caco2 Permeability Assay

Caco-2 cells (purchased from DSMZ Braunschweig, Germany) were seeded at a density of $4.5 \times 10^4$ cell per well on 24 well insert plates, 0.4 µm pore size, and grown for 15 days in DMEM medium supplemented with 10% fetal bovine serum, 1% GlutaMAX (100×, GIBCO), 100 U/ml penicillin, 100 µg/ml streptomycin (GIBCO) and 1% non essential amino acids (100×). Cells were maintained at 37° C. in a humified 5% $CO_2$ atmosphere. Medium was changed every 2-3 day. Before running the permeation assay, the culture medium was replaced by a FCS-free hepes-carbonate transport puffer (pH 7.2) For assessment of monolayer integrity the transepithelial electrical resistance (TEER) was measured. Test compounds were predissolved in DMSO and added either to the apical or basolateral compartment in final concentration of 2 µM. Before and after 2 h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions. The apparent permeability was calculated using following equation:

$$P_{app} = (V_r/P_o)(1/S)(P_2/t)$$

Where $V_r$ is the volume of medium in the receiver chamber, $P_o$ is the measured peak area of the test drug in the donor chamber at t=0, S the surface area of the monolayer, $P_2$ is the measured peak area of the test drug in the acceptor chamber after 2 h of incubation, and t is the incubation time. The efflux ratio basolateral (B) to apical (A) was calculated by dividing the $P_{app}$ B–A by the $P_{app}$ A–B. In addition the compound recovery was calculated. As assay control reference compounds were analyzed in parallel.

Example 6.0

In Vivo Rat Pharmacokinetics

For in vivo pharmacokinetic experiments test compounds were administered to male Wistar rats intravenously at doses of 0.3 to 1 mg/kg and intragastral at doses of 0.6 to 10 mg/kg formulated as solutions using solubilizers such as PEG400 in well-tolerated amounts.

For pharmacokinetics after intravenous administration test compounds were given as i.v. bolus and blood samples were taken at 2 min, 8 min, 15 min, 30 min, 45 min, 1 h, 2 h, 4 h, 6 h, 8 h and 24 h after dosing. Depending on the expected half-life additional samples were taken at later time points (e.g. 48 h, 72 h). For pharmacokinetics after intragastral administration test compounds were given intragastral to fasted rats and blood samples were taken at 5 min, 15 min, 30 min, 45 min, 1 h, 2 h, 4 h, 6 h, 8 h and 24 h after dosing. Depending on the expected half-life additional samples were taken at later time points (e.g. 48 h, 72 h). Blood was collected into Lithium-Heparintubes (Monovetten®, Sarstedt) and centrifuged for 15 min at 3000 rpm. An aliquot of 100 μL from the supernatant (plasma) was taken and precipitated by addition of 400 μL cold acetonitrile and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. PK parameters calculated from concentration time profiles after i.g.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0–tlast)norm: Area under the concentration-time curve from t=0 h to the last time point for which plasma concentrations could be measured divided by the administered dose (in kg*h/L); t1/2: terminal half-life (in h); F: oral bioavailability: AUCnorm after intragastral administration divided by AUCnorm after intravenous administration (in %).

The person skilled in the art will be aware of methods to show in vivo efficacy of anti-cancer compounds. By way of illustration, the following example describes methods of quantifying the in vivo efficacy in a mouse xenograft model. The skilled person will be able to apply such principles to derive models from alternative tumor material.

Example 7.0

In Vivo Xenograft Mechanism of Action Study

To demonstrate that compounds act in tumours by the anticipated mode of action phosphorylation of the AKT protein was investigated in PC3 prostate tumours treated once with 50 mg/kg compound.

To this extent PC3 human prostate tumours were xenografted onto athymic nude mice. PC3 tumour cells were cultivated according to ATCC protocols in recommended media contained 10% FCS and harvested for transplantation in a subconfluent (70%) state. $3\times10^6$ tumour cells suspended in 50% Matrigel were subcutaneously implantated into the inguinal region of male mice. Tumours were allowed to grow to the predetermined size of 60-80 mm$^2$. When the tumours were approximately in size, the animals were randomized to treatment and control groups (groups size: 9 animals) and treatment was started. Animals were treated once with 50 mg/kg compound or vehicle per oral administration (p.o.) carried out via a gastric tube. Treatment of each animal was based on individual body weight. At 2, 5 and 24 hours post treatment 3 animals each were sacrificed and the PC3 tumours excised. Tumour samples of approximately 5×5×5 mm were lysed on ice in MSD lysis buffer in the presence of protease and phosphatase inhibitors using Tissue Lyzer (Qiagen, Germany). The levels of p-AKT S473 in extracts from tumour tissue were analysed in an ELISA based assay. This assay is based on the "Akt Duplex" of the MULTI-SPOT® Assay System (Fa. Meso Scale Discovery, Cat# N41100B-1) following manufacturers instructions. Each assay used 20 μg of protein extract and measured total AKT and p-AKT content simultaneously in one well. All measurements where at least done in duplicates and confirmed by independent repetition.

Values for P-AKT are expressed as percentage of P-AKT level compared to total-AKT content of the extracts. Vehicle treated tumours were analyzed to determine the basal level of P-AKT in this model and used as a normalization control to determine the % P-AKT relative to vehicle levels.

Preferred compounds of the present invention show in this assay: relative to vehicle levels P-AKT <30% at 2 hours post treatment, more preferably at 5 hours post treatment, even more preferably at 24 hours post treatment.

The following Table gives selected data for selected Examples of the present invention.

| Example | P-AKT % relative to control at 2 hours | P-AKT % relative to control at 5 hours |
| --- | --- | --- |
| 1-9 | 32.2 | 21.1 |
| 1-13 | 95.7 | 151.8 |
| 2-00 | 4.7 | 6.3 |
| 2-18 | 8.0 | 7.7 |
| 2-41 | 10.2 | 8.8 |
| 2-52 | 34.9 | 47.9 |
| 2-73 | 9.1 | 9.3 |
| 2-75 | 5.5 | 6.2 |
| 2-81 | 33.6 | 69.6 |
| 2-90 | 51.6 | 53.7 |
| 2-92 | 34.6 | 22.0 |
| 2-93 | 46.0 | 79.2 |
| 2-96 | 12.2 | 11.4 |
| 2-110 | 10.2 | 16.4 |
| 2-114 | 47.0 | 57.2 |
| 2-140 | 26.0 | 18.0 |
| 2-144 | 6.3 | 8.0 |
| 2-145 | 33.0 | 38.0 |
| 2-146 | 17.5 | 22.3 |
| 6-0 | 5.8 | 6.0 |
| 6-1 | 7.7 | 7.5 |

Example 7.1

In Vivo Xenograft Efficacy Study

To determine the therapeutic efficacy and tolerability of compounds, tumour growth of PC3 prostate tumours xenografted onto nude mice may be observed.

Mice were treated either with vehicle or compounds. To this extent PC3 xenografts were established as described above. Tumours were allowed to grow to the predetermined size of 25-35 mm². When the tumours were approximately in size, the animals were randomized to treatment and control groups (groups size: 8 animals) and treatment was started. Treatment of each animal was based on individual body weight and oral administration (p.o.) was carried out via a gastric tube. The oral application volumes were 10 ml/kg for mice. Mice were treated once daily with 50 mg/kg compounds.

Tumour response was assessed by determination of the tumour area (product of the longest diameter and its perpendicular) using a calliper. The animal body weight was monitored as a measure for treatment-related toxicity. Measurement of tumour area and body weight were performed 2-3 times weekly. Statistical analysis was assessed using the SigmaStat software. A one way analysis of variance was performed, and differences to the control were compared by a pair-wise comparison procedure (Dunn's method). T/C ratios (Treatment/Control) were calculated with final tumour weights at study end.

The invention claimed is:
1. A compound of formula (I)

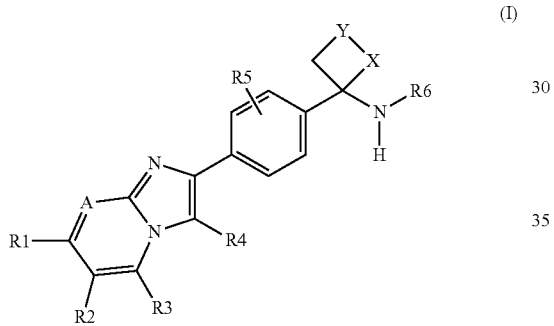

in which
R1 is hydrogen, hydroxy, halogen, cyano, CO-(1-6C-alkyl), C(O)OR10, CO(NR8R9), NR8R9, NH—C(O)NR8R9, NH—C(O)R11, 2-6C-alkinyl, or
 a group selected from 1-6C-alkyl, 2-6C-alkenyl, 1-6C-alkoxy, 3-7C-cycloalkyl, aryl, heteroaryl, -(1-6C-alkylen)-aryl, -(1-6C-alkylen)-heteroaryl, —O-(3-7C-cycloalkyl), —O-aryl, —O-(3-7C-heterocyclyl), —O-heteroaryl, —O-(1-6C-alkylen)-(3-7C-cycloalkyl), —O-(1-6C-alkylen)-aryl, —O-(1-6C-alkylen)-(3-7C-heterocyclyl), —O-(1-6C-alkylen)-heteroaryl,
  wherein said group is optionally substituted independently with one or more substituents selected from:
   hydroxy, halogen, 1-6C-alkyl, 1-4C-haloalkyl, 1-6C-alkoxy, —NR8R9, cyano, (=O), —C(O)NR8R9, —C(O)OR10, —NHC(O)R11, —NHS(O)₂R11, heteroaryl,
    wherein said substituent can be optionally substituted with 1-6C-alkoxy,
R2 is hydrogen, hydroxy, halogen, cyano, CO-(1-6C-alkyl),C(O)OR10, CO(NR8R9), NR8R9, —NH—C(O)R11, —NH—C(O)NR8R9, —NHS(O)₂R11 or
 a group selected from 1-6C-alkyl, 2-6C-alkenyl, 1-6C-alkoxy, 3-7C-cycloalkyl, aryl, heteroaryl,
  wherein said group is optionally substituted independently with one or more substituents selected from:
   hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11, NH-(1-6C-alkyl)-O-(1-6C-alkyl),
R3 is hydrogen, 1-6C-alkyl,
R4 is phenyl optionally substituted by 1-6C-alkyl, halogen, cyano,
R5 is hydrogen, halogen,
R6 is hydrogen, 1-6C-alkyl,
A is N, C(R7),
R7 is hydrogen, hydroxy, halogen, cyano, C(O)OR10, CO(NR8R9), 3-7C-cycloalkyl, or
 a group selected from 1-6C-alkyl, 2-6C-alkenyl, 1-6C-alkoxy, aryl, heteroaryl,
  wherein said group is optionally substituted independently with one or more substituents selected from:
   hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11,
X is —CH₂—,
Y is —CH₂—, —CH(OH)—,
R8, R9 which can be the same or different, is hydrogen, hydroxy, 3-7C-cycloalkyl or
 a group selected from 1-4C-alkyl, 1-6C-alkoxy, wherein said group is optionally substituted, independently with one or more substituents selected from:
  halogen, hydroxy, mono- or di-(1-4C-alkylamino), 1-4C-alkoxy, or 3-7C-cycloalkyl or,
 R8 and R9 together with the nitrogen to which they are attached may also form a saturated or unsaturated 3-6C-heterocyclic ring,
  which is optionally substituted by (=O)
R10 is hydrogen, 1-6C-alkyl,
R11 is 1-4C-alkyl (optionally substituted independently with one or more halogen or hydroxyl groups) or 3-7C-cycloalkyl,
or an N-oxide, a salt, a tautomer or a stereoisomer of said compound, or a salt of said N-oxide, tautomer or stereoisomer.

2. The compound of formula (I) according to claim 1, wherein
R1 is hydrogen, hydroxy, halogen, cyano, —CO-(1-6C-alkyl), C(O)OR10, CO(NR8R9), NR8R9, NH—C(O)NR8R9, NH—C(O)R11, 2-6C-alkinyl, or
 a group selected from 1-6C-alkyl, 2-6C-alkenyl, 1-6C-alkoxy, 3-7C-cycloalkyl, aryl, heteroaryl, -(1-6C-alkylen)-aryl, -(1-6C-alkylen)-heteroaryl, —O-(3-7C-cycloalkyl), —O-aryl, —O-(3-7C-heterocyclyl), —O-heteroaryl, —O-(1-6C-alkylen)-heteroaryl, —O-(1-6C-alkylen)-(3-7C-heterocyclyl), —O-(1-6C-alkylen)-aryl, —O-(1-6C-alkylen)-(3-7C-cycloalkyl)
  wherein said group is optionally substituted with one or more substituents selected from:
   hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)₂R11, heteroaryl,
    wherein said substituent can be optionally substituted with 1-6C-alkoxy,
R2 is hydrogen, hydroxy, halogen, cyano, C(O)OR10, CO(NR8R9), NR8R9, —NH—C(O)R11, —NH—C(O)NR8R9, —NHS(O)₂R11 or
 a group selected from 1-6C-alkyl, 2-6C-alkenyl, 1-6C-alkoxy, 3-7C-cycloalkyl, aryl, heteroaryl,
  wherein said group is optionally substituted independently with one or more substituents selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11, NH-(1-6C-alkyl)-O-(1-6-alkyl), R3 is hydrogen,
R4 is phenyl optionally substituted by 1-6C-alkyl, halogen, cyano,
R5 is hydrogen, halogen,
R6 is hydrogen,
A is N, C(R7),
R7 is hydrogen, hydroxy, halogen, cyano, C(O)OR10, CO(NR8R9), 3-7C-cycloalkyl, or
   a group selected from 1-6C-alkyl, 2-6C-alkenyl, 1-6C-alkoxy, aryl, heteroaryl,
      wherein said group is optionally substituted independently with one or more substituents selected from:
      hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)$_2$R11,
X is —CH$_2$—,
Y is —CH$_2$—, —CH(OH)—,
R8, R9 which can be the same or different, is hydrogen, hydroxy, or
   a group selected from 1-4C-alkyl, 1-6C-alkoxy, wherein said group is optionally substituted, independently with one or more substituents selected from:
      halogen, hydroxy, mono- or di-(1-4C-alkylamino), 1-4C-alkoxy, or 3-7C-cycloalkyl, or,
   R8 and R9 together with the nitrogen to which they are attached may also form a saturated or unsaturated 3-6C-heterocyclic ring,
      which is optionally substituted by (=O)
R10 is hydrogen, 1-6C-alkyl,
R11 is 1-4C-alkyl (optionally substituted independently with one or more halogen or hydroxyl groups) or 3-7C-cycloalkyl,
or an N-oxide, a salt, a tautomer or a stereoisomer of said compound, or a salt of said N-oxide, tautomer or stereoisomer.

3. The compound of formula (I) according to claim 1, wherein
R1 is hydrogen, hydroxy, halogen, cyano, —CO-(1-6C-alkyl), C(O)OR10, CO(NR8R9), NR8R9, NH—C(O)NR8R9, NH—C(O)R11, 2-6C-alkinyl, or
   a group selected from 1-6C-alkyl, 2-6C-alkenyl, 1-6C-alkoxy, 3-7C-cycloalkyl, aryl, heteroaryl, -(1-6C-alkylen)-aryl, -(1-6C-alkylen)-heteroaryl, —O -(3-7C-cycloalkyl), —O-aryl, —O-(3-7C-heterocyclyl), —O-heteroaryl, —O-(1-6C-alkylen)-heteroaryl, —O-(1-6C-alkylen)-(3-7C-heterocyclyl), —O-(1-6C-alkylen)-aryl, —O-(1-6C-alkylen)-(3-7C-cycloalkyl)
      wherein said group is optionally substituted independently with one or more substituents selected from:
      hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)2R11, heteroaryl,
         wherein said substituent can be optionally substituted with 1-6C-alkoxy,
R2 is hydrogen, hydroxy, halogen, cyano, C(O)OR10, CO(NR8R9), NR8R9, —NH—C(O)R11, —NH—C(O)NR8R9, —NHS(O)2R11 or
   a group selected from 1-6C-alkyl, 2-6C-alkenyl, 1-6C-alkoxy, 3-7C-cycloalkyl, aryl, heteroaryl,
      wherein said group is optionally substituted independently with one or more substituents selected from:

hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)2R11, NH-(1-6C-alkyl)-O-(1-6C-alkyl), R3 is hydrogen,
R4 is phenyl
R5 is hydrogen,
R6 is hydrogen,
A is N, C(R7),
R7 is hydrogen, hydroxy, halogen, cyano, C(O)OR10, CO(NR8R9), 3-7C-cycloalkyl, or
   a group selected from 1-6C-alkyl, 2-6C-alkenyl, 1-6C-alkoxy, aryl, heteroaryl,
      wherein said group is optionally substituted independently with one or more substituents selected from:
      hydroxy, halogen, 1-6C-alkyl, 1-4C-haloalkyl, 1-6C-alkoxy, —NR8R9, cyano, —C(O)NR8R9, —C(O)OR10, —NHC(O)R11, —NHS(O)2R11,
X is —CH$_2$—,
Y is —CH$_2$—, —CH(OH)—,
R8, R9 which can be the same or different, is hydrogen, hydroxy, or
   a group selected from 1-4C-alkyl, 1-6C-alkoxy, wherein said group is optionally substituted independently with one or more substituents selected from:
      halogen, hydroxy, mono- or di-1-4C-alkylamino), 1-4C-alkoxy, or 3-7C-cycloalkyl, or,
   R8 and R9 together with the nitrogen to which they are attached may also form a saturated or unsaturated 3-6C-heterocyclic ring,
      which is optionally substituted by (=O)
R10 is hydrogen, 1-6C-alkyl,
R11 is 1-4C-alkyl (optionally independently with one or more halogen or hydroxyl groups) or 3-7C-cycloalkyl,
or an N-oxide, a salt, a tautomer or a stereoisomer of said compound, or a salt of said N-oxide, tautomer or stereoisomer.

4. The compound of formula (I) according to claim 1, wherein,
R1 is hydrogen, 1-3C-alkyl, -(1-3C-alkylen)C(O)O(1-3C-alkyl), -(2-3Calkenylen)C(O)O(1-3C-alkyl), -(2-3Calkenylen)C(O)NH2, -(1-3C-alkylen)C(O)NH2, halogen, hydroxy, ONa, 1-3C-alkoxy, —O-cyclohexyl, —O-phenyl, —O-(1-3C-alkylen)-heteroaryl, —O-(1-3C-alkylen)-[(1-3C-alkoxy)heteroaryl], —O-(1-3C-alkylen)NH$_2$, —O-(1-3C-alkylen)O-(1-3C-alkyl), —O-(1-3C-alkylen)-cyclopropane-C(O)NH2, —O-(1-3C-alkylen)-CN, —O-(1-3C-alkylen)-C(O)O(1-3C-alkyl), —O-(1-3C-alkylen)-C(O)N(1-3C-alkyl)$_2$, —O-(1-3C-alkylen)-(heterocyclyl), -heteroaryl-(1-3Calkoxy), —O-(1-3C-alkylen)-(heteroaryl)-(1-3alkoxy), 3-7C-cycloalkyl, phenyl (which is optionally substituted with 1-3C-alkyl, halogen), cyano, —C(O)(1-3C-alkyl), —C(O)OH, —C(O)O(1-3C-alkyl), —CONH2, —C(O)NH(1-3C-alkyl), —C(O)NH-OH, —C(O)-heterocycyl, heteroaryl (which is optionally substituted with 1-3C-alkyl, (=O), 1-3Calkoxy,), NH—C(O)—NH-(1-3C-alkyl), amino, NH—C(O)-(1-3C-alkyl), NH—C(O)—NH2, N(1-3C-alkyl)-O-(1-3C-alkyl),
R2 is hydrogen, 1-3C-alkyl, trifluoromethyl, -(1-3C-alkylen)C(O)O-(1-3C-alkyl), 2-3C-alkenyl, -(2-3C-alkenylen)C(O)O-(1-3C-alkyl), -(2-3C-alkenylen)C(O)NH$_2$, -(1-3C-alkylen)-NH-(1-3C-alkylen)-O-(1-3C-alkyl), 1-3C-alkoxy, —O-(1-3C-alkylen)-CN, —O-(1-3C-alkylen)-C(O)O-(1-3C-alkyl), hydroxy, halogen, cyano, 3-7C-cycloalkyl, phenyl, —C(O)(1-3C-alkyl), C(O)O(1-3C-alkyl), —CONH$_2$, —CONH-(1-3C- alkyl), C(O)—N(1-3C-alkyl), C(O)—NH-(1-3C-alkylen)F, C(O)—NH-(1-3C-alkylen)OH, C(O)—NH-(1-3C-alkylen)O-(1-3C-alkyl), C(O)NH-3-7C-cycloalkyl, C(O)NH-(1-3C-alkyl)-3-7C-cycloalkyl, C(O)NH—OH, -(1-3C-alkyl)O-(1-3C-alkyl), —CH(OH)-(1-3C-alkyl), -(1-3C-alkylen)OH, heteroaryl (which is optionally substituted with 1-3C-alkyl), amino, NH—C(O)-(1-3C-alkyl), NH—C(O)—NH$_2$, NH—C(O)—NH-(1-3C-alkyl), NH—S(O)$_2$-(1-3C-alkyl), R3 is hydrogen, 1-3C-alkyl,
R4 is phenyl,
R5 is hydrogen,
R6 is hydrogen,
A is N, C(R7),
R7 is hydrogen, hydroxy, cyano, halogen, 1-3C-alkyl, 2-3C-alkenyl, 1-3C-alkoxy, -(1-3C-alkylen)OH, C(O)O-(1-3C-alkyl), —CONH$_2$, 3-7C-cycloalkyl, phenyl (which is optionally substituted with halogen, 1-3C-alkox),
R8 is hydrogen, 1-3C-alkyl, hydroxy, 1-3C-alkoxy, 3-7C-cycloalkyl,
  whereby 1-3C-alkyl is optionally substituted independently with one or more substituents selected from
  halogen, hydroxy, 1-3C-alkoxy, 3-7C-cycloalkyl,
R9 is hydrogen, 1-3C-alkyl,
or
R8 and R9 together with the nitrogen to which they are attached may also form a saturated or unsaturated 5- or 6-membered heterocyclic ring which optionally is substituted with (═O),
X is —CH$_2$—,
Y is —CH$_2$—, —CH(OH)—,
or an N-oxide, a salt, a tautomer or a stereoisomer of said compound, or a salt of said N-oxide, tautomer or stereoisomer.

5. The compound of formula (I) according to claim 1, which is selected from the group consisting of:
1-[4-(3-phenyl-imidazo[1,2-a]pyrimidin-2-yl)-phenyl]-cyclobutylamine,
1-[4-(7-methyl-3-phenyl-imidazo[1,2-a]pyrimidin-2-yl)-phenyl]-cyclobutylamine,
1-[4-(7-cyclopropyl-3-phenyl-imidazo[1,2-a]pyrimidin-2-yl)-phenyl]-cyclobutylamine,
1-[4-(3,7-diphenyl-imidazo[1,2-a]pyrimidin-2-yl)-phenyl]-cyclobutylamine,
1-[4-(3-phenyl-7-O-tolyl-imidazo[1,2-a]pyrimidin-2-yl)-phenyl]-cyclobutylamine,
1-[4-(6-chloro-3-phenyl-imidazo[1,2-a]pyrimidin-2-yl)-phenyl]-cyclobutylamine,
1-[4-(6-methyl-3-phenyl-imidazo[1,2-a]pyrimidin-2-yl)-phenyl]-cyclobutylamine,
1-[4-(6-methoxy-3-phenyl-imidazo[1,2-a]pyrimidin-2-yl)-phenyl]-cyclobutylamine,
1-[4-(6-ethoxy-3-phenyl-imidazo[1,2-a]pyrimidin-2-yl)-phenyl]-cyclobutylamine,
1-[4-(3,6-diphenyl-imidazo[1,2-a]pyrimidin-2-yl)-phenyl]-cyclobutylamine,
2-[4-(1-amino-cyclobutyl)-phenyl]-3-phenyl-imidazo[1,2-a]pyridine-6-carbonitrile,
1-[4-(7-methoxy-3-phenyl-imidazo[1,2-a]pyrimidin-2-yl)-phenyl]-cyclobutylamine,
2-[4-(1-amino-cyclobutyl)-phenyl]-3-phenyl-imidazo[1,2-a]pyrimidin-7-ol,
1-[4-(3-phenyl-7-propoxy-imidazo[1,2-a]pyrimidin-2-yl)-phenyl]-cyclobutylamine,
2-[4-(1-amino-cyclobutyl)-phenyl]-3-phenyl-imidazo[1,2-a]pyridine-8-carbonitrile,
1-[4-(7-methyl-3-phenyl-imidazo[1,2-a]pyridin-2-yl)-phenyl]-cyclobutyl amine,
1-[4-(8-methyl-3-phenyl-imidazo[1,2-a]pyridin-2-yl)-phenyl]-cyclobutyl amine,
2-[4-(1-amino-cyclobutyl)-phenyl]-3-phenyl-imidazo[1,2-a]pyridine-7-carbonitrile,
1-[4-(6-methyl-3-phenyl-imidazo[1,2-a]pyridin-2-yl)-phenyl]-cyclobutyl amine,
1-[4-(7-methoxy-3-phenyl-imidazo[1,2-a]pyridin-2-yl)-phenyl]-cyclobutylamine,
2-[4-(1-amino-cyclobutyl)-phenyl]-3-phenyl-imidazo[1,2-a]pyridine-6-carboxylic acid methylamide,
1-[4-(6-methoxymethyl-3-phenyl-imidazo[1,2-a]pyridin-2-yl)-phenyl]-cyclobutylamine,
1-[4-(3-phenyl-imidazo[1,2-a]pyridin-2-yl)-phenyl]-cyclobutylamine,
1-[4-(8-methoxy-3-phenyl-imidazo[1,2-a]pyridin-2-yl)-phenyl]-cyclobutylamine,
1-{2-[4-(1-amino-cyclobutyl)-phenyl]-3-phenyl-imidazo[1,2-a]pyridin-6-yl}-ethanol,
{2-[4-(1-amino-cyclobutyl)-phenyl]-3-phenyl-imidazo[1,2-a]pyridin-7-yl}-methanol,
{2-[4-(1-amino-cyclobutyl)-phenyl]-3-phenyl-imidazo[1,2-a]pyridin-8-yl}-methanol,
1-[4-(6-bromo-3-phenyl-imidazo[1,2-a]pyridin-2-yl)-phenyl]-cyclobutylamine,
1-[4-(6-methoxy-3-phenyl-imidazo[1,2-a]pyridin-2-yl)-phenyl]-cyclobutylamine,
2-[4-(1-amino-cyclobutyl)-phenyl]-3-phenyl-imidazo[1,2-a]pyridine-6-carboxylic acid amide,
1-[4-(8-ethoxy-3-phenyl-imidazo[1,2-a]pyridin-2-yl)-phenyl]-cyclobutylamine,
1-[4-(7-ethoxy-3-phenyl-imidazo[1,2-a]pyridin-2-yl)-phenyl]-cyclobutylamine,
1-[4-(7-ethyl-3-phenyl-imidazo[1,2-a]pyridin-2-yl)-phenyl]-cyclobutylamine,
1-{4-[3-phenyl-7-(1H-pyrazol-4-yl)-imidazo[1,2-a]pyridin-2-yl]-phenyl}-cyclobutylamine,
{2-[4-(1-amino-cyclobutyl)-phenyl]-3-phenyl-imidazo[1,2-a]pyridin-6-yl}-methanol,
1-{4-[7-(6-methoxy-pyridin-3-ylmethoxy)-3-phenyl-imidazo[1,2-a]pyrimidin-2-yl]-phenyl}-cyclobutylamine,
1-{4-[7-(2-methoxy-ethoxy)-3-phenyl-imidazo[1,2-a]pyrimidin-2-yl]-phenyl}-cyclobutylamine,
1-{4-[7-(2-methoxy-pyridin-4-ylmethoxy)-3-phenyl-imidazo[1,2-a]pyrimidin-2-yl]-phenyl}-cyclobutylamine,
1-[4-(7-ethoxy-3-phenyl-imidazo[1,2-a]pyrimidin-2-yl)-phenyl]-cyclobutylamine,
1-[4-(7-isopropoxy-3-phenyl-imidazo[1,2-a]pyrimidin-2-yl)-phenyl]-cyclobutylamine,
1-[4-(7-cyclohexyloxy-3-phenyl-imidazo[1,2-a]pyrimidin-2-yl)-phenyl]-cyclobutylamine,
1-[4-(7-phenoxy-3-phenyl-imidazo[1,2-a]pyrimidin-2-yl)-phenyl]-cyclobutylamine,
1-[4-(6-ethyl-3-phenyl-imidazo[1,2-a]pyrimidin-2-yl)-phenyl]-cyclobutylamine,
1-{4-[7-(4-fluoro-phenyl)-3-phenyl-imidazo[1,2-a]pyridin-2-yl]-phenyl}-cyclobutylamine,
1-[4-(7-cyclopropyl-3-phenyl-imidazo[1,2-a]pyridin-2-yl)-phenyl]-cyclobutylamine,
1-[4-(6-ethyl-3-phenyl-imidazo[1,2-a]pyridin-2-yl)-phenyl]-cyclobutylamine,
1-[4-(8-bromo-3-phenyl-imidazo[1,2-a]pyridin-2-yl)-phenyl]-cyclobutylamine, 1-[4-(7-bromo-3-phenyl-imidazo[1,2-a]pyridin-2-yl)-phenyl]-cyclobutylamine,
2-[4-(1-amino-cyclobutyl)-phenyl]-3-phenyl-imidazo[1,2-a]pyridine-7-carboxylic acid amide,
2-[4-(cis-1-amino-3-hydroxy-cyclobutyl)-phenyl]-3-phenyl-imidazo[1,2-a]pyrimidin-7-ol,
1-{4-[7-(2-amino-ethoxy)-3-phenyl-imidazo[1,2-a]pyrimidin-2-yl]-phenyl}-cyclobutylamine,
2-[4-(1-amino-cyclobutyl)-phenyl]-3-phenyl-imidazo[1,2-a]pyridin-6-ol,
2-[4-(1-amino-cyclobutyl)-phenyl]-3-phenyl-imidazo[1,2-a]pyridine-8-carboxylic acid amide,
1-[4-(3-Phenyl-7-pyrazol-1-yl-imidazo[1,2-a]pyridin-2-yl)-phenyl]-cyclobutylamine,
2-[4-(1-Amino-cyclobutyl)-phenyl]-8-methoxy-3-phenyl-imidazo[1,2-a]pyridine-6-carboxylic acid methyl ester,
2-[4-(1-Amino-cyclobutyl)-phenyl]-8-methoxy-3-phenyl-imidazo[1,2-a]pyridine-6-carboxylic acid amide,
1-{2-[4-(1-Amino-cyclobutyl)-phenyl]-3-phenyl-imidazo[1,2-a]pyridin-7-yl}-3-methyl-urea,
1-{2-[4-(1-Amino-cyclobutyl)-phenyl]-3-phenyl-imidazo[1,2-a]pyridin-7-yl}-1H-pyridin-2-one,
1-{4-[3-Phenyl-6-(1H-pyrazol-1-yl)imidazo[1,2-a]pyridin-2-yl]phenyl}cyclobutanamine,
{2[4-(1-Amino-cyclobutyl)-phenyl]-3-phenyl-imidazo[1,2-a]pyridin-7-yl}-pyrrolidin-1-yl-methanone,
2-[4-(1-Amino-cyclobutyl)-phenyl]-3-phenyl-imidazo[1,2-a]pyridine-8-carboxylic acid ethyl ester,
1-[4-(8-Fluoro-3-phenyl-imidazo[1,2-a]pyridin-2-yl)-phenyl]-cyclobutylamine,
1-[4-(8-Chloro-3-phenyl-imidazo[1,2-a]pyridin-2-yl)-phenyl]-cyclobutylamine,
1-[4-(6-Fluoro-3-phenyl-imidazo[1,2-a]pyridin-2-yl)-phenyl]-cyclobutylamine,
1-[4-(8-Cyclopropyl-3-phenyl-imidazo[1,2-a]pyridin-2-yl)-phenyl]-cyclobutylamine,
1-[4-(3-Phenyl-6-vinyl-imidazo[1,2-a]pyridin-2-yl)-phenyl]-cyclobutylamine,
1-[4-(3-Phenyl-8-vinyl-imidazo[1,2-a]pyridin-2-yl)-phenyl]-cyclobutylamine,
1-{4-[3-Phenyl-8-(1H-pyrazol-4-yl)-imidazo[1,2-a]pyridin-2-yl]-phenyl}-cyclobutylamine,
2-[4-(1-Amino-cyclobutyl)-phenyl]-3-phenyl-imidazo[1,2-a]pyridine-6-carboxylic acid hydrochloride salt,
1-[4-(6-Bromo-8-methoxy-3-phenyl-imidazo[1,2-a]pyridin-2-yl)-phenyl]-cyclobutylamine,
2-[4-(1-Amino-cyclobutyl)-phenyl]-3-phenyl-imidazo[1,2-a]pyridine-6-carboxylic acid isopropylamide,
2-[4-(1-Amino-cyclobutyl)-phenyl]-3-phenyl-imidazo[1,2-a]pyridine-6-carboxylic acid (2-fluoro-ethyl)-amide,
2-[4-(1-Amino-cyclobutyl)-phenyl]-3-phenyl-imidazo[1,2-a]pyridine-6-carboxylic acid (2-hydroxy-ethyl)-amide,
2-[4-(1-Amino-cyclobutyl)-phenyl]-3-phenyl-imidazo[1,2-a]pyridine-6-carboxylic acid (2-methoxy-ethyl)-amide,
2-[4-(1-Amino-cyclobutyl)-phenyl]-3-phenyl-imidazo[1,2-a]pyridine-6-carboxylic acid cyclopropylamide,
2-[4-(1-Amino-cyclobutyl)-phenyl]-3-phenyl-imidazo[1,2-a]pyridine-6-carboxylic acid cyclopropyl methylamide,
2-[4-(1-Amino-cyclobutyl)-phenyl]-3-phenyl-imidazo[1,2-a]pyridine-6-carboxylic acid hydroxyamide,
2-[4-(1-Amino-cyclobutyl)-phenyl]-8-chloro-3-phenyl-imidazo[1,2-a]pyridine-6-carboxylic acid methyl ester,
2-[4-(1-Amino-cyclobutyl)-phenyl]-3-phenyl-imidazo[1,2-a]pyridine-6-carboxylic acid dimethylamide,
2-[4-(1-Amino-cyclobutyl)-phenyl]-3-phenyl-imidazo[1,2-a]pyridine-6-carboxylic acid ethylamide,
1-[4-(6-Cyclopropyl-3-phenyl-imidazo[1,2-a]pyridin-2-yl)-phenyl]-cyclobutylamine,
1-(2-{2-[4-(1-Amino-cyclobutyl)-phenyl]-3-phenyl-imidazo[1,2-a]pyrimidin-7-yloxy}-ethyl)-pyrrolidin-2-one,
1-{2-[4-(1-Amino-cyclobutyl)-phenyl]-3-phenyl-imidazo[1,2-a]pyrimidin-7-yloxymethyl}-cyclopropanecarboxylic acid amide,
1-[4-(7-Chloro-3-phenyl-imidazo[1,2-a]pyridin-2-yl)-phenyl]-cyclobutylamine,
1-[4-(7-Fluoro-3-phenyl-imidazo[1,2-a]pyridin-2-yl)-phenyl]-cyclobutylamine,
1-{4-[8-(4-fluorophenyl)-3-phenyl-imidazo[1,2-a]pyridin-2-yl]-phenyl}-cyclobutylarnine,
1-{4-[8-(3-Fluorophenyl)-3-phenyl-imidazo[1,2-a]pyridin-2-yl]-phenyl}-cyclobutylamine,
1-{4-[8-(5-Methoxypyridin-3-yl)-3-phenyl-imidazo[1,2-a]pyridin-2-yl]-phenyl}-cyclobutylcarbarnine,
1-{4-[3-Phenyl-8-(2H-pyrazol-3-yl)-imidazo[1,2-a]pyridin-2-yl]-phenyl}-cyclobutylarnine,
1-{4-[8-(1H-indazol-6-yl)-3-phenyl-imidazo[1,2-a]pyridin-2-yl]-phenyl}-cyclobutylarnine,
1-[4-(6,8-Dimethyl-3-phenyl-imidazo[1,2-a]pyridin-2-yl)-phenyl]-cyclobutylamine,
1-[4-(8-Chloro-7-methyl-3-phenyl-imidazo[1,2-a]pyridin-2-yl)-phenyl]-cyclobutylamine,
1-[4-(7,8-Difluoro-3-phenyl-imidazo[1,2-a]pyridin-2-yl]-phenyl]-cyclobutylamine,
1-[4-(6-Chloro-8-methyl-3-phenyl-imidazo[1,2-a]pyridin-2-yl)-phenyl]-cyclobutylamine,
2-[4-(1-Arnino-cyclobutyl)-phenyl]-8-brorno-3-phenyl-imidazo[1,2-a]pyridine-6-carboxylic acid ethyl ester,
1-[4-(6,8-Dichloro-3-phenyl-imidazo[1,2-a]pyridin-2-yl)-phenyl]-cyclobutylamine,
2-[4-(1-Amino-cyclobutyl)-phenyl]-7-methoxy-3-phenyl-imidazo[1,2-a]pyridine -8-carbonitrile,
1-[4-(6,7-Dichloro-3-phenyl-imidazo[1,2-a]pyridin-2-yl)-phenyl]-cyclobutylamine,
1-[4-(8-Bromo-6-chloro-7-methyl-3-phenyl-imidazo[1,2-a]pyridin-2-yl)-phenyl]-cyclobutylamine,
1-[4-(6-Bromo-8-methyl-3-phenyl-imidazo[1,2-a]pyridin-2-yl)-phenyl]-cyclobutylamine,
1-[4-(8-Bromo-6-methyl-3-phenyl-imidazo[1,2-a]pyridin-2-yl)-phenyl]-cyclobutylamine,
1-[4-(6-Bromo-7,8-dimethyl-3-phenyl-imidazo[1,2-a]pyridin-2-yl)-phenyl]-cyclobutylamine,
1-[4-(8-Bromo-6-chloro-3-phenyl-imidazo[1,2-a]pyridin-2-yl)-phenyl]-cyclobutylamine,
1{-[4-(8-Bromo-3-phenyl-6-trifluoromethyl-imidazo[1,2-a]pyridin-2-yl]-phenyl}-cyclobutylamine,
1-{4-[6-Chloro-8-(4-fluorophenyl)-7-methyl-3-phenyl-imidazo[1,2-a]pyridin-2-yl]-phenyl}-cyclobutylamine,
1-{4-[6-Chloro-7-methyl-3-phenyl-8-(2H-pyrazol-3-yl)-imidazo[1,2-a]pyridin-2-yl]-phenyl}-cyclobutylamine,
1-{4-[7,8-Dimethyl-3-phenyl-6-(2H-pyrazol-3-yl)-imidazo[1,2-a]pyridin-2-yl]-phenyl}-cyclobutylamine,
1-{4-[6-Methyl-3-phenyl-8-pyridin-3-yl-imidazo[1,2-a]pyridin-2-yl]-phenyl}-cyclobutylamine,
1-{4-[8-(5-Methoxy-pyridin-3-yl)-6-methyl-3-phenyl-imidazo[1,2-a]pyridin-2-yl]-phenyl}-cyclobutylamine,
1-{4-[6-Methyl-3-phenyl-8-(2H-pyrazol-3-yl)-imidazo[1,2-a]pyridin-2-yl]-phenyl}-cyclobutylamine, 1-{4-[6-Methyl-3-phenyl-8-(1H-pyrazol-4-yl)-imidazo[1,2-a]pyridin-2-yl]-phenyl}-cyclobutylamine,
2-[4-(1-Amino-cyclobutyl)-phenyl]-6-bromo-3-phenyl-imidazo[1,2-a]pyridine-8-carboxylic acid amide,
2-[4-(1-Amino-cyclobutyl)-phenyl]-8-bromo-3-phenyl-imidazo[1,2-a]pyridine-6-carboxylic acid amide,
2-[4-(1-Amino-cyclobutyl)-phenyl]-6-methyl-3-phenyl-imidazo[1,2-a]pyridine-8-carboxylic acid amide,
2-[4-(1-Amino-cyclobutyl)-phenyl]-3-phenyl-6-(1H-pyrazol-4-yl)-imidazo[1,2-a]pyridine-8-carboxylic acid amide,
2-[4-(1-Amino-cyclobutyl)-phenyl]-3-phenyl-6-(2H-pyrazol-3-yl)-imidazo[1,2-a]pyridine-8-carboxylic acid amide,
2-[4-(1-Amino-cyclobutyl)-phenyl]-3-phenyl-6-pyridin-3-yl)-imidazo[1,2-a]pyridine-8-carboxylic acid amide,
2-[4-(1-Amino-cyclobutyl)-phenyl]-7,8-dimethyl-3-phenyl-imidazo[1,2-a]pyridine-6-carboxylic acid amide,
2-[4-(1-Amino-cyclobutyl)-phenyl]-8-methyl-3-phenyl-imidazo[1,2-a]pyridine-6-carboxylic acid amide,
1-{4-[8-Methyl-3-phenyl-6-(1H-pyrazol-4-yl)-imidazo[1,2-a]pyridin-2-yl]-phenyl}-cyclobutylamine,
1-{4-[8-Methyl-3-phenyl-6-(2H-pyrazol-3-yl)-imidazo[1,2-a]pyridin-2-yl]-phenyl}-cyclobutylamine,
1-{4-[8-Methyl-3-phenyl-6-pyridin-3-yl-imidazo[1,2-a]pyridin-2-yl]-phenyl}-cyclobutylamine,
1-{4-[8-Methyl-3-phenyl-6-(5-methyl-2H-pyrazol-3-yl)-imidazo[1,2-a]pyridin-2-yl]-phenyl}-cyclobutylamine,
1-[4-(3-phenyl-imidazo[1,2-a]pyridin-2-yl)-phenyl]-cyclobutylamine,
1-[4-(6-ethoxy-3-phenyl-imidazo[1,2-a]pyridin-2-yl)-phenyl]-cyclobutylamine,
1-[4-(3-phenyl-7-vinyl-imidazo[1,2-a]pyridin-2-yl)-phenyl]-cyclobutylamine,
1-[4-(3-phenyl-7-pyridin-4-yl-imidazo[1,2-a]pyridin-2-yl)-phenyl]-cyclobutylamine,
1-[4-(3-Phenyl-7-pyridin-3-yl-imidazo[1,2-a]pyridin-2-yl)-phenyl]-cyclobutylamine,
1-[4-(3-Phenyl-7-pyridin-2-yl-imidazo[1,2-a]pyridin-2-yl)-phenyl]-cyclobutylamine,
1-{4-[3-Phenyl-7-(1H-pyrazol-3-yl)-imidazo[1,2-a]pyridin-2-yl]-phenyl}-cyclobutylamine,
1-{4-[3-Phenyl-7-(1H-pyrazol-4-yl)-imidazo[1,2-a]pyridin-2-yl]-phenyl}-cyclobutylamine,
1-{4-[7-(1H-Imidazol-2-yl)-3-phenyl-imidazo[1,2-a]pyridin-2-yl]-phenyl}-cyclobutylamine HCl salt,
1-{4-[7-(3H-Imidazol-4-yl)-3-phenyl-imidazo[1,2-a]pyridin-2-yl]-phenyl}-cyclobutylamine HCl salt,
1-{4-[7-(3-Methyl-3H-imidazol-4-yl)-3-phenyl-imidazo[1,2-a]-pyridin-2-yl]-phenyl}-cyclobutylamine,
1-{4-[3-Phenyl-7-(2H-tetrazol-5-yl)-imidazo[1,2-a]pyridin-2-yl]-phenyl}-cyclobutylamine HCl salt ,
2-[4-(1-Amino-cyclobutyl)-phenyl]-3-phenyl-imidazo[1,2-a]-pyridine-7-carboxylic acid methyl ester,
2-[4-(1-Amino-cyclobutyl)-phenyl]-3-phenyl-imidazo[1,2-a]-pyridine-7-carboxylic acid ethyl ester,
2-[4-(1-Amino-cyclobutyl)-phenyl]-3-phenyl-imidazo[1,2-a]-pyridine-7-carboxylic acid HCl salt,
2-[4-(1-Amino-cyclobutyl)-phenyl]-3-phenyl-imidazo[1,2-a]-pyridine-7-carboxylic acid amide,
2-[4-(1-Amino-cyclobutyl)-phenyl]-3-phenyl-imidazo[1,2-a]-pyridine-7-carboxylic acid methylamide,
(E)-3-{2-[4-(1-Amino-cyclobutyl)-phenyl]-3-phenyl-imidazo[1,2-a]-pyridin-7-yl}-acrylic acid methyl ester,
(E)-3-{2-[4-(1-Amino-cyclobutyl)-phenyl]-3-phenyl-imidazo[1,2-a]-pyridin-7-yl}-acrylamide,
3-{2-[4-(1-Amino-cyclobutyl)-phenyl]-3-phenyl-imidazo[1,2-a]-pyridin-7-yl}-propionic acid methyl ester,
2-[4-(1-Amino-cyclobutyl)-phenyl]-3-phenyl-imidazo[1,2-a]-pyridine-7-carboxylic acid ethylamide,
2-[4-(1-Amino-cyclobutyl)-phenyl]-3-phenyl-imidazo[1,2-a]-pyridine-7-carboxylic acid hydroxyamide,
1-{2-[4-(1-Amino-cyclobutyl)-phenyl]-3-phenyl-imidazo[1,2-a]-pyridin-7-yl}-ethanone,
1-{4-[6-(3H-Imidazol-4-yl)-3-phenyl-imidazo[1,2-a]pyridin-2-yl]-phenyl}-cyclobutylamine HCl salt,
1-{4-[6-(1H-Imidazol-2-yl)-3-phenyl-imidazo[1,2a]pyridin-2-yl]-phenyl}-cyclobutylamine,
1-{4-[3-Phenyl-6-(1H-pyrazol-3-yl)-imidazo[1,2-a]pyridin-2-yl]-phenyl}-cyclobutylamine,
1-{4-[3-Phenyl-6-(1H-pyrazol-4-yl)-imidazo[1,2-a]pyridin-2-yl]-phenyl}-cyclobutylamine,
1-{4-[6-(3-Methyl-3H-imidazol-4-yl)-3-phenyl-imidazo[1,2-a]-pyridin-2-yl]-phenyl}-cyclobutylamine,
1-{4-[6-(1-Methyl-1H-pyrazol-4-yl)-3-phenyl-imidazo[1,2-a]-pyridin-2-yl]-phenyl}-cyclobutylamine,
1-{4-[3-Phenyl-6-(2H-tetrazol-5-yl)-imidazo[1,2-a]pyridin-2-yl]-phenyl}-cyclobutylamine HCl salt,
1-[4-(3-Phenyl-6-pyridin-4-yl-imidazo[1,2-a]pyridin-2-yl)-phenyl]-cyclobutylamine,
1-[4-(3-Phenyl-6-pyridin-3-yl-imidazo[1,2-a]pyridin-2-yl)-phenyl]-cyclobutylamine,
1-[4-(3-Phenyl-6-pyridin-3-yl-imidazo[1,2-a]pyridin-2-yl)-phenyl]-cyclobutylamine,
1-[4-(6-Bromo-3-phenyl-imidazo[1,2-a]pyridin-2-yl)-phenyl]-cyclobutylamine,
1-[4-(6-Chloro-3-phenyl-imidazo[1,2-a]pyridin-2-yl)-phenyl]-cyclobutylamine,
(E)-3-{2-[4-(1-Amino-cyclobutyl)-phenyl]-3-phenyl-imidazo[1,2-a]pyridin-6-yl}-acrylic acid methyl ester,
(E)-3-{2-[4-(1-Amino-cyclobutyl)-phenyl]-3-phenyl-imidazo[1,2-a]pyridin-6-yl}-acrylamide,
2-[4-(1-Amino-cyclobutyl)-3-phenyl-imidazo[1,2-a]pyridine-6-carboxylic acid ethyl ester ,
1-{2-[4-(1-Amino-cyclobutyl)-phenyl]-3-phenyl-imidazo[1,2-a]pyridin-6-yl}-ethanone,
1-[4-(6-Chloro-8-methoxy-3-phenyl-imidazo[1,2-a]pyridin-2-yl)-phenyl]-cyclobutylamine,
1-[4-(6,8-Dimethoxy-3-phenyl-imidazo[1,2-a]pyridin-2-yl)-phenyl]-cyclobutylamine,
1-[4-(6-Ethyl-8-methoxy-3-phenyl-imidazo[1,2-a]pyridin-2-yl)-phenyl]-cyclobutylamine,
1-{4-[6-(3H-Imidazol-4-yl)-8-methoxy-3-phenyl-imidazo[1,2-a]pyridin-2-yl]-phenyl}-cyclobutylamine,
1-{4-[6-(1H-Imidazol-2-yl)-8-methoxy-3-phenyl-imidazo[1,2-a]pyridin-2-yl]-phenyl}-cyclobutylamine,
1-{4-[7-(1-Methyl-1H-pyrazol-4-yl)-3-phenyl-imidazo[1,2-a]pyridin-2-yl]-phenyl}-cyclobutylamine,
2-[4-(1-Amino-cyclobutyl)-phenyl]-3-phenyl-imidazo[1,2-a]pyridin-7-ylamine,
N-{2-[4-(1-Amino-cyclobutyl)-phenyl]-3-phenyl-imidazo[1,2-a]pyridin-7-yl}-acetamide,
{2-[4-(1-Amino-cyclobutyl)-phenyl]-3-phenyl-imidazo[1,2-a]pyridin-7-yl}-urea,
2-[4-(1-Amino-cyclobutyl)-phenyl]-3-phenyl-imidazo[1,2-a]pyridine-7-carboxylic acid methoxy-methyl-amide,
2-[4-(1-Amino-cyclobutyl)-phenyl]-3-phenyl-imidazo[1,2-a]pyridin-6-ylamine,
N-{2-[4-(1-Amino-cyclobutyl)-phenyl]-3-phenyl-imidazo[1,2-a]pyridin-6-yl}-acetamide,
{2-[4-(1-Amino-cyclobutyl)-phenyl]-3-phenyl-imidazo[1,2-a]pyridin-6-yl}-urea , 1-{2-[4-(1-Amino-cyclobutyl)-phenyl]-3-phenyl-imidazo [1,2-a]pyridin-6-yl}-3-methyl-urea, N-{2-[4-(1-Amino-cyclobutyl)-phenyl]-3-phenyl-imidazo[1,2-a]pyridin-6-yl}-methanesulfonamide, 1-[4-(8-Methoxy-3-phenyl-6-yinyl-imidazo[1,2-a]pyridin-2-yl)-phenyl]-cyclobutylamine, 2-[4-(1-amino-cyclobutyl)-phenyl]-3-phenyl-imidazo[1,2-a]pyridin-8-ol, 2-[4-(1-amino-cyclobutyl)-phenyl]-3-phenyl-imidazo[1,2-a]pyridine-8-carboxylic acid amide, 1-[4-(7-ethynyl-3-phenyl-imidazo[1,2-a]pyridin-2-yl)-phenyl]-cyclo-butylamine, 3-{2-[4-(1-amino-cyclobutyl)-phenyl]-3-phenyl-imidazo [1,2-a]pyridin-7-yl}-propionamide, {2-[4-(1-amino-cyclobutyl)-phenyl]-3-phenyl-imidazo[1,2-a]pyridin-7-yloxy}-acetic acid methyl ester, 2-[4-(1-amino-cyclobutyl)-phenyl]-3-phenyl-imidazo[1,2-a]pyridin-7-ol, 3-{2-[4-(1-amino-cyclobutyl)-phenyl]-3-phenyl-imidazo [1,2-a]pyridin-6-yl}-pyridin-2-ol, 1-{4-[6(5-methyl-2H-pyrazol-3-yl)-3-phenyl-imidazo[1,2-a]pyridin-2-yl]-phenyl}-cyclobutylamine, 1-{4-[8-methoxy-3-phenyl-6-(1H-pyrazol-4-yl)-imidazo [1,2-a]pyridin-2-yl]-phenyl}-cyclobutylamine, 1-[4-(5-methyl-3-phenylimidazo[1,2-a]pyridin-2-yl)phenyl]cyclo-butanamine, and 2-[4-(1-aminocyclobutyl)phenyl]-8-chloro-3-phenylimidazo[1,2-a]pyridine-6-carbonitrile.

6. A pharmaceutical composition comprising at least one compound according to claim 1, together with at least one pharmaceutically acceptable auxiliary.

7. A pharmaceutical composition comprising at least one compound according to claim 1, and one or more second active ingredients selected from chemotherapeutic anti-cancer agents and target-specific anti-cancer agents.

8. Process for the manufacture of a compound of formula (I) according to claim 1, wherein a compound of formula (III)

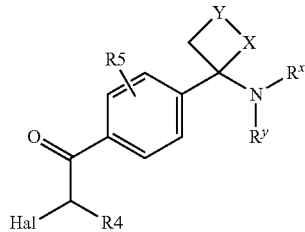

(III)

whereby R4, R5 and R6, X and Y are defined according to claim 1 and Rx is R6 or a protecting group; Ry is hydrogen or a protecting group, or Rx and Ry together, or Y and Rx together, may form a cyclic protecting group, Hal is halogen, is reacted with a compound of formula (IV)

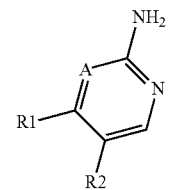

(IV)

whereby R1, R2, and A are defined according to claim 1, forming a compound of formula (IIa)

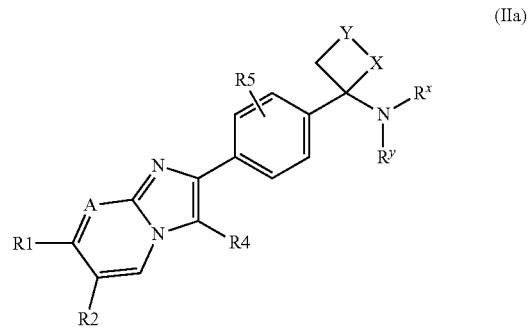

(IIa)

which is optionally subsequently deprotected to form a compound of general formula (I).

9. Process for the manufacture of a compound of formula (I) according to claim 1, wherein a compound of formula (XIV)

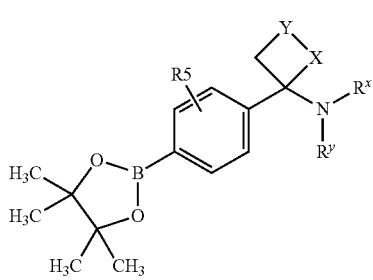

(XIV)

wherein

R5 is hydrogen or halogen, and

R6 is hydrogen or 1-6C-alkyl,

X is —CH2— and

Y is —CH2—, —CH(OH)— and

Rx is R6 or a protecting group;

Ry is hydrogen or a protecting group, or Rx and Ry together, or
Y and Rx together, may form a cyclic protecting group, is reacted with a compound of formula (XIII)

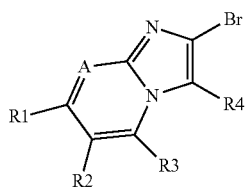

(XIII)

wherein R1, R2, R3, A and R4 are defined according to claim 1, to obtain a compound of formula (II) which is optionally deprotected, to obtain a compound of formula (I)

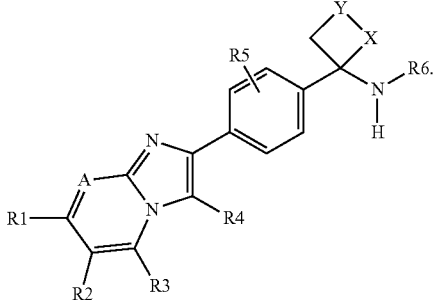

(I)

10. A method for the treatment of a hyperproliferative disease or disorder responsive to the induction of apoptosis selected from breast cancer, prostate cancer, melanoma, non-small cell lung cancer (NSCLC), and brain cancer comprising administering to a human or animal in need thereof an effective amount of a compound according to claim 1.

* * * * *